US012629394B2

(12) United States Patent
Regev et al.

(10) Patent No.: US 12,629,394 B2
(45) Date of Patent: May 19, 2026

(54) ATLAS OF CHOROID PLEXUS CELL TYPES AND THERAPEUTIC AND DIAGNOSTIC USES THEREOF

(71) Applicants: The Broad Institute, Inc., Cambridge, MA (US); Massachusetts Institute of Technology, Cambridge, MA (US); The Children's Medical Center Corporation, Boston, MA (US)

(72) Inventors: Aviv Regev, Cambridge, MA (US); Rebecca Herbst, Cambridge, MA (US); Naomi Habib, Cambridge, MA (US); Maria Lehtinen, Boston, MA (US); Neil Dani, Boston, MA (US); Ahram Jang, Boston, MA (US)

(73) Assignees: The Broad Institute, Inc., Cambridge, MA (US); Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 573 days.

(21) Appl. No.: 16/862,506

(22) Filed: Apr. 29, 2020

(65) Prior Publication Data

US 2020/0397828 A1 Dec. 24, 2020

Related U.S. Application Data

(60) Provisional application No. 62/840,351, filed on Apr. 29, 2019.

(51) Int. Cl.
*C12N 5/079* (2010.01)
*A61K 35/17* (2015.01)
*A61K 35/28* (2015.01)
*A61K 35/36* (2015.01)
*C12N 5/0775* (2010.01)

(52) U.S. Cl.
CPC .............. *A61K 35/36* (2013.01); *A61K 35/17* (2013.01); *A61K 35/28* (2013.01); *C12N 5/0666* (2013.01)

(58) Field of Classification Search
None
See application file for complete search history.

(56) References Cited

U.S. PATENT DOCUMENTS

| | | | |
|---|---|---|---|
| 4,737,323 A | 4/1988 | Martin et al. | |
| 4,816,567 A | 3/1989 | Cabilly et al. | |
| 4,837,028 A | 6/1989 | Allen | |
| 5,143,854 A | 9/1992 | Pirrung et al. | |
| 5,270,163 A | 12/1993 | Gold et al. | |
| 5,288,644 A | 2/1994 | Beavis et al. | |
| 5,324,633 A | 6/1994 | Fodor et al. | |
| 5,432,049 A | 7/1995 | Fischer et al. | |
| 5,470,710 A | 11/1995 | Weiss et al. | |
| 5,492,806 A | 2/1996 | Drmanac et al. | |
| 5,503,980 A | 4/1996 | Cantor | |
| 5,510,270 A | 4/1996 | Fodor et al. | |
| 5,525,464 A | 6/1996 | Drmanac et al. | |
| 5,547,839 A | 8/1996 | Dower et al. | |
| 5,580,732 A | 12/1996 | Grossman et al. | |
| 5,661,028 A | 8/1997 | Foote | |
| 5,800,992 A | 9/1998 | Fodor et al. | |
| 5,811,097 A | 9/1998 | Allison et al. | |
| 6,479,626 B1 | 11/2002 | Kim et al. | |
| 6,534,261 B1 | 3/2003 | Cox, III et al. | |
| 6,607,882 B1 | 8/2003 | Cox, III et al. | |
| 6,746,838 B1 | 6/2004 | Choo et al. | |
| 6,794,136 B1 | 9/2004 | Eisenberg et al. | |
| 6,824,978 B1 | 11/2004 | Cox, III et al. | |
| 6,866,997 B1 | 3/2005 | Choo et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,585,849 B2 | 9/2009 | Liu et al. | |
| 7,595,376 B2 | 9/2009 | Kim et al. | |
| 8,021,867 B2 | 9/2011 | Smith et al. | |
| 8,119,361 B2 | 2/2012 | Smith et al. | |
| 8,119,381 B2 | 2/2012 | Smith et al. | |
| 8,124,369 B2 | 2/2012 | Smith et al. | |

(Continued)

FOREIGN PATENT DOCUMENTS

| | | |
|---|---|---|
| EP | 0 785 280 A2 | 7/1997 |
| EP | 0 785 280 B1 | 4/2003 |

(Continued)

OTHER PUBLICATIONS

Gonzalez et al., (BMC Neuroscience 2011, 12:4, 12 pages (Year: 2011).*
Haddad et al., (Molecular Therapy, vol. 21, Supplement 1, May 2013, Abstract #383, p. S147 (Year: 2013).*
Konat et al., (Metab Brain Dis (2008) 23: 325-333 (Year: 2008).*
Qi et al., (Investigative Ophthalmology & Visual Science, Dec. 2007, vol. 48, No. 12, pp. 5360-5370 (Year: 2007).*
Schuster et al., (Frontiers in Neuroanatomy, Jun. 2014, vol. 8, Article 42, pp. 1-14 (Year: 2014).*
Nakane et al Stroke, Jan. 2001, pp. 184-189 (Year: 2001).*

(Continued)

*Primary Examiner* — Evelyn Y Pyla

(74) *Attorney, Agent, or Firm* — Foley & Lardner LLP; Sunit Talapatra

(57) ABSTRACT

A cell atlas of the Choroid Plexus is provided and includes novel markers for cell types. Novel cell types and methods of quantitating, detecting and isolating the cell types are disclosed. Methods of treatment, including for oxidative stress in the brain are provided, as well as methods for controlling differentiation, maintenance and/or function of the cell types disclosed herein.

7 Claims, 54 Drawing Sheets

Specification includes a Sequence Listing.

(56) References Cited

U.S. PATENT DOCUMENTS

| | | | |
|---|---|---|---|
| 8,129,134 | B2 | 3/2012 | Smith et al. |
| 8,133,697 | B2 | 3/2012 | Smith et al. |
| 8,163,514 | B2 | 4/2012 | Smith et al. |
| 2009/0312724 | A1 | 12/2009 | Pipkin et al. |
| 2016/0060691 | A1 | 3/2016 | Giresi et al. |
| 2016/0208323 | A1 | 7/2016 | Bernstein et al. |

FOREIGN PATENT DOCUMENTS

| | | |
|---|---|---|
| EP | 0 373 203 B2 | 2/2007 |
| WO | 89/10977 A1 | 11/1989 |
| WO | 95/21265 A1 | 8/1995 |
| WO | 96/31622 A1 | 10/1996 |
| WO | 96/40281 A2 | 12/1996 |
| WO | 97/10365 A1 | 3/1997 |
| WO | 97/27317 A1 | 7/1997 |
| WO | 2014/093622 A2 | 6/2014 |
| WO | 2014/204725 A1 | 12/2014 |
| WO | 2014/210353 A2 | 12/2014 |
| WO | 2016/040476 A1 | 3/2016 |
| WO | 2016/106236 A1 | 6/2016 |
| WO | 2016/168584 A1 | 10/2016 |
| WO | 2017/156336 A1 | 9/2017 |
| WO | 2017/164936 A1 | 9/2017 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/018423 A1 | 1/2019 |
| WO | 2019/060746 A1 | 3/2019 |
| WO | 2019/071048 A1 | 4/2019 |
| WO | 2019/126709 A1 | 6/2019 |
| WO | 2019/126716 A1 | 6/2019 |
| WO | 2019/126762 A2 | 6/2019 |
| WO | 2020/033601 A1 | 2/2020 |
| WO | 2020/131862 A1 | 6/2020 |

OTHER PUBLICATIONS

Neurosurgerypaedia—Cisterna magna (2024), retrieved from the internet: https://neurosurgerypaedia.org/wiki/doku.php?id=cisterna_magna (Year: 2024).*

Apparailly et al., Human Gene Therapy 16:426-434 (Apr. 2005) (Year: 2005).*

Geguchadze et al., J Dent Res 91(4) 2012, pp. 382-386 (Year: 2012).*

Georgiadis et al., Gene Therapy (2016) 23, 857-862 (Year: 2016).*

Yamazaki et al., Scientific Reports, 4:5506, 7 pages (2014) (Year: 2014).*

Carballo, et al., "A Highlight on Sonic Hedgehog Pathway", Cell Communication and Signaling, vol. 16, No. 11, 2018, 1-15.

Lehtinen, et al., "The Cerebrospinal Fluid Provides a Proliferative Niche for Neural Progenitor Cells", Neuron, vol. 69, Mar. 10, 2011, 893-905.

Lun, et al., "Spatially Heterogeneous Choroid Plexus Transcriptomes Encode Positional Identity and Contribute to Regional CSF Production", The Journal of Neuroscience, vol. 35, No. 12, Mar. 25, 2015, 4903-4916.

Purro, "Dysfunction of Wnt Signaling and Synaptic Disassembly in Neurodegenerative Diseases", Journal of Molecular Cell Biology, vol. 6, 2014, 75-80.

Aitkenhead et al., "Identification of endothelial cell genes expressed in an in vitro model of angiogenesis: induction of ESM-1, Beta-ig-h3, and NrCAM," Microvascular Research, 2002, vol. 63 (pp. 159-171).

Anzalone et al., "Search-and-replace genome editing without double-strand breaks or donor DNA," Nature Dec. 2019, vol. 576, No. 7785 (pp. 149-157).

Awatramani et al., "Cryptic boundaries in roof plate and choroid plexus identified by intersectional gene activation," Nature Genetics, Sep. 2003, vol. 35, No. 1 (pp. 70-75).

Balusu et al., "The choroid plexus-cerebrospinal fluid interface in Alzheimer's disease: more than just a barrier," Neural Regeneration Research, Apr. 2016, vol. 11, No. 4 (pp. 534-537).

Bartel et al., "MicroRNAs: Genomics, Biogenesis, Mechanism, and Function," Cell, Jan. 23, 2004, vol. 116, No. 2 (pp. 281-297).

Bartunek et al., Avian stem cell factor (SCF): production and characterization of the recombinant His-tagged SCF of chicken and its neutralizing antibody, Cytokine, Jan. 1996, vol. 8, Issue 1 (pp. 14-20).

Baskin et al., "Regional concentrations of insulin in the rat brain," Endocrinology, Mar. 1, 1983, vol. 112, No. 3 (pp. 898-903).

Ben-Zvi et al., "Mfsd2a is critical for the formation and function of the blood-brain barrier," Nature, May 22, 2014, vol. 509, No. 7501 (pp. 507-511).

Bielecki et al., "Skin inflammation driven by differentiation of quiescent tissue-resident ILCs into a spectrum of pathogenic effectors," bioRxiv, 2018, bioRxiv 461228; (43 pages).

Binz et al., "Engineering novel binding proteins from nonimmunoglobulin domains," Nature Biotechnology, 2005, vol. 23 (pp. 1257-1268).

Biswass et al., "CRISPRTarget: bioinformatic prediction and analysis of crRNA targets," RNA Biology, May 2013, vol. 10 (pp. 817-827).

Blei et al., "Latent Dirichlet Allocation," Journal of Machine Learning Research 3, 2003 (pp. 993-1022).

Brooks et al., "Multiciliated cells," Current Biology, Oct. 6, 2014, vol. 24, (pp. R973-R982).

Brown et al., "Propellant-Driven Aerosols of Proteins," Aerosol Science and Technology, Jan. 1996, vol. 24 (pp. 45-56).

Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).

Buenrostro et al., "Single-cell chromatin accessibility reveals principles of regulatory variation," Nature, Jul. 23, 2015, vol. 523, No. 7561 (pp. 486-490).

Burlingame et al., "Mass spectrometry," Analytical Chemistry, Aug. 15, 1998, vol. 70, No. 16 (pp. 647-716).

Butler et al., "Integrating Single-cell Transcriptomic Data Across Different Conditions, Technologies, and Species," Nature Biotechnology, May 2018, vol. 36, No. 5 (17 pages).

Camp et al., "Human cerebral organoids recapitulate gene expression programs of fetal neocortex development," Proceedings of the National Academy of Sciences, USA, Dec. 22, 2015, vol. 112, No. 51 (pp. 15672-15677).

Cao et al., "Comprehensive single cell transcriptional profiling of a multicellular organism by combinatorial indexing," bioRxiv preprint first posted online Feb. 2, 2017 (35 pages).

Cao et al., "Comprehensive single-cell transcriptional profiling of a multicellular organism," Science, Aug. 18, 2017, vol. 357, No. 6352 (pp. 661-667).

Carlson et al., "Identification of Amino Acids in the Glutamate Receptor, GluR3, Important for Antibody-binding and Receptor-specific Activation," The Journal of Biological Chemistry, Apr. 25, 1997, vol. 272, No. 17 (pp. 11295-11301).

Carr et al., "Genome Engineering," Nature Biotechnology, Dec. 2009, vol. 27, No. 12 (pp. 1151-1162).

Chang et al., "Zebrafish cerebrospinal fluid mediates cell survival through a retinoid signaling pathway," Developmental Neurobiology, 2015 (pp. 1-18).

Charman, "Lipids, Lipophilic Drugs, and Oral Drug Delivery-Some Emerging Concepts," Journal of Pharmaceutical Sciences, 2000, vol. 89, No. 8 (pp. 967-978).

Chau et al., "Progressive Differentiation and Instructive Capacities of Amniotic Fluid and Cerebrospinal Fluid Proteomes following Neural Tube Closure," Developmental Cell, Dec. 21, 2015, vol. 35, No. 6 (pp. 789-802).

Chen et al., Effects of Interleukin-1a, Interleukin-1 Receptor Antagonist, and Neutralizing Antibody on Proinflammatory Cytokine Expression by Human Squamous Cell Carcinoma Lines, Cancer Research, Aug. 15, 1998, vol. 58, No. 16 (pp. 3668-3678).

(56) References Cited

OTHER PUBLICATIONS

Choi et al., "Minocycline attenuates neuronal cell death and improves cognitive impairment in Alzheimer's disease models," Neuropsychopharmacology, 2007, vol. 32, No. 11 (pp. 2393-2404).

Chow et al., "The molecular constituents of the blood-brain barrier," Trends in Neuroscience, Oct. 2015, vol. 38, No. 10 (pp. 598-608).

Chuang et al., "Vertebrate Hedgehog signalling modulated by induction of a Hedgehog-binding protein," Nature, Feb. 18, 1999, vol. 397 (pp. 617-621).

Clackson et al., "Making antibody fragments using phage display libraries," Nature, Aug. 1991, vol. 352 (pp. 624-628).

Cohen et al., "Lung single-cell signaling interaction map reveals basophil role in macrophage imprinting," Cell, Nov. 1, 2018, vol. 175, No. 4 (pp. 1031-1044).

Coulter et al., "The ESCRT-III protein CHMP1A mediates secretion of sonic hedgehog on a distinctive subtype of extracellular vesicles," Cell Reports, Jul. 24, 2018, vol. 24, No. 4 (pp. 973-986).

Cusanovich et al., "Multiplex single-cell profiling of chromatin accessibility by combinatorial cellular indexing" Science, May 22, 2015, vol. 348, No. 6237 (34 pages—Supplementary materials).

Deng et al., "An Agonist Murine Monoclonal Antibody to the Human c-Mpl Receptor Stimulates Megakaryocytopoiesis," Blood, Sep. 1998, vol. 92, No. 6 (pp. 1981-1988).

Dietrich et al., "Clinical patterns and biological correlates of cognitive dysfunction associated with cancer therapy. Oncologist," Dec. 2008, vol. 13, No. 12 (pp. 1285-1295).

Diez-Roux et al., "A High-Resolution Anatomical Atlas of the Transcriptome in the Mouse Embryo," PLoS Biology, Jan. 2011 vol. 9, No. 1 (pp. 1-13).

Doench et al., "Optimized sgRNA design to maximize activity and minimize off-target effects of CRISPR-Cas9," Nature Biotechnology, Feb. 2016, vol. 34, No. 2 (pp. 184-191).

Donovan et al., "The iron exporter ferroportin/Slc40a1 is essential for iron homeostasis," Cell Metabolism, Mar. 2005, vol. 1, No. 3 (pp. 191-200).

Donsante et al., "ATP7A gene addition to the choroid plexus results in long-term rescue of the lethal copper transport defect in a Menkes disease mouse model," Molecular Therapy, 2011, vol. 19, No. 12 (pp. 2114-2123).

Doyon et al., "Enhancing zinc-finger-nuclease activity with improved obligate heterodimeric architectures," Nature Methods, Jan. 2011, vol. 8, No. 1 (pp. 74-79).

Ellington et al, "In vitro selection of RNA molecules that bind specific ligands," Nature, 1990, vol. 346, No. 6287 (pp. 818-822).

Esvelt et al., "Orthogonal Cas9 proteins for RNA-guided gene regulation and editing," Nature Methods, Nov. 2013, vol. 10, No. 11 (pp. 1116-1121).

Fardell et al., "Chemotherapy and cognitive impairment: treatment options," Clinical Pharmacological Therapy, Sep. 2011, vol. 90, No. 3 (pp. 366-376).

Faubel et al., "Cilia-based flow network in the brain ventricles," Science, Jul. 8, 2016, vol. 353, No. 6295 (pp. 176-178).

Fruttiger, M., "Development of the mouse retinal vasculature: angiogenesis versus vasculogenesis," Investigative Ophthalmology & Visual Science, Feb. 2002, vol. 43, No. 2 (pp. 522-527).

Gao et al., "Engineered Cpf1 enzymes with altered PAM specificities," bioRxiv preprint, Dec. 4, 2016 [pp. 1/14-14/14, pp. 1/3-3/3 of Figs, and pp. S1-S8 (25 pages)].

Gao et al., "Treatment of autosomal dominant hearing loss by in vivo delivery of genome editing agents," Nature, 2018, vol. 553, No. 7687 (pp. 217-221).

Gattazzo et al., "Extracellular matrix: a dynamic microenvironment for stem cell niche," Biochimica et Biophysica Acta (BBA) General Subjects, Aug. 2014, vol. 1840, No. 8 (pp. 2506-2519).

Gaudelli et al., "Programmable base editing of A-T to G-C in genomic DNA without DNA cleavage," Nature, Nov. 23, 2017, vol. 551, No. 7681 (pp. 464-471).

Gebauer and Skerra, "Engineered protein scaffolds as next-generation antibody therapeutics," Current Opinion in Chemical Biology, Jun. 2009, vol. 13, No. 3 (pp. 245-255).

Geiss et al., "Direct multiplexed measurement of gene expression with color-coded probe pairs," Nature Biotechnology, 2008, vol. 26, No. 3 (pp. 317-325).

Geraets et al., "Moving towards effective therapeutic strategies for Neuronal Ceroid Lipofuscinosis," Orphanet Journal of Rare Diseases, 2016, vol. 11, No. 40 (pp. 1-13).

Ghersi-Egea et al., "Molecular anatomy and functions of the choroidal blood-cerebrospinal fluid barrier in health and disease," Acta Neuropathologica, 2018, vol. 135 (pp. 337-361).

Gibson et al., "Methotrexate Chemotherapy Induces Persistent Tri-glial Dysregulation that Underlies Chemotherapy-Related Cognitive Impairment," Cell, Jan. 10, 2019, vol. 176, Nos. 1-2 (pp. 43-55).

Gierahn et al., "Seq-Well: Portable, Low-Cost RNA Sequencing of Single Cells at High Throughput," Nature Methods, Apr. 2017, vol. 14, No. 4 (8 pages).

Gilbert et al., "CRISPR-Mediated Modular RNA-Guided Regulation of Transcription in Eukaryotes," Cell, Jul. 18, 2013, vol. 154 (pp. 442-451).

Gilbert et al., "Genome-Scale CRISPR-Mediated Control of Gene Repression and Activation," Cell, Oct. 23, 2014, vol. 159, No. 3 (pp. 647-661).

Gill et al., "Biopharmaceutical drug discovery using novel protein scaffolds," Current Opinion in Biotechnology, 2006, vol. 17, No. 6 (653-658).

Girvan et al., "Community structure in social and biological networks," Proceedings of the National Academy of Sciences, USA, 2002, vol. 99 (pp. 7821-7826).

Gleditzsch et al., "PAM identification by CRISPR-Cas effector complexes: diversified mechanisms and structures," RNA Biology 2019, vol. 16, No. 4 (pp. 504-517).

Grapp et al., "Choroid plexus transcytosis and exosome shuttling deliver folate into brain parenchyma," Nature Communications, 2013, vol. 4, No. 2123 (pp. 1-13).

Gray et al., "Insulin regulates brain function, but how does it get there?" Diabetes, Dec. 2014, vol. 63, No. 12 (pp. 3992-3997).

Grissa et al., "CRISPRFinder: a web tool to identify clustered regularly interspaced short palindromic repeats," Nucleic Acids Research, 2007, vol. 35 (pp. W52-W57).

Gruber et al., "The Vienna RNA Websuite," Nucleic Acids Research, Apr. 19, 2008, vol. 36 (pp. W70-W74).

Habib et al., "Div-Seq: Single-nucleus RNA-Seq reveals dynamics of rare adult newborn neurons," Science, Aug. 26, 2016, vol. 353, No. 6302 (pp. 925-928).

Habib et al., "Massively parallel single-nucleus RNA-seq with DroNc-seq," Nature Methods, Oct. 2017, vol. 14, No. 10 (pp. 955-958).

Haddad et al., "Fetal Brain-directed AAV Gene Therapy Results in Rapid, Robust, and Persistent Transduction of Mouse Choroid Plexus Epithelia," Molecular Therapy, Nucleic Acids, 2013, vol. 2 (pp. 1-8).

Haghverdi et al., "Diffusion maps for high-dimensional single-cell analysis of differentiation data," Bioinformatics, 2015, vol. 31, No. 18 (pp. 2989-2998).

Haldar et al., "Heme-mediated SPI-C induction promotes monocyte differentiation into iron-recycling macrophages," Cell, Mar. 13, 2014, vol. 156 (pp. 1223-1234).

Hallmann et al., "The regulation of immune cell trafficking by the extracellular matrix," Current Opinion in Cell Biology, 2015, vol. 36 (pp. 54-61).

Hammond et al., "Single-Cell RNA Sequencing of Microglia throughout the Mouse Lifespan and in the Injured Brain Reveals Complex Cell-State Changes," CellPress, Jan. 15, 2019, Immunity, vol. 50 (pp. 253-271).

Harrop et al., "Antibodies to TR2 (Herpesvirus Entry Mediator), a New Member of the TNF Receptor Superfamily, Block T Cell Proliferation, Expression of Activation Markers, and Production of Cytokines," Journal of Immunology, 1998, vol. 161, No. 4 (pp. 1786-1794).

Hashimshony, et al., "CEL-Seq: Single-Cell RNA-Seq by Multiplexed Linear Amplification," Cell Reports, 2012, vol. 2, No., 3 (pp. 666-673).

(56)                References Cited

OTHER PUBLICATIONS

Hernberger et al., "The role of plasmalemma vesicle-associated protein (PLVAP) in endothelial cells of Schlemm's canal and ocular capillaries," Experimental Eye Research, Dec. 2012, vol. 105, (pp. 27-33).
Horowitz et al., "A Call for a Neuroscience Approach to Cancer-Related Cognitive Impairment," Trends in Neuroscience, Aug. 2018, vol. 41, No. 8 (pp. 493-496).
Horwell et al., "The 'peptoid' approach to the design of non-peptide, small molecule agonists and antagonists of neuropeptides," Trends in Biotechnology, Apr. 1995, vol. 13, No. 4 (pp. 132-134).
Howard et al., "Intracerebral drug delivery in rats with lesion-induced memory deficits," Journal of Neurosurgery, Jul. 1989, vol. 71, No. 1 (pp. 105-112).
Huang et al., "Dampened Hedgehog signaling but normal Wnt signaling in zebrafish without cilia," Development, Sep. 15, 2009, vol. 136, No. 18 (pp. 3089-3098).
Huang et al., "Transventricular delivery of Sonic hedgehog is essential to cerebellar ventricular zone development," Proceedings of the National Academy of Sciences, May 4, 2010, vol. 107, No. 18 (pp. 1-6).
Hunter et al., "Molecularly and temporally separable lineages form the hindbrain roof plate and contribute differentially to the choroid plexus," Development, 2007, vol. 134 (pp. 3449-3460).
Islam et al., "Characterization of the single-cell transcriptional landscape by highly multiplex RNA-seq," Genome Research, 2011, vol. 21, No. 7 (pp. 1160-1167).
Jiang et al., "RNA-guided editing of bacterial genomes using CRISPR-Cas systems," Nature Biotechnology, Mar. 2013, vol. 31 [30 pages, including supplementary information] (pp. 233-239).
Jordao et al., "Single-cell profiling identifies myeloid cell subsets with distinct fates during neuroinflammation," Science, Jan. 25, 2019, vol. 363, No. 6425 (pp. 1-18).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Karimy et al., "Inflammation-dependent cerebrospinal fluid hypersecretion by the choroid plexus epithelium in posthemorrhagic hydrocephalus," Nature Medicine, 2017, vol. 23 (pp. 997-1003).
Keskin et al., "Transcript-RNA-templated DNA recombination and repair," Nature, Nov. 20, 2014, vol. 515, No. 7527 (pp. 436-439).
Kim et al., "Hybrid restriction enzymes: Zinc finger fusions to Fok I cleavage domain," Proceedings of the National Academy of Science, USA, Feb. 1996, vol. 93, No. 3 (pp. 1156-1160).
Kim et al., "Chimeric restriction endonuclease.," Proceedings of the National Academy of Sciences, USA, Feb. 1994, vol. 91, No. 3 (pp. 883-887).
Klein et al., "Droplet Barcoding for Single-Cell Transcriptomics Applied to Embryonic Stem Cells," Cell, 2015, vol. 161, No. 5 (pp. 1187-1201).
Kleinridders et al., "Insulin action in brain regulates systemic metabolism and brain function," Diabetes, Jul. 2014, vol. 63, No. 7 (pp. 2232-2243).
Kleinstiver et al., "Engineered CRISPR-Cas9 nucleases with altered PAM specificities," Nature, Jul. 23, 2015, vol. 523, No. 7561 (pp. 481-485).
Klompe et al., "Transposon-encoded CRISPR-Cas systems direct RNA-guided DNA integration," Nature, Jul. 2019, vol. 571, No. 7764 (pp. 219-225).
Kohler et al., "Continuous cultures of fused cells secreting antibody of predefined specificity," Nature, 1975, vol. 256 (pp. 495-497).
Kohyama et al., "Role for Spi-C in the development of red pulp macrophages and splenic iron homeostasis," Nature, Jan. 15, 2009, vol. 457, No. 7227 (pp. 318-321).
Kojima et al., "Claudin 5 is transiently expressed during the development of the retinal pigment epithelium," The Journal of Membrane Biology, 2002, vol. 186 (pp. 81-88).

Kolmar, "Alternative binding proteins: biological activity and therapeutic potential of cystine-knot miniproteins," The FEBS Journal, 2008, 275 (pp. 2684-2690).
Komor et al., "Programmable editing of a target base in genomic DNA without double-stranded DNA cleavage," Nature, 2016, vol. 533 (pp. 420-424).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Koonin et al., "Origins and evolution of CRISPR-Cas systems," Philosophical Transactions of the Royal Society B. May 13, 2019, vol. 374, No. 1772 (16 pages).
Kriegstein et al., "The glial nature of embryonic and adult neural stem cells," Annual Review Neuroscience, 2009, vol. 32 (pp. 149-184).
Kuhn et al., "Quantification of C-reactive protein in the serum of patients with rheumatoid arthritis using multiple reaction monitoring mass spectrometry and 13C-labeled peptide standards," Proteomics, Apr. 2004 vol. 4, No. 4 (pp. 1175-1186).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Lamb et al., "The Connectivity Map: Using Gene-Expression Signatures to Connect Small Molecules, Genes, and Disease," Science, Sep. 29, 2006, vol. 313, Issue 5795 (pp. 1929-1935).
Lamb, "The Connectivity Map: A New Tool for Biomedical Research," Nature Reviews, Cancer, Jan. 2007, vol. 7, No. 1 (pp. 54-60).
Lau et al., "An Abundant Class of Tiny RNAs with Probably Regulatory Roles in Caenorhabditis elegans," Science, Oct. 26, 2001, vol. 294 (pp. 858-861).
Lee et al., "An Extensive Class of Small RNAs in Caenorhabditis elegans," Science, Oct. 26, 2001, vol. 294 (pp. 862-864).
Leek et al., "The sva package for removing batch effects and other unwanted variation in high-throughput experiments," Bioinformatics, Mar. 15, 2012, vol. 28, No. 6 (pp. 882-883).
Leenay et al., "Identifying and Visualizing Functional PAM Diversity across CRISPR-Cas Systems," Molecular Cell, vol. 62, 2016 (pp. 137-147).
Lehtinen et al., "Cystatin B deficiency sensitizes neurons to oxidative stress in progressive myoclonus epilepsy, EPM1," The Journal of Neuroscience, May 6, 2009, vol. 29, No. 18 (pp. 5910-5915).
Lehtinen et al., "Modeling oxidative stress in the central nervous system," Current Molecular Medicine, 2006, vol. 6 (pp. 871-881).
Lehtinen et al., "The choroid plexus and cerebrospinal fluid: emerging roles in development, disease, and therapy," The Journal of Neuroscience, Nov. 6, 2013 vol. 33, No. 45 (pp. 17553-17559).
Lein et al., "Genome-wide Atlas of Gene Expression in the Adult Mouse Brain," Nature, Jan. 11, 2007, vol. 445, No. 7124 (pp. 168-176).
Levy et al., "Cytosine and adenine base editing of the brain, liver, retina, heart and skeletal muscle of mice via adeno-associated viruses," Nature Biomedical Engineering, Jan. 2020, vol. 4, No. 1 (pp. 97-110).
Li et al., "Base editing with a Cpf1-cytidine deaminase fusion," Nature Biotechnology, Apr. 2018, vol. 36, No. 4 (pp. 324-327).
Li et al., "Developmental Heterogeneity of Microglia and Brain Myeloid Cells Revealed by Deep Single-Cell RNA Sequencing," CellPress, Neuron, Jan. 16, 2019, vol. 101 (pp. 207-223).
Liautard et al., "Specific Inhibition of IL-6 Signalling with Monoclonal Antibodies Against the gp130 Receptor," Cytokine, Apr. 1997, vol. 9, No. 4 (pp. 233-241).
Liddelow et al., "Development of the lateral ventricular choroid plexus in a marsupial, Monodelphis domestica," Cerebrospinal Fluid Research, 2010, vol. 7, No. 16 (pp. 1-10).

(56) References Cited

OTHER PUBLICATIONS

Lim et al., "Hyaluronan receptor LYVE-1-expressing macrophages maintain arterial tone through hyaluronan-mediated regulation of smooth muscle cell collagen" CellPress, Immunity, Aug. 21, 2018, vol. 49 (pp. 326-341).

Lim et al., "The microRNAs of Caenorhabditis elegans," Genes & Development, Apr. 15, 2003, vol. 17, No. 8 (pp. 991-1008).

Lim et al., "Vertebrate microRNA genes," Science, Mar. 7, 2003, vol. 299, No. 5612 (p. 1540).

Liu et al., "Engineering cell signaling using tunable CRISPR-Cpf1-based transcription factors," Nature Communications, 2017, vol. 8, No. 2095 (pp. 1-8).

Lun et al., "Development and functions of the choroid plexus-cerebrospinal fluid system," Nature Reviews Neuroscience, Aug. 2015, vol. 16, No. 8 (pp. 445-457).

Ma et al., "Targeted AID-mediated mutagenesis (TAM) enables efficient genomic diversification in mammalian cells," Nature Methods, Dec. 2016, vol. 13, No. 12 (pp. 1029-1035).

Macosko et al., "Highly Parallel Genome-wide Expression Profiling of Individual Cells Using Nanoliter Droplets," Cell, May 21, 2015, vol. 161 (pp. 1202-1214).

Makarova et al., "Evolutionary classification of CRISPR-Cas systems: a burst of class 2 and derived variants," Nature Reviews, Microbiology, Feb. 2020, vol. 18, No. 2 (pp. 67-83).

Mao et al., "Hedgehog signaling controls mesenchymal growth in the developing mammalian digestive tract," Development, May 15, 2010, vol. 137, No. 10 (pp. 1721-1729).

Marks et al., "By-passing immunization. Human antibodies from V-gene libraries displayed on phage," Journal of Molecular Biology, 1991, vol. 222, No. 3 (pp. 581-597).

Marques et al., "Blood-brain-barriers in aging and in Alzheimer's disease," Molecular Neurodegeneration, 2013, vol. 8, No. 38 (pp. 1-9).

Marraffini et al., "Self vs. non-self discrimination during CRISPR RNA-directed immunity," Nature, 2010, vol. 463 (pp. 568-571).

Martik et al., "Regulatory logic underlying diversification of the neural crest," Trends in Genetics, Oct. 2017, vol. 33, No. 10 (pp. 715-727).

Maruyama et al., "Targetability of novel immunoliposomes modified with amphipathic poly (ethylene glycol) s conjugated at their distal terminals to monoclonal antibodies," Biochimica et Biophysica Acta, 1995, vol. 1234 (pp. 74-80).

Mathew, D., "Haptic Responses to Emotional Stimulation," University of Tampere, School of Information Sciences, Interactive Technology, M.Sc. thesis, Apr. 2016 (40 pages).

Mojica et al., "Short Motif Sequences Determine the Targets of the Prokaryotic CRISPR Defence System," Microbiology, 2009, vol. 155 (pp. 733-740).

Moore et al., "Changes in Oxidant Defense, Apoptosis, and Cognitive Abilities During Treatment for Childhood Leukemia," Biological Research for Nursing, 2018, vol. 20, No. 4 (pp. 393-402).

Moore et al., "Increase in oxidative stress as measured by cerebrospinal fluid lipid peroxidation during treatment for childhood acute lymphoblastic leukemia," Journal of Pediatric Hematological Oncology, Mar. 2015, vol. 37, No. 2 (pp.s e86-e93).

Moskowitz et al., Neurotransmitters and the fifth cranial nerve: is there a relation to the headache phase of migraine? The Lancet, Oct. 27, 1979, vol. 314, No. 8148 (pp. 883-885).

Muller et al., "VEGF and the Fab fragment of a humanized neutralizing antibody: crystal structure of the complex at 2.4 A resolution and mutational analysis of the interface," Structure, 1998, vol. 6, No. 9 (pp. 1153-1167).

Myung et al., "The choroid plexus is an important circadian clock component," Nature communications, 2018, vol. 9, No. 1062 (pp. 1-13).

Nakayama et al., "Systematic review: generating evidence-based guidelines on the concurrent use of dietary antioxidants and chemotherapy or radiotherapy," Cancer Investigation, Dec. 2011, vol. 29, No. 10 (pp. 655-667).

Nielson et al., "Sonic hedgehog is required for vascular outgrowth in the hindbrain choroid plexus," Developmental Biology, 2010, vol. 340 (pp. 430-437).

Nishida et al., "Targeted nucleotide editing using hybrid prokaryotic and vertebrate adaptive immune systems," Science, Sep. 16, 2016, vol. 353, No. 6305 (9 Pages).

Nishimasu et al., "Crystal Structure of Cas9 in Complex with Guide RNA and Target DNA," Cell, Feb. 27, 2014, vol. 156 (pp. 935-949).

Nixon et al., "Engineered protein inhibitors of proteases," Current Opinion in Drug Discovery & Development, Mar. 1, 2006, vol. 9, No. 2 (pp. 261-268).

Nygren, "Alternative binding proteins: Affibody binding proteins developed from a small three-helix bundle scaffold," The FEBS Journal, 2008, vol. 275 (pp. 2668-2676).

Ota et al., "N-Glycosylation is essential for the secretion of extracellular superoxide dismutase," FEBS Letters, Oct. 2016, vol. 590, No. 19 (pp. 3357-3367).

Palha et al., "Do genes and environment meet to regulate cerebrospinal fluid dynamics? Relevance for schizophrenia," Frontiers in Neuroscience, Aug. 2012, vol. 6, No. 31 (pp. 1-8).

Pan et al., "Gene therapy restores auditory and vestibular function in a mouse model of Usher syndrome type 1c.," Nature Biotechnology, Mar. 2017, vol. 35, No. 3, (pp. 264-272).

Parnas et al., "A Genome-Wide CRISPR Screen in Primary Immune Cells to Dissect Regulatory Networks," 2015, vol. 162 (pp. 675-686) [with Supplementary Information].

Patel et al., "Targeting Oxidative Stress in Central Nervous System Disorders," Trends in Pharmacological Sciences, Sep. 2016, vol. 37, No. 9 (pp. 768-778).

Pattanayak et al., "High-throughput profiling of off-target DNA cleavage reveals RNA-programmed Cas9 nuclease specificity," Nature Biotechnology, vol. 31, 2013, pp. 839-843 [Including Supplementary Materials].

Peters et al., "Recruitment of CRISPR-Cas systems by Tn7-like transposons," Proceedings of the National Academy of Sciences, U.S.A, Online Aug. 15, 2017, vol. 29, No. 114 (pp. E7358-E7366).

Piazza et al., "Immunotherapy of Respiratory Syncytial Virus Infection in Cotton Rats(*Sigmodon fulviventer*) Using IgG in a Small-Particle Aerosol," The Journal of Infectious Diseases, vol. 166 (pp. 1422-1424).

Picelli et al. "Full-length RNA-seq from single cells using Smart-seq2," Nature Protocols, Jan. 2014, vol. 9, No. 1 (pp. 171-181).

Pitard et al., "Production and characterization of monoclonal antibodies against the leukemia inhibitory factor low affinity receptor, gp190," Journal of Immunological Methods, 1997, vol. 205 pp. (177-190).

Platt et al, "CRISPR-Cas9 Knockin Mice for Genome Editing and Cancer Modeling," Cell, 2014, vol. 159 (pp. 440-455).

Powell et al. "Compendium of Excipients for Parenteral Formulations," PDA Journal of Pharmaceutical Science and Technology, Sep./Oct. 1998, vol. 52, No. 2 (pp. 238-311).

Prat et al., "Agonistic monoclonal antibodies against the Met receptor dissect the biological responses to HGF," Journal of Cell Science, 1998, vol. 111 (pp. 237-247).

Protas et al., "Cerebrospinal fluid oxidative stress during chemotherapy of acute lymphoblastic leukemia in children," Pediatric Hematology and Oncology, Apr. 28, 2010, vol. 27, No. 4 (pp. 306-313).

Puelles et al., "Forebrain gene expression domains and the evolving prosomeric model," Trends in Neurosciences, Sep. 2003, vol. 26, No. 9 (pp. 469-476).

Qi et al., "Repurposing CRISPR as an RNA-Guided Platform for Sequence-Specific Control of Gene Expression," Cell, Feb. 28, 2013, vol. 152 (pp. 1173-1183).

Qi et al., "Repurposing CRISPR as an RNA-Guided Platform for Sequence-Specific Control of Gene Expression," Cell, 2013, vol. 152 (pp. 1173-1183).

Quadrato et al.,"Cell diversity and network dynamics in photosensitive human brain organoids," Nature, May 4, 2017, vol. 545, No. 7652 (pp. 48-53).

Qui et al., "Mutation detection using Surveyor™ nuclease," BioTechniques, Apr. 2004, vol. 36 (pp. 702-707).

(56) References Cited

OTHER PUBLICATIONS

Ramskold et al., "Full-length mRNA-Seq from single-cell levels of RNA and individual circulating tumor cells," Nature Biotechnology, Aug. 2012, vol. 30, No. 8 (777-782).

Ran et al., "Double Nicking by RNA-guided CRISPR Cas9 for enhanced genome editing specificity," Cell, Sep. 12, 2013, vol. 154 (pp. 1380-1389).

Ran et al., "In vivo genome editing using *Staphylococcus aureus* Cas9," Nature, vol. 520, 2015, (pp. 186-191). [Includes Supplemental information, 12 pages].

Reboldi et al., "C—C chemokine receptor 6-regulated entry of TH-17 cells into the CNS through the choroid plexus is required for the initiation of EAE," Nature Immunology, May 2009, vol. 10, No. 5 (pp. 514-523).

Rees et al., "Base editing: precision chemistry on the genome and transcriptome of living cells," Nature Reviews Genetics, Dec. 2018, vol. 19, No. 12 (pp. 770-788).

Replogle et al., "Combinatorial single-cell CRISPR screens by direct guide RNA capture and targeted sequencing," Nature Biotechnology, Aug. 2020, vol. 38, No. 8 (pp. 954-961).

Rodgers et al., "Fatigue and Oxidative Stress in Children Undergoing Leukemia Treatment," Biological Research for Nursing, 2016, vol. 18, No. 5 (pp. 515-520).

Rosenberg et al., "Scaling single cell transcriptomics through split pool barcoding," bioRxiv preprint first posted online Feb. 2, 2017 (13 pages).

Rosenberg et al., "Single-cell profiling of the developing mouse brain and spinal cord with split-pool barcoding," Science, Single Cell Genomics, 2018, vol. 360 (pp. 176-182).

Sanjana et al., "Improved vectors and genome-wide libraries for CRISPR screening," HHS Public Access Author Manuscript, 2014, vol. 11 (pp. 2145-2148).

Saudek et al., "A preliminary trial of the programmable implantable medication system for insulin delivery," New England Journal of Medicine, Aug. 31, 1989, vol. 321 (pp. 574-579).

Saunders et al., "Physiology and molecular biology of barrier mechanisms in the fetal and neonatal brain," The Journal of Physiology, 2018, vol. 596, No. 23 (pp. 5723-5756).

Saunders et al., "Recent Developments in Understanding Barrier Mechanisms in the Developing Brain: Drugs and Drug Transporters in Pregnancy, Susceptibility or Protection in the Fetal Brain?," Annual Review of Pharmacology and Toxicology, 2019, vol. 59 (pp. 487-505).

Saunders et al., "The rights and wrongs of blood-brain barrier permeability studies: a walk through 100 years of history," Frontiers in Neuroscience, Dec. 16, 2014, vol. 8, No. 404 (pp. 1-26).

Sawamoto et al., "New neurons follow the flow of cerebrospinal fluid in the adult brain," Science, Feb. 3, 2006, vol. 311 (pp. 629-632).

Schena et al., "Parallel human genome analysis: Microarray-based expression monitoring of 1000 genes," Proceedings of the National Academy of Science, Oct. 1996, vol. 93 (pp. 10614-10619).

Schiebinger et al., "Optimal-transport analysis of single-cell gene expression identifies developmental trajectories in reprogramming," Cell, Feb. 7, 2019, vol. 179 (pp. 928-943).

Schmitz et al., "Interleukin-1 Is Responsible for Acute Lung Immunopathology but Increases Survival of Respiratory Influenza Virus Infection," Journal of Virology, May 2005, vol. 79, No. 10 (pp. 6441-6448).

Schwartz et al., "Breaking peripheral immune tolerance to CNS antigens in neurodegenerative diseases: boosting autoimmunity to fight-off chronic neuroinflammation," Journal of Autoimmunity, 2014 (pp. 1-7).

Seigers et al., "Long-lasting suppression of hippocampal cell proliferation and impaired cognitive performance by methotrexate in the rat," Behavioural Brain Research, 2008, vol. 186, No. 2 (pp. 168-175).

Seigers et al., "Methotrexate decreases hippocampal cell proliferation and induces memory deficits in rats," Behavioural Brain Research, 2009, vol. 201, No. 2 (pp. 279-284).

Shababi et al., "A Direct Comparison of IV and ICV Delivery Methods for Gene Replacement Therapy in a Mouse Model of SMARD1," Molecular Therapy Methods and Clinical Development, Sep. 2018, vol. 10 (pp. 348-360).

Shalem et al., "Genome-Scale CRISPR-Cas9 Knockout Screening in Human Cells," Science, Jan. 3, 2014, vol. 343 (pp. 84-87).

Shalem et al., "High-throughput functional genomics using CRISPR-Cas9" Nature Review Genetics, 2015, vol. 16, No. 5 (pp. 299-311).

Shannon et al., "Mice Expressing Myc in Neural Precursors Develop Choroid Plexus and Ciliary Body Tumors," The American Journal of Pathology, Jun. 2018, vol. 188, No. 6 (pp. 1334-1344).

Shechter et al., "Recruitment of Beneficial M2 Macrophages to Injured Spinal Cord is Orchestrated by Remote Brain Choroid Plexus," Cell Press, Immunity, Mar. 21, 2013, vol. 38 (pp. 555-569).

Shen et al., "Early brain enlargement and elevated extra-axial fluid in infants who develop autism spectrum disorder," Brain, A Journal of Neurobiology, 2013, vol. 136 (pp. 2825-2835).

Shen et al., "Increased Extra-axial Cerebrospinal Fluid in High-Risk Infants who Later Develop Autism," Biological Psychiatry, Aug. 1, 2017, vol. 82, No. 3 (pp. 186-193).

Shmakov et al., "Discovery and Functional Characterization of Diverse Class 2 CRISPR-Cas Systems," Molecular Cell, Nov. 1, 2015, vol. 60, No. 3 (pp. 385-397).

Shuangshoti et al., "Histogenesis of choroid plexus in man," American Journal of Anatomy, Jan. 1966, vol. 118, No. 1 (pp. 283-315).

Silva-Vargas et al., "Age-dependent niche signals from the choroid plexus regulate adult neural stem cells," Cell Stem Cell, Nov. 3, 2016, vol. 19 (pp. 643-652).

Silverman et al., "Multivalent avimer proteins evolved by exon shuffling of a family of human receptor domains," Nature Biotechnology, 2005, vol. 23, No. 12 (pp. 1556-1561).

Skerra et al., "Alternative binding proteins: Anticalins-harnessing the structural plasticity of the lipocalin ligand pocket to engineer novel binding activities," The FEBS Journal, 2008, vol. 275 (pp. 2677-2683).

Skerra et al., "Alternative non-antibody scaffolds for molecular recognition." Current Opinion in Biotechnology, 2007, vol. 18 (pp. 295-303).

Skerra, "Engineered protein scaffolds for molecular recognition," Journal of Molecular Recognition, 2000, vol. 13 (pp. 167-187).

Stan et al., "PV-1 is a component of the fenestral and stomatal diaphragms in fenestrated endothelia," Proceedings of the National Academy of Sciences, Nov. 9, 1999, vol. 96, No. 23 (pp. 13203-13207).

Stegmaier et al., "Gene expression-based high-throughput screening (GE-HTS) and application to leukemia differentiation," Nature Genetics, 2004, vol. 36 (pp. 257-263).

Stumpp et al., "DARPins: a new generation of protein therapeutics," Drug Discovery Today, Aug. 2008, vol. 13, Nos. 15/16 (pp. 695-701).

Suzuki et al., "In vivo genome editing via CRISPR/Cas9 mediated homology-independent targeted integration," Nature, Dec. 1, 2016, vol. 540, No. 7631 (pp. 144-149).

Swiech et al., "In vivo interrogation of gene function in the mammalian brain using CRISPR-Cas9," Nature Biotechnology, 2014, vol. 33 (pp. 102-106) [Including Supplemental information, 4 pages].

Tang et al., "mRNA-Seq whole-transcriptome analysis of a single cell," Nature Methods, May 2009, vol. 6, No. 5 (pp. 377-382).

Tang et al., "RNA-Seq analysis to capture the transcriptome landscape of a single cell," Nature Protocols, Mar. 2010, vol. 5, No. 3 (pp. 516-535).

Tuerk et al., "Systematic evolution of ligands by exponential enrichment: RNA ligands to bacteriophage T4 DNa polymerase," Science, Aug. 3, 1990, vol. 249, No. 4968 (pp. 505-510).

Twyman et al., "Glutamate Receptor Antibodies Activate a Subset of Receptors and Reveal an Agonist Binding Site," Neuron, Apr. 1995, vol. 14 (pp. 755-762).

Van Den Brink et al., "Single-cell sequencing reveals dissociation-induced gene expression in tissue subpopulations," Nature Methods, Oct. 2017, vol. 14, No. 10 (pp. 935-936).

(56)             References Cited

OTHER PUBLICATIONS

Van Houten et al., "Insulin-binding sites in the rat brain: in vivo localization to the circumventricular organs by quantitative radioautography," Endocrinology, 1979, vol. 105, No. 3 (pp. 666-673).

Vanlandewijck et al., "A molecular atlas of cell types and zonation in the brain vasculature," Nature, Feb. 22, 2018, vol. 554 (pp. 475-480).

Vitak et al., "Sequencing thousands of single-cell genomes with combinatorial indexing," Nature Methods, Mar. 2017, vol. 14, No. 3 (pp. 302-308).

Wang et al., "One-Step Generation of Mice Carrying Mutations in Multiple Genes by CRISPR/Cas-Mediated Genome Engineering," Cell, May 9, 2013, vol. 153 (pp. 910-918).

Wang, Wei, "Lyophilization and development of solid protein pharmaceuticals," International Journal of Pharmaceutics, Aug. 2000, vol. 203, Issues 1-2 (pp. 1-60).

Watson et al., "Transduction of the choroid plexus and ependyma in neonatal mouse brain by vesicular stomatitis virus glycoprotein-pseudotyped lentivirus and adeno-associated virus type 5 vectors," Human Gene Therapy, Feb. 2005, vol. 16, No. 1 (pp. 49-56).

Wilting et al., "An experimental and ultrastructural study on the development of the avian choroid plexus," Cell and Tissue Research, 1989, vol. 255 (pp. 487-494).

Xie et al., "Sleep drives metabolite clearance from the adult brain," Science, Oct. 2013, vol. 342, No. 6156 (pp. 1-11).

Yang et al., "Engineering and optimising deaminase fusions for genome editing," Nature Communications, 2017 vol. 7. No. 13330 (pp. 1-12).

Yoon et al., "Antibodies to Domains II and III of the IL-1 Receptor Accessory Protein Inhibit IL-1f Activity But Not Binding: Regulation of IL-1 Responses Is Via Type I Receptor, Not the Accessory Protein," Journal of Immunology, 2019, vol. 160, No. 7 (pp. 3170-3179).

Zetsche et al., "A split-Cas9 architecture for inducible genome editing and transcription modulation," Nature Biotechnology, Feb. 2015, vol. 33, No. 2 (pp. 139-142).

Zheng et al. "Haplotyping germline and cancer genomes with high-throughput linked-read sequencing," Nature Biotechnology, Feb. 1, 2016, vol. 34, No. 3 (pp. 303-311) [with Supplemental Material].

Zheng et al., "Massively parallel digital transcriptional profiling of single cells," Nature Communications, Jan. 16, 2017, vol. 8, No. 14049 (12 pages).

Zhu et al., "Inhibition of Vascular Endothelial Growth Factor-induced Receptor Activation with Anti-Kinase Insert Domain-containing Receptor Single-Chain Antibodies from a Phage Display Library," Cancer Research, Aug. 1998, vol. 58 (pp. 3209-3214).

Zilionis et al., "Single-cell barcoding and sequencing using droplet microfluidics," Nature Protocols, 2017, vol. 12, No. 1 (pp. 44-73).

Zuker et al., "Optimal computer folding of large RNA sequences using thermodynamics and auxiliary information," Nucleic Acids Research, Jan. 10, 1981, vol. 9, No. 1 (pp. 133-148).

* cited by examiner

CX3CR1-GFP ● Pecam1 ● Hoechst

● CX3CR1-GFP ● PECAM1

● Cx3cr1-GFP ● Slc40a1 ● PECAM1

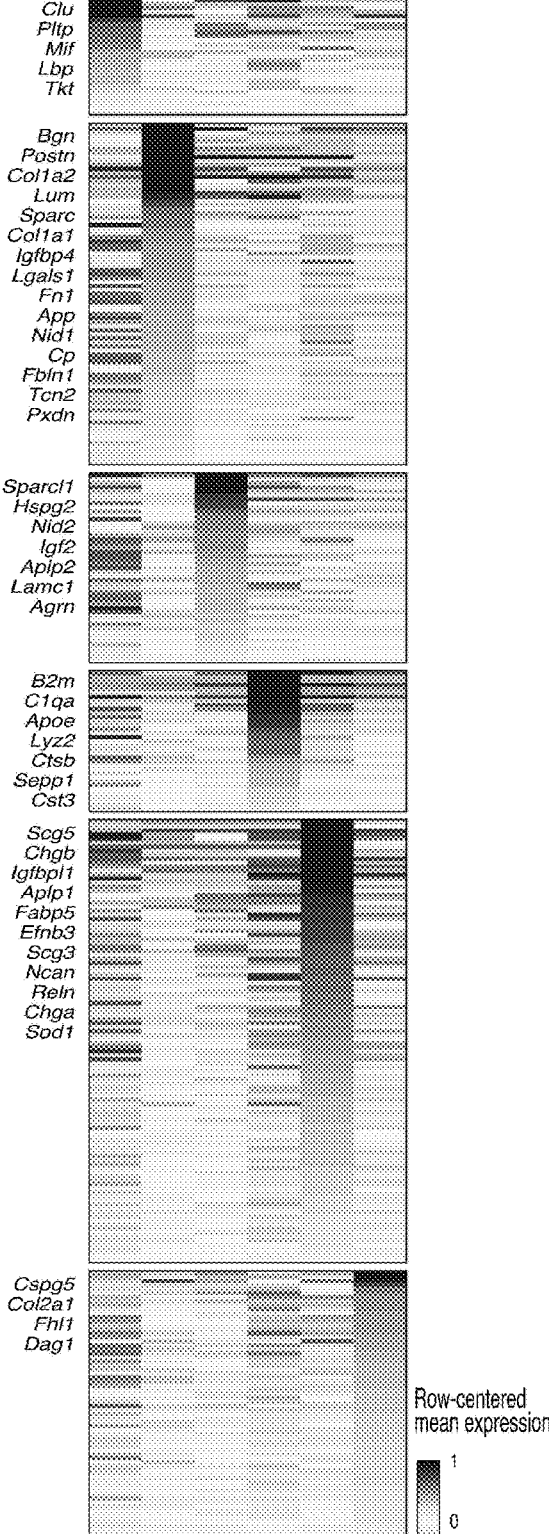
FIG. 6A

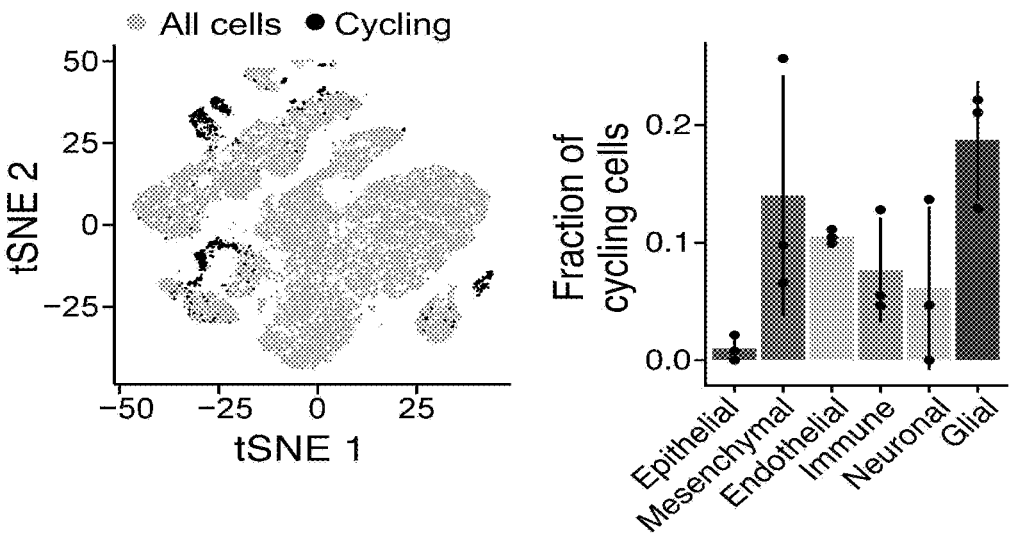
FIG. 8D
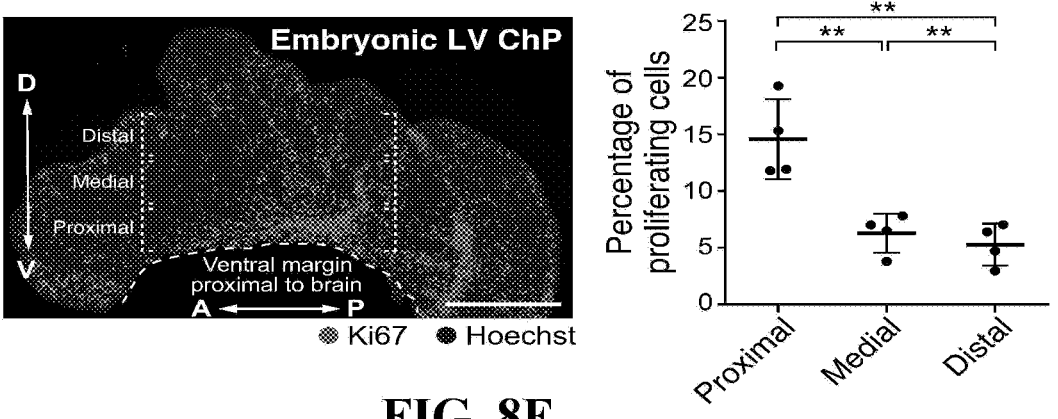
FIG. 8E
FIG. 8F

Lun et al, Journal of Neurosci 2015, Allen Brain Atlas

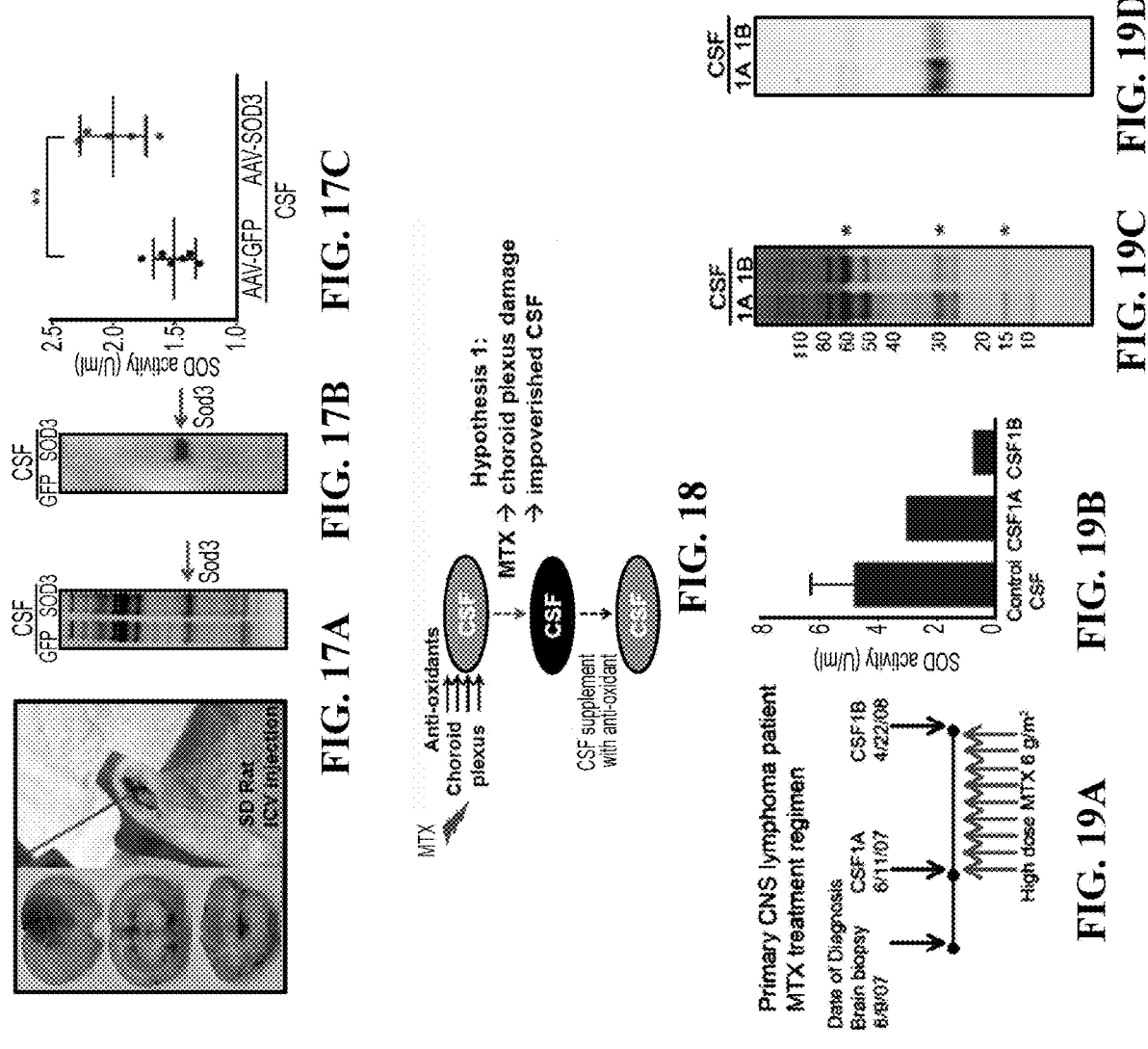

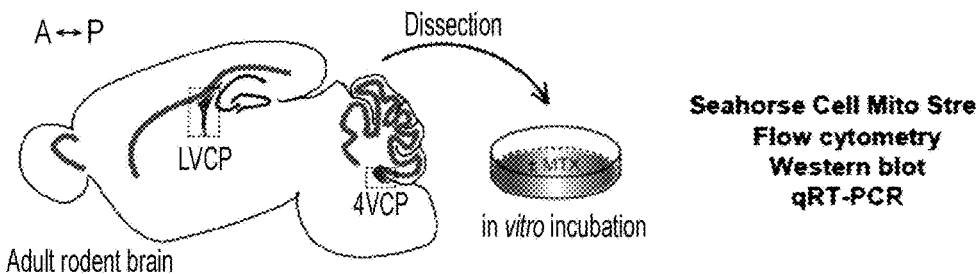
MTX induces ROS production and alters Mitochondrial Membrane Potential in choroid plexus
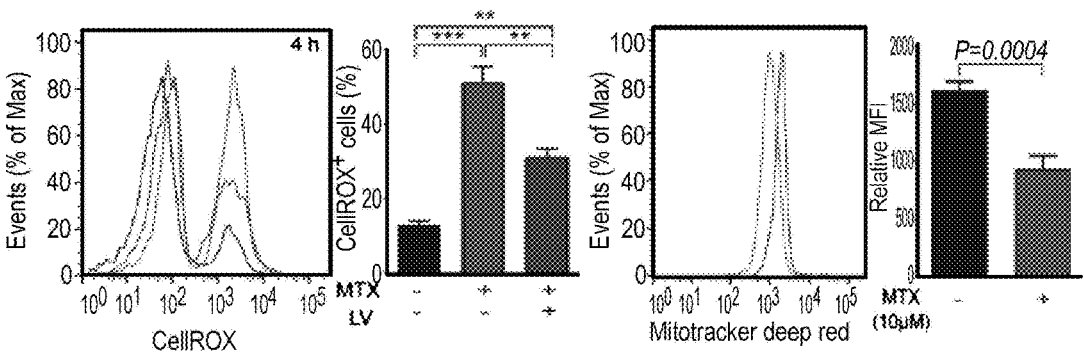
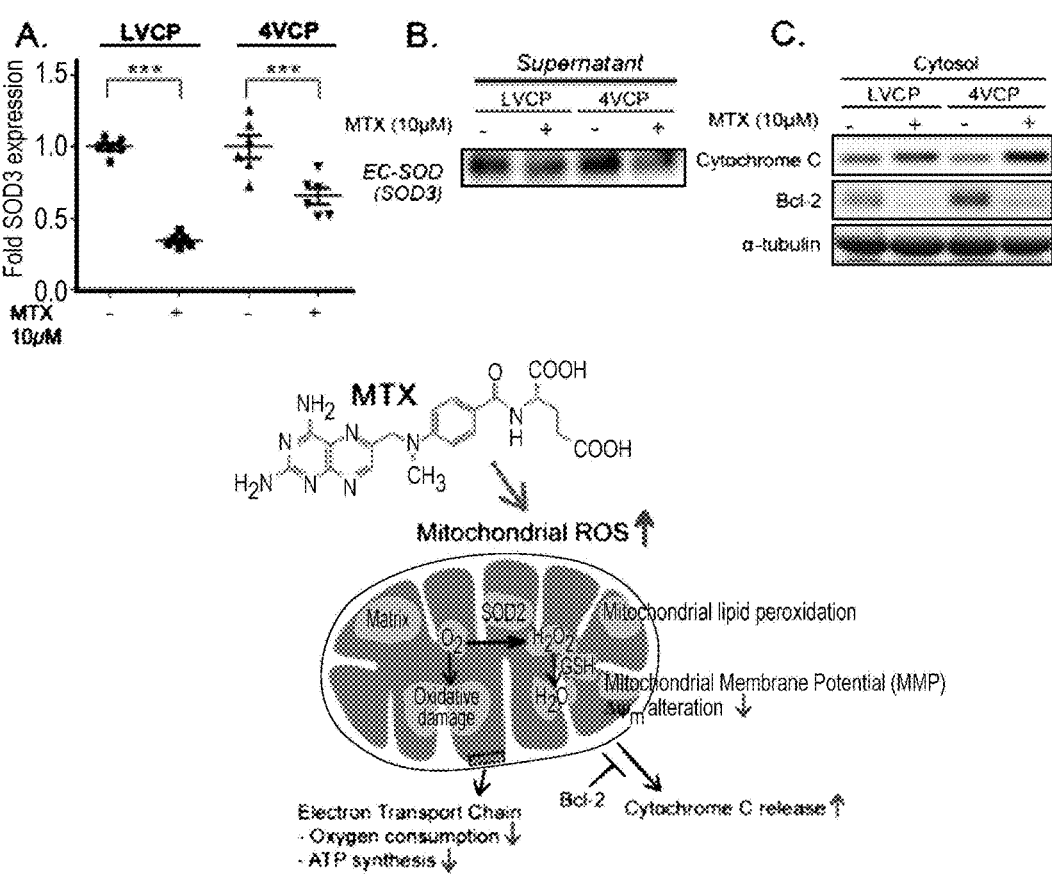
FIG. 21

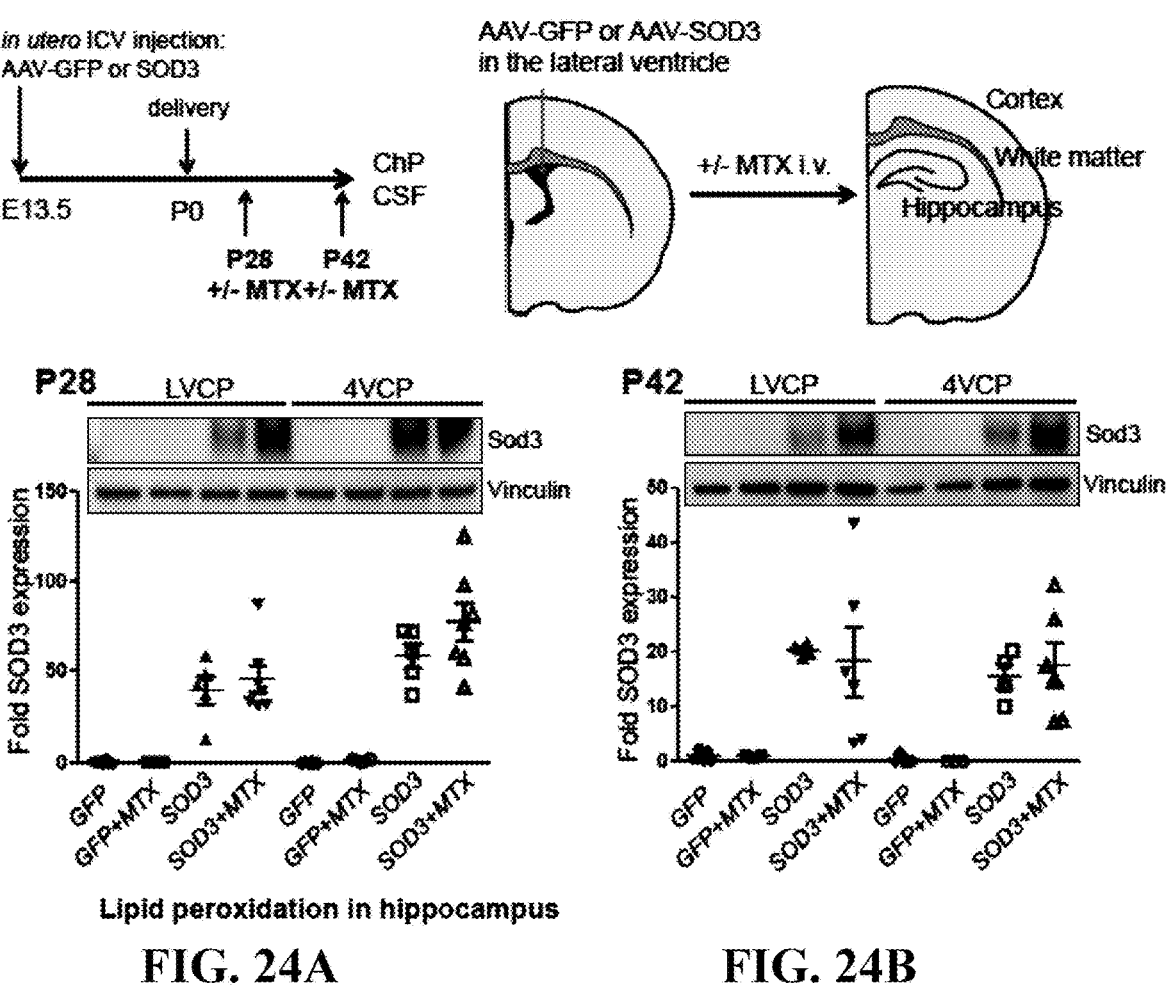
Lipid peroxidation in hippocampus
FIG. 24A
FIG. 24B
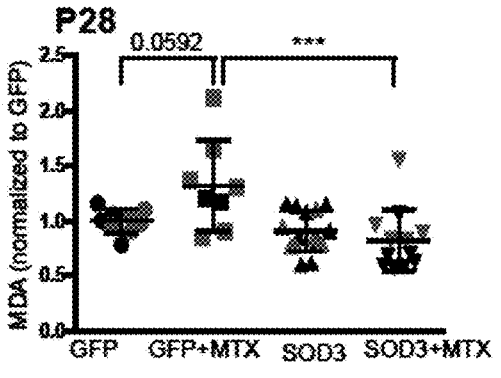
FIG. 24C
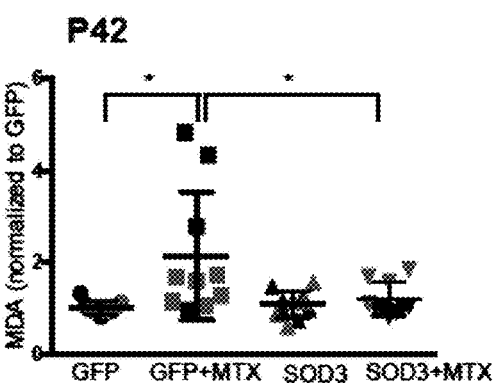
FIG. 24D

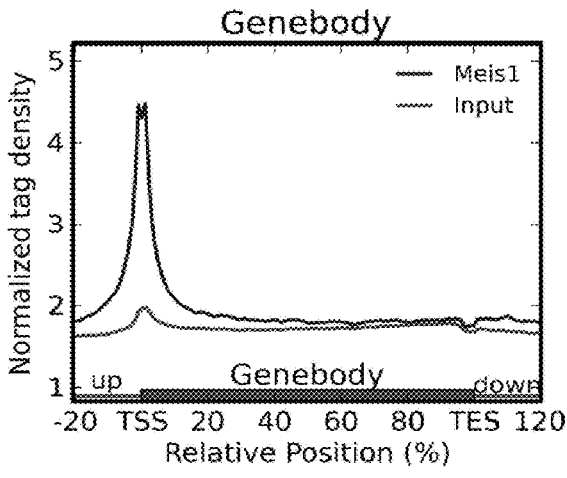
FIG. 28A
FIG. 28B
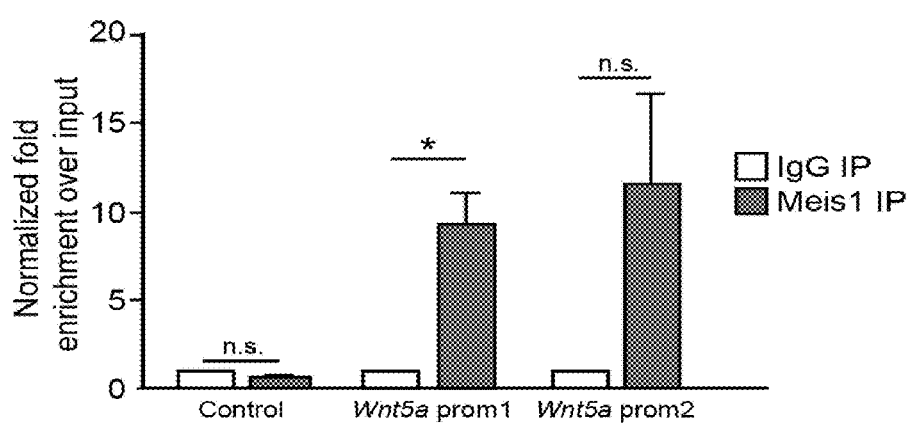
FIG. 28C
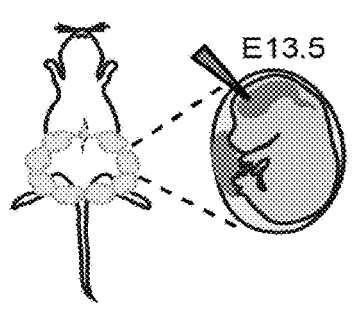
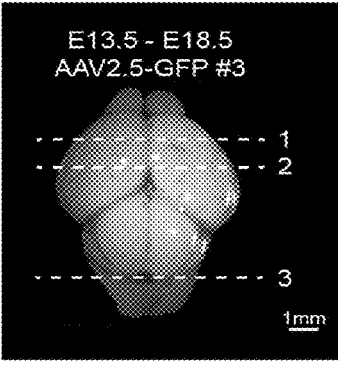
FIG. 29A                    FIG. 29B

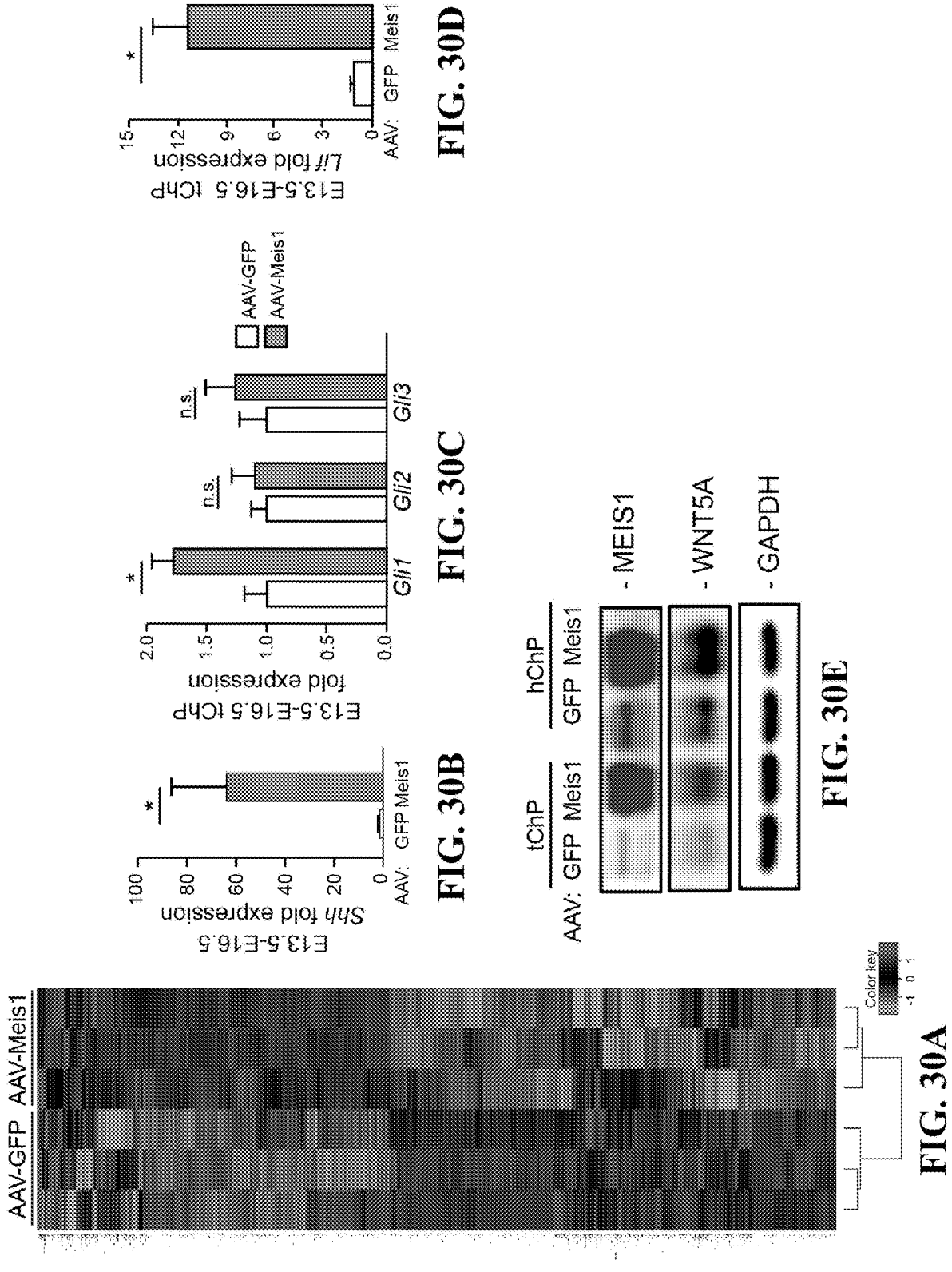

SEQUENCE LISTING

```
<160> NUMBER OF SEQ ID NOS: 17

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
```

-continued

```
1               5

<210> SEQ ID NO 2
<211> LENGTH: 10
<212> TYPE: PRT
<213> ORGANISM: Simian virus 40

<400> SEQUENCE: 2

Pro Lys Lys Lys Arg Lys Val Glu Ala Ser
1               5               10

<210> SEQ ID NO 3
<211> LENGTH: 16
<212> TYPE: PRT
<213> ORGANISM: Simian virus 40

<400> SEQUENCE: 3

Lys Arg Pro Ala Ala Thr Lys Lys Ala Gly Gln Ala Lys Lys Lys Lys
1               5               10              15

<210> SEQ ID NO 4
<211> LENGTH: 9
<212> TYPE: PRT
<213> ORGANISM: Homo sapiens

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Homo sapiens

<400> SEQUENCE: 5

Arg Gln Arg Arg Asn Glu Leu Lys Arg Ser Pro
1               5               10

<210> SEQ ID NO 6
<211> LENGTH: 38
<212> TYPE: PRT
<213> ORGANISM: Homo sapiens

<400> SEQUENCE: 6

Asn Gln Ser Ser Asn Phe Gly Pro Met Lys Gly Gly Asn Phe Gly Gly
1               5               10              15

Arg Ser Ser Gly Pro Tyr Gly Gly Gly Gly Gln Tyr Phe Ala Lys Pro
            20              25              30

Arg Asn Gln Gly Gly Tyr
        35

<210> SEQ ID NO 7
<211> LENGTH: 42
<212> TYPE: PRT
<213> ORGANISM: Homo sapiens

<400> SEQUENCE: 7

Arg Met Arg Ile Glx Phe Lys Asn Lys Gly Lys Asp Thr Ala Glu Leu
1               5               10              15

Arg Arg Arg Arg Val Glu Val Ser Val Glu Leu Arg Lys Ala Lys Lys
            20              25              30

Asp Glu Gln Ile Leu Lys Arg Arg Asn Val
        35              40
```

```
<210> SEQ ID NO 8
<211> LENGTH: 8
<212> TYPE: PRT
<213> ORGANISM: Homo sapiens

<400> SEQUENCE: 8

Val Ser Arg Lys Arg Pro Arg Pro
1               5

<210> SEQ ID NO 9
<211> LENGTH: 8
<212> TYPE: PRT
<213> ORGANISM: Homo sapiens

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Homo sapiens

<400> SEQUENCE: 10

Pro Gln Pro Lys Lys Lys Pro Leu
1               5

<210> SEQ ID NO 11
<211> LENGTH: 12
<212> TYPE: PRT
<213> ORGANISM: Mus sp.

<400> SEQUENCE: 11

Ser Ala Leu Ile Lys Lys Lys Lys Lys Met Ala Pro
1               5                   10

<210> SEQ ID NO 12
<211> LENGTH: 5
<212> TYPE: PRT
<213> ORGANISM: Influenza virus

<400> SEQUENCE: 12

Asp Arg Leu Arg Arg
1               5

<210> SEQ ID NO 13
<211> LENGTH: 7
<212> TYPE: PRT
<213> ORGANISM: Influenza virus

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Hepatitis virus

<400> SEQUENCE: 14

Arg Lys Leu Lys Lys Lys Ile Lys Lys Leu
1               5                   10
```

-continued

```
<210> SEQ ID NO 15
<211> LENGTH: 10
<212> TYPE: PRT
<213> ORGANISM: Mus sp.

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens

<400> SEQUENCE: 17

Arg Lys Cys Leu Gln Ala Gly Met Asn Leu Glu Ala Arg Lys Thr Lys
1               5                   10                  15

Lys
```

ATLAS OF CHOROID PLEXUS CELL TYPES AND THERAPEUTIC AND DIAGNOSTIC USES THEREOF

CROSS REFERENCE TO RELATED APPLICATIONS

This application claims the benefit of U.S. Provisional Application No. 62/840,351, filed Apr. 29, 2019. The entire contents of the above-identified application are hereby fully incorporated herein by reference.

STATEMENT REGARDING FEDERALLY SPONSORED RESEARCH

This invention was made with government support under Grant No.(s) NS088566 and HD090255 awarded by National Institutes of Health. The government has certain rights in the invention.

TECHNICAL FIELD

The subject matter disclosed herein is generally directed to a cell atlas of Choroid Plexus cell types. The subject matter further relates to novel cell specific markers and therapeutic targets.

REFERENCE TO AN ELECTRONIC SEQUENCE LISTING

The contents of the electronic sequence listing (BROD-4200US_ST25.txt"; Size is 3,778 bytes (4 KB on disk) was created on Apr. 29, 2020) is herein incorporated by reference in its entirety.

BACKGROUND

The choroid plexus (ChP) forms a blood-cerebrospinal fluid (CSF) barrier in each brain ventricle and is essential for the development and function of the brain. Built as an epithelial bilayer with an accompanying network of predominantly non-neural cell types and vasculature, the ChP regulates the secretion and composition of CSF that fills the brain's ventricles, bathes stem cells, and reaches neurons via exchange with the interstitial fluid (Lun et al., 2015a). CSF composition is regulated by de novo synthesis and secretion of signals by epithelial cells, as well as selective transcytosis of blood-borne factors (Ghersi-Egea et al., 2018; Grapp et al., 2013; Lun et al., 2015b; Saunders et al., 2018b), which regulate neurogenesis (Lehtinen et al., 2011; Silva-Vargas et al., 2016) or guide migration of newborn neurons (Sawamoto et al., 2006). The ChP is also sensitive to peripheral body signals, and arousal states (Mathew et al., 2016; Myung et al., 2018) and gates immune cell passage from body to brain (Ghersi-Egea et al., 2018; Reboldi et al., 2009; Schwartz and Baruch, 2014; Shechter et al., 2013). Disrupted ChP function and CSF composition, as well as abnormal CSF volume and ventricle space, are common to neurologic disease, including brain infection (Karimy et al., 2017), autism (Shen et al., 2013, 2017), Schizophrenia (Palha et al., 2012), and Alzheimer's disease (Balusu et al., 2016; Marques et al., 2013).

Despite these essential roles, remarkably little is known regarding the molecular mechanisms governing these functions of the choroid plexus, its cellular networks, and histology, limiting the ability to harness it for therapeutic benefit. In particular, knowledge of the cellular composition of the choroid plexus within each ventricle in developing and adult brain is limited. Each choroid plexus develops independently from distinct locations along the roof plate, where capillaries, mesenchymal and neural crest cells invaginate the neuroepithelium (Hunter and Dymecki, 2007; Lun et al., 2015a; Wilting and Christ, 1989). Earlier efforts to address these deficiencies were limited by the lack of techniques to access, isolate and comprehensively characterize ChPs, thus limiting the ability to understand their functions and harness them for therapeutic benefit. Identification of cell types, targets, and function in the ChP would provide a resource for creating tools to access and control this essential brain-body barrier.

SUMMARY

In certain example embodiments, an isolated cell characterized by signature defined in Table 1A, 1, or 1C is provided. In embodiments, the cell is selected from epithelial cell, endothelial cell, immune cell, mesenchymal cell, or progenitor glia-like cell. The isolated cell may be isolated from an autologous, allogenic, or xenogenic source and engineered to express one or more genes of the signature defined in: Table 2-epithelial cells of developing Choroid Plexus (ChP); Table 3—mesenchymal cells of developing ChPs; Table 4—endothelial cells of developing ChPs; Table 6—epithelial cell of adult ChPs; or Table 7—Mesenchymal cells of developing and adult ChPs.

In embodiments, the cell is an epithelial cell comprising one or more genes of the signature selected from Topic 3, 4, 6, 9, 11, 14, 16, 19, 23 or 24 from Table 2. In one aspect, the cell is a mesenchymal cell comprising one or more genes in the signature selected from Topic 2, 3, 5, 7, 8, 12, 16, or 18 of Table 3. In an aspect, the cell is an endothelial cell comprising one or more genes selected from Topic 3, 8, 10, 11 or 12 in Table 4. In an aspect, the cell is an epithelial cell comprising one or more genes selected from Topic 6, 8, 9 or 10 in Table 6. In an aspect, the cell is a mesenchymal cell comprising one or more genes selected from Topic 4, 5, 8, 12 or 15 from Table 7.

In certain embodiments, the isolated cell is engineered to express the signature comprising Rspo2+co-expressed with one or more of Rspo3, Lrp1b, Tpbg, Rspo1, Wls, Ezr, Ednrb, Clu, Wnt3a, Wnt8b, Sfrp1. The isolated cell is engineered to express the signature comprising Meis1, Wnt5a or both.

Tissue and/or organism models are provided comprising one or more cell types from the group consisting of epithelial cells, mesenchymal cells, endothelial cells, progenitor glia-like population or immune cells characterized by expression of the signature defined in Table 2, 3, 4, 6, or 7. In embodiments, the tissue or organism model is engineered to constitutively or conditionally express Meis 1, Ins2, Rspo$^{2+}$, Rspo3, Lrp1b, Tpbg, Rspo1, Ws, Ezr, Ednrb, Clu, Wnt3a, Wnt8b, Sfrp1, Hhip, Ptch1, Rbp4, Wisp1, BMp4/7, and/or Wnt5a, Wnt4/2, Penk and Shh. In embodiments, the cells herein are engineered using a CRISPR-Cas system.

A method of generating neural progenitors and/or specific neural cell types are provided comprising co-culturing a stem cell or iPS cell with one of the epithelial/fibroblast cell types of 4V ChP, expressing Hhip, Ptch1, Rbp4, and Wisp1 or a combination of epithelial/fibroblast cell types expressing one or more genes from a topic of Table 7.

A method of inducing growth factor expression in the brain comprises contacting the choroid plexus of one or more ventricles with an agent that increases/decrease expression of BMp4/7, and/or Wnt4/2. A method of increasing neural plasticity or neurodevelopmental potential is also disclosed, comprising modulating one or more of Rspo2+, Rspo3, Lrp1b, Tpbg, Rspo1, Wls, Ezr, Ednrb, Clu, Wnt3a, Wnt8b, Sfrp1, Penk or Shh.

A method of reducing oxidative stress in the central nervous system, in the brain, in the choroid plexus or in the LV, 3V or 4V of the ChP of a subject, comprising inducing or restoring ChP epithelial cells expression of one or more anti-oxidants is also disclosed. In embodiments, the one or more antioxidants is SOD3. In some embodiments, the subject suffers from a neurodegenerative or inflammatory disease. The neurodegenerative or inflammatory disease can be selected from Alzheimer's disease (AD), familial AD, Creutzfeldt-Jacob disease, dementia pugilistica, Down's Syndrome, Gerstmann-Straussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD), optic nerve drusen, optic neuropathy, optic neuritis, and lattice dystrophy, or atypical parkinsonism, acute disseminated encephalomyelitis (ADEM); Addison's disease; ankylosing spondylitis; antiphospholipid antibody syndrome (APS); aplastic anemia; autoimmune-associated infertility; autoimmune gastritis; autoimmune hepatitis; autoimmune hemophilia; autoimmune lymphoproliferative syndrome (ALPS); autoimmune thrombocytopenia; autoimmune uveoretinitis; Behget's disease; bullous pemphigoid; celiac disease; dermatomyositis; diabetes mellitus type I; glomerulonephritis (e.g., crescentic glomerulonephritis, proliferative glomerulonephritis); Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; insulin resistance; mixed connective tissue disease; multiple sclerosis (MS); myasthenia gravis (MG); opsoclonus myoclonus syndrome (OMS); optic neuritis; Ord's thyroiditis; pemphigus (e.g., pemphigus vulgaris); pernicious anaemia; polyarteritis nodosa; polymyositis; primary biliary cirrhosis; primary myxedema; psoriasis; rheumatic fever; rheumatoid arthritis; Reiter's syndrome; scleroderma with anti-collagen antibodies; Sjögren's syndrome; systemic lupus erythematosus (SLE); Takayasu's arteritis; temporal arteritis; vitiligo; warm autoimmune hemolytic anemia; or Wegener's granulomatosis. In embodiments, the subject is receiving a chemotherapeutic, optionally selected from methotrexate, Paclitaxel, and Adriamycin, or a combination thereof.

In embodiments, the methods disclosed herein provide inducing or restoring ChP epithelial cells expression of one or more anti-oxidants comprising administration of a vector encoding the one or more anti-oxidants. The method of inducing or restoring ChP epithelial cells expression can comprise administering one or more modulating agents that increase expression and/or secretion of one or more anti-oxidants. In certain embodiments, the one or more antioxidants comprises SOD3. Delivery of modulating agents may comprise a viral vector, preferably an AAV vector, which can be an AAV vector selected from AAV 2/5 or AAV9.

Methods of modulating the cell, tissue or organoid of may comprise a modulating agent selected from a CRISPR system, a zinc finger nuclease system, a TALEN, a meganuclease, or a RNAi system. In certain embodiments, the modulating agent is chemically or optically inducible.

Methods of modulating the cell-cell interaction network of the choroid plexus (ChP) are provided, comprising modulating the expression of cognate receptor-ligand pairs in a set of two or more cells from the ChP, wherein the cognate ligand pairs are selected from Table 5. The modulating the expression of ligands can be in mesenchymal cells, the ligands specific for cognate receptors in endothelial, immune, epithelial, neuronal and/or glial cells. In certain embodiments, the ligand-receptor pair comprises the receptor Pdgfra in a fibroblast and the ligand comprises Pdgfa in an epithelial cell. In embodiments, the ligand-receptor pair comprises the receptor Pdgfrb in a pericyte and the ligand comprises Pdgfb in an endothelial cell. The ligand receptor pair can comprise the receptor Csf1 in basophils and the receptor comprises Csf1R in macrophage or monocyte. In embodiments, the modulating the expression modulates myeloid cell maturation. In certain embodiments, the ligand-receptor pair comprises the receptor Il6 in a basophil and/or mast cell, and the receptor comprises IL6st in mesenchymal cells, or Il6ra in monocytes, macrophages, and/or dendritic cells.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 1A) ChP tissues from each brain ventricle. Location of ChP (horizontal dotted lines) in the E16.5 brain (top left panel, scale bar=1 mm). Representative images of intact LV ChP (a. top middle panel, scale bar=0.2 mm), 3V ChP (b. top right panel, scale bar=0.2 mm) and 4V ChP (c. bottom panel, scale bar=0.5 mm). Arrows: anterior-posterior (A/P), dorso-ventral (D/V) and medial-lateral (M/L) axes. (FIG. 1B) Workflow. (FIG. 1C) Major cell subsets of the embryonic ChP. A 2D t-stochastic neighborhood embedding (t-SNE) of 15,620 single cell profiles (n=9 mice, in pools of 3 animals per ventricle), colored by post hoc annotated cell type. (FIG. 1D) Canonical and novel cell type markers. Median expression level in expressing cells (color) and proportion of expressing cells (circle size) of selected genes (columns) in each major cell population (rows). (FIG. 1E) Immunostaining of major cell type markers reveal shared features of each ChP. Top panels: Coronal sections of E16.5 brain show LV (left), 3V (middle) and 4V (right) ChP in cross-section (H&E stained). Lower panels: Immunostaining of major cell type markers in the superficial epithelial cell layer (AQP1), sub-epithelial stromal space that contains mesenchymal (COL1A1), endothelial (PECAM1) and immune cells (SPI1, white arrowheads). Scale bar (LV ChP and 3V ChP)=20 µm, scale bar (4V ChP)=500 µm. (FIG. 1F) Neuronal and glia-like cell subsets. tSNE of neuronal and glia-like cell profiles, colored and numbered by cluster membership. (FIG. 1G) Neuronal cell bodies in the ChP. Whole explant imaging of LV ChP stained with TUBB3 antibodies White arrowheads: neuronal cell bodies within the plexus (Scale bar=100 µm), Inset a: Neuronal (TUBB3) cell morphology (scale bar=10 µm). Schematic with dotted outline (black): region of LV ChP depicted in immunostaining. Double headed arrows: A/P and D/V axes (as in A).

(FIG. 2A) Inferred differentiation trajectory from common progenitor to epithelial and neuronal cells. Diffusion map 2-D embedding of neuronal, glia-like and epithelial cell profiles (dots) from 3V ChP, displaying diffusion components 1 (x axis) and 3 (y axis), colored by $\log_2(\text{TP10K}+1)$ expression of marker genes of (from left to right): neuronal (Tubb3), progenitors (Rspo2), cycling (Mki67), ciliogenesis (Ccdc67), and mature epithelial (Krt18) cells. Right: Schematic model of suggested differentiation trajectories. (FIG. 2B) Multi-ciliated ChP epithelial cells. Left: Scanning electron microscope image of a multi-ciliated epithelial cell from a mouse ChP (Scale bar=1 µm). Right: Median expression level in expressing cells (color) and proportion of expressing cells (circle size) of markers of ciliogenesis and primary cilium (columns) across subsets of epithelial cells (rows, as in Figure S2E). (FIG. 2C) Ciliogenesis in a subset of epithelial cells. Left: Whole explant imaging of the LV ChP stained with anti-Ac-Tubulin (green) and anti-CCDC67/DEUP1 (red). Right: Images of individual ciliary tufts (green) stained with anti-CCDC67 (red, middle) or anti-SHISA8 (red, right). Scale bar=10 µm (left) or 5 µm (all other panels). (FIG. 2D) Spatial mapping of the differentiation trajectory in the LV ChP. In situ hybridization images from the LV ChP from Genepaint of markers of (from top): progenitors (Rspo2); differentiated epithelial cells (Krt18) ciliogenesis/basal body biogenesis (Ccdc67), neurons (Tubb3) and epithelial cells (Ttr) (Scale bar=100 µm). Top right: Model of proximal to distal organization of progenitor and differentiation states in the LV ChP. Progenitors at the base LV ChP and adjacent brain, ciliogenesis/basal body biogenesis epithelial 1 cells along the root of the LV ChP, followed by mature epithelial cells.

(FIG. 3A) Distinct epithelial cells clusters by ventricle. t-SNE of epithelial cell profiles (dots), colored by ventricle. (FIG. 3B) Ventricle associated transcriptional programs in epithelial cells. For each topic that is differentially weighted between ventricles, shown is a bar plot of topic scores for top ranked genes (left), and tSNE of the cell profiles (as in A) colored by topic's weight per cell (right). Bold: Genes highlighted in (3D, 3E). (FIG. 3C-3D) Key genes with regionalized expression in epithelial cells across ventricles. (FIG. 3C) Distribution of $\log_2(\text{TP10K}+1)$ expression (y axis) of each denoted gene across ventricles (x axis). (FIG. 3D) Top three panels: In situ hybridization from Genepaint of sagittal sections of the LV, 3V and 4V ChP (columns) of genes with regionalized expression (rows) (Scale bar=100 µm). Bottom panels: smFISH of Ins2 in whole explants (Scale bar=10 µm). (FIG. 3E) Regionalized expression within the 4V ChP epithelium. In situ hybridization from Genepaint of transcripts in sagittal sections of the 4V ChP (Scale bar=100 µm). (FIG. 3F) Rostral-caudal patterning within the 4V ChP epithelium. Model of regionalized expression in the medial core of the 4V ChP that lies within the 4th ventricle, with example genes identified by topic models and validated in situ (in 3E). (FIG. 3G) Mesenchymal cells largely cluster by ventricle. t-SNE of mesenchymal cell profiles (dots) colored by ventricle. (FIG. 3H) Ventricle associated transcriptional programs in mesenchymal cells. Each topic that is highly weighted in a significant fraction of mesenchymal cells (except cycling cells; FIG. 10H) is shown as in B, with the tSNE in G. Bold: genes highlighted in (3I). (FIG. 3I) Regionalized mesenchymal transcriptional programs. In situ hybridization in sagittal sections of the LV, 3V and 4V ChP (Genepaint) for a pericyte marker (Rgs5) and genes with ventricle specific enrichment in fibroblast in the 3V (Adamts2, Fbin1), 4V (Hhip), and LV (Lox) (Scale bar for LV=50 µm; 3V and 4V=10 µm).

(FIG. 4A) Immune cell subsets in the ChP. tSNE of immune cell profiles, colored by cluster membership. (FIG. 4B) Marker genes for eight immune cell types. Median expression level in expressing cells (color) and proportion of expressing cells (circle size) of selected marker genes (rows) across immune cell subsets (columns). (FIG. 4C) Macrophages phenotypic heterogeneity across three archetypes. Diffusion map embedding of macrophages, colored by $\log_2(\text{TP10K}+1)$ expression of a general marker (Cx3cr1) or each archetype specific gene (Slc40a1, Spic, Spp1, Lyve1). (FIG. 4D) Distinct macrophage archetype enriched in 4V ChP. Diffusion map embedding of macrophages (as in 4C) colored by ventricle. (FIG. 4E) Validation of macrophage subsets in 4V ChP. In situ hybridization (Genepaint) of Spic and Clec4n in LV, 3V, and 4V ChP (scale bar=10 µm). Dotted line outlines the ChP. (FIG. 4F) Cx3cr1$^+$ macrophages in the sub-epithelial stromal space and supra-epithelial epiplexus positions in the ChP. Cortical section of LV from CX3CR1-GFP mouse co-stained with antibodies against endothelial marker PECAM1 (red) and nuclei (Hoechst, blue). Arrows: epiplexus cells. Scale=10 µm. (FIG. 4G) Cx3cr1$^+$ macrophages in a tiled pattern closely associated with blood vessels in the ChP stromal space. Whole explants from CX3CR1-GFP mice co-stained with antibodies against PECAM1 (red). Scale=20 µm. (FIG. 4H) Diverse macrophages in the ChP stromal space. Whole explants from CX3CR1-GFP mice co-staining with antibodies against iron transporter FPN/SLC40A1 (red) and PECAM1 (grey). White arrow heads: macrophages localized to blood vessels that express the iron transporter. Scale=10 µm. (FIG. 4I) Diversity among epiplexus macrophages. Whole explants from CX3CR1-GFP mice co-stained with antibodies against hyaluronan receptor LYVE-1 (red). White arrow heads: LYVE1+ epiplexus macrophages in supra-epithelial positions (right panels: cross section. Scale bar=10 µm in whole explants; 5 µm in cross-section images).

(FIG. 5A) Endothelial cell transcriptional programs. For selected topics identified in endothelial cells, shown is tSNE of the cell profiles colored by topic's weight per cell (top), and bar plot of topic scores for top ranked genes (bottom). Bold: Genes of interest. (FIG. 5B) Arterio-venous zonation in developing and adult ChP. LV ChP whole explants stained with antibodies against PECAM1 (general endothelial, green), ACTA2 (red) and VWF (magenta), marking the arterial (ACTA2+, VWF+) and venous (ACTA2−, VWF+) zones. Left: Emerging zonation in embryonic ChP. Middle: Clear arterio-venous organization in adult. Right: Insets from adult image. Scale bar=100 µm. Zoomed inset scale bar=50 µm. (FIG. 5C) Angiogenic zonation. Whole explant stained with antibodies against PECAM1 (grey) and the angiogenic marker ESM1 (green) enriched along the free margin of the LV ChP. Scale=100 µm. Top: Inset: Localization of the image within the explant and orientation within the brain. Arrows: anterior-posterior (A/P) and dorso-ventral (D/V) axes. Bottom: Co-staining for ESM1 (green), PECAM1 (red) and nuclei stain (Hoechst, blue). Scale=10 µm). (FIG. 5D) Blood brain barrier zonation. Whole explant stained with antibodies against CLDN5 (green) and PECAM1 (red) showing BBB marker expression at the root of the LV ChP, along vessels that run from the brain into ChP. Scale bar=100 µm. Dotted line: barrier of the brain and the ChP. Right: Region a and b, scale bar=20 µm.

FIG. 6A-6C—Mesenchymal, endothelial and immune cells contribute to cellular cross-talk in ChP. (FIG. 6A) Many ChP cell types express genes encoding secreted factors. Mean expression (color bar, row centered) of genes (rows) coding for proteins measured in CSF from embryonic mice (Lun et al., 2015b) in each of six major cell types (columns). Genes are sorted by expression level in the cell type in which they were maximally expressed. Genes of interest are marked on the side. (FIG. 6B, 6C) Potential roles for mesenchymal, endothelial, and immune cells in cell-cell interactions. (FIG. 6B) Bipartite graph of cellular network of ligand (left) and cognate receptor (right) pairs. Nodes: sets of ligands (left) or receptor (right) genes, which are either cell type specific (Table S1) or subset specific (identified by differential expression for immune cells and neuronal/glia-like cells, or by top 50 scoring genes of topics, STAR Methods). Node color: cell type; Node size: degree in the full network. (FIG. 6C) Expression of examples (from 6B) of key ligand-receptor pairs (rows; groups of receptors and cognate ligands are separated by vertical dashed lines) across cell subtypes (columns). Dot size: fraction of expressing cells; color: median expression in expressing cells.

(FIG. 7A) Adult ChP. Whole explant images of the adult ChPs (Scale bar=1 cm). Arrows: anterior-posterior (A/P), dorso-ventral (D/V) and medial-lateral (M/L) axes. (FIG. 7B) snRNA-Seq from embryo and adult ChP. UMAP embedding of 29,727 sampled single nucleus profiles (STAR Methods, dots, adult: n=13 mice, processed in 3 pools of per ventricle, embryo: n=3 mice, processed in 1 pool of LV ChP), colored by annotated cell type (epithelial cell clusters were merged post-hoc), in either adult (left) or embryo (right). (FIG. 7C) Cell type marker genes in adult. Mean expression in expressing cells (color) and proportion of expressing cells (dot size) of selected genes (row) across the major cell populations (column). (FIG. 7D) Cell proliferation and ciliogenesis programs are specific to embryonic ChP cells. UMAP embedding (as in 7B) with cells colored by signature score of cell cycle (left) and ciliogenesis (right). (FIG. 7E) Regionalized expression of adult epithelial cells across ventricles conserved from the embryo. Regionalized gene expression in epithelial cells by ISH images (top) from Allen Brain Atlas (Lein et al., 2007) or smFISH (bottom), across the adult LV ChP, 3V ChP and 4V ChP (columns).

(FIG. 7F) Model of age-dependent changes in ChP cell types and tissue organization (left), and ventricle-specific gene expression in epithelial cells (right).

FIG. 8A-8K—Cellular markers, identity and organization within the ChP. (FIG. 8A) Cell quality of single-cells of embryo by cell type and replicate. Violin plot shows total number of unique molecular identifiers (nUMI, top) and total number of genes (nGene, bottom) per cell type (column) and experimental replicate (color). Y-axis is in $\log_{10}$ scale. (FIG. 8B) Proportions of cells captured from each ChP vary between experiments. Barplot shows the fraction of each major cell type identified per ventricle per experiment. Shades of color represents replicates. (FIG. 8C) Canonical markers identify cellular localization in LV ChP. In situ hybridization in sagittal sections within the LV ChP (Genepaint) show spatial expression pattern of cell-specific marker genes. (FIG. 8D) Neuronal and glia-like cells predominantly found in 3V ChP. tSNE embedding of neuronal and glia-like cells (as in FIG. 1F) colored by ventricle of origin. (E) tSNE embedding of neuronal and glia-like cells (as in FIG. 1F) colored by $\log_2$(TP10K+1) expression of neuronal marker Tubb3 (left) and glial marker Slc1a3 (right). (FIG. 8F) Neuronal-/glial subtype markers and neuropeptides. Dot-plot shows the expression of marker genes (column, left side) and neuropeptides (column, right side) across clusters (row). Size of dot represents the fraction of cells within each cell type that expresses a gene, and color indicates the median expression level when a gene is detected. (8A, 8B) Proliferating cell niche proximal to the brain. (FIG. 8G) Proliferating cells. Left: tSNE (as in FIG. 1C) of cell profiles (dots), with cells classified as cycling colored black (STAR Methods). Right: Mean fraction of cycling cells (y axis) in each cell type (x axis), and in each replicate (dots). Line: standard deviation (SD). (FIG. 8H) Proliferating cell niche. Left: KI67 staining (magenta) of whole explant of LV ChP. Double headed arrows: A/P and D/V axes. Right: Percent of proliferating cells (KI67+, y axis) in proximal, medial and distal regions of the LV ChP (x axis, relative to the ventral margin of the ChP near the brain) (n=4, Scale bar=500 µm; one-way ANOVA, **p<0.01. Error bars indicate S.E.M. Scale bar=500 µm). (FIG. 8I) Molecular expression in ChP neurons. Staining of the LV ChP. Top row: Representative images of a neuron labeled with serotonin anti-sera(5-HT) (red) and anti-TUBB3 (green) antibody. Bottom row: Representative images of neurons targeted by AAV expression of GFP driven by promoter of neuronal marker gene, Syn1, counterstained with anti-TUBB3 antibody. Across images: nuclei stained (blue), scale bar=10 µm. (FIG. 8J) Neuronal cells in the LV ChP. tSNE embedding (as in FIG. 1F) colored by $\log_2$(TP10K+1) expression of synaptic activity marker Syn1. (FIG. 8K) Organization of the developing 3V ChP. In situ hybridization images (Genepaint) of marker genes for developing pineal gland clusters (Krt19, Crx), of progenitor cells (Rspo3) and of epithelial cells (Ttr), localizing the progenitors adjacent to the pineal gland.

(FIG. 9A) Stem-like marker genes co-expressed in common progenitor population. Partial gene expression correlation with Rspo2 $\log_2$ (TP10K+1) expression (y axis), sorted (rank, x axis), across cells used for diffusion map (as in FIG. 2C). (FIG. 9B) Visualization of stem-like marker genes co-expressed with Rspo2 in common progenitor population. Diffusion map embedding (as in FIG. 2C), colored by $\log_2$(TP10K+1) expression of stem-like genes. (FIG. 9C) Proliferating cells emerge from the common progenitor cells on the inferred trajectory. Diffusion map embedding (as in FIG. 2C), colored by signature scores of G1/S and G2/M gene sets. (FIG. 9D) Epithelial cell sub-clusters. tSNE embedding of epithelial cells of the developing ChP, colored by cluster membership. (FIG. 9E)

FIG. 10A-10K—Regionalized transcriptional programs in epithelial and mesenchymal cell populations. (FIG. 10A) Single-cell data agrees with previous bulk RNAseq data. Differentially expressed genes between LV and 4V in bulk RNAseq (Lun et al., 2015b) (Top: up-regulated. Bottom: down regulated) averaged across single cell in 4V ChP (x axis) and LV ChP (y axis). Red line indicates x=y. All genes show a coordinated difference between the datasets. (FIG. 10B) Topic modeling of epithelial cells identifies transcriptional programs associated with immediate early gene expression (Topic 10, bottom) and ciliogenesis (Topic 12, top). Left: Bar plot shows the scores (x axis) of top ranked genes (y axis) of each topic. Right: 2D tSNE embedding (as in FIG. 3A), colored by each topic's weight in the cells. (FIG. 10C) Some epithelial topics are differentially weighted in cells across ventricles. Shown is the empirical cumulative distribution (y axis) of epithelial topic weights (x axis) across epithelial cells, grouped and colored by the ventricle the cells were collected from. (FIG. 10D) Immediate early gene (IEG) expression is likely an artifact from cell dissociation as expression of IEG genes is absent in single-nuclei RNA-seq data. Dotplot shows expression of immediate early genes (IEGs, column) across single-cell and single-nuclei RNA-seq datasets (row). Size of dot represents the fraction of cells within each cell type that expresses a gene, and color indicates the median expression level when a gene is detected. (FIG. 10E) Transporters can be differentially expressed in epithelial cells across ventricles. Dotplot shows expression of transporters (row) that were top scoring (within top 50 features) in topics that are regionalized across ventricles (Topic 2,7,8,9,10) in epithelial cells. Size of dot represents the fraction of cells within each cell type that expresses a gene, and color indicates the median expression level when a gene is detected. (FIG. 10F) Rostral and caudal gene expression pattern in 4V ChP epithelium. tSNE embedding of epithelial cells, colored by $\log_2$ (TP10K+1) expression of genes shown in FIG. 3E, F. (FIG. 10G) Mesenchymal cells partition into fibroblast and mural cells (pericytes and smooth muscle cells). tSNE embedding of mesenchymal cells colored by $\log_2$(TP10K+1) expression of marker genes for (from left to right): pericytes (Des), smooth muscle actin positive cells (Acta2) and fibroblasts (Pdgfra). (FIG. 10H) Topic modeling of mesenchymal cells identifies transcriptional programs associated with cell cycle (top: Topic 12, bottom: Topic 10). Left: Bar plot shows the scores (x axis) of top ranked genes (y axis) of each topic. Right: 2D tSNE embedding as is shown in FIG. 3G, colored by each topic's weight in the cells. (FIG. 10I) Some mesenchymal topics are differentially weighted in cells across ventricles. Shown is the empirical cumulative distribution (y axis) of mesenchymal topic weights (x axis) across mesenchymal cells, grouped and colored by the ventricle the cells were collected from. (FIG. 10J) Extracellular matrix (ECM) protein transcripts that are highly scoring in mesenchymal topics discussed. Dotplot shows expression of ECM protein transcripts (row) that were top scoring (within top 50 features) in topics (Topic 2,5,7,8,18) in mesenchymal cells. Size of dot represents the fraction of cells within each cell type that expresses a gene, and color indicates the median expression level when a gene is detected. (FIG. 10K) Regionalized transcriptional programs across ventricles in epithelial and mesenchymal cells show different functional enrichments. GO analysis enrichment of union of top 50 features of regionalized topics are shown for epithelial cells (top) and mesenchymal cells (bottom). FDR (x axis) of top ten significant biological processes (y axis) are shown.

(FIG. 11A-11B) Dot-plots showing gene expression of cytokines (FIG. 11A) and chemokines (FIG. 11B) across immune cell types. Size of dot represents the fraction of cells within each cluster that expresses a gene, and color indicates the level of expression when expressed. (FIG. 11C) SPIC+ macrophages in ChP stromal space. LV ChP explants in CX3CR1-GFP mice stained with antibody against SPIC (magenta), showing a subset of macrophages in the stroma express Spic (white arrow heads). (FIG. 11D) Correlated gene expression in Spic+ macrophages. Partial gene expression correlation (normalized for cell quality, y axis) with cell scores for diffusion component 2 from diffusion map embedding of macrophages (from FIG. 4C) reveals gene expression profiles of 4V ChP enriched macrophages.

(FIG. 12A) Subsets of endothelial cells (EC) score highly for arterial and venous transcriptional programs. tSNE embedding of endothelial cells, colored by signature scores for gene sets expressed in arterial EC (left) or venous EC (right) (signatures taken from (Vanlandewijck et al., 2018)). (FIG. 12B) Topic modeling of EC identifies a transcriptional program associated with immediate early gene expression (Topic 10) Left: Bar plot shows the scores (x axis) of top ranked genes (y axis). Right: 2D tSNE embedding (as in FIG. 12A), colored by the topic's weight in the cells. (12C-12D) Endothelial cells do not show significant transcriptional shifts between ventricles. (FIG. 12C) tSNE embedding of EC colored and faceted by ventricle the cells were sampled from. All cells are shown in grey in the background. (FIG. 12D) The empirical cumulative distribution (y axis) of EC topic weights (x axis) across EC cells, grouped and colored by the ventricle the cells were collected from. (FIG. 12E) Blood brain barrier gene expression identified in EC of the developing ChP. tSNE embedding of endothelial cells colored by expression of BBB genes Cldn5 (top left), Mfsd2a (top right), Esm1 (bottom left) and Plvap (bottom right). (FIG. 12F) Transmission electron microscopy image of developing fenestrae in the embryonic vessels (top, black arrow heads), as compared to well-defined fenestrae in the adult endothelia (bottom, black arrow heads). Scale bar=100 nm.

(FIG. 13A) Dotplot shows expression of Igfbp2 and Igf2, examples of secreted genes, across all cells. Size of dot represents the fraction of cells within each cell type that expresses a gene, and color indicates the median expression level when a gene is detected. (FIG. 13B) Bipartite graph representation of cellular network of ligand (left) and cognate receptor (right) pairs (STAR Methods). Dots represent gene sets, which are either generally expressed by a cell type compared to all other cell types (Table 1), or specific to a subset of cells identified either by differential expression for immune cells and neuron-/glial-like cells, or by top 50 scoring genes of topics. Dots are colored by the cell type a gene sets was identified in, and size is proportional to the degree of each vertex of the fully connected network. Shown are two subnetworks, where only connections to receptor vertices of neuronal-like cells (top) and glial-like cells (bottom) are shown.

(FIG. 14A) A trained random forest classifier assigns cell types across development. Dot-plot shows the results of a random forest classifier trained on adult nuclei data, and applied on embryo single-cell data. For each cell that belongs to the six major cell type in the embryo, the classifier predicted the cell type in the adult dataset. The dots (both size and color) indicate percent of cells per cell type (column) that were classified to which of the adult cluster (row). Hence, columns add up to 1. (FIG. 14B) Cells captured by sNuc-Seq data are dominated by epithelial cells. Barplot showing the fractions of cells that were sampled per cell type (x axis, color). (FIG. 14C) Adult epithelial cells separate strongly by ventricle. UMAP embedding of all sNuc-Seq data, where each cell is colored by ventricle it was sampled from. All cells in grey as orientation. Adult ChP was sampled form all three ventricles, and embryo from LV only. (FIG. 14D) Composition of each cell cluster by ventricle the cells were sampled from. Barplot shows the fraction of cells of each cluster by ventricle. (FIG. 14E) Immune cells in the adult ChP. Whole explant imaging of the LV ChP shows immune cells labeled with antibodies against MRC1 (mannose receptor C-type) and CD45 (protein tyrosine phosphatase). Nuclei shaded. (FIG. 14F) GFAP+ cells identified in the adult ChP. Right: Violin plot (top) shows the expression of glial cell markers in the embryonic and adult brain ChP (only glia-like cells shown), which shows common expression of Slcla3, expression of Rspo3 in embryonic, and expression of the glial markers (Gfap) in adults. Left: Immunohistochemistry with antibody against GFAP (gray, nuclei shaded) in the adult LV ChP explants (scale bar=10 μm). (FIG. 14G) Topic modeling of adult epithelial cells reveals conserved regionalization of transcriptional programs. Bar plot shows the scores (x axis) of top ranked genes (y axis). Right: Shown is the empirical cumulative distribution (y axis) of topic weights (x axis) in adult epithelial cells, grouped and colored by the ventricle the cells were collected from. (FIG. 14H) Dotplot shows expression of genes that are regionalized in epithelial cells across ventricles, some of which are conserved across development (Wls, Tbcld1, Sulf1, Ins2) and some are age-specific (Slc35f1, Penk, Ttr). Size of dot represents the fraction of cells of epithelial cells discretized by age and ventricle that expresses a gene, and color indicates the median expression level when a gene is detected. (FIG. 14I) Topic modeling of mesenchymal cells. Top: Bar plot shows the scores (x axis) of top ranked genes (y axis) for cluster specific topics. Bottom: Shown is the empirical cumulative distribution (y axis) of topic weights (x axis) in adult epithelial cells, grouped and colored by the ventricle the cells were collected from (left) or by cluster membership (right).

(FIG. 15B) images of MTX treatment on rat hippocampal neurons; (FIG. 15C) relative SOD activity in CSF of adult tissue; (FIG. 15D) expression of SOD3 by qRT-PCR; (FIG. 15E) imaging of SPD3 ISH in LVCP and 4VCP, adapted from Lun et al, J of Neurosci 2015, Allen Brain Atlas, incorporated herein by reference.

(FIG. 16A) Postnatal 42 measurements of SOD3 in LVCP and 4VCP; (FIG. 16B) shows SOD3 band at P28 and P43 of SOD3.

FIG. 17A-17C—(FIG. 17A) CSF delivery of GFP and SOD3, (FIG. 17B) shows band of Sod3 delivery, (FIG. 17C) charts SOD activity with AAV-GFP (Control) and AAV-SOD3.

FIG. 18—Depiction of overview of hypothesis and research plan.

FIG. 19A-19D—Example of (FIG. 19A) patient CSF sample with reduced (FIG. 19B) SOD activity compared to disease-free control CSF and (FIG. 19C-19D) CSF proteins. Asterisks denotes SOD3 band.

FIG. 21—depicts study of in vitro incubation; results of MTX inducing ROS production and alters mitochondrial membrane potential in ChP; MTX impairs mitochondrial respiration in choroid plexus in vitro; MTX decreases SOD expression and secretion in vitro; with depiction of the MTX effects on expression of SOD.

FIG. 22A depicts study parameters, with MTX injection of 4 mg/kg i.v. to mouse, with evaluation at 48 hours, FIG. 22B measures CSF Sod3 and Albumin, FIG. 22C SOD activity, FIG. 22D 8-OHdG.

FIG. 24A-24D—CHP SOD3 rescues oxidative stress against MTX in hippocampus. measurement of lipid peroxidation in hippocampus at p24 (FIG. 24A) and at p42 (FIG. 24B); MDA normalized to GFP for GFP, GFP+ MTX, SOD3, SOD3+ MTX for p28 (FIG. 24C) and for p42 (FIG. 24D).

(FIG. 25E) Adult rats (8 wks) expressing AAV2/5-SOD3 for one week show higher CSF-SOD enzymatic activity vs. ctrl, p<0.05, t-test.

(FIG. 26B) Schematic of chemotherapy delivery via tail vein injection to rodents, which induces (FIG. 26C) lipid damage and reduces antioxidant activity in (FIG. 26D) cortex and (FIG. 26E) CSF. (FIG. 26F) CSF from Primary CNS lymphoma patient shows reduced CSF-SOD expression levels after receiving high dose MTX (sample 1B) compared to pretreatment (sample 1A).

FIG. 28A-28C Meis1 binds Wnt5a promoter in hindbrain choroid plexus.

FIG. 29A-29C-3 Selective infection of choroid plexus epithelium by AAV2.5.

FIG. 30A-30E Meis1 overexpression in telencephalic choroid plexus (tChP) of the lateral ventricles, increases expression of Wnt and Sonic signaling pathway components.

Figures 1A, 1B, 1C, 1D:
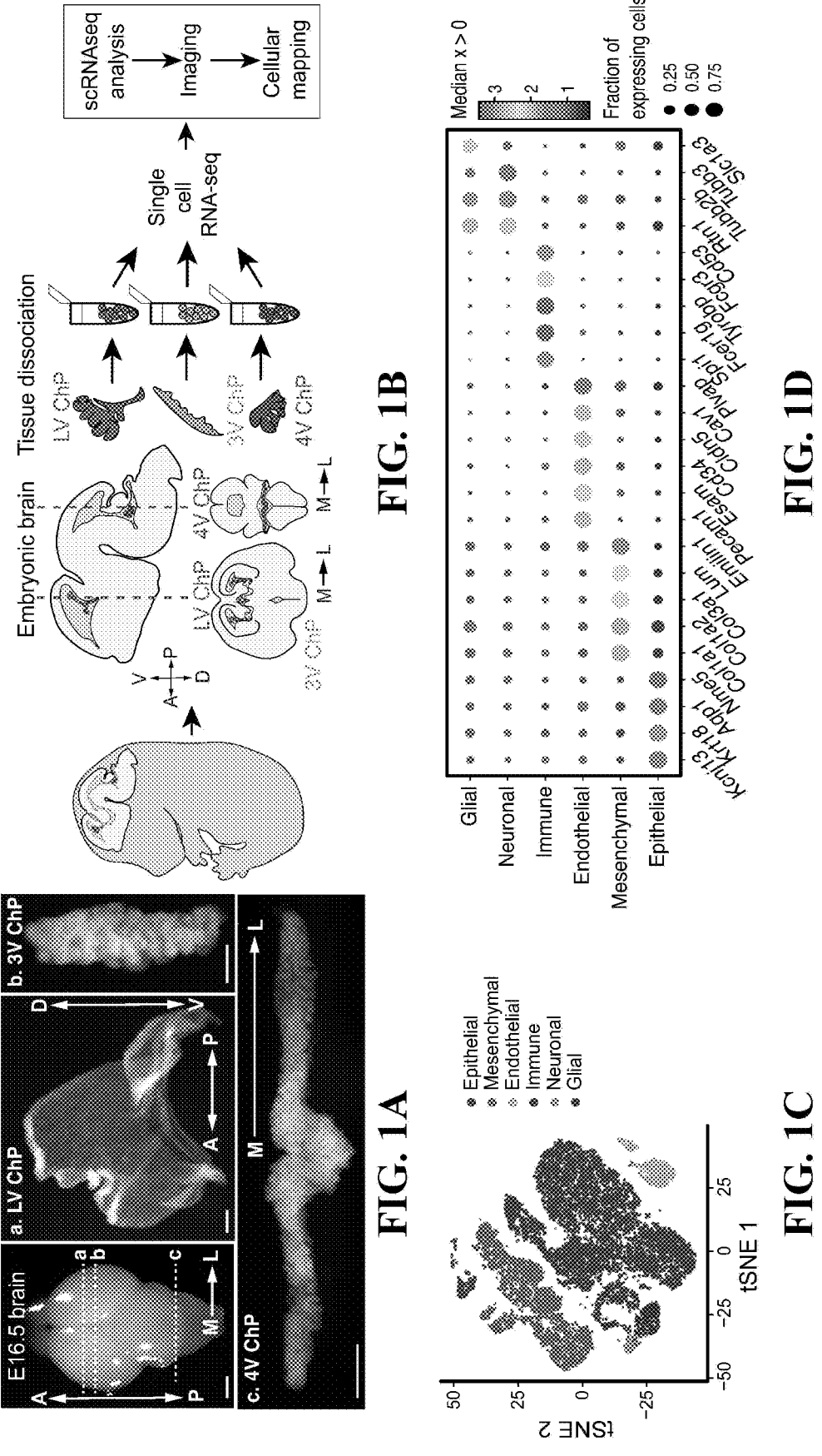
FIG. 1A-1G—Single cell RNA-Seq of the cellular composition of ChPs.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "developmental stage" refers to a stage of a cell that may include cell states and may include stages of development from a new born cell to a mature cell, or maturation of a progenitor undifferentiated cell, such as a stem cell, to a mature cell and all stages in between.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide isolated cells of the choroid plexus, and engineered ChP cells expressing modified to express particular gene signatures as provided herein. In embodiments, the cells may be provided in a tissue or organism model. Methods of modulating expression of the gene signatures or topics are also provided. Embodiments disclosed herein also provide for methods of detecting gene signatures and biomarkers for use in diagnostic assays or for screening assay, e.g. assays for screening therapeutics or genetic perurbations. In certain embodiments, the methods of modulating include methods for reducing oxidative stress, which can comprise supplementing choroid plexus secretion of anti-oxidants such as SOD3 by adeno-associated virus (AAV)-mediated approaches.

Signature

In certain example embodiments, the therapeutic, diagnostic, and screening methods disclosed herein target, detect, or otherwise make use of one or more biomarkers of an expression signature. As used herein, the term "biomarker" can refer to a gene, an mRNA, cDNA, an antisense transcript, a miRNA, a polypeptide, a protein, a protein fragment, epigenetic element, or any other nucleic acid sequence or polypeptide sequence that indicates either gene expression levels or protein production levels. Accordingly, it should be understood that reference to a "signature" in the context of those embodiments may encompass any biomarker or biomarkers whose expression profile or whose occurrence is associated with a specific cell type, subtype, or cell state of a specific cell type or subtype within a population of cells (e.g., ChP cells) or a specific biological program. As used herein the term "module" or "biological program" can be used interchangeably with "expression program" and refers to a set of biomarkers that share a role in a biological function (e.g., an activation program, cell differentiation program, proliferation program). Biological programs can include a pattern of biomarker expression that result in a corresponding physiological event or phenotypic trait. Biological programs can include up to several hundred biomarkers that are expressed in a spatially and temporally controlled fashion. Expression of individual biomarkers can be shared between biological programs. Expression of individual biomarkers can be shared among different single cell types; however, expression of a biological program may be cell type specific or temporally specific (e.g., the biological program is expressed in a cell type at a specific time). Expression of a biological program may be regulated by a master switch, such as a nuclear receptor or transcription factor. As used herein, the term "topic" refers to a biological program. Topics are described further herein. The biological program (topic) can be modeled as a distribution over expressed biomarkers. In topic modeling, a cell can be modeled as a mixture of a small number of transcriptional programs ("topics"), where each topic is a distribution over genes. A gene can belong to multiple topics with different weights, reflecting the gene's role in each topic. Likewise, a topic's weight for a given cell reflects the relative prominence of the corresponding biological process associated with that topic in that cell. Topic models for all epithelial cells were learned, and then topics were searched for that were differentially weighted across subsets of individual cells or that described an interpretable biological process, based on the associated genes.

In certain embodiments, the expression of the signatures disclosed herein is dependent on epigenetic modification of the biomarkers or regulatory elements associated with the signatures (e.g., chromatin modifications or chromatin accessibility). Thus, in certain embodiments, use of signature biomarkers includes epigenetic modifications of the biomarkers that may be detected or modulated. As used herein, the terms "signature", "expression profile", or "expression program" may be used interchangeably (e.g., expression of genes, expression of gene products or polypeptides). It is to be understood that also when referring to proteins (e.g. differentially expressed proteins), such may fall within the definition of "gene" signature. Levels of expression or activity may be compared between different cells in order to characterize or identify, for instance, signatures specific for cell (sub)populations. Increased or decreased expression or activity or prevalence of signature biomarkers may be compared between different cells in order to characterize or identify for instance specific cell (sub)populations. The detection of a signature in single cells may be used to identify and quantitate for instance specific cell (sub)populations. A signature may include a biomarker whose expression or occurrence is specific to a cell (sub)

population, such that expression or occurrence is exclusive to the cell (sub)population. An expression signature as used herein, may thus refer to any set of up- and/or down-regulated biomarkers that are representative of a cell type or subtype. An expression signature as used herein, may also refer to any set of up- and/or down-regulated biomarkers between different cells or cell (sub)populations derived from a gene-expression profile. For example, an expression signature may comprise a list of biomarkers differentially expressed in a distinction of interest.

The signature according to certain embodiments of the present invention may comprise or consist of one or more biomarkers, such as for instance 1, 2, 3, 4, 5, 6, 7, 8, 9, 10 or more. In certain embodiments, the signature may comprise or consist of two or more biomarkers, such as for instance 2, 3, 4, 5, 6, 7, 8, 9, 10 or more. In certain embodiments, the signature may comprise or consist of three or more biomarkers, such as for instance 3, 4, 5, 6, 7, 8, 9, 10 or more. In certain embodiments, the signature may comprise or consist of four or more biomarkers, such as for instance 4, 5, 6, 7, 8, 9, 10 or more. In certain embodiments, the signature may comprise or consist of five or more biomarkers, such as for instance 5, 6, 7, 8, 9, 10 or more. In certain embodiments, the signature may comprise or consist of six or more biomarkers for instance 6, 7, 8, 9, 10 or more. In certain embodiments, the signature may comprise or consist of seven or more biomarkers, such as for instance 7, 8, 9, 10 or more. In certain embodiments, the signature may comprise or consist of eight or more biomarkers, such as for instance 8, 9, 10 or more. In certain embodiments, the signature may comprise or consist of nine or more biomarkers, such as for instance 9, 10 or more. In certain embodiments, the signature may comprise or consist of ten or more biomarkers, such as for instance 10, 11, 12, 13, 14, 15, or more. It is to be understood that a signature according to the invention may for instance also include different types of biomarkers combined (e.g. genes and proteins).

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different cells found in the ChP, e.g. epithelial, endothelial, mesenchymal, immune, neuronal or glial cells or the cell (sub)populations (e.g., fibroblast cells), as well as comparing a ChP cell population or cell (sub)populations with other cell populations or cell (sub)populations, e.g. anatomical location, including ventricle specific cell population or (sub) population, age, developmental, or differentiation state. It is to be understood that "differentially expressed" biomarkers include biomarkers which are up- or down-regulated as well as biomarkers which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art. Differential expression of biomarkers may also be determined by comparing expression of biomarkers in a population of cells or in a single cell. In certain embodiments, expression of one or more biomarkers is mutually exclusive in cells having a different cell state or subtype (e.g., two genes are not expressed at the same time). In certain embodiments, a specific signature may have one or more biomarkers upregulated or downregulated as compared to other biomarkers in the signature within a single cell. Thus a cell type or subtype can be determined by determining the pattern of expression in a single cell.

As discussed herein, differentially expressed biomarkers may be differentially expressed on a single cell level, or may be differentially expressed on a cell population level. Preferably, the differentially expressed biomarkers as discussed herein, such as constituting the expression signatures as discussed herein, when as to the cell population level, refer to biomarkers that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., fibroblasts) which can be distinguished or are uniquely identifiable and set apart from other cells of this cell type. The cell subpopulation may be phenotypically characterized, and is preferably characterized by the signature as discussed herein. A cell (sub) population as referred to herein may constitute of a (sub) population of cells of a particular cell type characterized by a specific cell state.

The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression at a site of inflammation. The signature gene may indicate the presence of one particular cell type. In one embodiment, the expression may indicate the presence of inflammatory or protective cell types. Not being bound by a theory, a combination of cell subtypes in a subject may indicate an outcome.

When referring to induction, or alternatively suppression of a particular signature, preferable is meant induction or alternatively suppression (or upregulation or downregulation) of at least one biomarker of the signature, such as for instance at least two, at least three, at least four, at least five, at least six, or all biomarkers of the signature.

Isolated Cells

Isolated cells of the Choroid Plexus are provided. In embodiments, the cell type may be detected by measuring one or more markers for each cell type selected from Table 1A-1C. In certain embodiments, the cell type as defined by expression of the markers described herein may be obtained by sorting cells based on expression of one or more markers for each cell type according to Table 1A-1C. In certain example embodiments, the quantity of cells may be determined by cell specific markers and gene expression assigned to each cell. The isolated cell can be from an autologous, allogenic, or xenogenic source and engineered to express one or more genes of the signature defined in Table 2, epithelial cells of developing Choroid Plexus (ChP); Table 3, mesenchymal cells of developing ChPs; Table 4, endothelial cells of developing ChPs; Table 6, epithelial cells of adult ChPs; or Table 7, Mesenchymal cells of developing and adult ChPs. The isolated cell may be engineered to express a signature comprising Rspo2+co-expressed with one or more of Rspo3, Lrp1b, Tpbg, Rspo1, Ws, Ezr, Ednrb, Clu, Wnt3a, Wnt8b, Sfrp1. The isolated and/or engineered cells may provided as a tissue or organism model. The tissue or organism model may comprise one or more cell types from the group consisting of epithelial cells, mesenchymal cells, endothelial cells, progenitor glia-like population or immune cells characterized by expression of the signature defined in Table 2, 3, 4, 6, or 7.

In another aspect, the present invention provides methods for detecting or quantifying ChP cells in a biological sample of a subject can be isolated, detected or quantified. The isolated cells may be detected or quantified using one or more cell surface markers for a cell type selected from Table 1A-1C. In another aspect, the present invention provides for a method of isolating a ChP cell from a biological sample of a subject, the method comprising isolating from the biological sample ChP cells as defined as defined in any embodiment herein. The cell may be isolated using one or more surface markers for a cell type selected from Table 1A-1C. In certain embodiments, the cell may be isolated, detected or quantified using a technique selected from the group consisting of RT-PCR, RNA-seq, single cell RNA-seq, western blot, ELISA, flow cytometry, mass cytometry, fluorescence activated cell sorting, fluorescence microscopy, affinity separation, magnetic cell separation, microfluidic separation, and combinations thereof.

Sources of isolated cells may be autologous, allogeneic or xenogeneic source, which can then be engineered to express a gene signature as defined in Table 2, 3, 4, 6 or 7. In preferred embodiments, the cells are from a mammal, more preferably, a mouse or a human.

In embodiments, the cell is an epithelial cell comprising one or more genes of the signature selected from Topic 3, 4, 6, 9, 11, 14, 16, 19, 23 or 24 from Table 2. The isolated cell can be a mesenchymal cell comprising one or more genes in the signature selected from Topic 2, 3, 5, 7, 8, 12, 16, or 18 of Table 3. The isolated cell can be an endothelial cell comprising one or more genes selected from Topic 3, 8, 10, 11 or 12 in Table 4. In one aspect, the cell is an epithelial cell comprising one or more genes selected from Topic 6, 8, 9 or 10 in Table 6. In another aspect, the cell is a mesenchymal cell comprising one or more genes selected from Topic 4, 5, 8, 12 or 15 from Table 7.

Tissue or Organism Model

Embodiments can include tissue or organism models comprising cells, the cells comprising one or more cell types from the group comprising epithelial cells, mesenchymal cells, endothelial cells, progenitor glia-like population or immune cells. The cells can be characterized by expression of one or more signatures as defined herein. The signatures can comprise markers of cell types as described in Tables 1A-1C, may comprise gene expression signatures as described in any one of Tables 2, 3, 4, 6, or 7, or a combination thereof.

The tissue or organism model may be engineered to constitutively or conditionally express one or more targets of interest from the gene signatures as described herein. As described herein, the tissue or organism models can be utilized with assays, including perturbations. In particular embodiments, the targets of interest are from the gene signatures of developing ChPs, adult ChPs. In embodiments, the targets of interest are from a gene signature of a cell of the LV, 3V or 4V. In certain embodiments, the targets of interest comprise a signature of a particular cell population or (sub) population and may comprise an immune cell, an epithelial cell, a neuronal cell, a mesenchymal cell, endothelial cell, or progenitor glia-like population. In certain embodiments, the cell is a fibroblast or macrophage.

The signature genes of the present invention were discovered by analysis of expression profiles of single-cells within a population of ChP cells, thus allowing the discovery of novel cell subtypes that were previously invisible in a population of cells within one or more ventricle sof the ChP. The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a ventricle. The signature genes may indicate the presence of one particular cell type. In one embodiment, the expression may indicate the presence of proliferating cell types.

Detection and Isolation Using Biomarkers

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

Detection may comprise one or more markers of topic 3 in a developing epithelial cell. In an aspect, the one or more genes may be selected from Ly6e, Ly6a, Ltc4s, Prr32, Macrod1, Gm17750, X0610012G03Rik, Pcbp3, Dcaf12ll, Gzmm, Gm11744, Actr3, Ptp4a3, X1110065P20Rik, Gm15932, Cisd1, Cdkl5, Krt1, Bex2, Shisa4, Mgmt, Tex40, Gm15631, Gstm1, Mrps6, Arsg, X2310015A1ORik, Eri3, Pla2g5, Hscb, Cmtm8, Sys1, Ccdcl2, Gata3, Cibl, Scp2, Nefm, Fam47e, Nfasc, X2900011008Rik, X1500011B03Rik, Il17rc, Gadd45g, X1700024G13Rik, Ephx2, Hemkl, Pigyl, Pla2gl2a, Adra2c, or Mrpl34. In embodiments, the one or more markers is from Topic 3, Topic 4, Topic 6, Topic 9, Topic 11, Topic 14, Topic 16, Topic 19, Topic 23 or Topic 24 of Table 2.

Detection and/or isolation may comprise one or more markers of a topic in a mesenchymal cell of a developing ChP. In embodiments, the one or more genes from Topic 2, from Topic 3, Topic 5, Topic 7, Topic 8, Topic 12, Topic 16, and/or Topic 18 of Table 3.

Detection and/or isolation may comprise one or more markers of a topic in an endothelial cell of developing ChPs from Table 4. In embodiments, the one or more markers can be from Topic 3, Topic 8, Topic 10, Topic 11 and/or Topic 12 of Table 4.

Detection and/or isolation may comprise one or more markers of a topic in an endothelial cell of adult ChPs. In embodiments, the one or more markers is from Topic 6, from Topic 8, from Topic 9 and/or from Topic 10 of Table 6.

Detection and/or isolation may comprise one or more markers of a topic in mesenchymal cells of developing and adult ChPs from Table 7. In certain embodiments, the one or more markers is from Topic 4, from Topic 5, from Topic 8, from Topic 12 and/or from Topic 14.

In embodiments, detection and/or isolation may comprise one or more markers in a mesenchymal cell. In embodiments, the detection and/or isolation is of a fibroblast cell, optionally within the LV, 3V, or 4V. In embodiments, the one or more markers is from Topic 8 or 18 in the LV, one or more markers from Topic 2 and 7 in the 3V, and/or one or more markers from Topic 5 in the 4V. In particular embodiments, the one or markers encode growth factors. In particular embodiments, the one or more markers are Bmp4/7 and or Wnt4/2. In some embodiments, the one or more markers are Hhip, Ptch1, RBP4 and/or Wisp1 in fibroblasts, in some preferred embodiments, in the 4V.

In embodiments, the detection and/or isolation is of immune cells. Macrophages may be detected or isolated, which in some embodiments, may comprise one or markers for comprising Lyve 1, Spp1, Slc40a1, Spic and/or Clec4n. In embodiments, the immune cell is a basophil and the one or more markers is a proinflammatory chemokine. The proinflammatory chemokine marker can be selected from Ccl3, Ccl4, Ccl6, or Ccl9.

In certain embodiments, the detection and/or isolation is of endothelial cells. In particular embodiments, the one or more genes is associated with transcription programs of Topic 8 (arterial), Topic 11 (venous) or Topic 3 (arteriolar gene expression). In certain embodiments, the one or more markers is Esm1 and/or Plvap, Cldn5 and/or Mfsd2a.

In certain embodiments, the detection and/or isolation is of Insulin like growth factor 2 (Igf2), in epithelial cells, endothelial cells, and/or mesenchymal cells. One or more markers may comprise Penk and Shh in epithelial cells, and/or Ttr, Slc35fl.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or the like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, μl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

In certain embodiments, the CD8+ and/or CD4+ T cell subtypes may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH), Flow-FISH and combinations thereof. The technique may employ one or more agents capable of specifically binding to one or more gene products expressed or not expressed by the CD8+ T cells, preferably on the cell surface of the CD8+ T cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see Immunoassay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, an instrument-control system, and a data system. Differences in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

Separation

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854, 5,288,644, 5,324,633, 5,432,049, 5,470,710, 5,492,806, 5,503,980, 5,510,270, 5,525,464, 5,547,839, 5,580,732, 5,661,028, and 5,800,992, the disclosures of which are herein incorporated by reference, as well as WO 95/21265, WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B. V. (1993) and Kricka, "Nonisotopic DNA Probe Techniques", Academic Press, San Diego, Calif. (1992).

Sequencing and Single Cell Sequencing

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule) may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nano-liter Droplets" Cell 161, 1202-1214; International Patent Application No. PCT/US2015/049178, published as WO 2016/040476 on Mar. 17, 2016; Klein et al., 2015, "Droplet Barcoding for Single-Cell Transcriptomics Applied to Embryonic Stem Cells" Cell 161, 1187-1201; International Patent Application No PCT/US2016/027734, published as WO 2016/168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), the contents and disclosures of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International Patent Application No. PCT/US2016/059239, published as WO 2017/164936 on Sep. 28, 2017, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US Patent Publication Nos. US 20160208323A1 and US 20160060691A1; and International Patent Publication No. WO 2017/156336A1).

Modulating Agents

As used herein the term "altered expression" may particularly denote altered production of the recited gene products by a cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve affecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

The modulating agent may target or modulate one or more genes of topic 3 in a developing epithelial cell. In an aspect, the one or more genes may be selected from Ly6e, Ly6a, Ltc4s, Prr32, Macrod1, Gm17750, X0610012G03Rik, Pcbp3, Dcafl211, Gzmm, Gm11744, Actr3, Ptp4a3, X1110065P20Rik, Gm15932, Cisd1, Cdkl5, Krt1, Bex2, Shisa4, Mgmt, Tex40, Gm15631, Gstm1, Mrps6, Arsg, X2310015A1ORik, Eri3, Pla2g5, Hscb, Cmtm8, Sys1, Ccdcl2, Gata3, Cibl, Scp2, Nefm, Fam47e, Nfasc, X2900011008Rik, X1500011B03Rik, Il17rc, Gadd45g, X1700024G13Rik, Ephx2, Hemkl, Pigyl, Pla2gl2a, Adra2c, or Mrp134. In embodiments, the one or more genes is from Topic 3, Topic 4, Topic 6, Topic 9, Topic 11, Topic 14, Topic 16, Topic 19, Topic 23 or Topic 24 of Table 2.

The modulating agent may target or modulate one or more genes of topic 23 in an epithelial cell. In an aspect, the one or more genes may comprise Meis1 and one or more genes selected from Penk, Pmch, Wnt5a, Shh, Gpx3, Ctsc, Ocln, Fam69a, Slc22a19, Atel, Slc4a10, Lgil, D730045A05Rik, Wls, Slcl6a10, Lmol, Prps2, Cpxml, Pdgfra, Sema3c, Negr1, Adamtsl3, Defb9, Tpd5211, Mapk4, Abca4, Dlkl, Meis2, Grbl4, Fxyd7, Scd2, Hotairml, Tspan33, Plagll, Rapgef4, Jam3, Cltb, Plppr4, Slc24a5, Peg10, Col8al, Hpgd, Marveld2, Npnt, Id4, Oca2, E130308A19Rik, Dtx2, Cep162.

The modulating agent may target or modulate one or more genes of topic 23 in an epithelial cell. In an aspect, the one or more genes may comprise Wnt5a and one or more genes selected from Penk, Pmch, Shh, Gpx3, Ctsc, Ocln, Fam69a, Slc22a19, Atel, Slc4a10, Lgil, D730045A05Rik, Wls, Slcl6a10, Lmol, Meis1, Prps2, Cpxml, Pdgfra, Sema3c, Negr1, Adamtsl3, Defb9, Tpd5211, Mapk4, Abca4, Dlkl, Meis2, Grbl4, Fxyd7, Scd2, Hotairml, Tspan33, Plagll, Rapgef4, Jam3, Cltb, Plppr4, Slc24a5, Peg10, Col8al, Hpgd, Marveld2, Npnt, Id4, Oca2, E130308A19Rik, Dtx2, Cep162.

The modulating agent may target or modulate one or more genes of a topic in a mesenchymal cell of a developing ChP. In embodiments, the agent may target or modulate one or more genes from Topic 2, from Topic 3, Topic 5, Topic 7, Topic 8, Topic 12, Topic 16, and/or Topic 18 of Table 3.

The modulating agent may target or modulate one or more genes of a topic in an endothelial cell of developing ChPs from Table 4. In embodiments, agent may target or modulate one or more genes from Topic 3, Topic 8, Topic 10, Topic 11 and/or Topic 12 of Table 4.

The modulating agent may target or modulate one or more genes of a topic in an endothelial cell of adult ChPs. In embodiments, the agent may target or modulate one or more genes from Topic 6, from Topic 8, from Topic 9 and/or from Topic 10 of Table 6.

The modulating agent may target or modulate one or more genes of a topic in mesenchymal cells of developing and adult ChPs from Table 7. The modulating agent may target or modulate one or more genes from Topic 4, from Topic 5, from Topic 8, from Topic 12 and/or from Topic 14.

In embodiments, the modulating agent is targeted to a mesenchymal cell. In embodiments, the modulating agent targets a fibroblast cell, optionally within the LV, 3V, or 4V. In embodiments, the modulating agent targets one or more genes from Topic 8 or 18 in the LV, one or more genes from Topic 2 and 7 in the 3V, and/or one or more genes from Topic 5 in the 4V. In particular embodiments, the modulating agent targets genes encoding growth factors. In particular embodiments, the modulating agent targets Bmp4/7 and or Wnt4/2. In some embodiments, the modulating agent targets Hhip, Ptch1, RBP4 and/or Wisp1 in fibroblasts, in some preferred embodiments, in the 4V.

In embodiments, the modulating agent modulates or targets immune cells. Macrophages may be targeted, which in some embodiments, comprise Lyve 1, Spp1, Slc40a1, Spic and/or Clec4n. In embodiments, the immune cell is a basophil and the target is a proinflammatory chemokine. The proinflammatory chemokine modulated can be selected from Ccl3, Ccl4, Ccl6, or Ccl9.

In certain embodiments, the modulating agent modulates endothelial cells. In particular embodiments, the modulating agent may modulate one or more genes associated with transcription programs of Topic 8 (arterial), Topic 11 (venous) or Topic 3 (arteriolar gene expression). In certain embodiments, the modulating agent targets or modulates Esm1 and/or Plvap, Cldn5 and/or Mfsd2a.

In certain embodiments, the modulating agent modulates Insulin like growth factor 2 (Igf2), in epithelial cells, endothelial cells, and/or mesenchymal cells. Modulating agents may target or modulate Penk and Shh in epithelial cells, and/or Ttr, Slc35fl.

In a preferred embodiment, the modulating agent modulated SOD expression, in particular embodiments, the modulating agent targets SOD3, or gene expression of other antioxidants.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). Cmap can be used to screen for drugs capable of modulating one or more signatures of the ChP cells in silico.

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

Genetic Modifying Agents

In certain embodiments, the one or more modulating agents may be a genetic modifying agent. The genetic modifying agent may comprise a CRISPR system, a zinc finger nuclease system, a TALEN, a meganuclease or RNAi system.

CRISPR-CAS Systems

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

Class 1 Systems

The methods, systems, and tools provided herein may be designed for use with Class 1 CRISPR proteins. In certain example embodiments, the Class 1 system may be Type I, Type III or Type IV Cas proteins as described in Makarova et al. "Evolutionary classification of CRISPR-Cas systems: a burst of class 2 and derived variants" Nature Reviews Microbiology, 18:67-81 (Feb 2020)., incorporated in its entirety herein by reference, and particularly as described in FIG. 1, p. 326. The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g. Cas1, Cas2, RNA nuclease), and/or one or more accessory proteins (e.g. Cas 4, DNA nuclease), CRISPR associated Rossman fold (CARF) domain containing proteins, and/or RNA transcriptase. Although Class 1 systems have limited sequence similarity, Class 1 system proteins can be identified by their similar architectures, including one or more Repeat Associated Mysterious Protein (RAMP) family subunits, e.g. Cas 5, Cas6, Cas7. RAMP proteins are characterized by having one or more RNA recognition motif domains. Large subunits (for example cas8 or cas10) and small subunits (for example, cas11) are also typical of Class 1 systems. See, e.g., FIGS. 1 and 2. Koonin E V, Makarova K S. 2019 Origins and evolution of CRISPR-Cas systems. Phil. Trans. R. Soc. B 374: 20180087, DOI: 10.1098/rstb.2018.0087. In one aspect, Class 1 systems are characterized by the signature protein Cas3. The Cascade in particular Class 1 proteins can comprise a dedicated complex of multiple Cas proteins that binds pre-crRNA and recruits an additional Cas protein, for example Cas6 or Cas5, which is the nuclease directly responsible for processing pre-crRNA. In one aspect, the Type I CRISPR protein comprises an effector complex comprises one or more Cas5 subunits and two or more Cas7 subunits. Class 1 subtypes include Type I-A, I-B, I-C, I-U, I-D, I-E, and I-F, Type IV-A and IV-B, and Type III-A, III-D, III-C, and III-B. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al, the CRISPR Journal, v. 1, n5, FIG. 5.

Class 2 Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (Feb 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), Cas12d (CasY), Cas12e (CasX), and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sept 12; 154(6):1380-1389), Cas12 (Liu et al. Nature Communications, 8, 2095 (2017), and Cas13 (International Patent Publication Nos. WO 2019/005884 and WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and International Patent Publication WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein, "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1$b$, 2$a$-2$c$, 3$a$-3$f$, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in International Patent Publication Nos. WO 2018/213708, WO 2018/213726, and International Patent Applications No. PCT/US2018/067207, PCT/US2018/067225, and PCT/US2018/067307, each of which is incorporated herein by reference.

In certain example embodiments, the base editing system may be an RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA base editor may be used to delete or introduce a post-translation modification site in the expressed mRNA. In contrast to DNA base editors, whose edits are permanent in the modified cell, RNA base editors can provide edits where finer, temporal control may be needed, for example in modulating a particular immune response. Example Type VI RNA-base editing systems are described in Cox et al. 2017. Science 358: 1019-1027, International Patent Publication Nos. WO 2019/005884, WO 2019/005886, and WO 2019/071048, and International Patent Application Nos. PCT/US20018/05179 and PCT/US2018/067207, which are incorporated herein by reference. An example FnCas9 system that may be adapted for RNA base editing purposes is described in International Patent Publication No. WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system. See e.g. Anzalone et al. 2019. Nature. 576: 149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion and combinations thereof. Generally, a prime editing system, as exemplified by PE1, PE2, and PE3 (Id.), can include a reverse transcriptase fused or otherwise coupled or associated with an RNA-programmable nickase and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRIPSR-Cas systems along with few byproducts and greater or similar efficiency as compared to traditional CRISPR-Cas systems.

In some embodiments, the prime editing guide molecule can specify both the target polynucleotide information (e.g., sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1*b*, 1*c*, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2*a*, 3*a*-3*f*, 4*a*-4*b*, Extended data FIGS. 3*a*-3*b*, 4, The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2*a*-2*b*, and Extended Data FIGS. 5*a*-*c*.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class 1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4) 702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT US2019/045582, specifically paragraphs [0178]-[0333]. Which is incorporated herein by reference.
Target Sequences, PAMs, and PFSs
Target Sequences
In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.
PAM and PFS Elements
PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 3 (from Gleditzsch et al. 2019) below shows several Cas polypeptides and the PAM sequence they recognize.

TABLE 3

Example PAM Sequences

| Cas Protein | PAM Sequence |
| --- | --- |
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. Doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LshCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Sequences Related to Nucleus Targeting and Transportation

In some embodiments, one or more components (e.g., the Cas protein and/or deaminase) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO:1) or PKKKRKVEAS (SEQ ID NO:2); the NLS from nucleoplasmin (e.g., the nucleoplasmin bipartite NLS with the sequence KRPAATKKAGQAKKKK (SEQ ID NO:3)); the c-myc NLS having the amino acid sequence PAAKRVKLD (SEQ ID NO:4) or RQRRNELKRSP (SEQ ID NO:5); the hRNPA1 M9 NLS having the sequence NQSSNFGPMKGGNFGGRSSGPYGGGGQYFAK-PRNQGGY (SEQ ID NO:6); the sequence RMRIZFKNKGKDTAELRRRRVEVSVELRKAKKD-EQILKRRNV (SEQ ID NO:7) of the IBB domain from importin-alpha; the sequences VSRKRPRP (SEQ ID NO:8) and PPKKARED (SEQ ID NO:9) of the myoma T protein; the sequence PQPKKKPL (SEQ ID NO:10) of human p53; the sequence SALIKKKKKMAP (SEQ ID NO:11) of mouse c-abl IV; the sequences DRLRR (SEQ ID NO:12) and PKQKKRK (SEQ ID NO:13) of the influenza virus NS1; the sequence RKLKKKIKKL (SEQ ID NO:14) of the Hepatitis virus delta antigen; the sequence REKKKFLKRR (SEQ ID NO:15) of the mouse Mx1 protein; the sequence KRKGDEVDGVDEVAKKKSKK (SEQ ID NO:16) of the human poly(ADP-ribose) polymerase; and the sequence RKCLQAGMNLEARKTKK (SEQ ID NO:17) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to a nucleotide deaminase or catalytic domain thereof. When such a guide forms a CRISPR complex (e.g., CRISPR-Cas protein binding to guide and target), the adapter proteins bind and the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include a sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Perturbations

In some embodiments, CRISPR-Cas systems may be used to knockout protein-coding genes by frameshifts (indels). Embodiments include efficient and specific CRISPR-Cas9 mediated knockout (Gilbert, L. A., Horlbeck, M. A., Adamson, B., Villalta, J. E., Chen, Y., Whitehead, E. H., Guimaraes, C., Panning, B., Ploegh, H. L., Bassik, M. C., Qi, L. S., Kampmann, M. & Weissman, J. S. Genome-Scale CRISPR-Mediated Control of Gene Repression and Activation. Cell. 159, 647-661, doi:10.1016/j.cell.2014.09.029 (2014). PMCID:4253859; Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. Nature. 520, 186-191, doi:10.1038/nature14299 (2015). PMCID:4393360), including a CRISPR mediated double-nicking to efficiently modify both alleles of a target gene or multiple target loci (Ran, F. A., Hsu, P. D., Lin, C. Y., Gootenberg, J. S., Konermann, S., Trevino, A. E., Scott, D. A., Inoue, A., Matoba, S., Zhang, Y. & Zhang, F. Double nicking by RNA-guided CRISPR Cas9 for enhanced genome editing specificity. Cell. 154, 1380-1389, doi:10.1016/j.cell.2013.08.021 (2013). PMCID: 3856256; Wang, H., Yang, H., Shivalila, C. S., Dawlaty, M. M., Cheng, A. W., Zhang, F. & Jaenisch, R. One-step generation of mice carrying mutations in multiple genes by CRISPR-Cas-mediated genome engineering. Cell. 153, 910-918, doi:10.1016/j.cell.2013.04.025 (2013). PMCID: 3969854) and implementation of a smaller Cas9 protein for delivery on smaller vectors (Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. Nature. 520, 186-191, doi:10.1038/nature14299 (2015). PMCID:4393360).

CRISPR-mediated activation or inactivation (CRISPRa/i) systems may be used to activate or inactivate gene transcription, which can be used to interrogate cells, tissues, organoids, or animal models. Briefly, a nuclease-dead (deactivated) Cas9 RNA-guided DNA binding domain (dCas9) (Qi, L. S., Larson, M. H., Gilbert, L. A., Doudna, J. A., Weissman, J. S., Arkin, A. P. & Lim, W. A. Repurposing CRISPR as an RNA-guided platform for sequence-specific control of gene expression. Cell. 152, 1173-1183, doi: 10.1016/j.cell.2013.02.022 (2013). PMCID:3664290) tethered to transcriptional repressor domains that promote epigenetic silencing (e.g., KRAB) forms a "CRISPRi" (Gilbert, L. A., Larson, M. H., Morsut, L., Liu, Z., Brar, G. A., Torres, S. E., Stern-Ginossar, N., Brandman, O., Whitehead, E. H., Doudna, J. A., Lim, W. A., Weissman, J. S. & Qi, L. S. CRISPR-mediated modular RNA-guided regulation of transcription in eukaryotes. Cell. 154, 442-451, doi:10.1016/j.cell.2013.06.044 (2013). PMCID:3770145; Konermann, S., Brigham, M. D., Trevino, A. E., Hsu, P. D., Heidenreich, M., Cong, L., Platt, R. J., Scott, D. A., Church, G. M. & Zhang, F. Optical control of mammalian endogenous transcription and epigenetic states. Nature. 500, 472-476, doi: 10.1038/nature12466 (2013). PMCID:3856241) that represses transcription. To use dCas9 as an activator (CRISPRa), a guide RNA may be engineered to carry RNA binding motifs (e.g., MS2) that recruit effector domains fused to RNA-motif binding proteins, increasing transcription (Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. Nature. 517, 583-588, doi:10.1038/nature14136 (2015). PMCID:4420636).

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimising deaminase fusions for genome editing, Nat Commun. 7:13330; Hess et al, 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65 may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

Direct-capture Perturb-seq, a versatile screening approach in which expressed sgRNAs are sequenced alongside single-cell transcriptomes can also be used, allowing pooled single-cell CRISPR screens paired with combinatorial perturbation libraries that contain dual-guide expression vectors. Replogle et al., Combinatorial single-cell CRISPR screens by direct guide RNA capture and targeted sequencing, Nat Biotechnol. (2020); doi: 10.1038/s41587-020-0470-y.

CRISPR-Cas systems may also be used for the deletion of regulatory elements. To target non-coding elements, pairs of guides may be designed and used to delete regions of a defined size, and tile deletions covering sets of regions in pools. The delivery of two sgRNAs may mediate efficient excision of 500 bp genomic fragments.

CRISPR-Cas systems may also be used for gene editing, e.g., by RNA-templated homologous recombination. Keskin, H., Shen, Y., Huang, F., Patel, M., Yang, T., Ashley, K., Mazin, A. V. & Storici, F. Transcript-RNA-templated DNA recombination and repair. Nature. 515, 436-439, doi: 10.1038/nature13682 (2014).

CRISPR transgenic mice may be used to derive 'CRISPR-ready' cells. 'CRISPR-mice' are mice where the mouse germ line is engineered to harbor key elements of a CRISPR system, and cells require only the programmable (sgRNA) element to activate the CRISPR-Cas system. CRISPR mice include Cas9-transgenic mice (Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. Cell. 159, 440-455, doi:10.1016/j.cell.2014.09.014 (2014). PMCID:4265475; Parnas O., Jovanovic M., Eisenhaure™., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. Cell Jul 15. (2015) 2015 Jul 30; 162(3): 675-86. doi: 10.1016/j.cell.2015.06.059. Epub 2015 Jul 16).

CRISPR-Cas based perturbations, including single order or higher order perturbations, may be implemented in pooled format. The perturbation (screen) may be performed with expression readouts or reporter expression readout (genome-wide reporter-based pooled screens).

CRISPR-Cas functional genomics assays that may be used to cause sets of genetic perturbations are described in Shalem O., Sanjana N E., Zhang F. High-throughput functional genomics using CRISPR-Cas9. Nat Rev Genet. May; 16(5):299-311. (2015). doi: 10.1038/nrg3899. Epub 2015 Apr 9.

sgRNA libraries, including genome-wide libraries of sgR-NAs, may be designed as described in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. Cell Jul 15. (2015) 2015 Jul 30; 162(3):675-86. doi: 10.1016/j.cell.2015.06.059. Epub 2015 Jul 16; Sanjana, N. E., Shalem, O. & Zhang, F. Improved vectors and genome-wide libraries for CRISPR screening. Nat Methods. 11, 783-784, doi:10.1038/nmeth.3047 (2014); Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. Science. 343, 84-87, doi:10.1126/science.1247005 (2014). PMCID:4089965; Shalem, O., Sanjana, N. E. & Zhang, F. High-throughput functional genomics using CRISPR-Cas9. Nat Rev Genet. 16, 299-311, doi:10.1038/ nrg3899 (2015).

A pooled genome-wide screen for CRISPR-mediated KO (knock-out) may be performed as in Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. Science. 343, 84-87, doi:10.1126/science.1247005 (2014). PMCID:4089965.

An expression marker-based genome-wide CRISPR screen may be performed as in Parnas O., Jovanovic M., Eisenhaure™., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. Cell Jul 15. (2015) 2015 Jul 30; 162(3):675-86. doi: 10.1016/ j.cell.2015.06.059. Epub 2015 Jul 16.

A pooled, genome-scale, CRISPRa screen may be performed as in Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. Nature. 517, 583-588, doi:10.1038/nature14136 (2015). PMCID:4420636.

Pooled combinatorial perturbations may be performed, where the delivered perturbations and impact (molecular profiling) are determined post hoc, in either a conventional readout (e.g., sorting followed by sequencing) or with high-content single cell genomics.

In some embodiments, the CRISPR-Cas screen is performed by co-delivering multiple sgRNA using virale vector delivery (eg, sgRNA encoding vectors at a relatively high MOI) into cells pre-expressing the Cas9 enzyme to obtain as many higher order combinations as possible. For small sets of ~5 genes one may generate a combinatorially complete ascertained set of all 32 perturbations.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514, 8,133,697, 8,021,867, 8,119,361, 8,119,381, 8,124,369, and 8,129,134, which are specifically incorporated herein by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In embodiments the target of interest is one or more of the genes in the Tables 2, 3, 4, 6, or 7. In embodiments, the target of interest is selected from Rspo2, Rspo3, Lrp1b, Tpbg, Rspo1, Wls, Ezr, Ednrb, Clu, Wnt3a, Wnt8b, Sfrp1, and/or Shisa8. In certain embodiments, the cell is from 4V ChP, expressing one or more of Hhip, Ptch1, Rbp4, and Wisp1.

In certain embodiments, the target of interest is one or more genes in a cell from the lateral ventricle (LV), the 3V or the 4V. In preferred embodiments, the cell is a fibroblast.

In certain embodiments, target of interest is in a cell from the LV, comprising one or more genes from Topic 8 and/or Topic 18. In certain embodiments, target of interest is in a cell from the 3V, comprising one or more genes from Topic 2 and/or Topic 7. In certain embodiments, target of interest is in a cell from the 4V, comprising one or more genes from Topic 5.

In embodiments, modulating vascular cell types in the ChP is desired. In particular embodiments, the modulating can comprise one or more targets of a transcriptional program selected from Topic 8 (arterial), Topic 11 (venous), and Topic 3 (arteriolar).

Tissues and Organoids

Neural tissues have the potential to be tractable models for studying the human brain and neurological disorders, but to achieve this potential, they must closely reflect the cell composition, ECM, and gene expression profiles of the human brain. One or more types of isolated cells disclosed herein can be grown as a three dimensional model, allowing for brain organoids to be cultured, or for three dimensional tissue cultures. Accordingly, conventional culturing models can be used to grow one or more cells to organoids.

See., e.g., Quadrato, G. et al. Cell diversity and network dynamics in photosensitive human brain organoids. Nature 545, 48-+, doi:10.1038/nature22047 (2017); Camp, J. G. et al. Human cerebral organoids recapitulate gene expression programs of fetal neocortex development. Proceedings of the National Academy of Sciences of the United States of America 112, 15672-15677, doi:10.1073/pnas.1520760112 (2015). Tissues of higher complexity can be grown, utilizing the blueprint of spatially resolved cells and cell signatures provided herein, which can be further utilized with the Allen brain atlas for comparison and matching, see, brain-map.org.

Methods

Detection of Cell (Sub)Populations

In one embodiment, the method comprises detecting or quantifying cells in a biological sample obtained from the ChP. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "sample" or "biological sample" as used throughout this specification include any biological specimen obtained from a subject. Particularly useful samples are those known to comprise, or expected or predicted to comprise gut cells as taught herein. Preferably, a sample may be readily obtainable by minimally invasive methods, such as blood collection or tissue biopsy, allowing the removal/isolation/provision of the sample from the subject (e.g., colonoscopy).

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $1 \times SE$ or $\pm 2 \times SE$ or $\pm 3 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Methods of Detection and Isolation of Cell Types Using Biomarkers

In certain embodiments, the cell types disclosed herein may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the gut cells, preferably on the cell surface of the gut cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilized metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. The cell of origin is determined by a cellular barcode. In certain embodiments, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nano-liter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified cells from the tested object such as the biological sample may increase the abundance of the specified cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample. By means of example, isolating or purifying the specified cells from the tested object such as the biological sample may yield a cell population, in which the specified cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

The method may allow to detect or conclude the presence or absence of the specified cells in a tested object (e.g., in a cell population, tissue, organ, organism, or in a biological sample of a subject). The method may also allow to quantify the specified cells in a tested object (e.g., in a cell population, tissue, organ, organism, or in a biological sample of a subject). The quantity of the specified cells in the tested object such as the biological sample may be suitably expressed for example as the number (count) of the specified immune cells per standard unit of volume (e.g., ml, p1 or nl) or weight (e.g., g or mg or ng) of the tested object such as the biological sample. The quantity of the specified cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Use of Specific Binding Agents for Detection

In certain embodiments, the aforementioned detection methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $KA$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilized on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about 104-fold, or at least about 105-fold, or at least about 106-fold or more greater, than its affinity for a non-target molecule, such as for a suitable control molecule (e.g., bovine serum albumin, casein).

Preferably, the specific binding agent may bind to its intended target(s) with affinity constant (KA) of such binding KA >1×106 M-1, more preferably KA >1×107 M-1, yet more preferably KA >1×108 M-1, even more preferably KA >1×109 M-1, and still more preferably KA >1×1010 M-1 or KA >1×1011 M-1 or KA >1×1012 M-1, wherein KA=[SBA_T]/[SBA][T], SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')₂, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')₂, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant.

Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos*, *Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs may typically be capable of annealing with (hybridizing to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies. Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as 32p 33p, 35$^{12}$51, $^{131}$I; electron-dense reagents; enzymes (e.g., horseradish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilized in the probe:binding partner arrangement may be any, and includes, for example biotin:streptavidin, his-tag:metal ion (e.g., Ni2+), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.
Methods of Use Methods provided herein include methods of inducing growth factor expression in the brain by contacting the choroid plexus of one or more ventricles with an agent that increases or decreases expression of Bmp4/7, or Wnt4/2.

Methods provided herein include methods of enhancing, increasing, or facilitating choroid plexus development in the brain, or increasing neurodevelopmental potential, by contacting the choroid plexus, for example, hindbrain choroid plexus, with an agent that increases the expression of Wnt pathway (see, e.g. Purro et al., J Mol Cell Biol. 2014 February; 6(1):75-80. doi: 10.1093/jmcb/mjt049) and/or Sonic hedgehog (Shh) signaling pathway (see, e.g. Carballo et al., A highlight on Sonic hedgehog pathway. Cell Commun Signal 16, 11 (2018); doi:10.1186/s12964-018-0220-7) components. In an aspect, the method comprises increasing expression of Meis1, Wnt5a, or a combination thereof. In an aspect, the method can comprise contacting the telencephalic choroid plexus (tChP) of the lateral ventricles with an agent that increases the expression of Meis1, Wnt5a, or a combination thereof.

The methods of modulating one or more gene signatures provided herein can be utilized for increasing neural plasticity or neurodevelopmental potential. In particular embodiments, the method modulating comprises modulating one or more of Rspo2+, Rspo3, Lrp1b, Tpbg, Rspo1, Wls, Ezr, Ednrb, Clu, Wnt3a, Wnt8b, Sfrp1, Penk or Shh.

Modulating may comprise modulating any of the isolated cells as described herein, including modulation of epithelial cell development in an epithelial cell isolated from a ChP or in the ChP, comprising modulating the expression of Rspo2 associated with progenitor cells. Ccdc671Deup1 associated with newly differentiated epithelial cells, or Krt18, associated with mature epithelial cells. Modulating may comprise upregulating Slc40a1/Fpn-expressing macrophage in the ChP. In certain embodiments, the modulation of the macrophage modulated brain iron homeostasis. In embodiments, the method of modulating may comprise regulating Ins2 expression in epithelial cells of the ChP. The epithelial cells in preferred embodiments, are from the 3V of the ChP and can comprise newly differentiated epithelial cells, mature epithelial cells, or progenitor cells. In embodiments, the modulating of a cell comprises a basophil. In particular embodiments, the modulating comprises differentially expressing Ccl3, Ccl4, Ccl6, and Ccl9 relative to other cells.
Reducing Oxidative Stress Methods of reducing oxidative stress in the central nervous system, in the brain, in the ChP, or a ventricle of the ChP is provide, comprising increasing anti-oxidant expression from ChP epithelial cells comprising.

In particular embodiments, the subject suffers from a neurodegenerative disease, an inflammatory disease, is receiving chemotherapy, or a combination of the above. In particular embodiments, the chemotherapy is methotrexate (MTX).

In particular embodiments, the methods of reducing oxidative stress comprise administration of an antioxidant. In embodiments, the antioxidant is SOD3. The methods comprise gene delivery of SOD3 to augment SOD3 production in the ChP. IDelivery can be by any of the methods discussed herein, in certain instances, the gene delivery is by AAV. AAV2/5 is one preferred method of delivery. Administration of the AAV-SOD3 can comprise delivery transdermally or intravenously. In preferred embodiments, the delivery comprises injection into the lateral ventricle.

Monitoring of a reduction in oxidative stress can comprise monitoring SOD3 expression, SOD levels and CSF antioxidant capacity as further detailed herein. Further monitoring may comprise evaluating markers of redox homeostasis and oxidative damage, which may comprise markers found in cortical and hippocampal tissues, as well as white matter and CSF. In embodiments, monitoring the CSF may be of interest. The CSF comprises exosomes as well as circulating cells, and monitoring by spinal tap may be of interest. Additionally, circulating blood may aid in monitoring health of the brain, as CSF is absorbed through blood vessels over the surface of the brain back into the bloodstream. Additional monitoring may comprise diseases.
Diseases The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, indisposition, or affliction. The disease or disorder may result in oxidative stress, or treatment of the diseases or disorders herein, for example, by chemotherapy may result in oxidative stress in the subject.

In embodiments, the methods of reducing oxidative stress comprise treating a subject with Alzheimer's disease (AD), familial AD, Creutzfeldt-Jacob disease, dementia pugilistica, Down's Syndrome, Gerstmann-Straussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy, or atypical parkinsonism.

As well understood by the skilled artisan, autoimmune diseases or autoimmune disorders refer to diseases or disorders caused by an immune response against a self-tissue or tissue component (self-antigen) and include a self-antibody response and/or cell-mediated response. These encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune-associated infertility; autoimmune gastritis; autoimmune hepatitis; autoimmune hemophilia; autoimmune lymphoproliferative syndrome (ALPS); autoimmune thrombocytopenia; autoimmune uveoretinitis; Behget's disease; bullous pemphigoid; coeliac disease; dermatomyositis; diabetes mellitus type I; glomerulonephritis (e.g., crescentic glomerulonephritis, proliferative glomerulonephritis); Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; insulin resistance; mixed connective tissue disease; multiple sclerosis (MS); myasthenia gravis (MG); opsoclonus myoclonus syndrome (OMS); optic neuritis; Ord's thyroiditis; pemphigus (e.g., pemphigus vulgaris); pernicious anaemia; polyarteritis nodosa; polymyositis; primary biliary cirrhosis; primary myxedema; psoriasis; rheumatic fever; rheumatoid arthritis; Reiter's syndrome; scleroderma with anti-collagen antibodies; Sjögren's syndrome; systemic lupus erythematosus (SLE); Takayasu's arteritis; temporal arteritis; vitiligo; warm autoimmune hemolytic anemia; or Wegener's granulomatosis. Autoimmune disease has been recognized also to encompass atherosclerosis and Alzheimer's disease.

Modulating Cell-Cell Interaction Network

As described herein, there is a robust cell-cell interaction network of the ChP. In certain embodiments, methods of modulating the cell-cell interaction network of the ChP comprises modulating the expression of cognate receptor-ligand pairs in a set of two or more cell of the ChP, which may be selected from the pairs in Table 5. In embodiments, the modulating the expression of ligands is in mesenchymal cells, the ligands specific for cognate receptors in endothelial, immune, epithelial, neuronal and/or glial cells. In certain embodiments, the ligand-receptor pair comprises the receptor Pdgfra in a fibroblast and the ligand comprises Pdgfa in an epithelial cell. The ligand-receptor pair can comprise the receptor Pdgfrb in a pericyte and the ligand comprises Pdgfb in an endothelial cell. In an embodiment, the ligand receptor pair comprises the ligand Csf1 in basophils and the receptor comprises Csf1R in macrophage or monocyte. In particular instance, the modulating the expression of Csf1 modulates myeloid cell maturation. In embodiments, the ligand-receptor pair comprises the receptor Il6 in a basophil and/or mast cell, and the receptor comprises IL6st in mesenchymal cells, or Il6ra in monocytes, macrophages, and/or dendritic cells.

Administration

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., SOD3, antioxidants) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or prodrug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

In another embodiment, the delivery system may be an administration device. As used herein, an administration device can be any pharmaceutically acceptable device adapted to deliver a composition of the invention (e.g., to a subject's nose). A nasal administration device can be a metered administration device (metered volume, metered dose, or metered-weight) or a continuous (or substantially continuous) aerosol-producing device. Suitable nasal administration devices also include devices that can be adapted or modified for nasal administration. In some embodiments, the nasally administered dose can be absorbed into the bloodstream of a subject.

A metered nasal administration device delivers a fixed (metered) volume or amount (dose) of a nasal composition upon each actuation. Exemplary metered dose devices for nasal administration include, by way of example and without limitation, an atomizer, sprayer, dropper, squeeze tube, squeeze-type spray bottle, pipette, ampule, nasal cannula, metered dose device, nasal spray inhaler, breath actuated bi-directional delivery device, pump spray, pre-compression metered dose spray pump, monospray pump, bispray pump, and pressurized metered dose device. The administration device can be a single-dose disposable device, single-dose reusable device, multi-dose disposable device or multi-dose reusable device. The compositions of the invention can be used with any known metered administration device.

A continuous aerosol-producing device delivers a mist or aerosol comprising droplet of a nasal composition dispersed in a continuous gas phase (such as air). A nebulizer, pulsating aerosol nebulizer, and a nasal continuous positive air pressure device are exemplary of such a device. Suitable nebulizers include, by way of example and without limitation, an air driven jet nebulizer, ultrasonic nebulizer, capillary nebulizer, electromagnetic nebulizer, pulsating membrane nebulizer, pulsating plate (disc) nebulizer, pulsating/vibrating mesh nebulizer, vibrating plate nebulizer, a nebulizer comprising a vibration generator and an aqueous chamber, a nebulizer comprising a nozzle array, and nebulizers that extrude a liquid formulation through a self-contained nozzle array.

In certain embodiments, the device can be any commercially available administration devices that are used or can be adapted for nasal administration of a composition of the invention (see, e.g., US patent publication US20090312724A1).

The amount of the agents (e.g., SOD3) which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent are generally about 5-500 micrograms (g) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 g/human and preferably approximately 5 to 500 g/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions of the present invention.

Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxy-propyl-p-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g., edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxy-propylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, traga-canth, carboxyvinyl polymers, magnesium-aluminum sili-cates, Carbopol®, hydrophilic polymers such as, e.g. starch or cellulose derivatives such as, e.g., carboxymethylcellu-lose, hydroxyethylcellulose and other cellulose derivatives, water-swellable hydrocolloids, carrageenan, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and poly-sorbates.

Examples of other excipients are polymers such as car-mellose, sodium carmellose, hydroxypropylmethylcellu-lose, hydroxyethylcellulose, hydroxypropylcellulose, pec-tin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 g to 1 g, preferably 1-1000 g, more preferably 2-500, even more preferably 5-50, most prefer-ably 10-20 g per unit dosage form. In certain embodiments, infusion of antibodies of the present invention may range from 10-500 mg/m².

There are a variety of techniques available for introducing nucleic acids into viable cells. The techniques vary depend-ing upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The cur-rently preferred in vivo gene transfer techniques include transfection with viral (typically retroviral) vectors and viral coat protein-liposome mediated transfection.

In another aspect, provided is an administration device, pharmaceutical pack or kit, comprising one or more con-tainers filled with one or more of the ingredients of the pharmaceutical compositions, such as antioxidants (e.g., SOD3), and/or additional therapeutic agents.

The invention is further described in the following examples, which do not limit the scope of the invention described in the claims.

Methods of Screening

A further aspect of the invention relates to a method for identifying an agent capable of modulating one or more phenotypic aspects of a cell or cell population as disclosed herein, comprising: a) applying a candidate agent to the cell or cell population; b) detecting modulation of one or more phenotypic aspects of the cell or cell population by the candidate agent, thereby identifying the agent. The pheno-typic aspects of the cell or cell population that is modulated may be a gene signature or biological program specific to a cell type or cell phenotype or phenotype specific to a population of cells (e.g., an inflammatory phenotype or suppressive immune phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, sub-stance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modu-lation takes place.

Agents may include any potential class of biologically active conditions, substances or agents, such as for instance antibodies, proteins, peptides, nucleic acids, oligonucle-otides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, star-vation, a chemical (for example a therapeutic agent or potential therapeutic agent) and the like. After the stress is applied, a representative sample can be subjected to analy-sis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin archi-tecture, epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Identifying Immunomodulators

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place (e.g. using functional assays, detecting biomarkers and/or gene signatures).

Immunomodulants may include any potential class of biologically active conditions, substances or agents, such as for instance antibodies, proteins, peptides, nucleic acids, oligonucleotides, small molecules, or combinations thereof.

In Vitro Cell-Based Systems

In certain embodiments, modulation of glucocorticoid and IL-27 signaling and/or downstream targets are used to generate dysfunctional cells that recapitulate in vivo dysfunctional cells. Embodiments disclosed herein provide for in vitro cell-based systems that faithfully recapitulate an in vivo dysfunctional phenotype and methods of generating and using the cell-based systems. In certain embodiments, in vitro dysfunctional T cells can be used to screen for immunomodulators.

In certain embodiments, T cells are obtained from a biological sample subject (e.g., from a mouse or human subject). The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

In certain embodiments, T cells are obtained from peripheral blood mononuclear cells (PBMC) (e.g., using Dynabeads® described further herein). In certain embodiments, the T cells are treated with Glucocorticoid (dexamethasone) and IL-27 in combination. In certain embodiments, the T cells are treated with an agent that modulates a downstream target of combined glucocorticoid and TL-27 signaling. In certain embodiments, dysfunctional cells are characterized by assaying dysfunctional markers as described herein.

The invention is further described in the following examples, which do not limit the scope of the invention described in the claims.

EXAMPLES

Figures 1E, 1F, 1G:
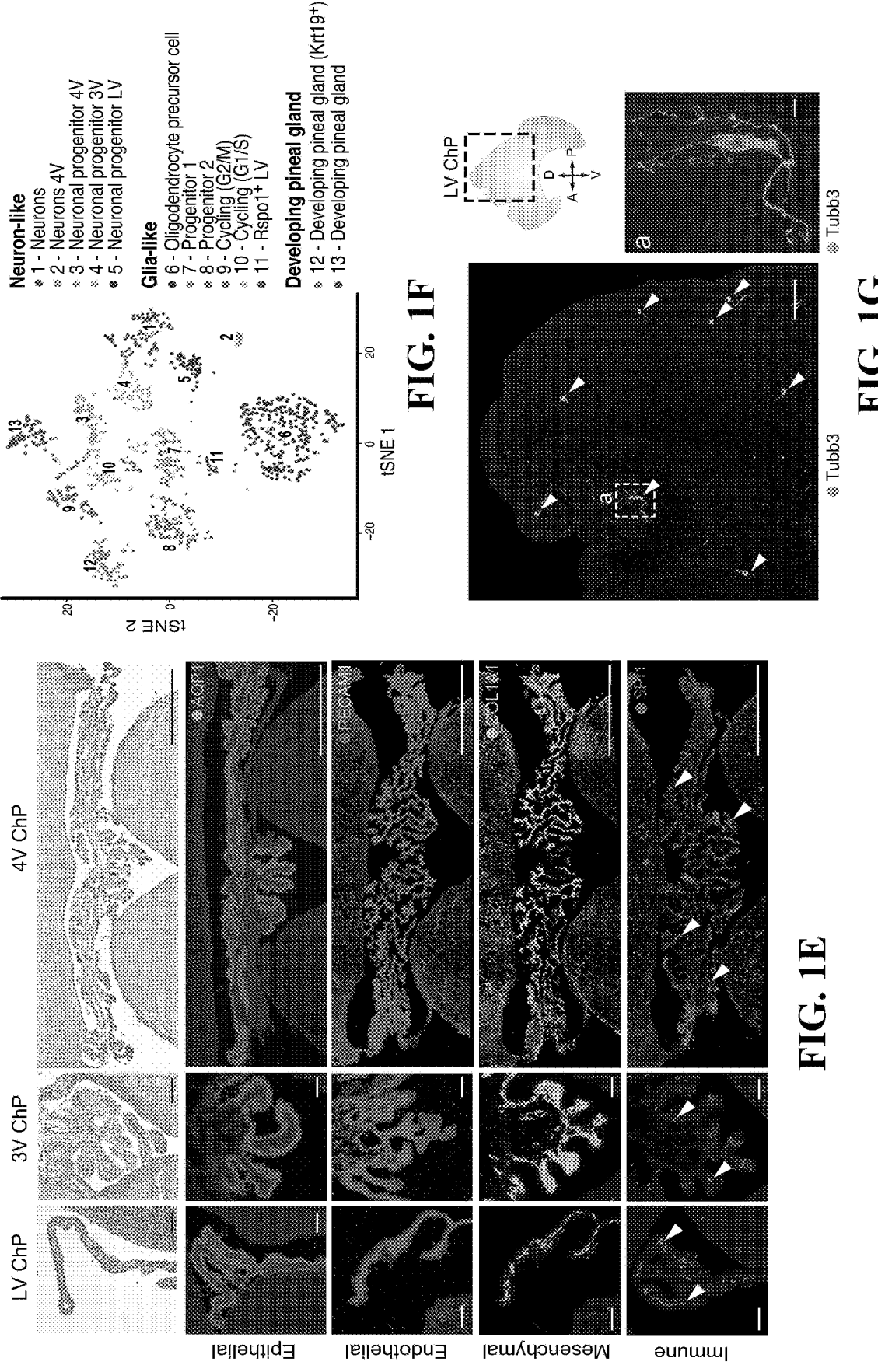

Example 1—A Cellular and Spatial Map of the Choroid Plexus Across Brain Ventricles and Ages Molecular Survey Defines the Cellular Composition of the Developing ChP Across Ventricles To chart a cell atlas of the developing ChP, Applicants profiled 15,620 single cells from the ChP of each brain ventricle (lateral, third and fourth ventricles; LV, 3V, 4V) at embryonic day [E]16.5 (FIGS. 1A, 1B, 1C). Microdissection techniques were first refined to isolate the ChPs in the developing mouse brain (FIG. 1A) and optimized tissue dissociation. Next, healthy cells were collected by fluorescence-activated cell sorting (FACS) across three independent experiments and nine litters of mice and profiled them by droplet-based single cell RNA-seq (scRNA-Seq, STAR Methods, FIG. 1B, 8A). The cells were partitioned into clusters (STAR Methods) followed by post hoc annotation by expression of canonical cell markers, which identified epithelial, mesenchymal (mural and fibroblast), endothelial, immune, neuron and glia-like cell types in each ChP from all ventricles (FIGS. 1C, 1D, 8B), and associated each cell type with marker genes (FIG. 1D, Table 1). Canonical markers were used to determine the spatial positions of each major cell type within the ChP tissue from each ventricle (FIGS. 1E, 8C). Notably, actively cycling cell subsets were present within each of the six major cell classes (FIG. 8D), and positionally enriched along the base of the ChP proximal to the brain based on staining for the proliferation marker Ki67 (FIG. 8E).

Neurogenic and Gliogenic Cell Populations are Found within all Developing ChPs

Figures 8A, 8B, 8C:
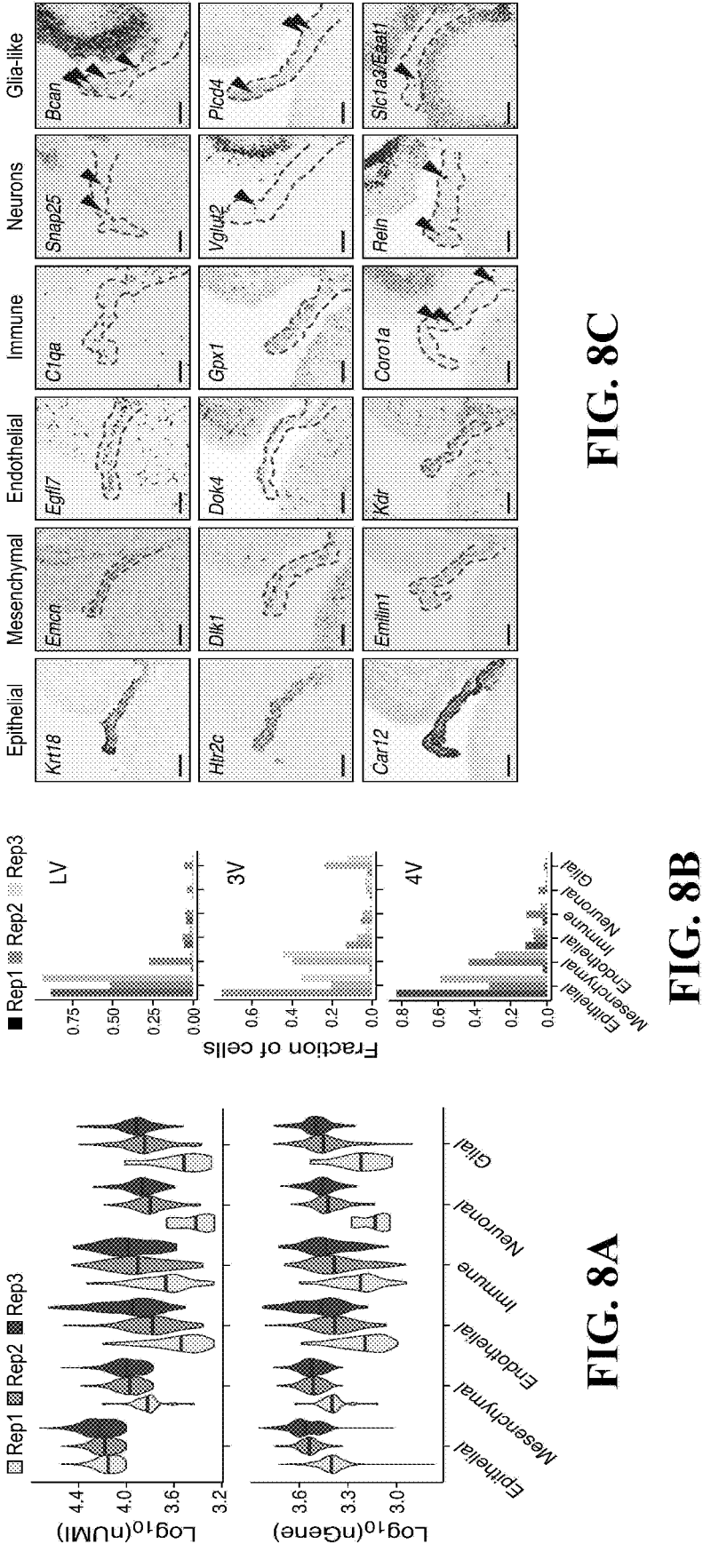
Figures 8G, 8H:
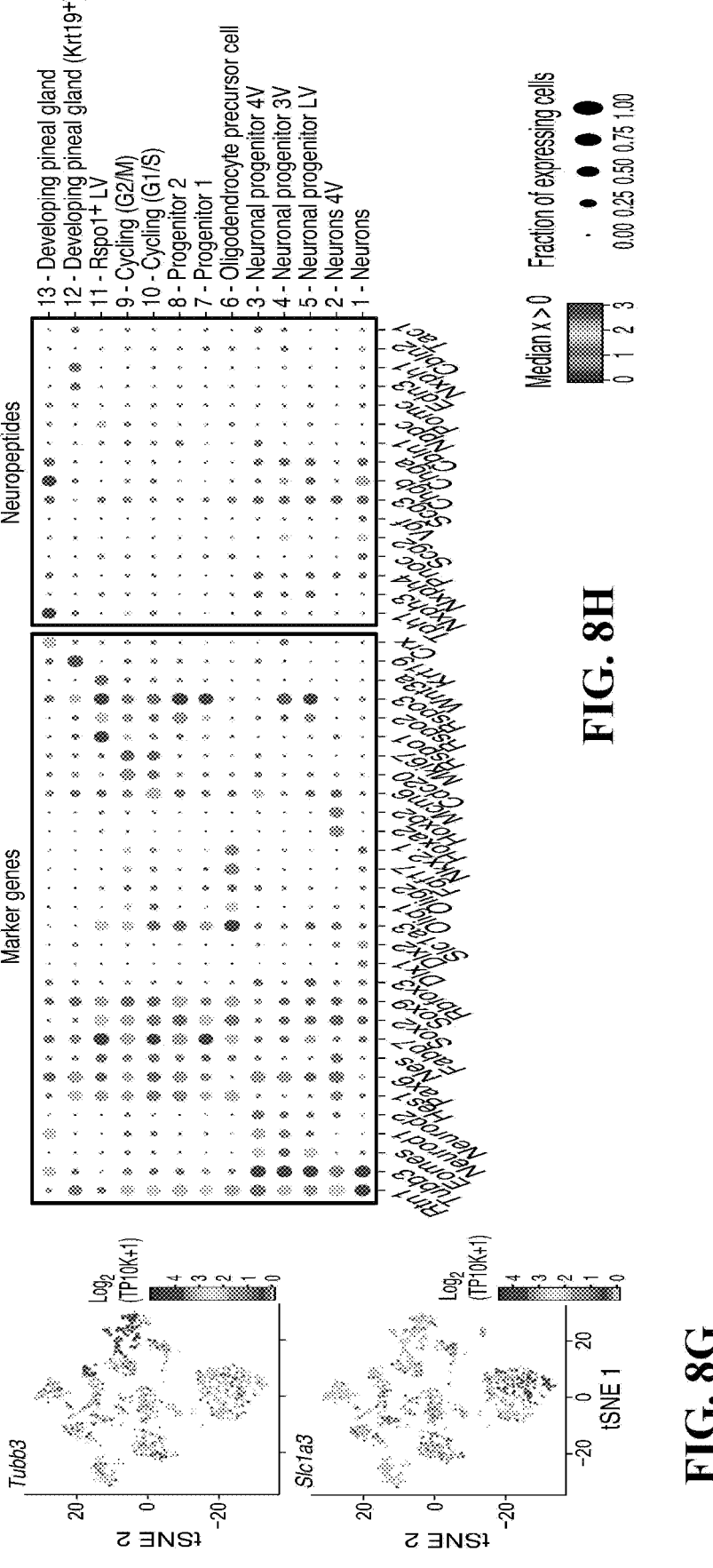
Figures 8I, 8J, 8K:
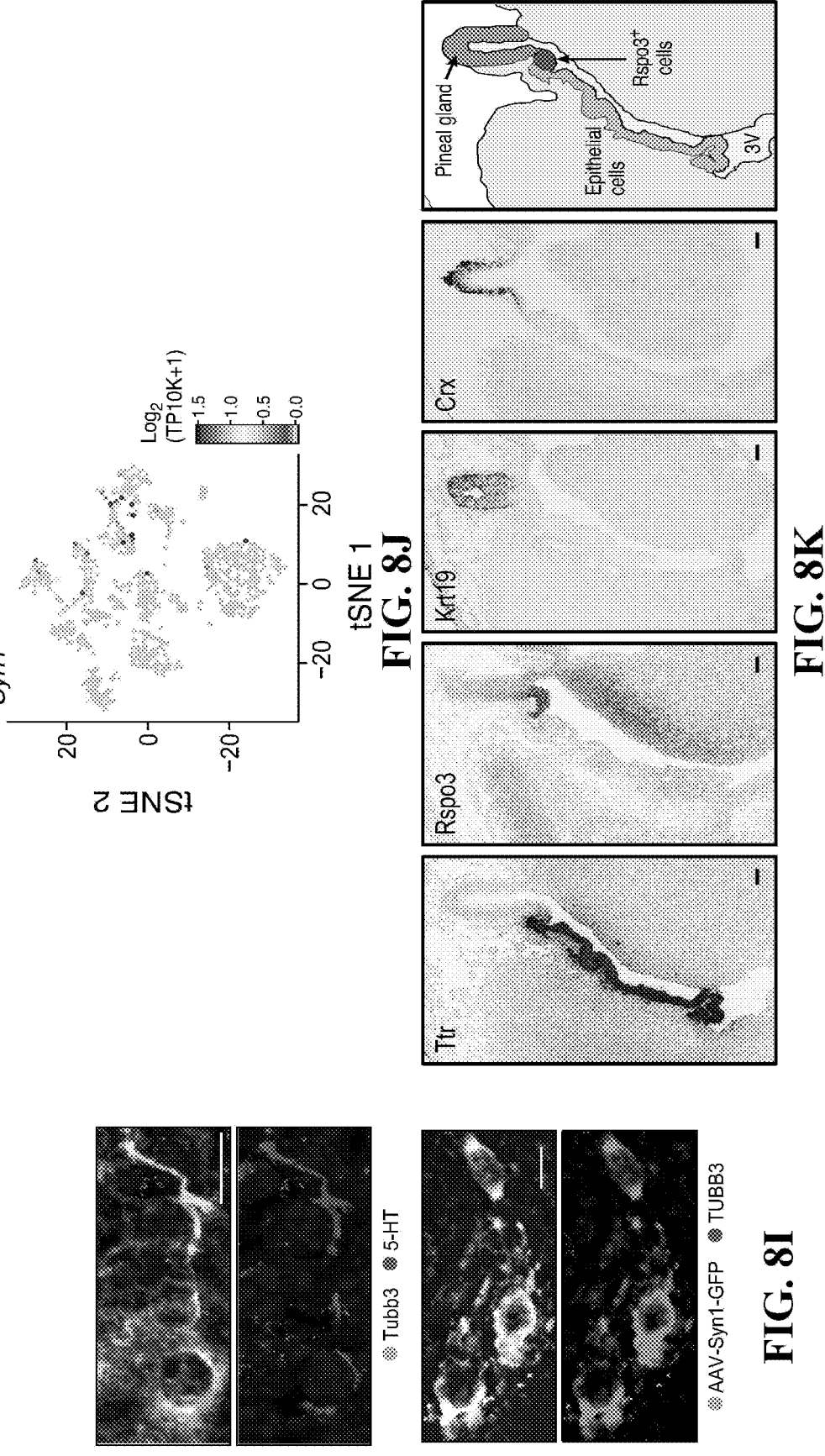

In agreement with previous studies documenting the presence of neuronal cell bodies and neural innervation of the ChP (Lindvall et al., 1978), both neuronal (Tubb3 expressing) and glial-like (Slc1a3/EAAT1 expressing) populations were captured in each developing ChP (FIGS. 8F, 8G) in all developing ChPs (FIG. 8B). Subsets of glial-like cells expressed markers of glia-neuron progenitors/stem-like cells (Rspo2/3, Nes, Sox2, Fabp7, Hes1, Pax6) as well as oligodendrocyte precursor cells (OPCs, Olig1, Olig2) (Kriegstein and Alvarez-Buylla, 2009) (FIGS. 1F, 8H). Subsets of neurons expressed markers of immediate progenitor (Eomes Tbr2) and immature neurons (Neurod1/2, Dlx 2, FIGS. 1F, 8H), which also expressed a range of neuropeptides (FIG. 8H). The presence of differentiated neurons were confirmed using whole LV ChP explants (STAR Methods, FIG. 1G), leveraging the relatively simpler three-dimensional structure of LV ChP (FIG. 1A) to facilitate whole tissue imaging, reconstruction and cell identification. Moreover, some of the neuronal cell bodies with processes within the LV ChP stained positive for the neurotransmitter serotonin (5-UT) (FIG. 8I). This may be related to earlier findings in the adult brain that serotonergic axons from brain regions such as the raphe nucleus innervate the ChP (Moskowitz et al., 1979). Finally, some of these ChP neurons express Syn1, another marker of neuronal identity (FIG. 8J), and were correspondingly amenable to adeno-associated viral transduction (AAV1.Syn1, FIG. 8I), emphasizing the potential for their transgenic perturbations.

TABLE 1

Figures 4A, 4B:
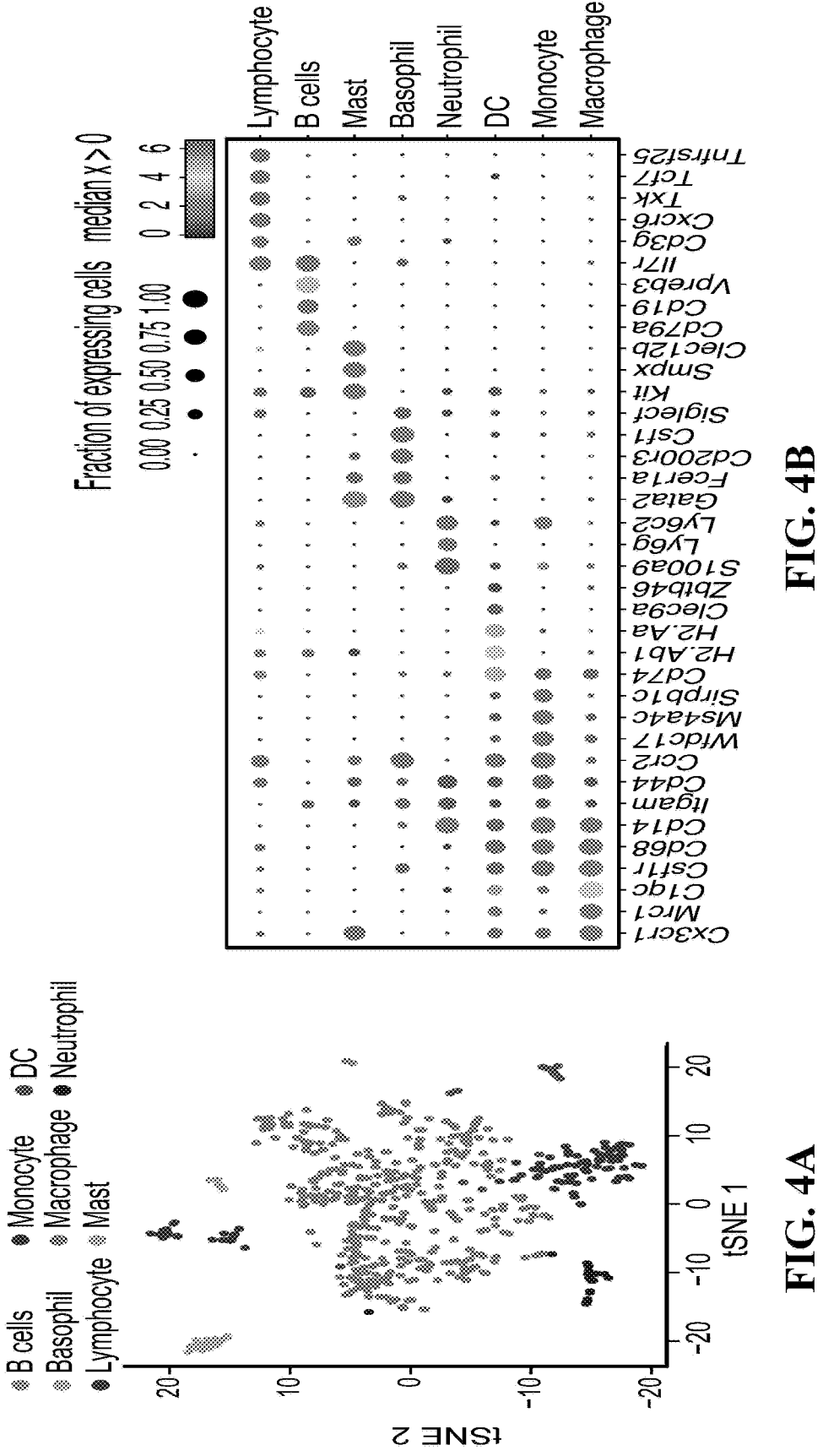
FIG. 4A-4I-Immune cell diversity in the ChP and macrophage niches within and across ChPs.

Markers for cell types (FIG. 1C), neuronal and glia-like clusters (FIG. 1F) and immune clusters (FIG. 4A).

Table 1A: Markers for Cell Types

| Epithelial | Mesenchymal | | Endothelial | |
|---|---|---|---|---|
| Acaa2 | A830082K12Rik | Pdlim2 | Aars | Pam |
| Aqp1 | Aamp | Pgf | Abhd17c | Parvb |
| Arsg | Aard | Pir | Ablim1 | Pcdh1 |
| Atp1b1 | Abcc9 | Pkd2 | Acat1 | Pcdh12 |
| Atp5g1 | Abi3bp | Pkdcc | Acot9 | Pcdh17 |
| Bphl | Ace2 | Pla2g4a | Actn4 | Pdcd10 |
| Bsg | Actn1 | Pofut2 | Adgrf5 | Pdcl3 |
| Calml4 | Adam10 | Postn | Adgrl4 | Pde2a |
| Capsl | Adam12 | Praf2 | Adrm1 | Pde8a |
| Car12 | Adamts1 | Pros1 | Afap1l1 | Pdgfb |
| Car14 | Adamts2 | Prr5 | Agrn | Pecam1 |
| Car2 | Adamts9 | Prrc2c | Airn | Pgm1 |
| Ccdc113 | Add3 | Prrx1 | Apbb2 | Phldb2 |
| Cfap126 | Aip | Prrx2 | Apln | Piezo2 |
| Chchd10 | Akt1 | Pten | Aplnr | Pim3 |
| Clic6 | Alcam | Ptges | Aplp2 | Plagl1 |
| Clu | Aldh7a1 | Pth1r | Apold1 | Plekha1 |
| Col8a2 | Alpl | Ptk7 | Arap3 | Plod1 |
| Col9a3 | Angptl4 | Ptpn9 | Arhgap18 | Plp2 |
| Cox8a | Apod | Ptprd | Arhgap29 | Pls3 |
| Crb3 | Arcn1 | Pxdn | Arhgef15 | Plscr2 |
| Dcaf12l1 | Arfgap1 | Rab22a | Arl6ip5 | Plvap |
| Dnajb13 | Arhef25 | Rarb | Arpc5l | Plxnd1 |
| Dpcd | B3gnt9 | Rarres2 | Asb4 | Pnkd |
| Dynlrb2 | Bcat2 | Rasl11a | Atox1 | Podxl |
| Enpp2 | Bend5 | Rbbp7 | AU021092 | Polr2e |
| Fam183b | Bet1 | Rbms2 | Babam1 | Pomp |
| Fbxo36 | Bicc1 | Rbms3 | Bace2 | Pon2 |
| Fhit | Bmper | Rem1 | Bak1 | Ppdpf |
| Folr1 | Bok | Rest | Bcl6b | Ppp1r16b |
| Fxyd1 | Brinp1 | Rgs5 | Bhlhe40 | Pqlc1 |
| Gm29538 | Btbd2 | Rhod | Btbd3 | Prdx6 |
| Gpx8 | Calr | Rnf26 | Bvht | Prex2 |
| Htr2c | Ccdc127 | Rora | C130074G19Rik | Prkch |
| Igfbp2 | Ccdc3 | Rpl10.ps3 | Card19 | Procr |
| Kcne2 | Ccdc8 | Rps12.ps3 | Cav1 | Psmb1 |
| Kcnj13 | Cd248 | Rps26.ps1 | Cav2 | Psmc2 |
| Klk4 | Cd38 | Runx1t1 | Ccdc12 | Ptp4a3 |

TABLE 1-continued

Markers for cell types (FIG. 1C), neuronal and
glia-like clusters (FIG. 1F) and immune clusters (FIG. 4A).

| | | | | |
|---|---|---|---|---|
| Krt18 | Cdc26 | Saraf | Ccdc28b | Ptprb |
| Krt8 | Cdc42ep4 | Scarf2 | Ccdc85a | Pvrl2 |
| Lbp | Cdc42ep5 | Sct | Ccdc85b | Pxn |
| Lrpap1 | Cdh10 | Sdc1 | Cct4 | Rab1a |
| Lrrc51 | Cdh11 | Sec31a | Cd34 | Rab1b |
| Mcee | Chpf | Sec61a1 | Cd93 | Rab2a |
| Mlf1 | Cldn11 | Sec62 | Cda | Rab35 |
| Msx1 | Clmp | Serpine2 | Cdc42ep1 | Ralgps2 |
| Mt3 | Cmc2 | Serpinf1 | Cdc42ep2 | Ramp3 |
| Ndufa13 | Col16a1 | Serping1 | Cdc42ep3 | Rapgef3 |
| Ndufa4 | Col1a1 | Sfrp2 | Cdipt | Rarg |
| Nme5 | Col23a1 | Sh3pxd2a | Cds2 | Rasgrp3 |
| Perp | Col26a1 | Shc1 | Chmp2b | Rasip1 |
| Pifo | Col3a1 | Six1 | Chmp6 | Rassf3 |
| Pla2g16 | Col5a1 | Slc50a1 | Chst15 | Rbck1 |
| Prr32 | Col5a2 | Smad6 | Ciapin1 | Rbm42 |
| Ptgds | Col6a1 | Smad7 | Cldn5 | Rer1 |
| Riiad1 | Col6a2 | Smarca2 | Clec14a | Rgl2 |
| Rsph1 | Col6a3 | Snai1 | Clec1a | Rgs3 |
| Rsph9 | Colec11 | Sned1 | Clptm1 | Robo4 |
| Serpinb1b | Colec12 | Snhg18 | Cnih4 | Rps27rt |
| Sfrp1 | Copa | Spats2l | Coa3 | S1pr1 |
| Slc16a2 | Copb2 | Sphk1 | Col15a1 | Samm50 |
| Slc16a8 | Copg1 | Spon2 | Cope | Sbds |
| Slc22a17 | Copz2 | Spred1 | Cpsf3l | Scarb1 |
| Slc31a1 | Coq10b | Srm | Cr1l | Scarf1 |
| Slc4a2 | Cox4i2 | Srpx | Cracr2b | Sdhb |
| Slc6a15 | Cp | Ssr1 | Crem | Sdpr |
| Slc7a10 | Cped1 | Stbd1 | Crk | Sec14l1 |
| Slco1a4 | Cpxm1 | Stt3a | Ctla2a | Sept4 |
| Sostdc1 | Creb3l1 | Stx16 | Ctnna1 | Sgk1 |
| Spa17 | Crispld1 | Surf4 | Ctnnbip1 | Sh2b3 |
| Spint2 | Crtap | Svil | Cyb5r3 | Sh2d3c |
| Sulf1 | Cryl1 | Svopl | Cyyr1 | Sh3glb2 |
| Tmem9 | Crym | Tbx18 | Dapk3 | She |
| Trpm3 | Ctdsp1 | Tcf21 | Dcbld1 | Sigirr |
| Ttr | Ctsk | Thbs2 | Dcps | Slc31a2 |
| Ubxn11 | Ctsl | Tlcd2 | Ddx54 | Slc39a8 |
| Vat1l | Cxcl12 | Tmed3 | Degs1 | Slc43a3 |
| Wfikkn2 | Cygb | Tmem100 | Dll4 | Slc44a2 |
| X1110017D15Rik | Cyp1b1 | Tmem119 | Dok4 | Slc7a5 |
| X1500015O10Rik | Cyth3 | Tmem159 | Dusp3 | Slco2a1 |
| X1700012B09Rik | Dact1 | Tmem45a | Dysf | Slmo2 |
| X1700016K19Rik | Dcn | Tmem86a | Ece1 | Smarcd2 |
| X1700088E04Rik | Ddx50 | Tnfsf12 | Ecscr | Smtn |
| X1810058I24Rik | Dnajb1 | Tomm5 | Efna1 | Snrk |
| X2410004P03Rik | Dnaic10 | Topors | Efnb2 | Sod1 |
| X4833427G06Rik | Dpep1 | Tpd5212 | Egfl7 | Sox17 |
| | Ebpl | Tpm2 | Elf2 | Sox18 |
| | Ech1 | Tpst1 | Ephb4 | Sox7 |
| | Ecm1 | Trip6 | Erf | Ssna1 |
| | Ednra | Twist1 | Erg | Ssu72 |
| | Efemp2 | Txndc5 | Esam | St3gal5 |
| | Efnb1 | Uba5 | Ets2 | St6galnac3 |
| | Erp44 | Ube2s | Exoc31 | Stk25 |
| | Errfi1 | Unc5b | F11r | Sult1a1 |
| | F3 | Vgll4 | Fam101b | Supt4a |
| | Fam110b | Vkorc1 | Fam114a2 | Syf2 |
| | Fam114a1 | Vstm4 | Fam129b | Sypl |
| | Fap | Wisp1 | Fam13c | Tbxa2r |
| | Fbln1 | X1500009L16Rik | Fam167b | Tcf15 |
| | Fbn2 | X1700123O20Rik | Fam198b | Tek |
| | Fhl2 | X2810428I15Rik | Fam43a | Tgfbr2 |
| | Figf | X2810474O19Rik | Fbxw2 | Thoc7 |
| | Fkbp14 | Zfp260 | Fgd5 | Thsd1 |
| | Flna | Zfp950 | Fis1 | Tie1 |
| | Fn1 | Zfyve21 | Flt1 | Tjp1 |
| | Fnta | | Fmnl3 | Tln2 |
| | Foxc1 | | Foxo1 | Tm2d3 |
| | Foxc2 | | Fzd4 | Tmed9 |
| | Foxd1 | | Gadd45g | Tmem109 |
| | Foxn3 | | Gchfr | Tmem123 |
| | Fzd2 | | Ggta1 | Tmem204 |
| | G0s2 | | Gimap1 | Tmem252 |
| | Gata6 | | Gimap4 | Tmem255a |
| | Gdf10 | | Gimap5 | Tmem44 |
| | Ggnbp2 | | Gimap6 | Tmem88 |

TABLE 1-continued

Markers for cell types (FIG. 1C), neuronal and
glia-like clusters (FIG. 1F) and immune clusters (FIG. 4A).

| | | |
|---|---|---|
| Ghr | Ginm1 | Tnfaip8l1 |
| Gjb2 | Gja4 | Tnfrsf11b |
| Gjb6 | Gm11808 | Tonsl |
| Gjc1 | Gm13889 | Traf7 |
| Glipr2 | Gmpr | Tspan14 |
| Gm10073 | Gne | Tspan15 |
| Gm13305 | Gpihbp1 | Tspan18 |
| Gm26917 | Gpr182 | Tspan9 |
| Gm42418 | Grasp | Uba52 |
| Gmds | Grrp1 | Ubald2 |
| Golgb1 | Gtf2e2 | Ubb |
| Golim4 | Hbegf | Ube2a |
| Golt1b | Hdac7 | Ubn1 |
| Gsn | Heg1 | Unc45b |
| Gucy1a3 | Hmbox1 | Uqcc3 |
| Gucy1b3 | Hmg20b | Uqcrc1 |
| Hdlbp | Homer3 | Urm1 |
| Hic1 | Hspa12b | Ushbp1 |
| Hmgcs2 | Hspg2 | Vamp5 |
| Hpca | Hyal2 | Vwa1 |
| Hpgd | Icam1 | Wwtr1 |
| Hspa5 | Icam2 | X0610037L13Rik |
| Ikbip | Ier3ip1 | X1700020I14Rik |
| Il11ra1 | Isf2r | X1810011O10Rik |
| Il33 | Igfbp3 | X2900026A02Rik |
| Il6st | Ipo11 | X4930523C07Rik |
| Inafm1 | Irx3 | X4931406P16Rik |
| Islr | Itga5 | X8430408G22Rik |
| Isyna1 | Itpkb | X9430020K01Rik |
| Itga8 | Jup | Yes1 |
| Kansl3 | Kank3 | Zdhhc20 |
| Kcnj8 | Kctd12b | |
| Kcnq1ot1 | Kctd20 | |
| Kdelr3 | Kdr | |
| Lama2 | Klhl4 | |
| Lamb1 | Kti12 | |
| Lancl1 | Lamc1 | |
| Lasp1 | Lifr | |
| Lhfp | Limch1 | |
| Lima1 | Lpar4 | |
| Lix1l | Lrg1 | |
| Lman1 | Lrp10 | |
| Lox | Lrrc8c | |
| Loxl2 | Lta4h | |
| Lpp | Ltbr | |
| Lrp1 | Luzp1 | |
| Lrrc17 | Ly6c1 | |
| Lum | Macf1 | |
| Map1lc3a | Map3k11 | |
| Matn2 | Map4 | |
| Mbtps1 | Marc2 | |
| Mfap4 | Mast4 | |
| Mfsd10 | Mcam | |
| Mgp | Mcf2l | |
| Mmp2 | Med10 | |
| Morf4l1 | Med28 | |
| Moxd1 | Mef2a | |
| Mrap | Mgat1 | |
| Mrc2 | Mgll | |
| Mrps17 | Mgst3 | |
| mt.Co2 | Mkl2 | |
| mt.Co3 | Mllt4 | |
| Mxra8 | Mmrn2 | |
| Mycbp2 | Mob2 | |
| Myl9 | Mrpl4 | |
| Mylip | Mrps11 | |
| Mylk | Mrps24 | |
| Naalad2 | Mum1 | |
| Nab2 | Myct1 | |
| Nbl1 | Myl6 | |
| Ndufa4l2 | Myo18a | |
| Nenf | Myo6 | |
| Nfat5 | Myzap | |
| Nfatc4 | Naa20 | |
| Nfic | Napa | |
| Nr1h3 | Nck1 | |
| Nr2f1 | Ndfip2 | |

TABLE 1-continued

Markers for cell types (FIG. 1C), neuronal and
glia-like clusters (FIG. 1F) and immune clusters (FIG. 4A).

| | |
|---|---|
| Nr2f2 | Ndrg1 |
| Nr3c1 | Ndufa10 |
| Nudt16l1 | Ndufv1 |
| Oaf | Nelfb |
| Olfml3 | Net1 |
| Osr1 | Nfkb1 |
| Ost4 | Nid2 |
| P2ry14 | Nme2 |
| P3h1 | Notch1 |
| Pard6g | Npr1 |
| Pcdh18 | Nrarp |
| Pck2 | Nsmce1 |
| Pcolce | Oit3 |
| Pddc1 | Orai1 |
| Pde6d | Oxa1l |
| Pdgfra | Pak2 |
| Pdgfrb | Pald1 |

Table 1A: Markers for Cell Types

| Immune | | Neuronal | | Glial-like |
|---|---|---|---|---|
| AB124611 | Il6ra | Aatf | Shmt2 | Acyp2 |
| Abca1 | Imp4 | Abca4 | Siah1a | Aifl1 |
| Abhd12 | Inpp5d | Acly | Slc17a6 | Ak2 |
| Abi1 | Irf5 | Acvr2b | Slc38a1 | Aldoc |
| Acads | Irf8 | Afap1 | Slc39a6 | Amd1 |
| Acp5 | Itgb2 | Aggf1 | Smarcc2 | Armcx2 |
| Acsl5 | Khk | Ahi1 | Smarcd1 | Arxes1 |
| Actr3 | Lamtor4 | Akap9 | Sms | Arxes2 |
| Adgre1 | Lap3 | Alkbh1 | Snap25 | Asf1a |
| Adrb2 | Laptm5 | Amn1 | Snapc3 | Atp1a2 |
| Adrbk1 | Lbr | Ankrd12 | Socs2 | B3galnt1 |
| AF251705 | Lcp2 | Ap1ar | Soga3 | Bcan |
| AI413582 | Lgals3 | Ap3b2 | Srpk1 | Bcat1 |
| AI607873 | Lilrb4a | Arf2 | Srrm4 | Bckdk |
| AI662270 | Lipa | Arid4b | St8sia2 | Bfar |
| Aif1 | Lpxn | Armc10 | Stau1 | Btbd1 |
| Akap13 | Lrmp | B630019K06Rik | Stmn2 | Btf3l4 |
| Akr1b3 | Lrrc25 | Barhl1 | Stmn3 | Camk2d |
| Alox5aP | Lsp1 | Bax | Stmn4 | Capn6 |
| Amdhd2 | Lst1 | Baz2b | Strip1 | Cask |
| Anxa1 | Ltc4s | Bcl2l1 | Synpr | Cbx3 |
| Ap1b1 | Ly86 | Bcl7a | Tagln3 | Ccdc90b |
| Ap2a2 | Ly96 | Bhlhe22 | Tbc1d16 | Ccna2 |
| Apbb1iP | Lyve1 | Brwd1 | Tbpl1 | Cdc123 |
| Apobec1 | Lyz2 | Btbd9 | Tcerg1 | Cdca3 |
| Arhgap17 | Maf | Cab39 | Tdrkh | Cdca8 |
| Arhgap19 | Man2b1 | Cacna2d1 | Tecpr1 | Cdo1 |
| Arhgap25 | Map2k1 | Cacnb3 | Timm50 | Cenpf |
| Arhgap30 | Mbnl1 | Cadm3 | Tmcc1 | Cenpm |
| Arhgap9 | Mfsd1 | Camta1 | Tmeff1 | Cisd2 |
| Arhgdib | Milr1 | Ccng2 | Tmem57 | Ckap5 |
| Arid3a | Mknk1 | Ccnt1 | Tmod2 | Cks2 |
| Arl8b | Mndal | Cdk5r1 | Tmx4 | Cnot2 |
| Arrb2 | Mpeg1 | Celf1 | Tomm70a | Col2a1 |
| Asah1 | Mrc1 | Celf4 | Top2b | Cops2 |
| Asnsd1 | Mrps15 | Cep170 | Tram1l1 | Creb5 |
| Atf3 | Ms4a6b | Chd3os | Trim2 | Cspg5 |
| Atp13a2 | Ms4a6c | Chga | Trp53bp1 | Cstf2t |
| Atp6ap1 | Ms4a6d | Chgb | Tsg101 | Cux1 |
| Aup1 | Ms4a7 | Clcn4 | Ttc9b | Cwc15 |
| B4galnt1 | Msr1 | Cmip | Tubb3 | Cxcr4 |
| Baz1a | Msrb1 | Cnot7 | Tubb4a | D1Ertd622e |
| Bcl2a1b | Mvp | Col8a1 | Txnrd1 | Dab1 |
| Bin1 | Myo1f | Cplx2 | Ube2b | Dcaf8 |
| Bin2 | Myo5a | Crmp1 | Ubqln1 | Dclk1 |
| Bin3 | N4bp2l1 | Csnk2a1 | Usf1 | Dfna5 |
| Blvra | Nadk | Ctps | Usp11 | Dhrs1 |
| C1qa | Nagpa | Cxxc5 | Usp3 | Dkc1 |
| C1qb | Napsa | Cyp51 | Usp5 | Dnajc24 |
| C1qc | Ncf1 | Dach1 | Vamp2 | Dok5 |
| C3ar1 | Ncf2 | Dcc | Whsc1 | Dut |
| C5ar1 | Ncf4 | Dcx | Wrb | Ebna1bp2 |
| Capza1 | Nckap1l | Dda1 | X1700037H04Rik | Eif4e |
| Casp1 | Neat1 | Ddx24 | X4833420G17Rik | Eln |
| Ccdc50 | Nfam1 | Dll3 | Yeats4 | Elp4 |

TABLE 1-continued

Markers for cell types (FIG. 1C), neuronal and
glia-like clusters (FIG. 1F) and immune clusters (FIG. 4A).

| | | | | |
|---|---|---|---|---|
| Ccl12 | Nfe2l2 | Dnajb6 | Ypel1 | Emc10 |
| Ccl2 | Nfkbid | Dnajc2 | Yrdc | Epha7 |
| Ccl24 | Nfkbiz | Dnajc5 | Zcchc12 | Eprs |
| Ccl3 | Nme4 | Dner | Zdhhc16 | Etf1 |
| Ccl4 | Nmt1 | Dohh | Zfp292 | Fam204a |
| Ccl6 | Npl | Dpysl4 | Zfp358 | Fam92a |
| Ccl7 | Nrm | Draxin | Zfp444 | Fbxo2 |
| Ccl9 | Ntpcr | Dync1li1 | Zfp512 | Fgf15 |
| Ccr1 | Ocel1 | Ehmt1 | Zfp553 | Fgf17 |
| Ccr2 | Ogfrl1 | Elavl2 | Zfp68 | Fgf8 |
| Ccrl2 | P2rx4 | Elavl3 | Zfp821 | |
| Cd14 | P2ry12 | Elavl4 | Gart | |
| Cd180 | P2ry6 | Eomes | Gcsh | |
| Cd200r1 | Paox | Ephb2 | Gdpd2 | |
| Cd300a | Parvg | Fam110a | Glg1 | |
| Cd36 | Pdcd6ip | Fam134b | Gm28050 | |
| Cd37 | Pepd | Fam210b | Gm29478 | |
| Cd44 | Pf4 | Fam57b | Gpd2 | |
| Cd48 | Pgd | Fam96b | Gtf2i | |
| Cd52 | Pglyrp1 | Fdft1 | Gufl | |
| Cd53 | Pim1 | Fdps | Hadh | |
| Cd68 | Pkib | Fiz1 | Hdac3 | |
| Cd74 | Pkn1 | Fnbp1l | Hes5 | |
| Cd79b | Pla2g15 | Fsd1 | Hnrnpll | |
| Cd83 | Pld4 | Fyttd1 | Hs2st1 | |
| Cd84 | Plek | Gadd45gip1 | Hspa13 | |
| Cd86 | Plekhj1 | Gamt | Htra1 | |
| Cdk2ap2 | Plekho2 | Gap43 | Id4 | |
| Cebpa | Plgrkt | Gatad2b | Igfbp5 | |
| Cela1 | Plin2 | Gch1 | Il17rd | |
| Cept1 | Por | Gdap1l1 | Ilkap | |
| Cfp | Ppp1r18 | Gdpd1 | Immt | |
| Chst12 | Prkcd | Glyr1 | Ipo5 | |
| Clec10a | Prr13 | Gnb3 | Irf2bpl | |
| Clec12a | Psap | Gng3 | Jarid2 | |
| Clec4a1 | Psmb10 | Gpr162 | Kif21a | |
| Clec4a2 | Psmb8 | Gramd1a | Kitl | |
| Clec4a3 | Psmb9 | Gse1 | Klhl9 | |
| Clec4n | Ptgs1 | Gtf2f2 | Krt19 | |
| Cln8 | Ptpn18 | Hap1 | Lect1 | |
| Clta | Ptpn6 | Hdgfrp3 | Lix1 | |
| Cltc | Ptprc | Hist3h2a | Lockd | |
| Cmtm7 | Ptpre | Homer2 | Lrrn1 | |
| Cndp2 | Pycard | Hsdl1 | Lsm6 | |
| Cnppd1 | Rab32 | Hsp90aa1 | Lyar | |
| Cnpy3 | Rac2 | Hsph1 | Magoh | |
| Commd4 | Rasgef1b | Htatsf1 | Mapre2 | |
| Commd8 | Rbfa | Huwe1 | Maz | |
| Coro1a | Reep5 | Igsf21 | Mbip | |
| Creg1 | Renbp | Ina | Mcm2 | |
| Crlf3 | Rgs1 | Insm1 | Mcm5 | |
| Cryba4 | Rgs10 | Islr2 | Med25 | |
| Crybb1 | Rhoh | Itfg2 | Med4 | |
| Csf1r | Rnase4 | Jkamp | Megf11 | |
| Csf2ra | Rnasel | Jmjd1c | Mettl9 | |
| Csf2rb | Rnf115 | Kctd13 | Mff | |
| Csrnp1 | Rnf13 | Kctd5 | Mgst1 | |
| Cstb | Rnf130 | Kdm1a | Mid1ip1 | |
| Ctla2b | Rnf149 | Khdrbs2 | Mlc1 | |
| Ctsa | Rnpep | Kif5b | Mllt3 | |
| Ctsb | Rragc | Kif5c | Mpp6 | |
| Ctss | Rtfdc1 | Klhl7 | Mpst | |
| Cx3cr1 | Rtp4 | Lcmt1 | Mrpl3 | |
| Cxcl1 | Runx1 | Lhx2 | Mrpl50 | |
| Cxcl2 | S100a6 | Lhx5 | Msh2 | |
| Cybb | S100a8 | Lhx9 | Myh10 | |
| Cyfip1 | Samhd1 | Lmo1 | Naa10 | |
| Cyth4 | Samsn1 | Lsm14b | Naa50 | |
| Dab2 | Scamp2 | Luc7l | Nars | |
| Daglb | Sdf2l1 | Lzts1 | Ncaph2 | |
| Dcxr | Sec11c | Mab21l1 | Ndnl2 | |
| Dera | Selplg | Map2 | Nipbl | |
| Dhrs3 | Serp1 | Mapk8 | Nkx2.1 | |
| Dnase2a | Sesn1 | Mapk8ip1 | Nol7 | |
| Dok1 | Sgpl1 | Mapt | Nop10 | |
| Dok2 | Sh3kbp1 | 43525 | Npm3 | |
| Dok3 | Shisa5 | 43529 | Nsfl1c | |

TABLE 1-continued

Markers for cell types (FIG. 1C), neuronal and
glia-like clusters (FIG. 1F) and immune clusters (FIG. 4A).

| | | | |
|---|---|---|---|
| Dtnbp1 | Sirpa | Mdga1 | Nusap1 |
| Dusp11 | Sirt2 | Med22 | Nxn |
| Dusp2 | Sirt7 | Med27 | Olig1 |
| Dusp5 | Skap2 | Mex3b | Otx1 |
| E2f4 | Sla | Mgarp | Oxct1 |
| Ebi3 | Slc11a1 | Midn | Paics |
| Ebp | Slc15a3 | Mllt11 | Paqr4 |
| Edem1 | Slc40a1 | Mpp3 | Pbdc1 |
| Efhd2 | Slc7a7 | Mrpl34 | Pbk |
| Egr2 | Slc9a9 | Mrto4 | Pcnp |
| Ehbp1l1 | Slco2b1 | Msantd3 | Pfdn6 |
| Elf1 | Slfn2 | Mtf2 | Pfkl |
| Emilin2 | Smap2 | Mycl | Plcd4 |
| Eps15 | Snx2 | Mycn | Poldip3 |
| Ethe1 | Snx20 | Mzt1 | Polr3h |
| Evi2a | Snx8 | Nap1l5 | Ppp1r1a |
| F13a1 | Sp110 | Nbea | Prkag1 |
| Fam105a | Spg21 | Ndrg3 | Prkca |
| Fam111a | Spi1 | Neurod1 | Prpf19 |
| Fam213b | Spic | Neurod4 | Prr7 |
| Fam96a | Ssh2 | Nipsnap1 | Psat1 |
| Fcer1g | Stab1 | Nmral1 | Psmd13 |
| Fcgr1 | Stard8 | Nova2 | Psmd3 |
| Fcgr2b | Stk17b | Npepps | Psmd5 |
| Fcgr3 | Stk24 | Nsg2 | Ptpra |
| Fcna | Stra13 | Nt5c3 | Ptprz1 |
| Fcrls | Stx7 | Ntm | Puf60 |
| Fermt3 | Stxbp2 | Ntmt1 | Pvrl3 |
| Fes | Syk | Numbl | Pygb |
| Fgd2 | Syngr1 | Olfm1 | Racgap1 |
| Folr2 | Syngr2 | Onecut2 | Rad21 |
| Fyb | Szrd1 | Pabpn1 | Rad23b |
| G6pdx | Taf6l | Pafah1b1 | Rfc1 |
| Gas7 | Taok3 | Palm | Rfc3 |
| Gatm | Tapbp | Panx1 | Rhno1 |
| Gbp7 | Tbxas1 | Parp6 | Rnf10 |
| Glipr1 | Tifa | Patz1 | Rnf2 |
| Gm100116 | Tifab | Pcmt1 | Rnps1 |
| Gm12166 | Tlr2 | Pfdn4 | Rp9 |
| Gm16286 | Tmem106a | Pkm | Rpa2 |
| Gm26522 | Tmem219 | Plppr3 | Rpa3 |
| Gm26532 | Tmem261 | Pnmal2 | Rrm1 |
| Gm2a | Tmem55b | Ppa2 | Rrm2 |
| Gm6377 | Tmem8 | Ppil4 | Rrp1 |
| Gna12 | Tmem9b | Ppm1b | Sap30 |
| Gna15 | Tnfaip3 | Ppp1r8 | Sema6d |
| Gpr183 | Tnfaip8l2 | Ppp2r5e | Sesn3 |
| Gpr34 | Tnfrsf13b | Prkaca | Sf3b6 |
| Gpr65 | Tor1aip1 | Proser1 | Sfxn5 |
| Gpsm3 | Tpp1 | Psmb7 | Siva1 |
| Gsdmd | Traf3ip3 | Psmd14 | Six3 |
| Gusb | Trem2 | Ptbp2 | Skp1a |
| H2.DMa | Trib1 | Rab3a | Slc1a3 |
| Hacd4 | Tuba1c | Rab3b | Slc27a1 |
| Hck | Twf1 | Rabep1 | Slc39a1 |
| Hcls1 | Tyrobp | Raf1 | Slit2 |
| Hcst | Uap1l1 | Ralgds | Smarcd3 |
| Hexa | Ubald1 | Rcor2 | Smu1 |
| Hexb | Ubl3 | Reln | Snx1 |
| Hk2 | Ucp2 | Rgs16 | Sox2 |
| Hk3 | Unc93b1 | Rnd2 | Spc25 |
| Hmgcl | Vav1 | Rnd3 | Spcs2 |
| Hmha1 | Vps26a | Rnf165 | Spry2 |
| Hpgds | Vrk1 | Rnf5 | Srsf9 |
| Ifi202b | Vsir | Rnmt | Ssbp1 |
| Ifi27l2a | Was | Rpf2 | Stoml2 |
| Ifi30 | Wdr26 | Rrn3 | Tardbp |
| Ifnar2 | Wfdc17 | Rsrc1 | Tbl1x |
| Igf1 | Wwp1 | Rtn2 | Tceal3 |
| Igsf6 | X1600014C10Rik | Rufy3 | Tfg |
| Ikzf1 | X2510039O18Rik | Rundc3a | Tgfb2 |
| Il16 | Zeb2os | Sag | Thoc3 |
| Il18 | Zfp622 | Sbk1 | Tipin |
| Il1b | | Scg3 | Tmem132c |
| Il21r | | 43711 | Tmem47 |
| Il4ra | | Sez6l2 | Tnpo3 |
| | | | Top2a |

TABLE 1-continued

Markers for cell types (FIG. 1C), neuronal and
glia-like clusters (FIG. 1F) and immune clusters (FIG. 4A).

Tpx2
Tst
Ttyh1
U2surp
Ube2c
Ubxn4
Unc119
Upf3b
Usp1
Usp51
Wdr6
Wls
X0610007P14Rik
X1110001J03Rik
X1810022K09Rik
X2810004N23Rik
X4930402H24Rik
X4931429I11Rik
Xrn2
Zfhx3
Zfhx4
Zfp664
Zmynd11

Table1B. Immune Clusters

| Monocyte | Neutrophil | DC | Mast | Basophil | B cells | Lymphocyte |
|---|---|---|---|---|---|---|
| Abracl | AA467197 | BC028528 | Bfsp2 | Acss2 | Atp1b3 | Abhd8 |
| Acer3 | Abhd5 | Calml4 | Cd55 | Adck4 | Bcl2l1 | Ankrd54 |
| Actr3 | Acsl1 | Car14 | Clec12b | Adora2b | Bcl7a | Aqp3 |
| Adgre4 | Adgrg3 | Cd74 | Cma1 | Aldoa | Cd19 | Arfgap2 |
| Adgre5 | Adpgk | Cdkn1c | Cmtm7 | Alox15 | Cd79a | Arg1 |
| Ahnak | Agpat2 | Cfap126 | Dtwd1 | Amigo2 | Cd79b | Arhgef1 |
| AI662270 | Alas1 | Clec9a | Errfi1 | Anxa6 | Cecr2 | Arl2bp |
| AI839979 | Ankrd22 | Clu | Gm11697 | Aqp9 | Chchd10 | Ash21 |
| Ap1s2 | Ankzf1 | Col9a3 | Gna14 | Atp2a3 | Cyth1 | Auts2 |
| Apbb1ip | Asns | Crip2 | Gnaz | Bmp4 | Dnajc21 | AW112010 |
| Arhgap9 | Asprv1 | Cxx1b | Gnb4 | Capn2 | Ebf1 | Bcl2 |
| Arpc2 | B230208H11Rik | Dpp4 | Gzmb | Cd200r3 | Erg | Camk4 |
| Asap1 | Baz1a | Ezr | Homer2 | Cd200r4 | Fam53b | Ccr6 |
| Atp5c1 | BC100530 | Folr1 | Hs3st1 | Cd244 | Igll1 | Ccr7 |
| B4galnt1 | BC117090 | Fxyd1 | Kcne3 | Cd53 | Lef1 | Ccr9 |
| C1galt1c1 | Birc5 | Gpx8 | Kit | Cd69 | Lrmp | Cct2 |
| Ccdc109b | Camp | Gsta4 | Ldha | Cdh1 | Metap2 | Cct5 |
| Ccdc88a | Ccdc125 | H2.Aa | Lxn | Cdkn1a | Mknk2 | Cd160 |
| Cd34 | Cd177 | H2.Ab1 | Mfge8 | Cela3b | Mzb1 | Cd2 |
| Cd44 | Cd3d | H2.DMb1 | Mpl | Chic2 | Pafah1b3 | Cd27 |
| Cdc42se1 | Ceacam1 | H2.Eb1 | Nap1l5 | Cmc2 | Pgls | Cd28 |
| Cebpb | Ceacam10 | Ifi205 | Patz1 | Csf1 | Polr2m | Cd3g |
| Cers6 | Chil3 | Igfbp2 | Pdlim1 | Csf2rb | Prep | Cd82 |
| Clec4e | Ckap4 | Igfbp11 | Plgrkt | Csf2rb2 | Ptgr1 | Cd96 |
| Cmpk1 | Cks2 | Kcne2 | Prkcb | Ddit4 | Ptp4a3 | Clcn3 |
| Coro1b | Clec4b2 | Kcnj13 | Rab27b | Ddx28 | Rag2 | Cldnd1 |
| Csf3r | Clec5a | Mdk | Rexo2 | Dnase2b | Rasgrp2 | Clnk |
| Cycs | Degs1 | Mest | Slc18a2 | Dtnbp1 | Rcsd1 | Cnot6l |
| Dynll1 | Dhrs7 | Msx1 | Slc22a3 | Dut | Rhoh | Crbn |
| Ear1 | Dstn | Mycl | Slc45a3 | Ecm1 | Slc38a1 | Ctsw |
| Ear2 | Elane | Ntrk2 | Slc6a4 | Eif1 | Smarca4 | Cxcr5 |
| Emp3 | F5 | Olfm1 | Slc7a5 | Ept1 | Sox4 | Cxcr6 |
| Eno1 | F630028O10Rik | Otx2 | Smc5 | Etf1 | Stambpl1 | D16Ertd472e |
| Epsti1 | Fam101b | Phf11a | Smpx | Fam65b | Stk3 | Dalrd3 |
| Ethe1 | Fcnb | Ppm1m | Tpsab1 | Fat3 | Tcf3 | Dazap1 |
| F10 | G0s2 | Psmb9 | Tpsb2 | Fbxo9 | Trp53i11 | Dlk1 |
| Fam111a | Gca | Ptgds | Zfp386 | Fcer1a | Tspan13 | Dnajc1 |
| Fam69a | Gm5416 | Serpinh1 | | Fis1 | Usp3 | Eif3k |
| Fam96a | Gm5483 | Slamf7 | | Flot1 | Vpreb1 | Eif3m |
| Fes | Gm6594 | Slc22a17 | | Furin | Vpreb3 | Eif4b |
| Flna | Gmfg | Slc6a15 | | Fut8 | Xrcc6 | Emid1 |
| Fn1 | Golim4 | Sostdc1 | | Gm20186 | | Espn |
| Galnt9 | Gpc1 | Spint2 | | Gm42806 | | Eya2 |
| Gapdh | Gpsm3 | Sulf1 | | Gpx4 | | Fam110a |
| Gch1 | Grk6 | Tmem108 | | Grm6 | | Fam189b |
| Gm21975 | Hmgn2 | Tmem9 | | H2.Oa | | Fcho1 |
| Gm5150 | Hsd11b1 | Tnni2 | | Hgf | | Fli1 |
| Gm9733 | Hvcn1 | Ttr | | Htr1b | | Gata3 |
| Gpr35 | Inhba | X1500015O10Rik | | Igfbp7 | | Gem |

TABLE 1-continued

Markers for cell types (FIG. 1C), neuronal and
glia-like clusters (FIG. 1F) and immune clusters (FIG. 4A).

| | | | | |
|---|---|---|---|---|
| Gpx1 | Itgb21 | Zfp536 | Il18rap | Gimap3 |
| Hiatl1 | Lamtor4 | | Il3ra | Gimap4 |
| Hopx | Lbp | | Il6 | Gimap5 |
| I830077J02Rik | Lcn2 | | Inpp5b | Gnas |
| Ifi204 | Lmnb1 | | Itgb1 | Gramd1a |
| Ifi27l2a | Lockd | | Itgb3 | Hilpda |
| Ifitm3 | Lrg1 | | Jak2 | Hmgn5 |
| Ikzf1 | Lta4h | | Jarid2 | Hnrpll |
| Il13ra1 | Ltf | | Klhl6 | Ikzf3 |
| Il17ra | Ly6g | | L1cam | Il17re |
| Iqgap1 | Ly75 | | Lcp1 | Il18r1 |
| Irf7 | Mapk13 | | Ldhc | Il1r1 |
| Itga4 | Mbnl3 | | Lgalsl | Il2rb |
| Itgal | Med31 | | Lilr4b | Impdh2 |
| Kdm7a | Megf9 | | Limd2 | Jak11 |
| Klf4 | Mettl9 | | Man2b1 | Kcnk1 |
| Klra2 | Mgst2 | | Mapkapk3 | Klrd1 |
| Lilra6 | Mrgpra2a | | Max | Lasl1 |
| Limd1 | Mrgpra2b | | Mboat1 | Lax1 |
| Lyn | Ms4a3 | | Mboat7 | Lck |
| Magohb | Msra | | Mcpt8 | Lingo4 |
| Map3k1 | Ncf1 | | Mfsd6 | Lonp2 |
| Mndal | Neil3 | | Ms4a2 | Lta |
| Mrpl30 | Ngp | | Myh9 | Map4k4 |
| Ms4a4c | Nudt4 | | Myo1d | Mif4gd |
| Mthfd2 | Olfm4 | | Neat1 | Mob4 |
| Mycbp2 | Orm1 | | Nfkbia | Ncl |
| Myo1f | Pde4d | | Nlrp3 | Ncor1 |
| Myo1g | Pgd | | Nt5c3 | Nfkb1 |
| Nadk | Pgp | | Nt5e | Nrgn |
| Ncf2 | Pilrb2 | | Oaf | Nrip1 |
| Nuak2 | Pnkp | | P2rx1 | Nudt21 |
| Nupr1 | Ppp1cb | | P2ry1 | Orai2 |
| Pabpc1 | Pram1 | | P2ry10 | Pacsin1 |
| Pid1 | Prom1 | | P2ry14 | Pbxip1 |
| Pilra | Pygl | | Pdzd4 | Pdcd1 |
| Pira2 | R3hdm4 | | Pecam1 | Pdcd4 |
| Pmaip1 | Rab3d | | Perp | Plaa |
| Ppp2r5a | Rdh12 | | Pfn1 | Podnl1 |
| Pqlc3 | Retnlg | | Phf2011 | Pole4 |
| Prelid1 | Rpa3 | | Pkp3 | Ppm1b |
| Prkcd | Rrm2 | | Plek | Ppp1r12a |
| Psma2 | S100a9 | | Plk3 | Ppp1r16b |
| Psma7 | Sec11c | | Prr7 | Ppp2r4 |
| Psme2 | Serpinb10 | | Ptger3 | Prkcq |
| Ptpn1 | Siglece | | Ptk2b | Prr29 |
| Ptprc | Ska1 | | Ptpre | Prrc2c |
| Pyhin1 | Slbp | | Pyurf | Pycr1 |
| Rara | Slco4c1 | | Rab4a | Qars |
| Rnase6 | Sp140 | | Rabac1 | Rasal3 |
| Samhd1 | St3gal5 | | Rcn1 | Rassf5 |
| Sec61b | Stfa1 | | Rgs5 | Rbck1 |
| Sema4a | Stfa2 | | S100a13 | Rbm39 |
| Sgk3 | Stfa2l1 | | Selm | Rftn1 |
| Sik1 | Stfa3 | | Siglecf | Rhof |
| Sirpb1b | Tinagl1 | | Slc41a3 | Rock1 |
| Sirpb1c | Tmem216 | | Smap1 | Rora |
| Slfn1 | Tmem40 | | Smim3 | Rorc |
| Slfn2 | Tmem45a2 | | Spn | Rpl21 |
| Smpdl3a | Trem3 | | Spns3 | Rpl30 |
| Snrpb | Treml2 | | Spry2 | Rpl31 |
| Snrpe | Triobp | | Sptssa | Rsl1d1 |
| Sorl1 | Tst | | St14 | Rtf1 |
| Sp100 | Txn1 | | Stx3 | Runx3 |
| St3gal4 | Vamp5 | | Sytl3 | Satb1 |
| St8sia4 | Wfdc21 | | Tax1bp1 | Sdc1 |
| Thbs1 | X1700020L24Rik | | Tes | Senp6 |
| Tmem167 | X1810037I17Rik | | Tesc | 43719 |
| Tmpo | X2010005H15Rik | | Tmem154 | Serbp1 |
| Trps1 | X4930438A08Rik | | Tmem71 | Set |
| Uqcrfs1 | X9830107B12Rik | | Tnfaip3 | Sfr1 |
| Vcan | Xpc | | Tpm4 | Sh2d2a |
| Vsir | Zmpste24 | | Vcl | Sh2d3c |
| Wfdc17 | | | Wdr95 | Skp1a |
| X1600010M07Rik | | | Zc3h12a | Sla |
| X1600014C10Rik | | | | Sla2 |
| Zbp1 | | | | Slc9a3r1 |

TABLE 1-continued

Markers for cell types (FIG. 1C), neuronal and
glia-like clusters (FIG. 1F) and immune clusters (FIG. 4A).

Smc3
Socs1
Spon2
Srpk1
Srsf3
Ssrp1
St6galnac3
Stat4
Suclg1
Tcf7
Tecpr1
Thy1
Tnfrsf25
Tnik
Tns4
Tox
Tox2
Txk
Ugcg
Unc119b
Uqcrh
Vps37b
X0610011F06Rik
Xlr4a
Xlr4b
Xlr4c
Ywhaq
Zbtb16
Zfp207
Znrf1

Table 1C. Neuron Glia-like Clusters

| Neurons | Neurons 4V | Neuronal progenitor 4V | Neuronal progenitor 3V | Neuronal progenitor LV | OPC |
| --- | --- | --- | --- | --- | --- |
| A730017C20Rik | Abracl | Arhgef2 | Clybl | Bcl11a | Amd1 |
| Actl6b | Atp6v0d1 | Barx2 | Ghr | Bcl7a | Anxa5 |
| Agtr1a | Cntn2 | Bhlhe22 | Gm26872 | Cdkn1a | Atp5g2 |
| Ahi1 | Crabp1 | Cxcl14 | Mpp3 | Csnk1e | AY036118 |
| Aplp1 | Eln | Ddah2 | Nono | Emx2 | B3gat2 |
| Arpc5 | Hey1 | E2f1 | Olfm1 | Hdac2 | Cdkn1c |
| Asic4 | Hoxa2 | Ebf3 | Prdx2 | Lhx1os | Col1a2 |
| Atcay | Hoxb2 | Fabp5 | Tcf7l2 | Lhx2 | Crybb1 |
| Atpif1 | Hoxb3 | Fam107b | | Nhlh2 | Ctsl |
| B630019K06Rik | Hoxb3os | Fam134b | | Reln | Cxcr4 |
| Bex2 | Hoxb4 | Fam210b | | Sept3 | Cyb561 |
| Cadm1 | Hoxd4 | Fscn1 | | Smad1 | Etv5 |
| Celf3 | Meis1 | Gm2694 | | Tbr1 | F11r |
| Celf6 | Mfap4 | Gsc | | Trp73 | Fgf17 |
| Chd3 | Nav2 | Hnrnpab | | Wrap73 | Gm10709 |
| Chd3os | Rab15 | Hpcal1 | | | Gm9493 |
| Cnih2 | Rassf4 | Mab21l2 | | | Gng12 |
| Ctxn1 | RP24.402O2.2 | Neurod2 | | | Hexb |
| Cyth2 | Vps37b | Nt5dc2 | | | Il17rd |
| D930028M14Rik | | Pcsk9 | | | Islr |
| Dbn1 | | Pde1c | | | Kitl |
| Dlgap4 | | Rnd2 | | | Lmo1 |
| Dlk1 | | Rpl10 | | | Lpar1 |
| Dll4 | | Rpl19 | | | Mbip |
| Dlx1 | | Sstr2 | | | mt.Atp6 |
| Dlx2 | | Tpt1 | | | mt.Co2 |
| Dlx5 | | Trpc3 | | | mt.Co3 |
| Dlx6os1 | | Uncx | | | Mxd4 |
| Dnaja1 | | | | | Nkx2.1 |
| Dnajb6 | | | | | Nrp2 |
| Dner | | | | | Olig1 |
| Dync1li1 | | | | | Pax8 |
| Dynll2 | | | | | Pcp4 |
| Evl | | | | | Pmp22 |
| Fxyd6 | | | | | Ppdpf |
| Gabarapl2 | | | | | Prnp |
| Gdap1l1 | | | | | Rpl15 |
| Gdi1 | | | | | Rpl27a |
| Gm1673 | | | | | Rpl29 |
| Gria2 | | | | | Rpl35a |
| Hap1 | | | | | S100a16 |

TABLE 1-continued

Markers for cell types (FIG. 1C), neuronal and
glia-like clusters (FIG. 1F) and immune clusters (FIG. 4A).

| | |
|---|---|
| Hist3h2a | Sema6d |
| Hspa8 | Serf2 |
| Ip6k2 | Slc6a6 |
| Kctd13 | Sox1 |
| Kifap3 | Sparcl1 |
| Klc1 | Spon1 |
| Lhx5 | Sumo2 |
| Mapk10 | Thrsp |
| Mapt | Tomm20 |
| Myt1l | Uba52 |
| Nap1l5 | Vax1 |
| Nav1 | |
| Ncam1 | |
| Ndn | |
| Nol4 | |
| Nrxn3 | |
| Onecut2 | |
| Pafah1b3 | |
| Pak3 | |
| Pcsk1n | |
| Pebp1 | |
| Phyhipl | |
| Pmaip1 | |
| Prmt2 | |
| Ptp4a1 | |
| Ptpn5 | |
| R3hdm4 | |
| Rab6a | |
| Rasgrp1 | |
| Resp18 | |
| Rit2 | |
| Rnf187 | |
| Rufy3 | |
| Scg2 | |
| Scg5 | |
| Serf1 | |
| Sez6l2 | |
| Sh3bp1 | |
| Sh3bp5 | |
| Shtn1 | |
| Slc32a1 | |
| Snhg11 | |
| Srrm3 | |
| St8sia3 | |
| Stmn4 | |
| Syt1 | |
| Tmem130 | |
| Tmem57 | |
| Tmod2 | |
| Ttc9b | |
| Tuba1a | |
| Tubb2a | |
| Ubqln2 | |
| Uchl1 | |
| Wsb1 | |
| X1700086L19Rik | |
| X2010107G23Rik | |
| Ypel3 | |
| Ywhaq | |
| Zcchc12 | |

Table 1C. Neuron Glia-like Clusters

| Progenitor 1 | Progenitor 2 | Cycling (G2/M) | Cycling (G1/S) | Rspo1 + LV | Developing pineal gland (Krt19+) | Developing pineal gland |
|---|---|---|---|---|---|---|
| Eef1g | Chadl | Anp32e | Anp32b | | AI593442 | Adrb1 |
| Fgf15 | Cmtm5 | Arl6ip1 | Atad2 | | Aqr | Aipl1 |
| Rpl28 | Grb10 | Aurka | Dctpp1 | | Bmp4 | Bcl2l1 |
| Rpl36a | Kcna1 | Aurkb | Dek | | C1ql2 | Casz1 |
| Rpl38 | Kcna5 | Bub1b | Dnajc9 | | Ccnd3 | Cdhr1 |
| Rplp2 | Mdfi | Bub3 | Dut | | Cldn19 | Cdk2ap2 |
| | Prss35 | C330027C09Rik | Fen1 | | Clic1 | Cntn1 |
| | Rpl35 | Casc5 | Gins2 | | Col23a1 | Cox4i1 |
| | Scube2 | Ccna2 | Gmnn | | Col9a3 | Cplx3 |
| | Sfrp1 | Ccnb1 | Hat1 | | Cp | Crx |

TABLE 1-continued

Markers for cell types (FIG. 1C), neuronal and
glia-like clusters (FIG. 1F) and immune clusters (FIG. 4A).

| St3gal6 | Ccnb2 | Lig1 | Ctsb | Ctsf |
|---|---|---|---|---|
| | Cdc20 | Mcm5 | Efna5 | Dctn3 |
| | Cdc25c | Mcm6 | Eva1a | Ddc |
| | Cdca2 | Nasp | Fam155a | F2rl1 |
| | Cdca3 | Ranbp1 | Gucy1a3 | Fam19a1 |
| | Cdk1 | Rfc4 | Gyg | Gm11744 |
| | Cdkn2c | Rrm1 | Hspb8 | Gnb3 |
| | Cdkn3 | Rrm2 | Igfbp7 | Gngt2 |
| | Cenpa | Siva1 | Kcnip4 | Insm1 |
| | Cenpe | Tipin | Krt15 | Isl2 |
| | Cenpf | Tk1 | Krt19 | Lhx3 |
| | Cenpq | Tyms | Lgals1 | Lhx4 |
| | Cep55 | | Mcoln3 | Lrrc38 |
| | Cep89 | | mt.Cytb | Mir124a.1hg |
| | Ckap2 | | Mxra7 | Mrfap1 |
| | Ckap2l | | Ngf | Mrpl49 |
| | Cks2 | | Nrxn1 | Msi1 |
| | Ddx39 | | Nxph1 | Napa |
| | Dlgap5 | | Parm1 | Ndufv3 |
| | Dynll1 | | Pcdh8 | Pcbp3 |
| | Ect2 | | Ppfibp1 | Pdc |
| | Eif4e | | Prdx4 | Pde6g |
| | Fam64a | | Prrx2 | Platr17 |
| | G3bp1 | | Rab38 | Ralgds |
| | H1fx | | Rab3b | Rbp3 |
| | H2afx | | Rbms1 | Rorb |
| | Hmgb1 | | Rgs2 | Sag |
| | Hmgb3 | | Robo2 | Sall1 |
| | Hmmr | | Scn3b | Samd11 |
| | Incenp | | Sdpr | Setdb2 |
| | Kif11 | | Sepw1 | Slc17a6 |
| | Kif20a | | Sgk1 | Slc25a33 |
| | Kif20b | | Slc2a1 | Ssu72 |
| | Kif22 | | Slc6a15 | Tlx2 |
| | Kif23 | | Srpx2 | Tma7 |
| | Kif2c | | Stac | Tmem215 |
| | Kifc1 | | Syngr1 | Tpd52 |
| | Knstrn | | Tpi1 | Tph1 |
| | Kpna2 | | | Trappc21 |
| | Lockd | | | Tulp1 |
| | Lsm3 | | | Unc119 |
| | Mad2l1 | | | Wbscr17 |
| | Mis18bp1 | | | Wdr66 |
| | Mki67 | | | X9330179D12Rik |
| | Ncapd2 | | | |
| | Ndc80 | | | |
| | Nde1 | | | |
| | Nucks1 | | | |
| | Nudcd2 | | | |
| | Nuf2 | | | |
| | Plk1 | | | |
| | Prc1 | | | |
| | Psip1 | | | |
| | Psrc1 | | | |
| | Pttg1 | | | |
| | Racgap1 | | | |
| | Rad21 | | | |
| | Ran | | | |
| | Rangap1 | | | |
| | Rnf26 | | | |
| | Sapcd2 | | | |
| | Sgol1 | | | |
| | Shcbp1 | | | |
| | Smc4 | | | |
| | Spc24 | | | |
| | Spdl1 | | | |
| | Tacc3 | | | |
| | Tpx2 | | | |
| | Troap | | | |
| | Tuba1c | | | |
| | Tubb4b | | | |
| | Ube2c | | | |
| | X2700094K13Rik | | | |

65

Two subsets of neurons in the 3V expressed markers of developing pinealocytes (e.g., Crx, Krt19; FIGS. 1F, clusters 12 and 13, FIGS. 8F, 8H). The pineal gland develops caudal to the 3V ChP, and these two secretory tissues form together the roof of the 3V (Puelles and Rubenstein, 2003). Applicants leveraged the inclusion of ChP adjacent brain tissue in the cell atlas to molecularly map the boundary between the 3V ChP and developing pineal gland (FIG. 8K).

Figures 2A, 2B, 2C, 2D:
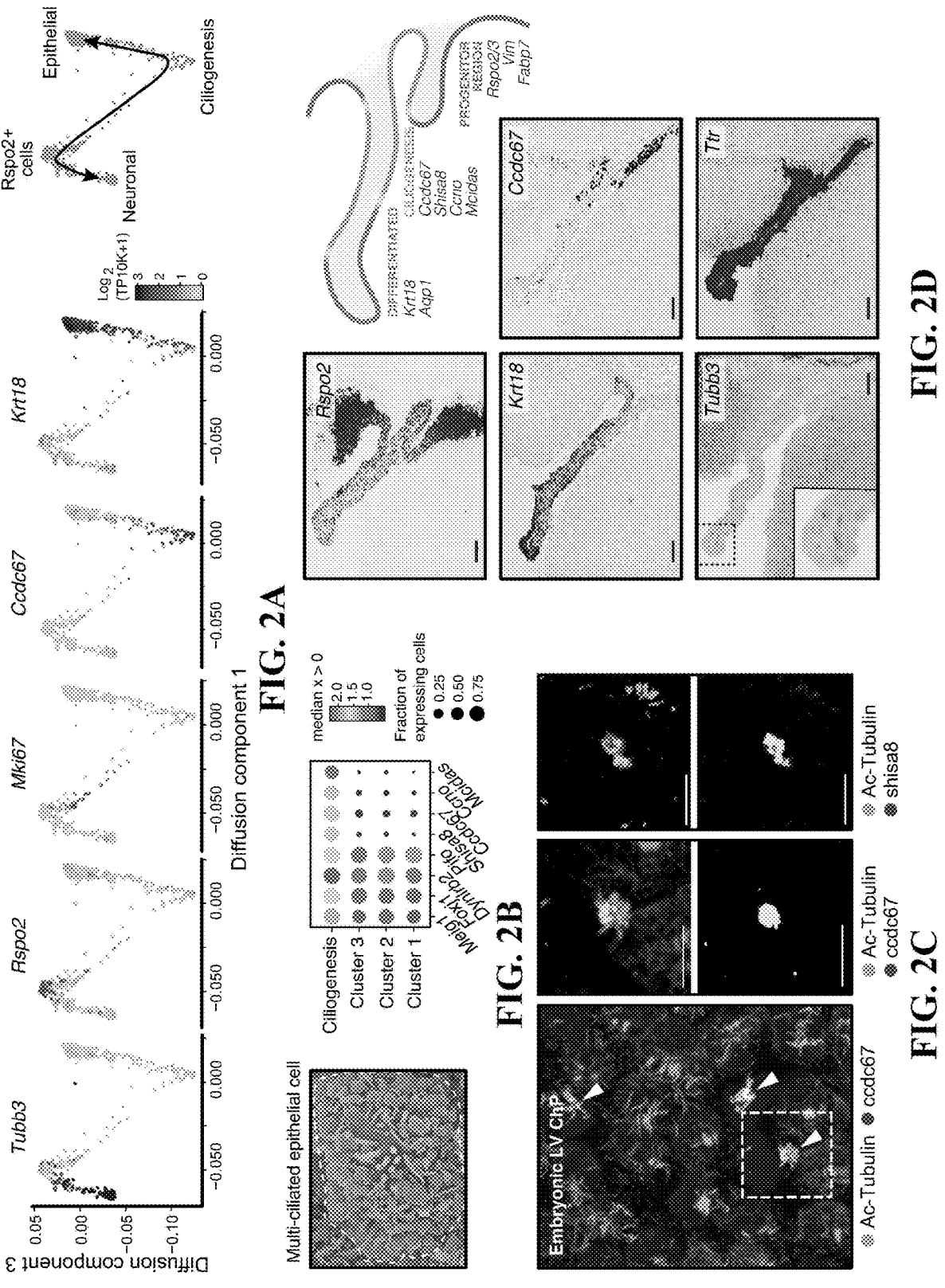
FIG. 2A-2D—An epithelial differentiation trajectory suggests a common progenitor of epithelial and neural cells.
Figures 9A, 9B:
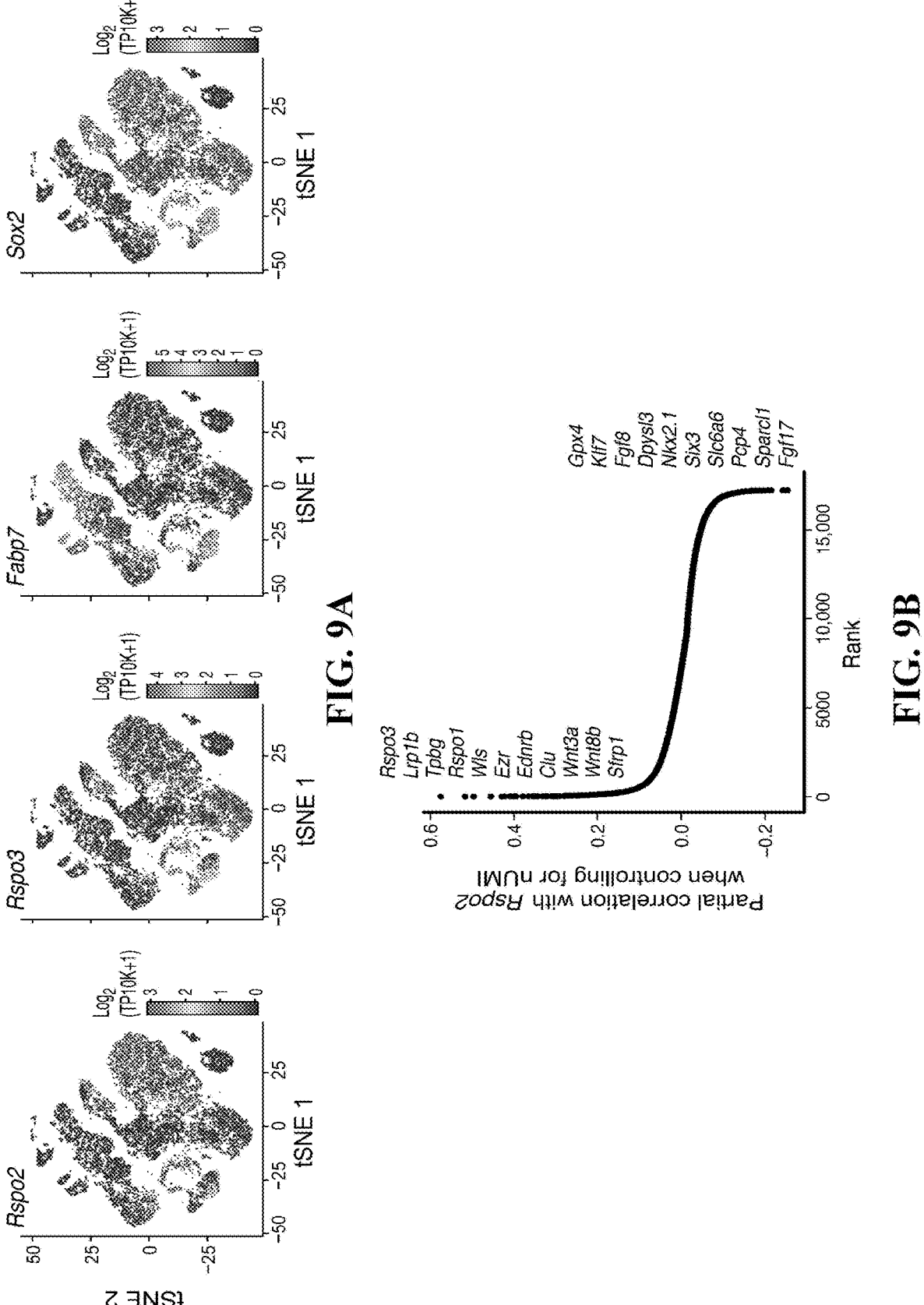
FIG. 9A-9E—Common progenitors of neural epithelium divide to become mature epithelial cells.
Figure 9C:
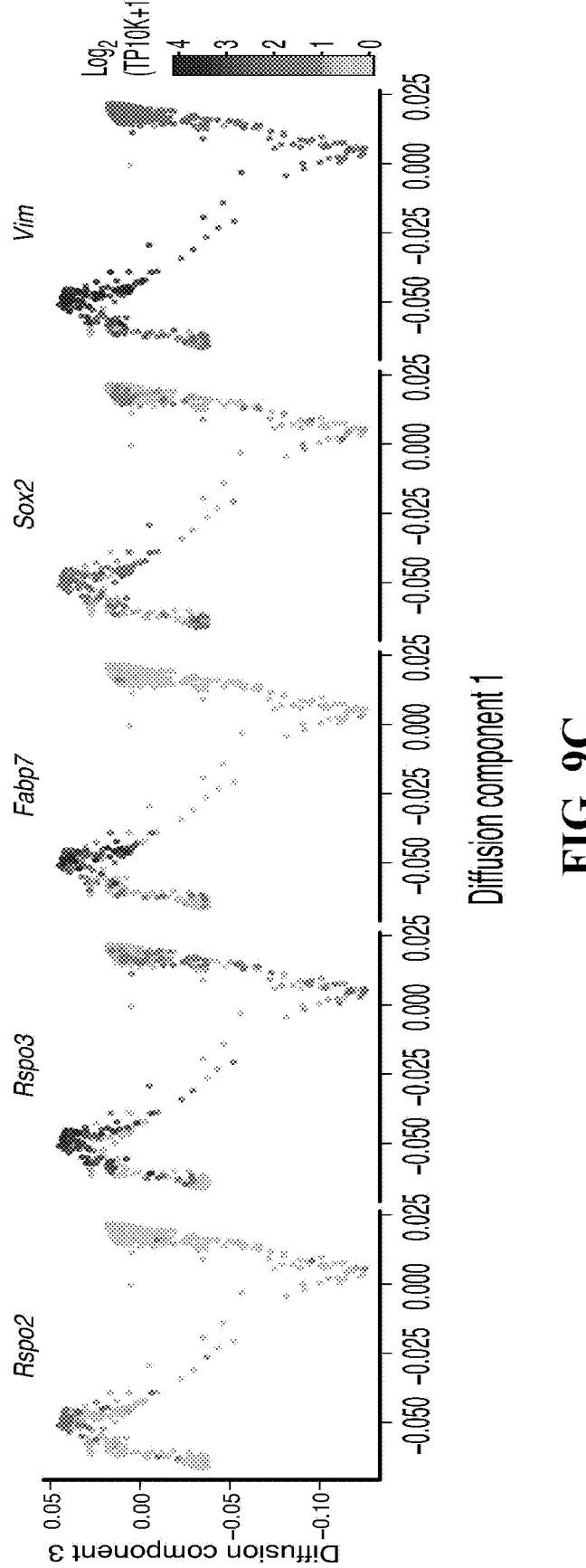

An Inferred Differentiation Continuum Suggests a Common Progenitor of Epithelial and Neural Cells Surprisingly, the epithelial and neuronal/glia-like cells were not discretely separable (FIG. 1C) by any low-dimensional embedding analyses that were attempted (STAR Methods), and stem cell marker genes were expressed in cells at their intersection point (FIG. 9A), suggesting a model where a common progenitor pool for both epithelial and neuronal cells may exist in the ChP. To explore this hypothesis, the predicted phenotypic continuum between neuronal, glia-like and epithelial cells were modeled using a diffusion map (Haghverdi et al., 2015) of cells of the 3V ChP. The diffusion embedding arranged neurons and mature epithelial cells at two opposite ends of a trajectory, with a progenitor glia-like population (Rspo2+) between them (FIG. 2A). Rspo2+progenitor like cells also expressed several stem markers (FIGS. 9B, 9C, progenitor 1 and 2 populations in FIG. 1F; STAR Methods), which have previously been shown in precursor cells of the developing cortex that have glia like properties and give rise to ependymal cells (modified epithelial cells) and neurons (Kriegstein and Alvarez-Buylla, 2009).

Figure 9E:
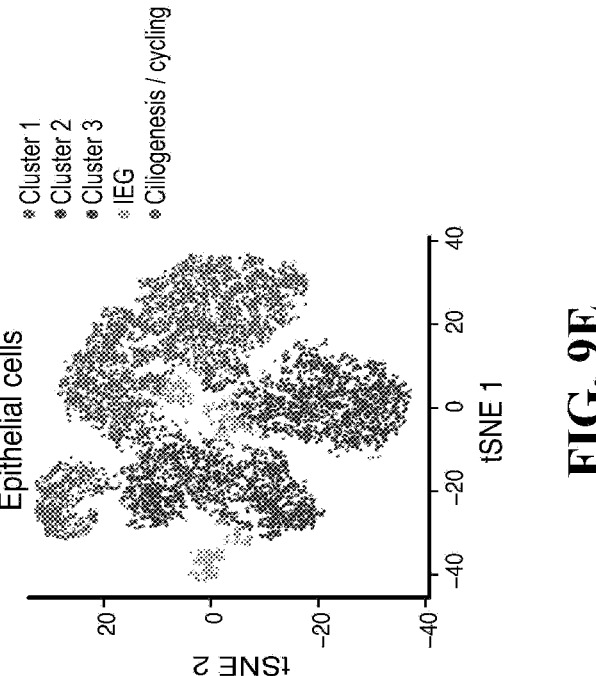

Applicants' analysis also highlighted newly differentiated, post-mitotic epithelial cells (FIG. 9D) that transiently expressed ciliogenesis genes (FIG. 2A) and were associated with distinct marker genes (FIGS. 2B, 9E), including Ccdc67/Deup1, which drives centriole biogenesis, an essential step of multi-ciliation (Brooks and Wallingford, 2014). Another marker, Shisa8, was expressed near the base of acetylated-tubulin tufts in multi-ciliated epithelial cells (FIG. 2C), and was recently identified as a regulator in iPSC reprogramming (Schiebinger et al., 2019).

These populations had distinct spatial boundaries: progenitor cells were located near the ChP-brain boundary (by ISH of Rspo2; FIG. 2D); newly differentiated epithelial cells localized near the base of the LV ChP proximal to the brain (by ISH of Ccdc67/Deupl; FIG. 2D), whereas more mature epithelial cells were positioned along the length of the ChP, extending distally into the LV (ISH by Krt18) (FIG. 2D). This maturation gradient of ChP epithelial cells matches models based on classic electron microscopy (Liddelow et al., 2010; Shuangshoti and Netsky, 1966) and provide a molecular handle for investigating these distinct stages of epithelial cell development.

Figures 3A, 3B:
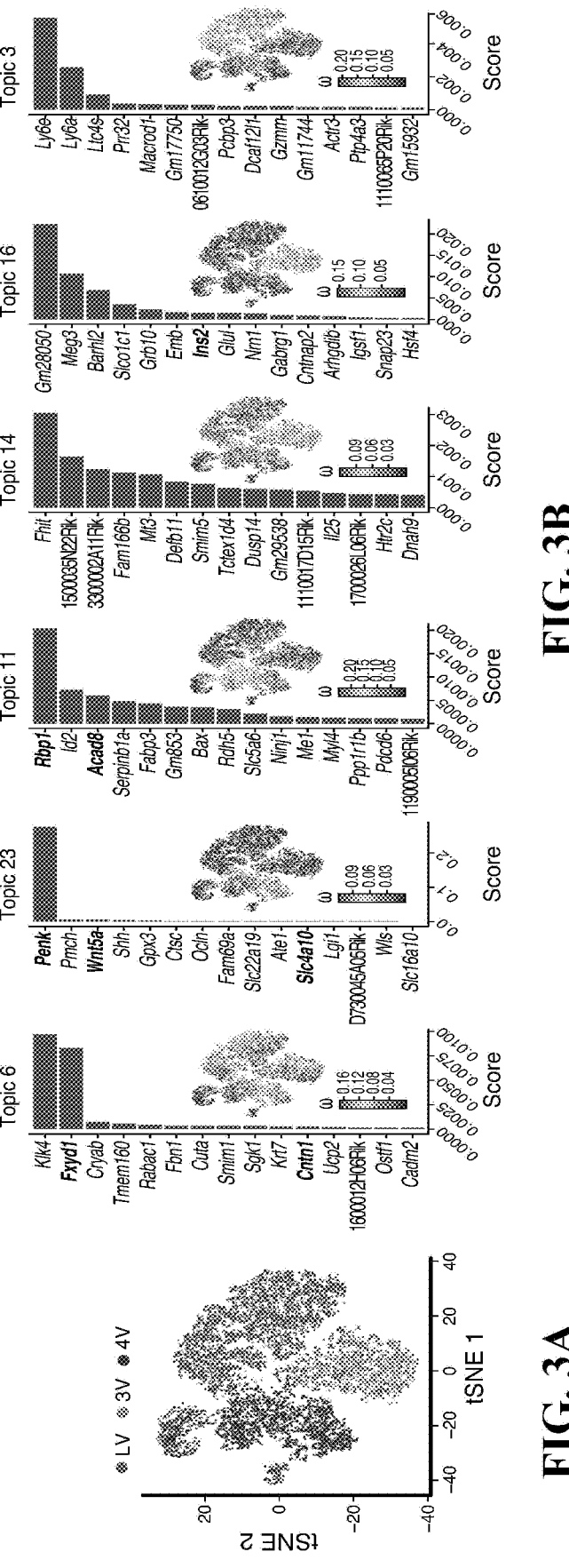
FIG. 3A-3I—Regionalized epithelial and mesenchymal transcriptional programs across ventricles.
Figure 9D:
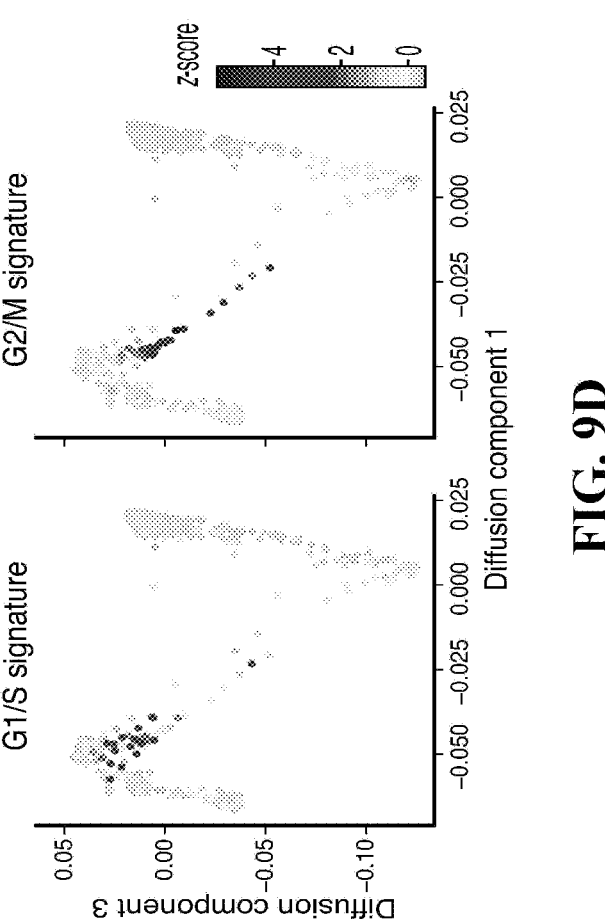
Figures 10A, 10B, 10C:
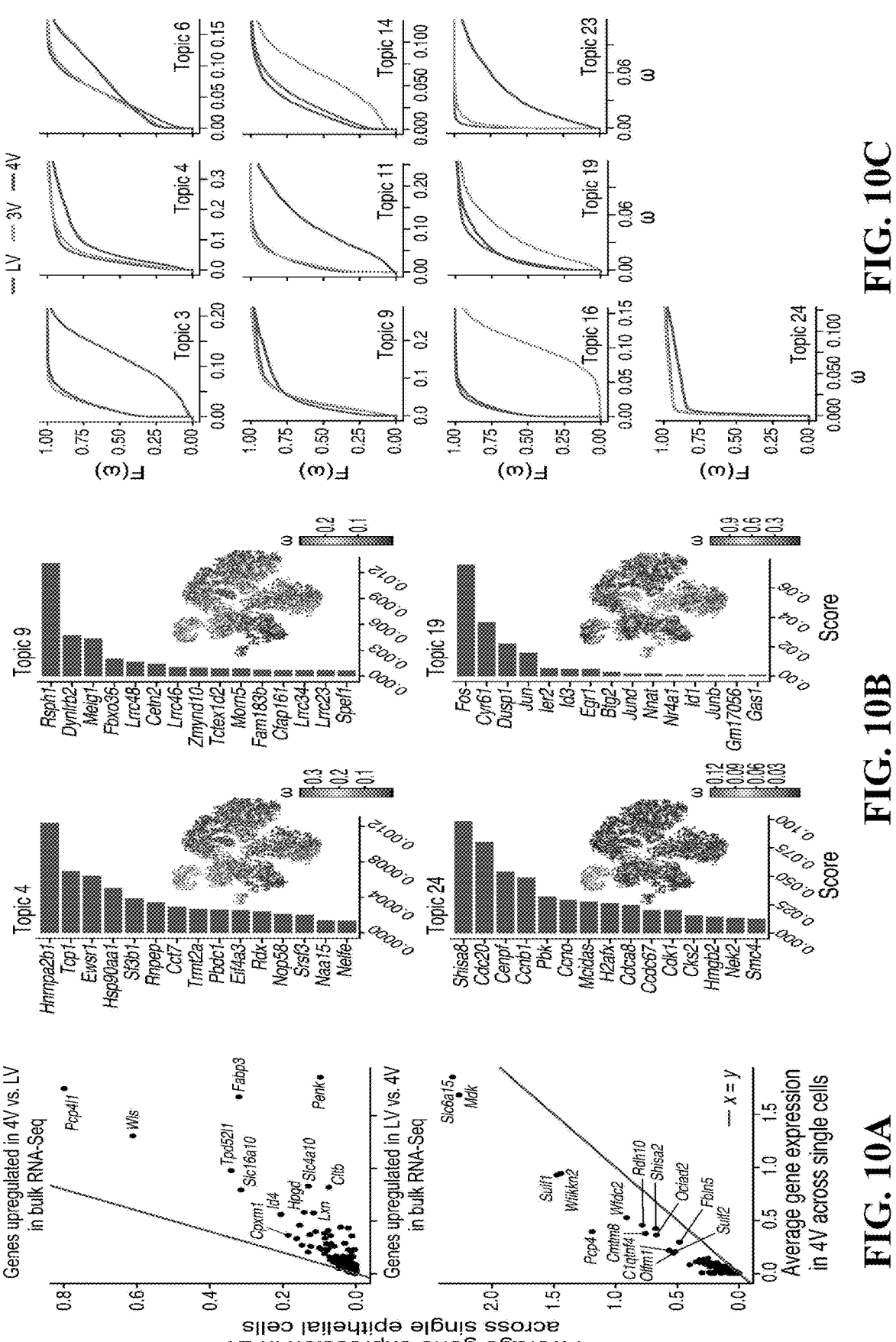

Epithelial and Mesenchymal Cell Programs are Regionalized Across Brain Ventricles Epithelial cells formed the largest cell class in each ChP and partitioned into several clusters representing cycling, newly differentiated cells undergoing ciliogenesis (above), and mature cells with ventricle-specific differences (FIGS. 9D, 3A). On average, the scRNA-seq data recapitulated differential gene expression between epithelial cells from LV and 4V ChP from bulk RNA-seq (Lun et al., 2015b) (FIG. 10A).

To identify the transcriptional programs that drive the distinction of differentiated ChP epithelial cells by brain ventricle, topic modeling was applied using Latent Dirichlet Allocations (Blei et al., 2003), originally developed for natural language processing and recently applied to scRNA-seq data (Bielecki et al., 2018). In topic modeling, a cell is modeled as a mixture of a small number of transcriptional programs ("topics"), where each topic is a distribution over genes. A gene can belong to multiple topics with different weights, reflecting the gene's role in each topic. Likewise, a topic's weight for a given cell reflects the relative prominence of the corresponding biological process associated with that topic in that cell. Topic models were learned for all epithelial cells, and then searched for topics that were differentially weighted across subsets of individual cells or that described an interpretable biological process, based on the associated genes (FIGS. 3B, 10B, 10C, STAR Methods, Table 2), such as ciliogenesis (Topic 12, FIGS. 10B, 2D), or immediate early genes (Topic 16, which may reflect a response to tissue dissociation (van den Brink et al., 2017), as it was absent from single nucleus RNA-seq (snRNA-Seq, FIGS. 10B, 10D)).

TABLE 2

| Top 50 genes in each topic revealed by topic modeling on epithelial cells of developing ChPs. | | | | | |
|---|---|---|---|---|---|
| topic_3 | topic_4 | topic_6 | topic_9 | topic_11 | topic_14 |
| Ly6e | Hnrnpa2b1 | Klk4 | Rsph1 | Rbp1 | Fhit |
| Ly6a | Tcp1 | Fxyd1 | Dynlrb2 | Id2 | X1500035N22Rik |
| Ltc4s | Ewsr1 | Cryab | Meig1 | Acad8 | X3300002A11Rik |
| Prr32 | Hsp90aa1 | Tmem160 | Fbxo36 | Serpinb1a | Fam166b |
| Macrod1 | Sf3b1 | Rabac1 | Lrrc48 | Fabp3 | Mt3 |
| Gm17750 | Rnpep | Fbn1 | Cetn2 | Gm853 | Defb11 |
| X0610012G03Rik | Cct7 | Cuta | Lrrc46 | Bax | Smim5 |
| Pcbp3 | Trmt2a | Smim1 | Zmynd10 | Rdh5 | Tctex1d4 |
| Dcaf12l1 | Pbdc1 | Sgk1 | Tctex1d2 | Slc5a6 | Dusp14 |
| Gzmm | Eif4a3 | Krt7 | Morn5 | Ninj1 | Gm29538 |
| Gm11744 | Rdx | Cntn1 | Fam183b | Me1 | X1110017D15Rik |
| Actr3 | Nop58 | Ucp2 | Cfap161 | Myl4 | Il25 |
| Ptp4a3 | Srsf3 | X1600012H06Rik | Lrrc34 | Ppp1r1b | X1700026L06Rik |
| X1110065P20Rik | Naa15 | Ostf1 | Lrrc23 | Pdcd6 | Htr2c |
| Gm15932 | Nelfe | Cadm2 | Spef1 | X1190005I06Rik | Dnah9 |
| Cisd1 | Ddx39b | Hfe | Dnaic2 | Car10 | Usp32 |
| Cdk15 | Ppan | Cox20 | Ift43 | Slc31a1 | Cfap43 |
| Krt1 | Ptges3 | Bst2 | X6820408C15Rik | Acat1 | Slco1a4 |
| Bex2 | Csrp2 | Sema3f | Ppp1r32 | Acss1 | Lhb |
| Shisa4 | Psmd7 | Nid2 | Tmem107 | Cab39l | Dcdc2b |
| Mgmt | Hspa9 | Stk39 | Tekt1 | Fads3 | Dydc2 |
| Tex40 | Cmas | Crtap | X1700012B09Rik | Ndufa8 | Cetn4 |
| Gm15631 | Scpep1 | Klk8 | Cfap52 | Slc4a5 | Efcab10 |
| Gstm1 | Stip1 | Metrn | Cfap206 | Rbp4 | Brwd3 |
| Mrps6 | Dxo | Clic3 | Ccdc113 | Hrasls | Iqgap1 |

TABLE 2-continued

| Top 50 genes in each topic revealed by topic modeling on epithelial cells of developing ChPs. | | | | | |
|---|---|---|---|---|---|
| Arsg | Ppp1cb | Apoc1 | Chchd6 | Kcnip2 | Slc16a12 |
| X2310015A10Rik | Vta1 | Adora2b | Spag6l | Oaz2 | Ndrg2 |
| Eri3 | Casp7 | Gas6 | Crip2 | Cyc1 | Klhl31 |
| Pla2g5 | Ppid | Prr13 | X1700028P14Rik | Acadm | Hcfc1r1 |
| Hscb | Cwc15 | Bcam | Bphl | Ssu72 | Col8a2 |
| Cmtm8 | Me2 | Col4a3 | Fank1 | Bdh1 | Myo16 |
| Sys1 | Psmg2 | Sdf2 | Hist1h1c | Taf4b | X9530053A07Rik |
| Ccdc12 | Vdac2 | Sfrp1 | Elof1 | Me3 | X4933434E20Rik |
| Gata3 | Trim27 | Tmem248 | Ak7 | Eci1 | Colec12 |
| Cib1 | March5 | Rexo2 | Hspa2 | Fuom | Crb3 |
| Scp2 | Cyth2 | Vkorc1 | X1700007G11Rik | A2m | Cfap44 |
| Nefm | Smarca5 | Itpr1 | Ppp1r36 | Gpi1 | Gm14964 |
| Fam47e | Tomm40 | Gstm2 | Mdh1b | Npr3 | Tmem108 |
| Nfasc | Zcrb1 | Itga3 | Nudc | Aqp1 | Slc16a2 |
| X2900010O008Rik | Slmo2 | Agtpbp1 | Ndufaf3 | Hadha | Tcea3 |
| X1500011B03Rik | Fmr1 | X2310009B15Rik | Ccdc65 | Lxn | Perp |
| Il17rc | Nsmce1 | Zdhhc12 | Ulk4 | Atp1a1 | Akip1 |
| Gadd45g | Mphosph8 | Pnp | X1700016K19Rik | Got1 | Lrrc51 |
| X1700024G13Rik | Morf4l2 | Fam174a | Mns1 | Fam195a | Hs6st2 |
| Ephx2 | Hnrnpll | Abca1 | B9d1 | Hopx | X1810037I17Rik |
| Hemk1 | Psma5 | Ubxn6 | Ccdc189 | Hoxaas3 | Serpinb6b |
| Pigyl | Pdap1 | Izumo4 | Efhc1 | Bnip3 | Cog7 |
| Pla2g12a | Cct3 | Scamp3 | Drc1 | Slc25a11 | Lrrc8c |
| Adra2c | Mpi | Fam198a | Psmd9 | Ggt7 | Larp1b |
| Mrpl34 | Wdr92 | Ccdc126 | BC005624 | Haus7 | Ttll5 |

| | | topic_16 | topic_19 | topic_23 | topic_24 |
|---|---|---|---|---|---|
| | | Gm28050 | Fos | Penk | Shisa8 |
| | | Meg3 | Cyr61 | Pmch | Cdc20 |
| | | Barhl2 | Dusp1 | Wnt5a | Cenpf |
| | | Slco1c1 | Jun | Shh | Ccnb1 |
| | | Grb10 | Ier2 | Gpx3 | Pbk |
| | | Emb | Id3 | Ctsc | Ccno |
| | | Ins2 | Egr1 | Ocln | Mcidas |
| | | Glul | Btg2 | Fam69a | H2afx |
| | | Nrn1 | Jund | Slc22a19 | Cdca8 |
| | | Gabrg1 | Nnat | Ate1 | Ccdc67 |
| | | Cntnap2 | Nr4a1 | Slc4a10 | Cdk1 |
| | | Arhgdib | Id1 | Lgi1 | Cks2 |
| | | Igsf1 | Junb | D730045A05Rik | Hmgb2 |
| | | Snap23 | Gm17056 | Wls | Nek2 |
| | | Hsf4 | Gas1 | Slc16a10 | Smc4 |
| | | Galnt12 | Ccnd2 | Lmo1 | Ccnb2 |
| | | Zfand5 | Pnrc1 | Meis1 | H2afz |
| | | S100a6 | Fosb | Prps2 | Cenpa |
| | | Il3ra | Dusp5 | Cpxm1 | Dlgap5 |
| | | Steap1 | Tob1 | Pdgfra | X2810417H13Rik |
| | | Cers4 | Fgf17 | Sema3c | Aurka |
| | | Camk2d | Lect1 | Negr1 | Ube2t |
| | | Six3 | Ccnd1 | Adamtsl3 | Pttg1 |
| | | Pdgfc | Nr4a2 | Defb9 | Knstrn |
| | | Otx1 | Nfkbia | Tpd52l1 | Cks1b |
| | | Cmpk1 | Csnk1a1 | Mapk4 | Plk4 |
| | | Ace | Atf3 | Abca4 | Cdca3 |
| | | Gsn | Bckdk | Dlk1 | Top2a |
| | | E530001K10Rik | Ppp1r15a | Meis2 | Racgap1 |
| | | Dmgdh | Hes1 | Grb14 | Melk |
| | | Dach2 | Sptssa | Fxyd7 | Birc5 |
| | | Krt8 | Aldoc | Scd2 | H2afv |
| | | Fap | Irf2bpl | Hotairm1 | Prc1 |
| | | Gabarapl1 | Cthrc1 | Tspan33 | Casc5 |
| | | Hspb6 | Mageh1 | Plagl1 | Stmn1 |
| | | Nov | Csrnp1 | Rapgef4 | Ckap2l |
| | | Arf4 | Rcan1 | Jam3 | Smc2 |
| | | Crhr2 | Frat2 | Cltb | Tpx2 |
| | | Mip | Ddit4l | Plppr4 | Ccdc61 |
| | | Ndufb4 | Grn | Slc24a5 | Cdkn2c |
| | | Mirg | Ier3 | Peg10 | Kif20a |
| | | Stmn2 | Rab11b | Col8a1 | Cdc20b |
| | | Osmr | Arc | Hpgd | Tacc3 |
| | | Thsd7a | Nppc | Marveld2 | Bub3 |
| | | Anxa2 | Ube2d3 | Npnt | Rad51ap1 |
| | | Galnt7 | Prkaca | Id4 | Rrm1 |
| | | Mapk10 | Rnf115 | Oca2 | Kif2c |
| | | X4930523C07Rik | Hdac3 | E130308A19Rik | Cenpe |

TABLE 2-continued

| Top 50 genes in each topic revealed by topic modeling on epithelial cells of developing ChPs. | | | |
|---|---|---|---|
| Noct | Tgfb3 | Dtx2 | Cdca2 |
| Fuca2 | X1810011O10Rik | Cep162 | Aard |

Figures 3C, 3D, 3E, 3F, 3G:
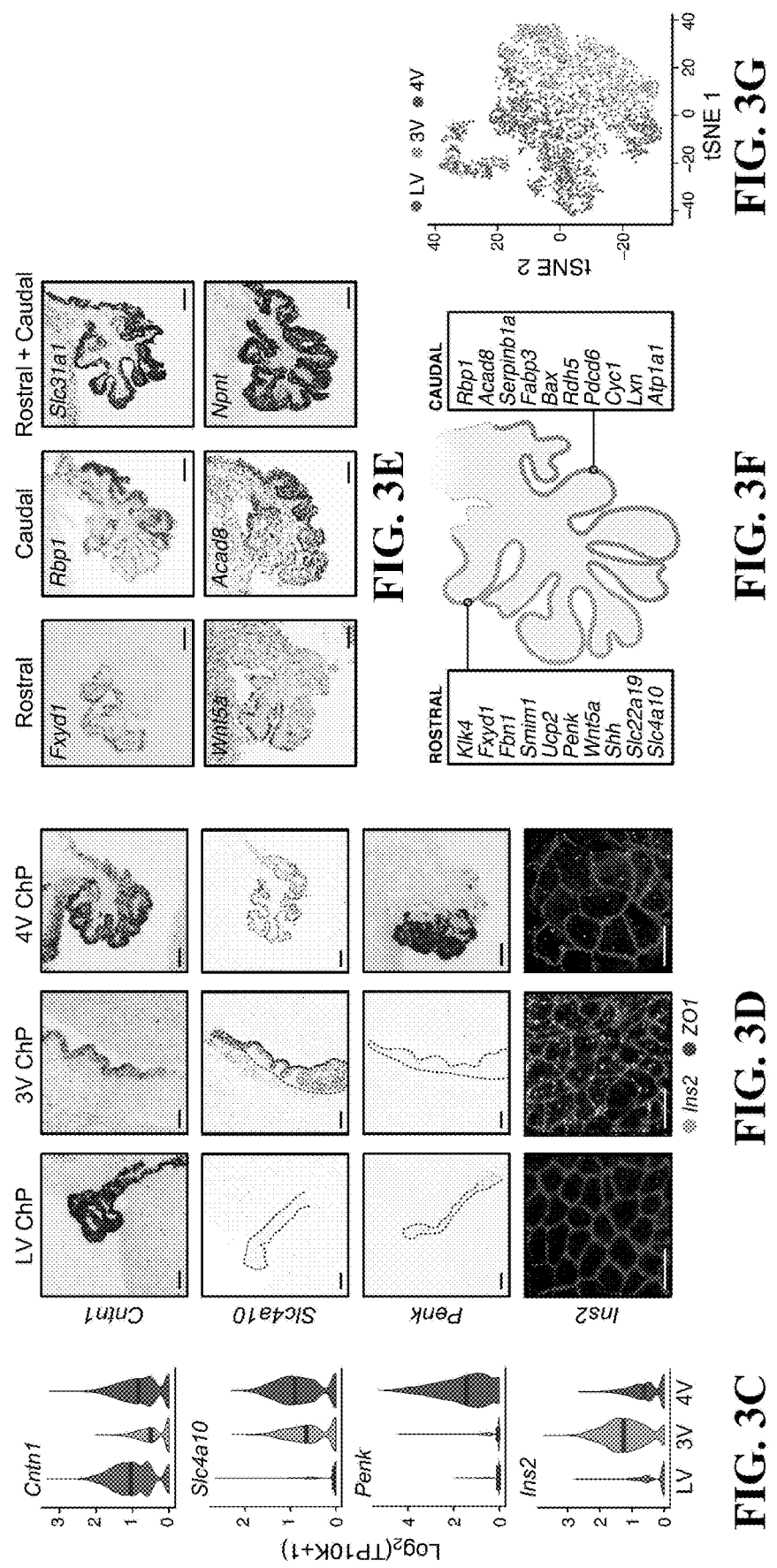
Figures 10D, 10E, 10F:
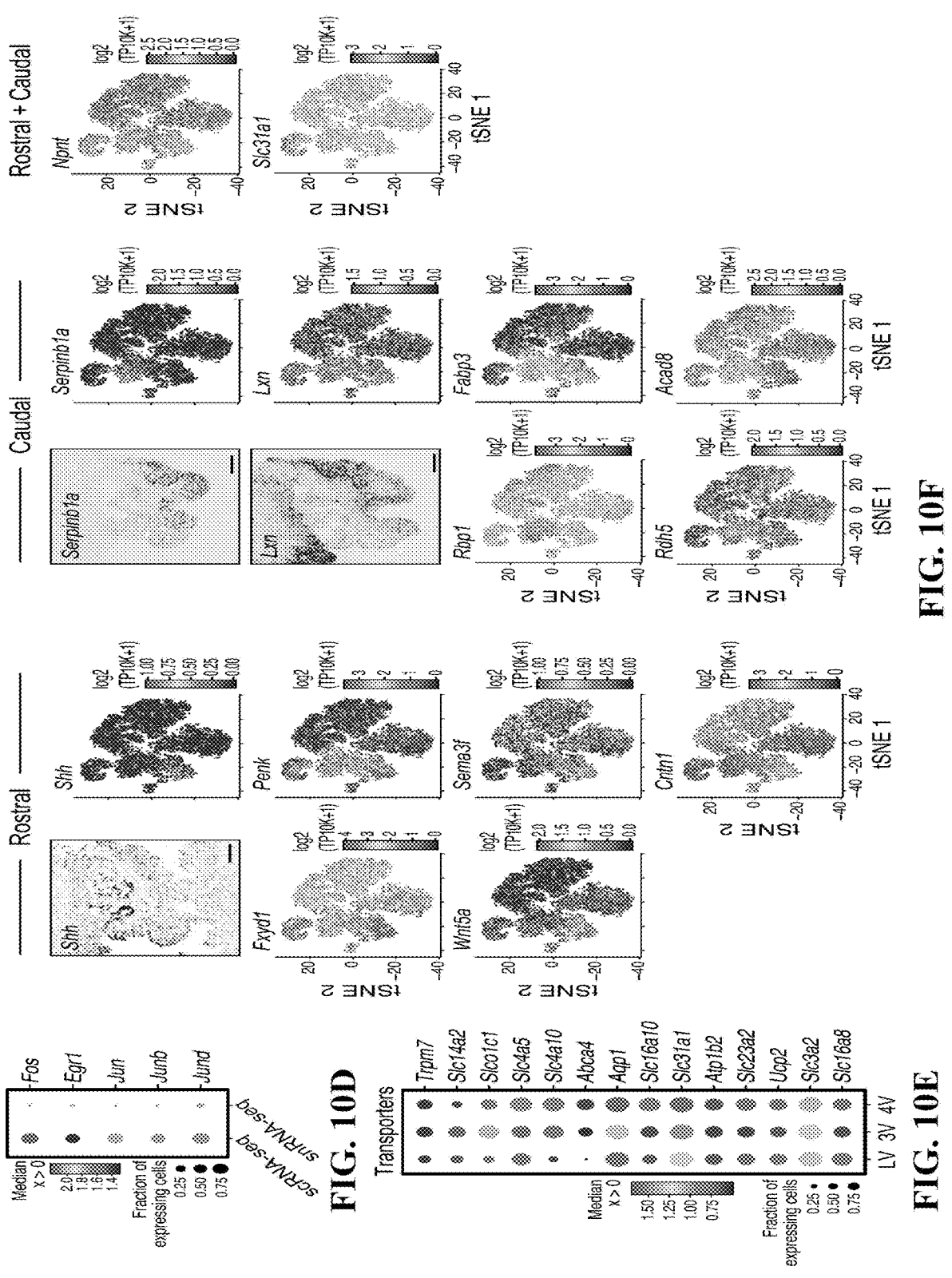

Several topics (2,7,8,9,10) were differentially weighted across cells from the different brain regions (FIG. 10C), including genes encoding transporters (FIG. 10E). The ventricle specific enrichment of key associated genes was validated using single molecule fluorescence in situ hybridization (smFISH) and published data (Diez-Roux et al., 2011) (FIGS. 3C, 3D). Notably, Ins2, encoding an insulin precursor and associated with Topic 10, was over-expressed in 3V epithelial cells (FIGS. 3B, 3C, 3D), suggesting the 3V ChP as an internal source of insulin within the developing brain. Moreover, epithelial cells within the 4V ChP could be distinguished in two different ways by their weights of topic 8 or 9 (FIGS. 3B, 3E, 10F). Mapping the expression of highly scoring genes for these two topics within the 4V ChP identified a rostro-caudal gradient of gene expression along the medial core of the plexus within the fourth ventricle (FIGS. 3E, 3F). These gradients may derive from the earliest stages of development, when roof plate progenitors originating from distinct rhombomeres give rise to hindbrain and 4V ChP (Hunter and Dymecki, 2007).

Figures 3H, 3I:
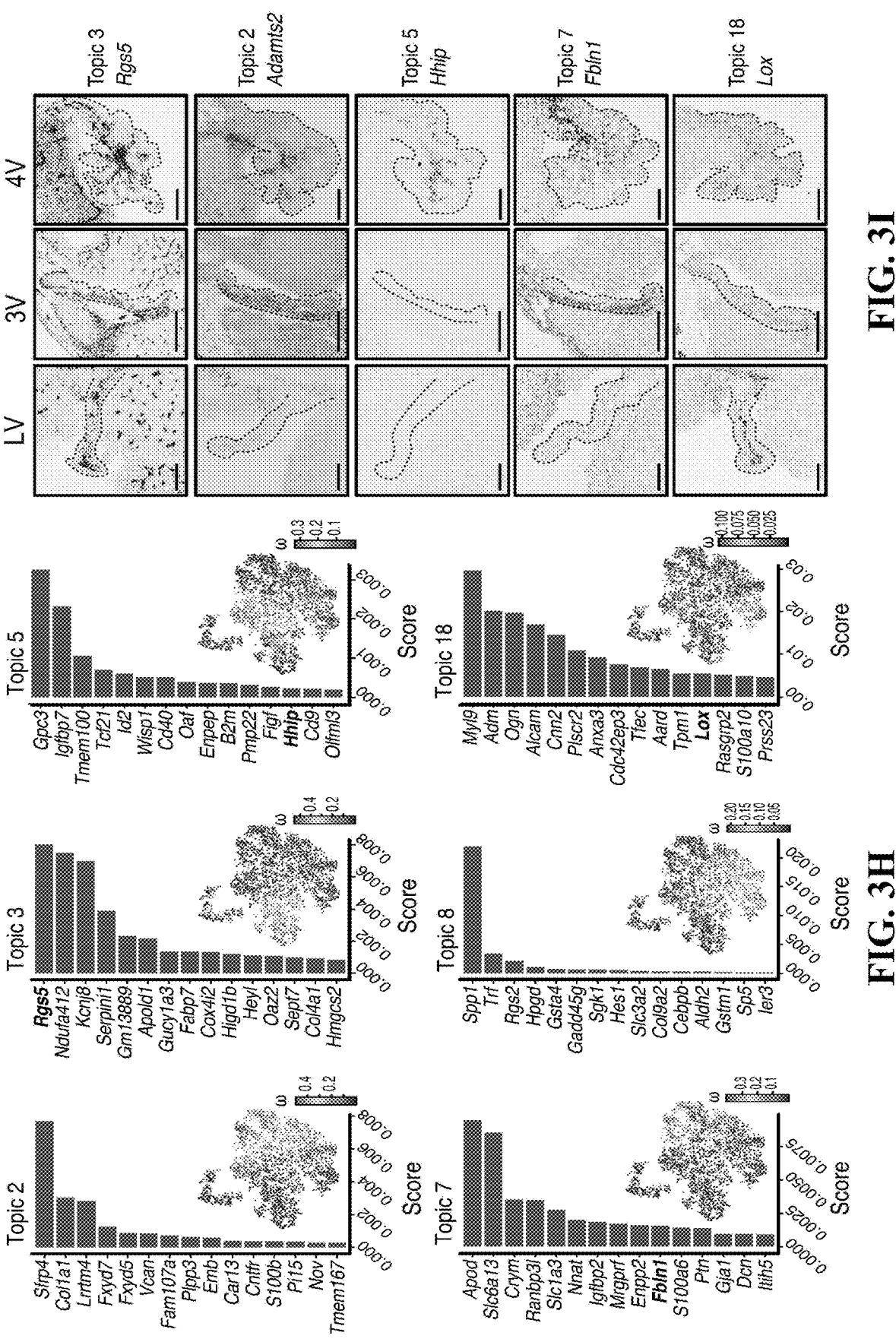
Figures 10G, 10H:
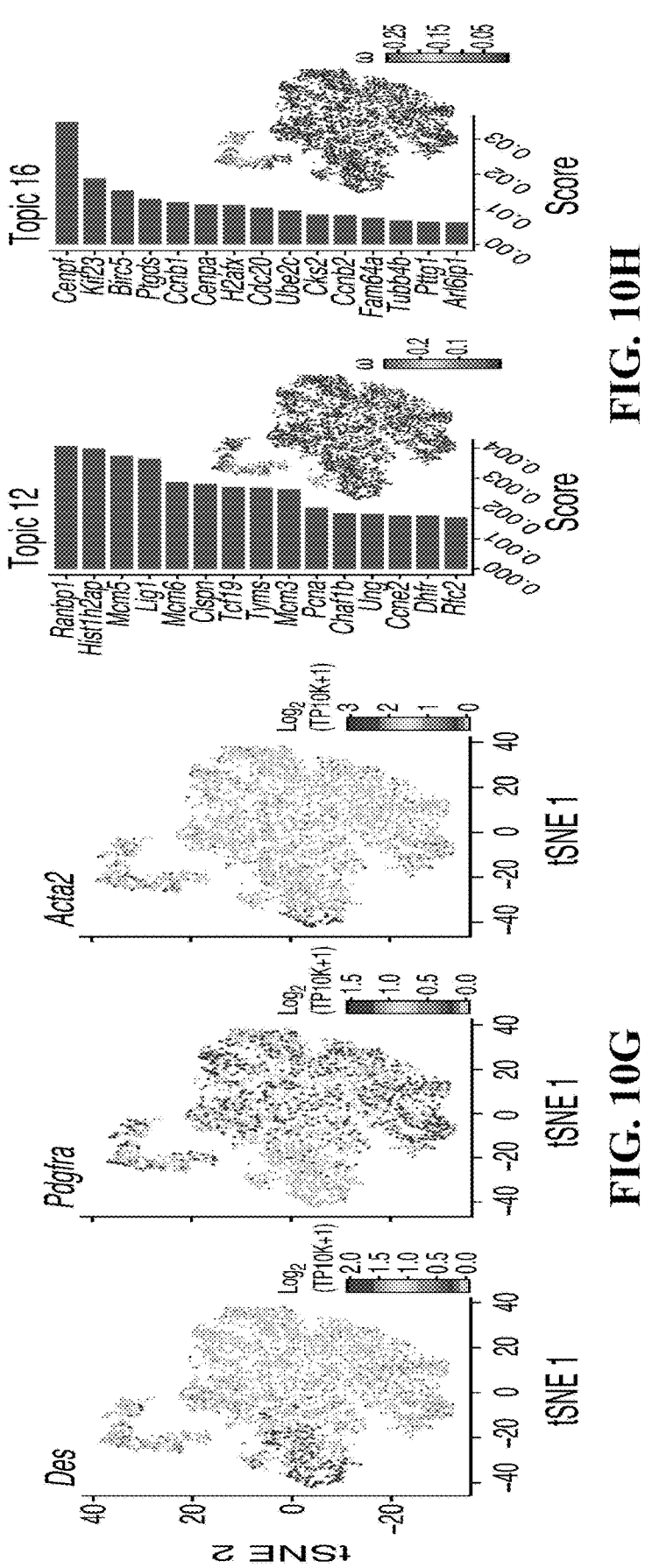
Figures 10I, 10J:
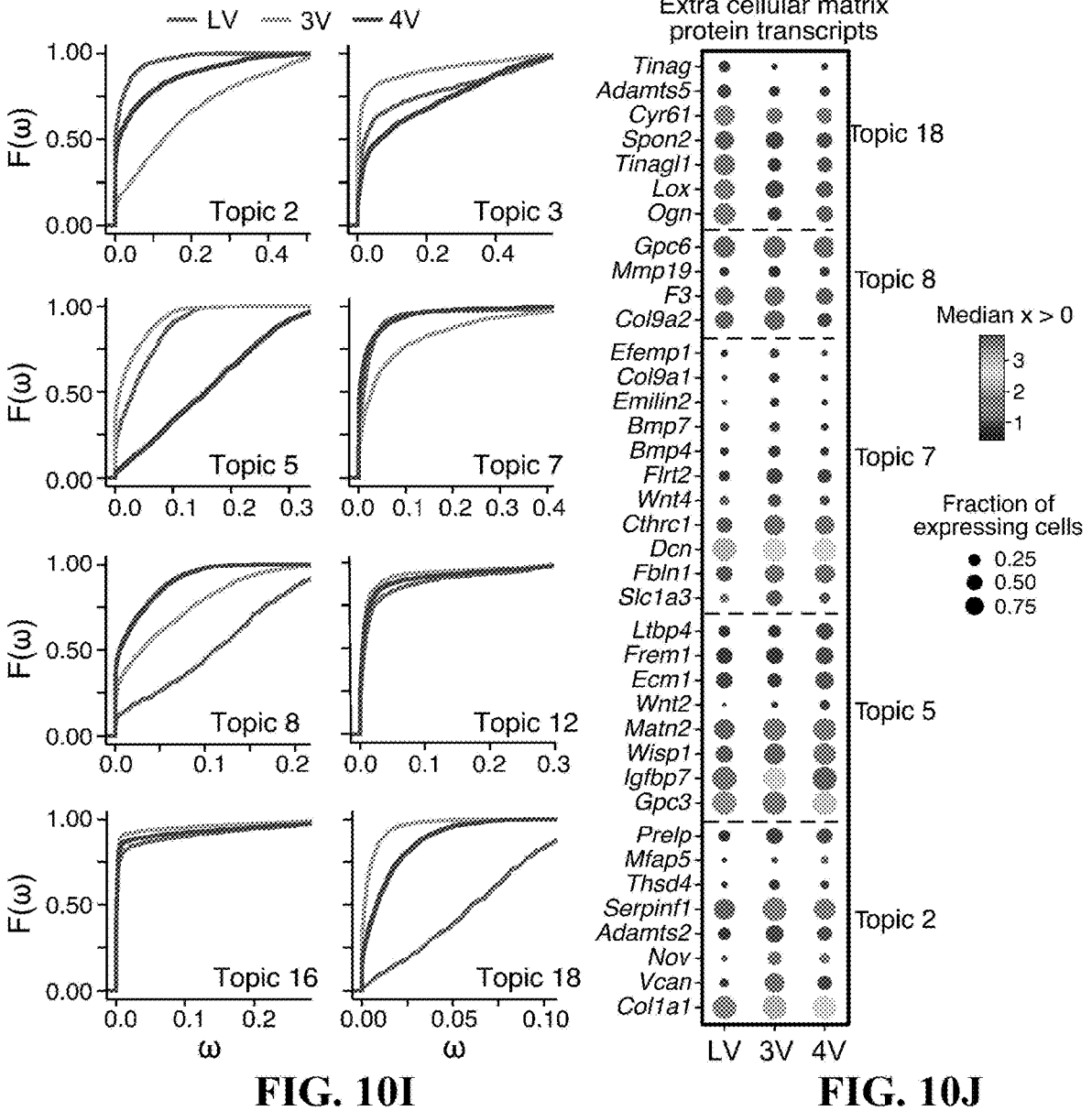
Figure 10K:
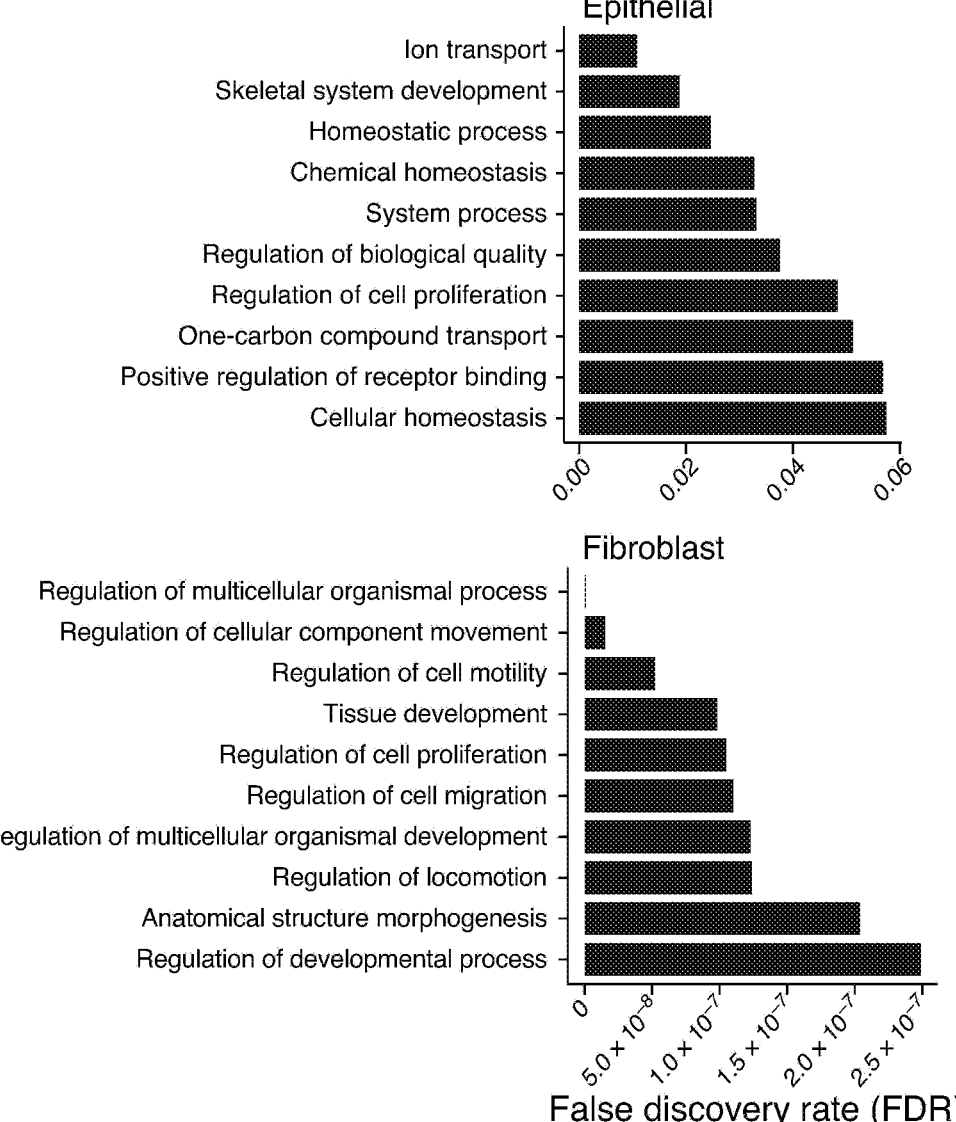

A similar analysis was used to characterize regionalized features in the large and heterogeneous population of mesenchymal cells in the ChP. Mesenchymal cells comprised of fibroblasts and mural cells (including pericytes and smooth muscle actin [SMA] positive cells) (FIG. 10G), consistent with cranial mesenchyme and neural crest contributions to the stromal space (Martik and Bronner, 2017; Wilting and Christ, 1989). While pericytes were similar in each ChP, topic modeling identified transcriptional programs of fibroblasts significantly enriched in specific ventricles; LV (Topic 8 and 18), 3V (Topic 2 and 7) and 4V (Topic 5) (FIGS. 3G, 3H, 10H, 10I), which were validated using published data (FIG. 3I, (Diez-Roux et al., 2011)). These topics revealed ventricle-dependent expression of genes encoding growth factors (Bmp4/7, Wnt4/2) and extracellular matrix proteins (FIGS. 3H, 10J, Table 3). For example, 4V ChP fibroblasts expressed high levels of genes encoding signaling molecules critical for hindbrain development (e.g., Hhip (Chuang and McMahon, 1999), Ptch1 (Huang et al., 2009), Rbp4 (Chang et al., 2016), and Wisp1, (FIG. 3H, 3I). More generally, genes involved in regulation of cell migration and tissue development were significantly enriched in region-associated topics in fibroblasts (FIG. 10K), underscoring the potential regulatory roles of fibroblasts in the developing ChP.

TABLE 3

| Embryo Fibroblast Top 50 Features - Top 50 genes in each topic revealed by topic modeling on mesenchymal cells of developing ChPs. | | | | | | | |
|---|---|---|---|---|---|---|---|
| topic_2 | topic_3 | topic_5 | topic_7 | topic_8 | topic_12 | topic_16 | topic_18 |
| Sfrp4 | Rgs5 | Gpc3 | Apod | Spp1 | Ranbp1 | Cenpf | Myl9 |
| Col1a1 | Ndufa4l2 | Igfbp7 | Slc6a13 | Trf | Hist1h2ap | Kif23 | Adm |
| Lrrtm4 | Kcnj8 | Tmem100 | Crym | Rgs2 | Mcm5 | Birc5 | Ogn |
| Fxyd7 | Serpini1 | Tcf21 | Ranbp3l | Hpgd | Lig1 | Ptgds | Alcam |
| Fxyd5 | G13889 | Id2 | Slc1a3 | Gsta4 | Mcm6 | Ccnb1 | Cnn2 |
| Vcan | Apold1 | Wisp1 | Nnat | Gadd45g | Clspn | Cenpa | Plscr2 |
| Fam107a | Gucy1a3 | Cd40 | Igfbp2 | Sgk1 | Tcf19 | H2afx | Anxa3 |
| Plpp3 | Fabp7 | Oaf | Mrgprf | Hes1 | Tyms | Cdc20 | Cdc42ep3 |
| Emb | Cox4i2 | Enpep | Enpp2 | Slc3a2 | Mcm3 | Ube2c | Tfec |
| Car13 | Higd1b | B2m | Fbln1 | Col9a2 | Pcna | Cks2 | Aard |
| Cntfr | Heyl | Pmp22 | S100a6 | Cebpb | Chaf1b | Ccnb2 | Tpm1 |
| S100b | Oaz2 | Figf | Ptn | Aldh2 | Ung | Fam64a | Lox |
| Pi15 | Sept7 | Hhip | Gja1 | Gstm1 | Ccne2 | Tubb4b | Rasgrp2 |
| Nov | Col4a1 | Cd9 | Dcn | Sp5 | Dhfr | Pttg1 | S100a10 |
| Tmem167 | Hmgcs2 | Olfml3 | Itih5 | Ier3 | Rfc2 | Arl6ip1 | Prss23 |
| Pygb | Slc12a2 | Rbp4 | Fam162b | Bicc1 | Dut | Cdc25c | Ehd3 |
| Adamts2 | Tspan15 | Col13a1 | Lsr | Xist | Mcm2 | Kif20a | X2310022B05Rik |
| Serpinf1 | Mcam | Laptm4b | Aldh1a2 | Ier5 | Hells | Cenpe | Sdpr |
| Gng11 | Mef2c | G0s2 | Pid1 | Zfand6 | Tipin | Tubb6 | Tinagl1 |
| Phlda2 | Abcc8 | Sct | Cthrc1 | Pdgfra | Fam111a | Sapcd2 | Tpm4 |
| Thsd4 | IFi203 | Camk2n1 | Nkd1 | Avl9 | Mcm7 | Prc1 | Angpt2 |
| Slc15a2 | P2ry14 | Foxl1 | Wnt4 | Ddc | Hat1 | Plk1 | Fhl2 |
| Pde6d | Pir | Pgf | Tpbg | F3 | Dscc1 | Nusap1 | Plvap |
| H19 | Gja4 | Klf14 | Flrt2 | Cox14 | Nasp | Cdca8 | Fhl1 |
| Sel1l3 | Nrarp | Matn2 | Igf1 | Clmp | Cdc45 | Ccna2 | Plat |
| Efnb1 | Timp3 | Slc38a5 | Cxcl12 | Gadd45b | Dctpp1 | Kif2c | Mt1 |
| Epha5 | Tbx3os1 | Limch1 | Atp1a2 | Appbp2 | Fen1 | Tacc3 | Arxes2 |
| Wfdc2 | Efhd2 | Bhlhe22 | Bmp4 | Wbp11 | Mcm4 | Cdca3 | Spon2 |
| Prdm6 | Esam | Isoc1 | Stra6 | Aldh6a1 | Dek | Hn1 | Arhgdib |
| Mfap5 | Tslp | Wnt2 | Bmp7 | Ctnna1 | Prim1 | Depdc1a | Flna |
| Crispld1 | Myo1b | Ecm1 | Itih2 | Dapk1 | Dtymk | Hmgb2 | Naaladl2 |
| Bet1 | Tmem178 | Gsn | Kcnk2 | Atg101 | Gins2 | Knstrn | Hacd4 |
| Prelp | Steap4 | Moxd1 | Ntm | Tmem205 | Gmnn | Hmmr | Fabp5 |
| Tubb2a | Mndal | Asb4 | Edn3 | Fam20a | Zfp367 | Racgap1 | Cyr61 |
| Khk | Aspn | Frem1 | Mpped2 | Rin2 | Rpa2 | Aurka | Hspb1 |
| Stard3nl | Rasl12 | Vstm4 | Mdga2 | Nisch | Atad2 | Tpx2 | Amotl2 |

TABLE 3-continued

Embryo Fibroblast Top 50 Features - Top 50 genes in each topic revealed
by topic modeling on mesenchymal cells of developing ChPs.

| topic_2 | topic_3 | topic_5 | topic_7 | topic_8 | topic_12 | topic_16 | topic_18 |
|---|---|---|---|---|---|---|---|
| Ntng1 | Des | S100a13 | Emilin2 | Isyna1 | Tubg1 | H1f0 | Serpinb6b |
| Smim5 | Ifngr2 | Mcc | Tfap2b | Irf2bpl | Rpa1 | Kif22 | Bst2 |
| Cdh11 | Ebf1 | Ppp1r3d | Cited1 | Mat2a | Tk1 | Stmn1 | Adamts5 |
| Tmem176b | Pea15a | Fam198b | Msx1 | C6 | Dnmt1 | Lockd | Gpx3 |
| Stk39 | Msn | Ltbp4 | Tubb2b | Nr4a2 | Mms221 | Fam83d | Tagln |
| Rab15 | Tbx2 | Itga8 | Gap43 | Sphk1 | Mrpl18 | Tuba1c | Gstm2 |
| Atp2b1 | Raph1 | Gm5127 | Agtr2 | Bambi | Chafla | Mki67 | Tspan4 |
| Thbs3 | Vasp | Sys1 | Ptgdr | G3bp2 | Fignl1 | Cdkn3 | Dmd |
| Ppp1r3b | Cd93 | Fam217b | Col9a1 | Ccnd3 | Skp2 | Mis18bp1 | Tinag |
| Msx2 | Pde8b | Clec14a | Sidt1 | Eml4 | Nxt1 | Nuf2 | Smap2 |
| Gbp8 | Vtn | Myadm | Mthfd11 | Ankrd50 | Rad51ap1 | Ckap2 | Dhrs3 |
| Pcdh7 | Foxs1 | Ptger3 | Efemp1 | Mrap | Nap1l1 | Rnf26 | Ndufa4 |
| Oat | Mustn1 | S100a16 | Arhgap20 | Mmp19 | Rnaseh2a | Bub1b | Dusp9 |
| Pgm5 | Septl1 | Hoxa2 | Nbl1 | Gpc6 | Cdk4 | Nucks1 | Serping1 |

Homeostatic Macrophage Diversity within and Across the Developing ChP

Figure 11A:
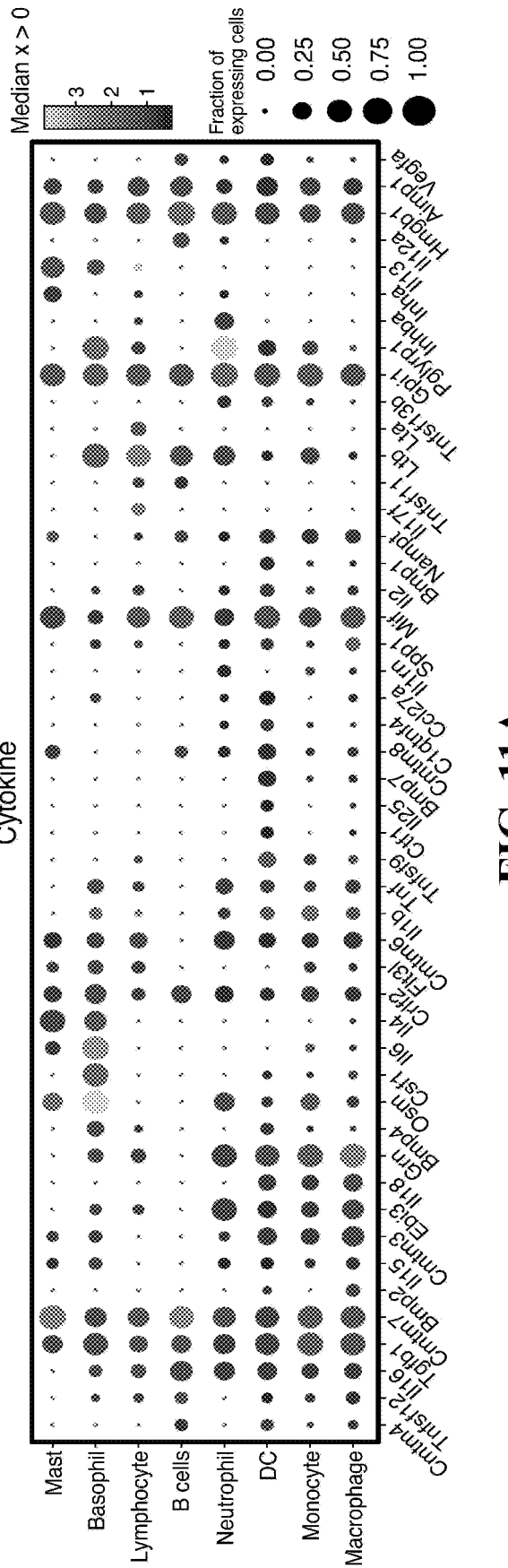
FIG. 11A-11D—Cytokine and chemokine expression across ChP immune cells.
Figures 11B, 11C:
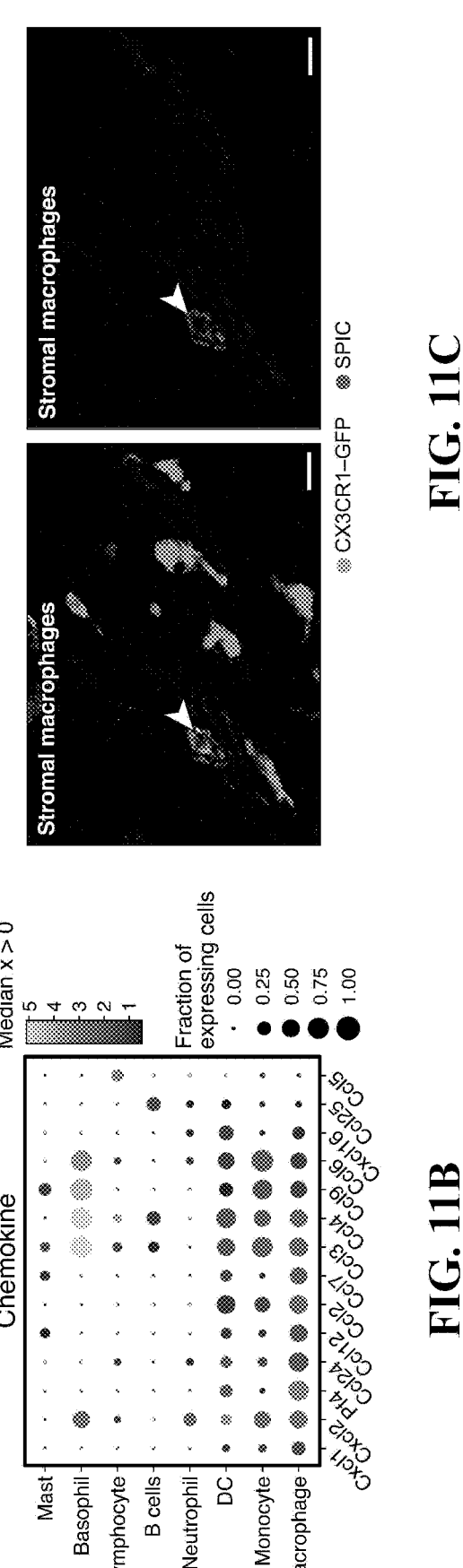

The ChP is an entry point for immune cells and immune signaling into the central nervous system in health and disease (Ghersi-Egea et al., 2018; Schwartz and Baruch, 2014). Recent studies have identified a diversity of immune cells in the choroid plexus in adult (Jordao et al., 2019) and postnatal (Li et al., 2019) brain, yet the diversity of immune cells within and across the developing ChPs is not well understood. Eight subsets of immune cells were identified: B cells, lymphocytes, macrophages, basophils, mast cells, dendritic cells, monocytes and neutrophils (FIGS. 4A, B), each expressing specific immune regulatory genes encoding cytokines, chemokines, and complement components (FIGS. 11A, 11B). For example, basophils expressed high levels of proinflammatory chemokines (Ccl3, Ccl4, Ccl6, Ccl9, FIGS. 11A, 11B), suggesting that they may provide signals to trigger activation of signaling cascades necessary for leukocyte recruitment.

Figures 4C, 4D, 4E:
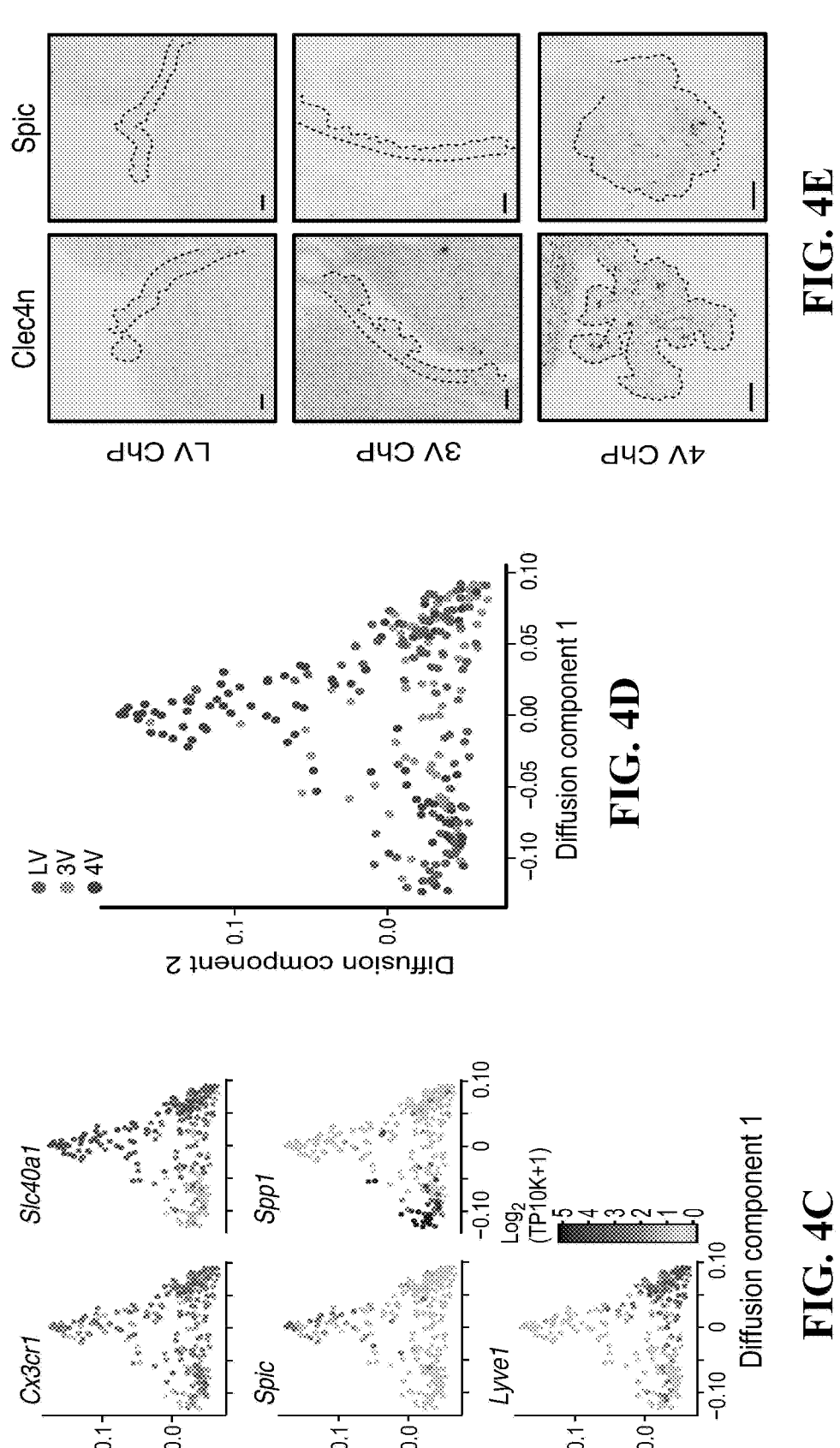
Figure 11D:
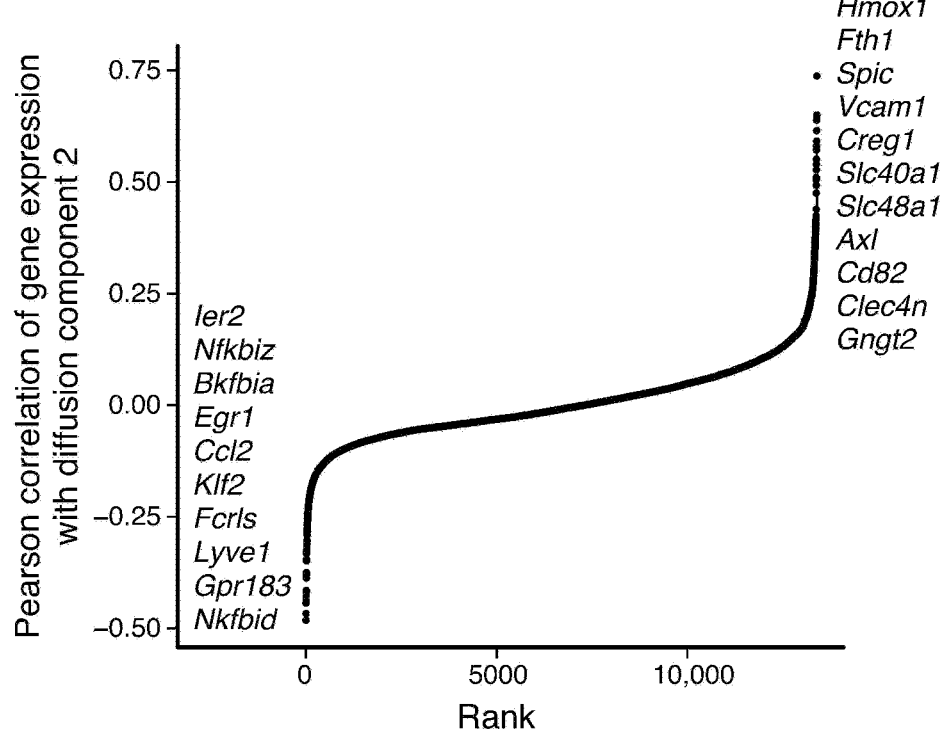

Cx3cr1+CsfJR+ macrophages were the largest class of immune cells in the ChP and showed graded gene expression patterns by diffusion map embedding (FIG. 4C, STAR Methods), spanning states between three "archetypes". All archetypes expressed Mrc1 and CD68, which are involved in macrophage phagocytosis. Genes differentially expressed between archetypes included the hyaluronan receptor Lyve1 (Lim et al., 2018); Spp1, a potential regulator of phagocytosis in the brain (Hammond et al., 2019); Slc40al, an iron transporter; and Spic, which marks red pulp macrophages (Haldar et al., 2014) and bone marrow macrophages (Kohyama et al., 2009) (FIGS. 4C, 11C). A subset of Slc40al macrophages expressed Spic and Clec4n (corresponding to recently described Clec4n* macrophages in postnatal ChP (Li et al., 2019)), and was enriched in the 4V ChP (FIG. 4D, 4E, 11D). This highlights potential regionalization of ChP macrophages across the developing brain ventricles.

Figures 4F, 4G, 4H, 4I:
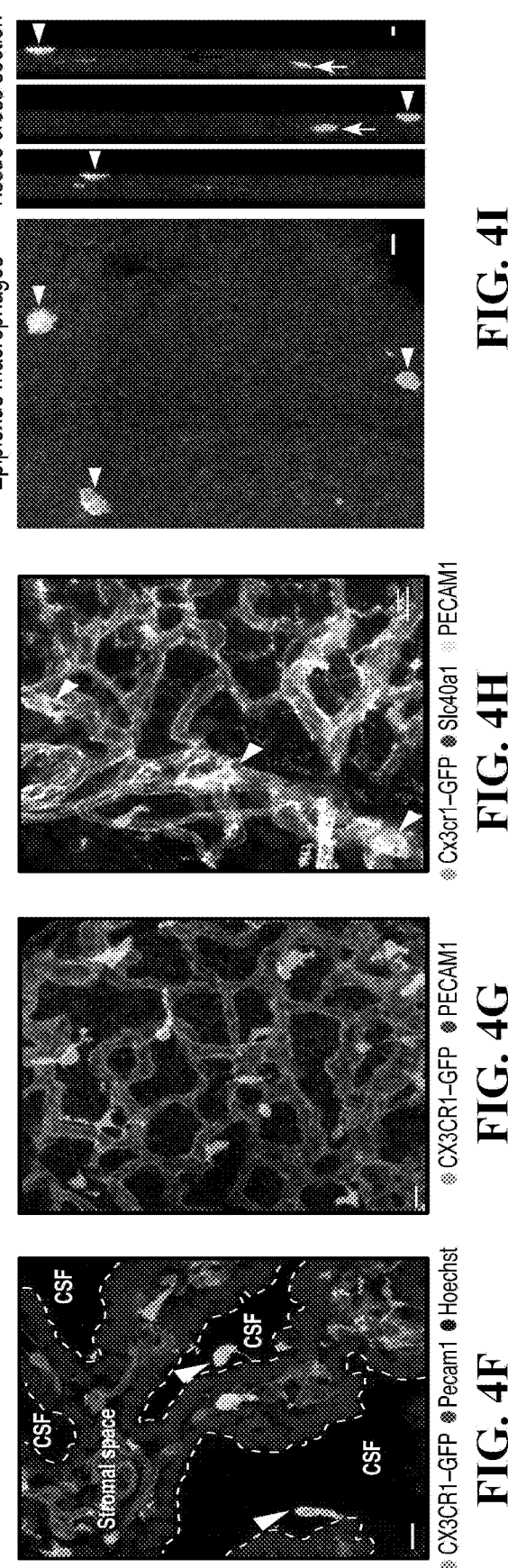

The archetypal expression patterns are also differentially associated with distinct spatial niches in the ChP, either basally under the epithelial cell monolayer or on the apical surface (e.g., epiplexus positions: FIG. 4F). Imaging the distribution of macrophages using Cx3cr1-GFP transgenic mice (STAR Methods) revealed a "tiled" pattern of cells in proximity with blood vessels (FIG. 4G). A subset of these macrophages stained for Slc40a1 Ferroportin, suggesting potential roles in regulating local iron homeostasis (FIG. 4H). Of the Cx3cr1+ macrophages located on the apical ChP surface, a subset expressed Lyve1, potentially revealing molecular identity of CSF-facing Kolmer/epiplexus cells (FIG. 4I). Together, this immune cell diversity in the ChP provides a platform for investigating the multiple roles that immune cells have in the ChP in homeostasis and in disease conditions.

Figures 12A, 12B, 12C:
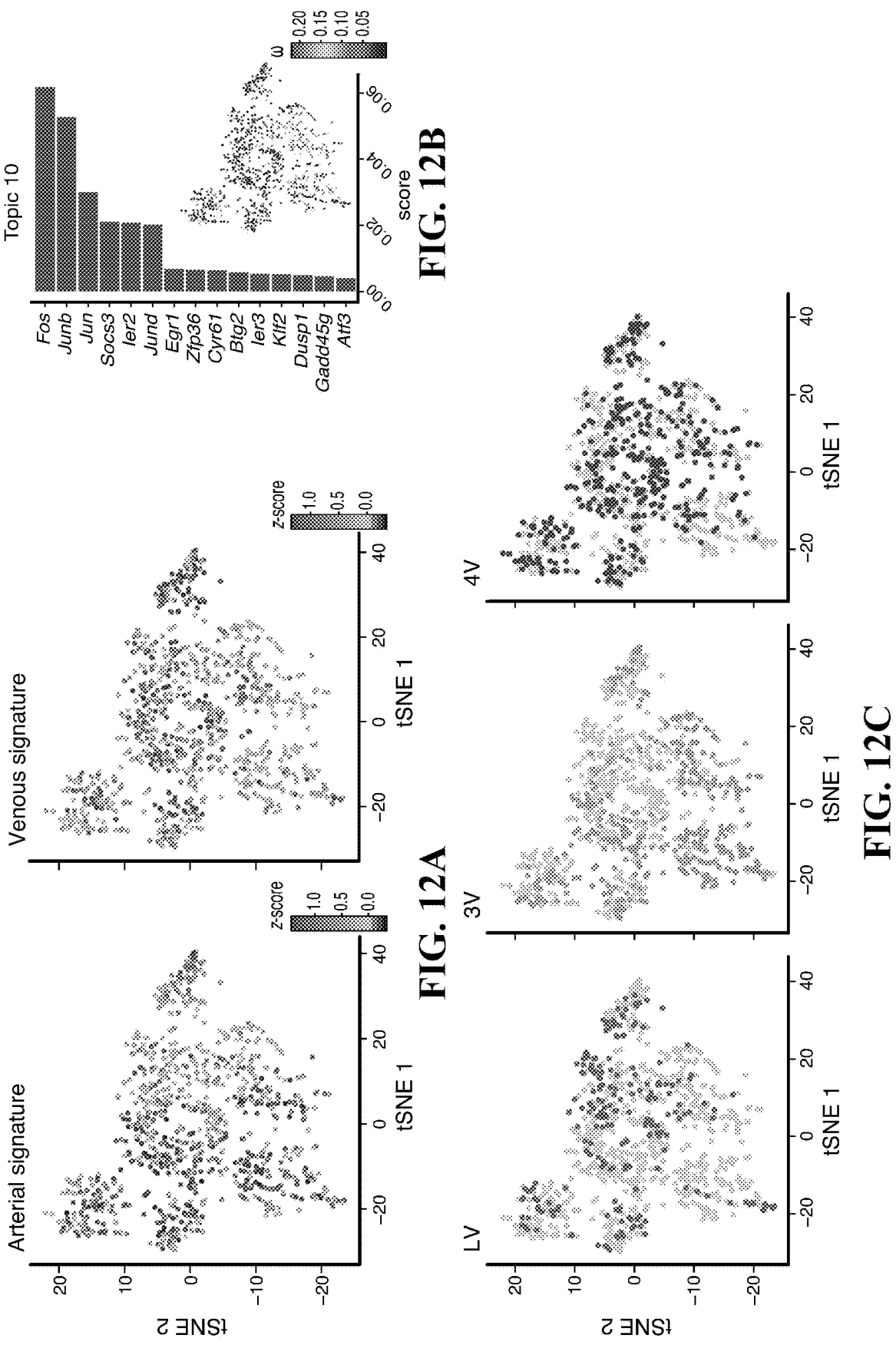
FIG. 12A-12F—Molecular identities of ChP endothelial cells.
Figure 12D:
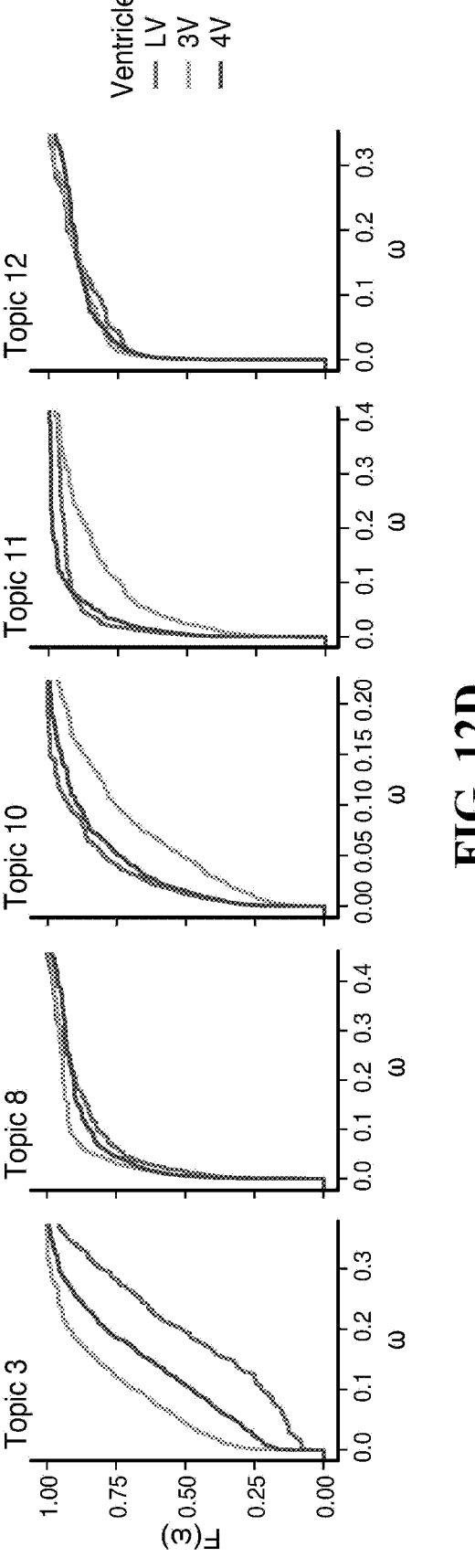

Arterio-Venous Zonation and Blood Brain Barrier Protein Expression in ChP Vasculature The choroidal artery delivers blood to each ChP (Damkier et al., 2013), but the identity, structure and development of vascular cell types in the ChP remain largely unknown. Using topic modeling, transcriptional programs associated with arterial (Topic 8), venous (Topic 11) and arteriolar gene expression (Topic 3) (FIGS. 5A, 12A, 12B, Table 4) were found. In contrast to epithelial cells and fibroblasts, little evidence for regionalization of endothelial cells across ventricles was identified (FIGS. 12C, 12D).

TABLE 4

Top 50 genes in each topic revealed by topic modeling
on endothelial cells of developing ChPs.

| topic_3 | topic_8 | topic_10 | topic_11 | topic_12 |
|---|---|---|---|---|
| Sparc | Gja4 | Fos | Fth1 | Birc5 |
| Esm1 | Gja5 | Junb | Cldn5 | Top2a |
| Gpihbp1 | Glul | Jun | Slc7a5 | X2810417H13Rik |
| Sparcl1 | Stmn2 | Socs3 | Tmsb10 | Hmgb2 |
| 43712 | Egfl8 | Ier2 | Sepp1 | Fam64a |
| Mest | Vim | Jund | Slc38a5 | Tuba1b |
| Igfbp7 | X8430408G22Rik | Egr1 | Slc3a2 | Rrm2 |
| Scarb1 | Tm4sf1 | Zfp36 | Slc7a1 | Ccnb2 |
| Mfge8 | Col18a1 | Cyr61 | Hs3st1 | Nuf2 |
| Sh3bp5 | Cxcl12 | Btg2 | Mfsd2a | Cenpa |
| Kcne3 | Fbln2 | Ier3 | Ptgis | Cdc20 |
| Gpx3 | Bmx | Klf2 | Slc1a4 | Tk1 |
| Trp53i11 | Cav1 | Dusp1 | Gatm | Nusap1 |
| Plvap | Sox17 | Gadd45g | Pglyrp1 | Pbk |
| Eva1b | H19 | Atf3 | Grap | Tubb5 |
| Hlx | Sat1 | Ppp1r15a | Lefl | Ccna2 |
| Tmem204 | Hey1 | Fosb | Fgfr4 | Cdca8 |
| Sult1a1 | Nebl | Nr4a1 | Foxq1 | H2afz |
| Gimap6 | Sema3g | Apold1 | Lsr | H1f0 |
| Tspan15 | Cthrc1 | Csrnp1 | Mmrn1 | H2afx |
| Robo4 | Unc5b | Rhob | Slc39a8 | Cks1b |
| Tnfrsf11b | Ssu2 | Pnrc1 | Best1 | Kif11 |
| Cd3001g | Itgal | Klf6 | Slc35f2 | Cenpf |
| Tagln2 | Rbp7 | Nr4a2 | Tmem252 | Spc24 |
| Arhgap18 | Azin1 | Sgk1 | Maoa | Racgap1 |
| Mpzl1 | Amd1 | Bhlhe40 | Aplnr | Cks2 |
| Adgrl4 | Lims2 | Adamts1 | Prcp | Hist1h2ap |
| Ivns1abp | Ecscr | Plk2 | St3gal6 | Lrr1 |
| Gm12002 | Crip2 | Irf1 | Mfsd7c | Prc1 |

TABLE 4-continued

| Top 50 genes in each topic revealed by topic modeling on endothelial cells of developing ChPs. | | | | |
|---|---|---|---|---|
| topic_3 | topic_8 | topic_10 | topic_11 | topic_12 |
| Dcbld1 | Kctd10 | Rasd1 | Spock2 | Cdk1 |
| Anxa6 | Myo10 | Nfkbiz | Rhox5 | Plk1 |
| Mgll | Ptprr | Dusp6 | Arl4a | Smc4 |
| Dok3 | Vegfc | Dnajb1 | Trf | Lmnb1 |
| Gng2 | Cdkn1c | Klf4 | Gm694 | Tyms |
| Pde2a | Tpd52 | Gm26802 | Ocln | Ccnb1 |
| Kcna5 | Ebf1 | Rlim | Tsc22d1 | Aurkb |
| Ciapin1 | Tmem255b | Fam174b | Foxf1 | Sapcd2 |
| F2r | Mos | Cxcl1 | Fendrr | X2700094K13Rik |
| Ptp4a3 | Alas1 | Egr2 | Slc40a1 | Cenpe |
| Oaz2 | Mecom | Trib1 | Rassf9 | Ube2c |
| Gja1 | Pcsk5 | Zfp36l1 | Cadm1 | Pttg1 |
| Ppp1r2 | Mannr | Rcan1 | Tln2 | Kif22 |
| Lrrfip1 | Igfbp3 | Cebpb | Stc2 | Tacc3 |
| Eng | Slc26a10 | Tnfsf8 | Fam13a | Knstrn |
| Cdc42ep3 | Ptchd1 | Sertad1 | Reep1 | Hn1 |
| Pcdh17 | Hrg | Neurl3 | Tnfrsf19 | Cenpm |
| Zdhhc20 | C2cd4c | Dusp5 | Prnp | Spc25 |
| Tprgl | Tubb2b | Gm26571 | Tmem182 | Tubb4b |
| Plpp3 | Adgre5 | Stx3 | Slc38a3 | Tpx2 |
| Mmd | Icam2 | Gem | Net1 | Aunip |

Figure 5A:
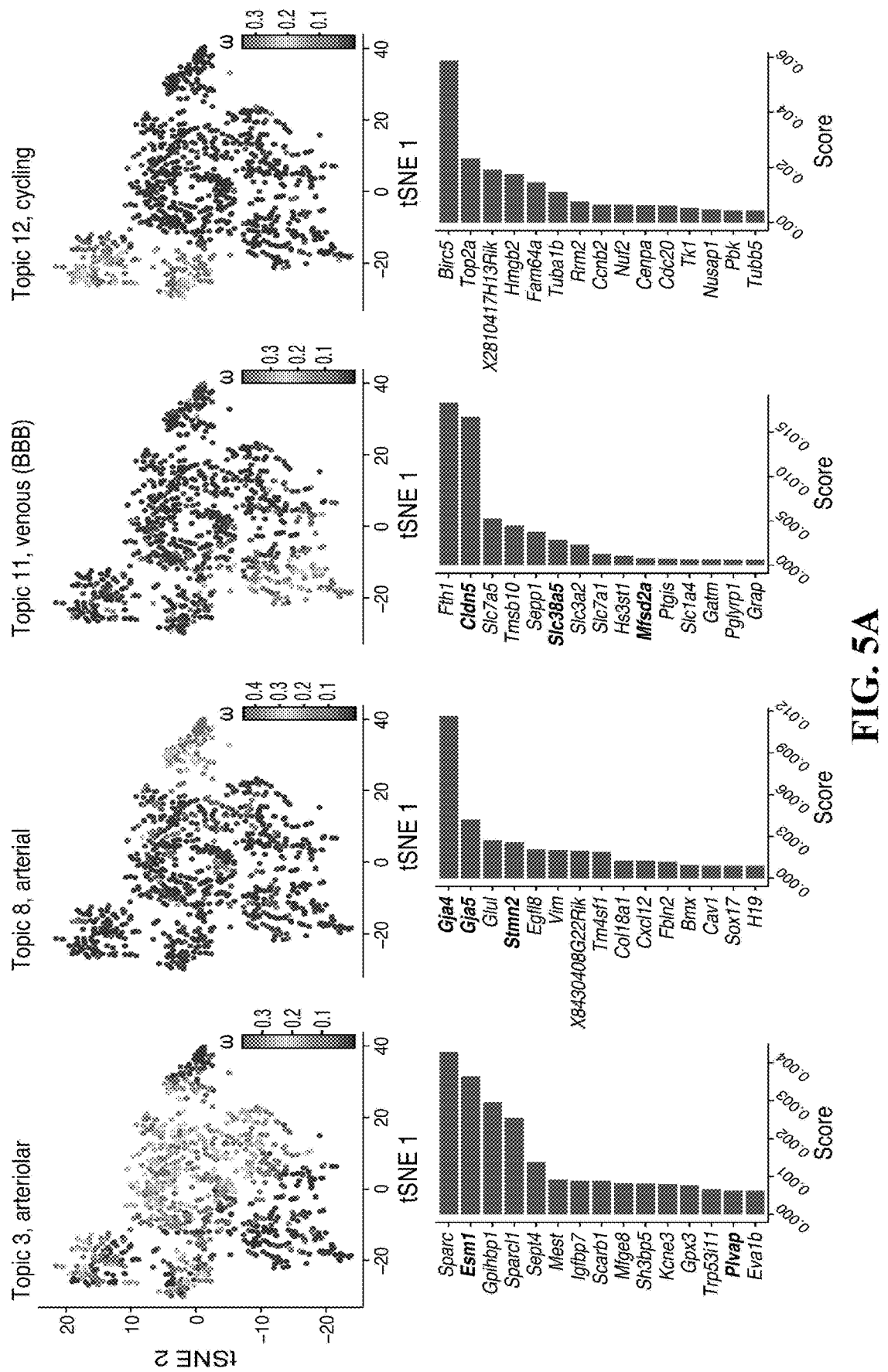
FIG. 5A-5D—Vascular identity and BBB proteins are zonated within the ChP.
Figures 5B, 5C, 5D:
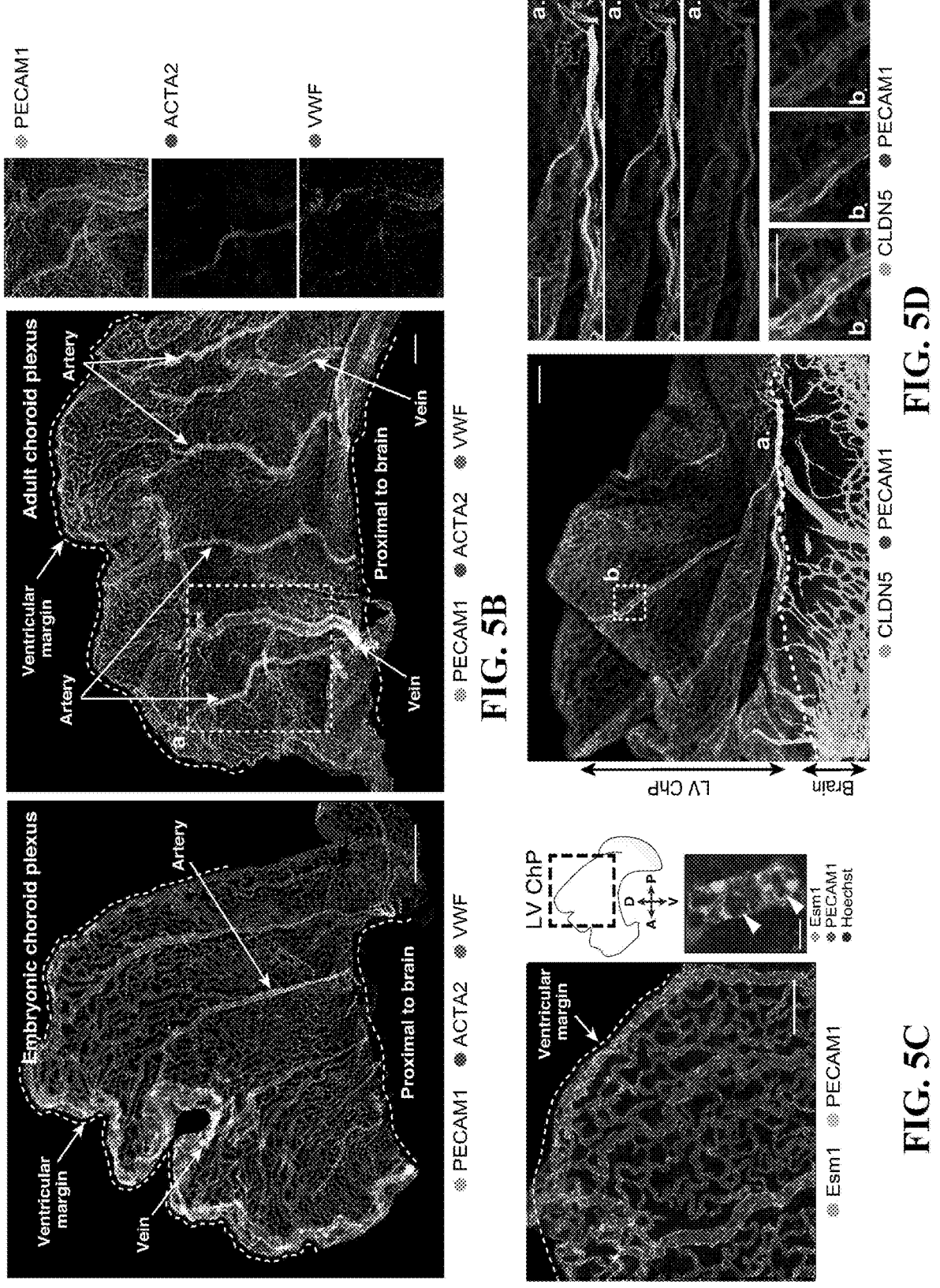
Figures 12E, 12F:
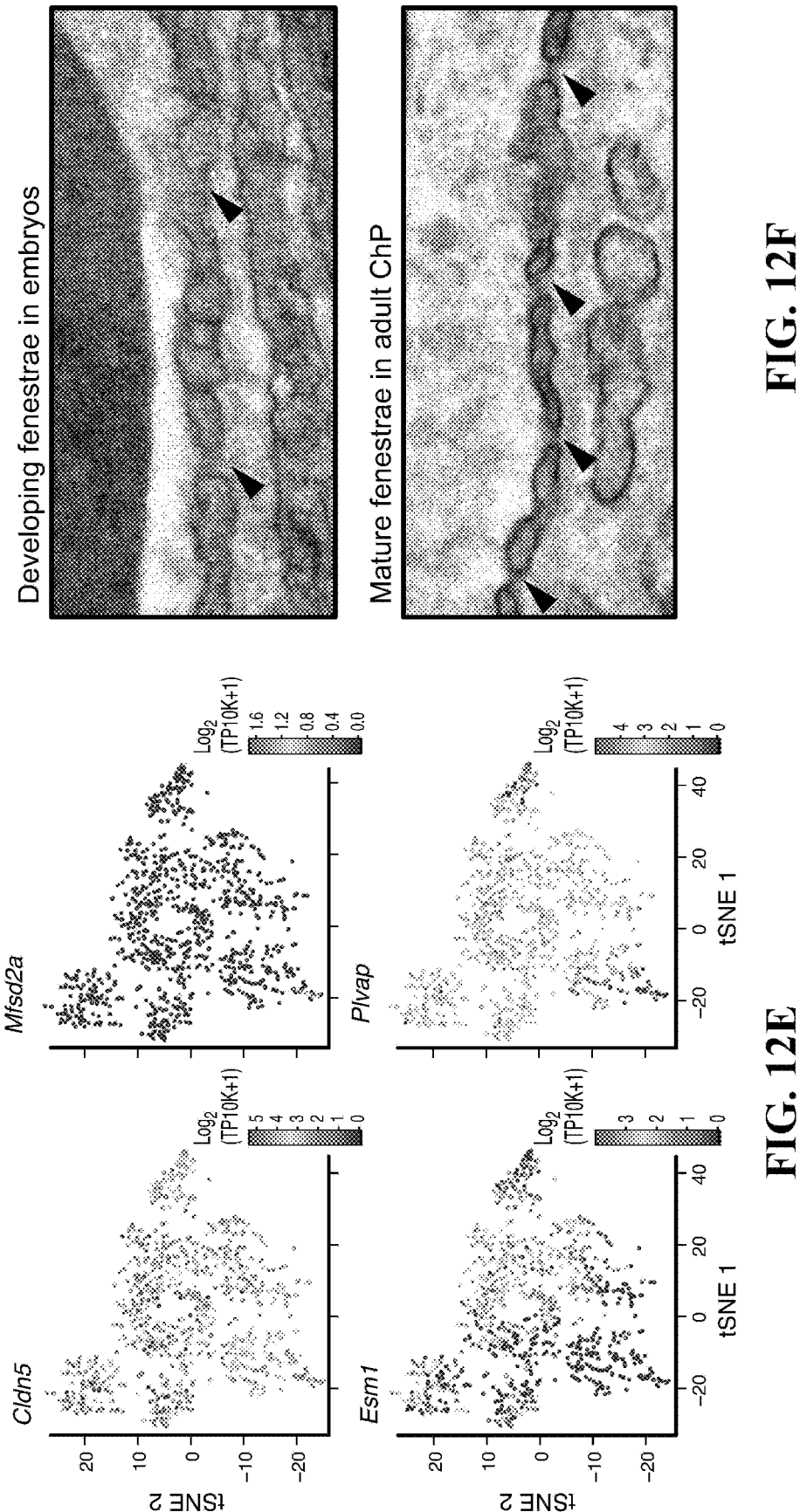

Applicants spatially mapped the developing arterio-venous zonation in the LV ChP in whole explants, by combining the pan-endothelial marker PECAM1 with markers for arteries (Acta2+, Vwf+) and veins (Acta2−, Vwf+) (Vanlandewijck et al., 2018), revealing arterial vessels oblique to the plexus and venous vessels along the ventricular margin of the tissue (FIG. 5B). By comparison, in the adult ChP there were regularly spaced arteries and veins across and expanded capillary-like network along the ventricular margin (FIG. 5B). This is reminiscent of the radially spreading vascular plexus in the developing retina (Fruttiger, 2002). The immature endothelial marker, Esm1, which marks angiogenic cells (Aitkenhead et al., 2002; Rocha et al., 2014) was expressed in endothelial cells along the ventricular margin of the developing LV ChP (FIG. 5C), suggesting these cells may contribute to the expansion of LV ChP during maturation. Both Esm1 and Plvap, which marks diaphragm of fenestrae in fenestrated endothelial cells (Herrnberger et al., 2012), scored highly in topic 3, suggesting the presence of developing fenestrations in the ChP as early as E16.5 (Stan et al., 1999) (FIGS. 5A, 12E, 12F).

Surprisingly, the non-angiogenic endothelial cells expressed blood brain barrier proteins (topic 11), even though ChP lacks a classic blood brain barrier. These included Cldn5 and Mfsd2a, which was expressed in cells with particularly high Cldn5 expression (Ben-Zvi et al., 2014) (FIGS. 5A, 12E). CLDN5 was expressed in endothelial cells in situ and was enriched in the brain and along the ChP region proximal to the brain (FIG. 5D). Such BBB-like expression may be a transient developmental feature of the ChP, analogous to that observed in the developing vasculature along retinal pigmented epithelium (Kojima et al., 2002).

A Network of Potential Cellular Crosstalk in the ChP

Figure 6B:
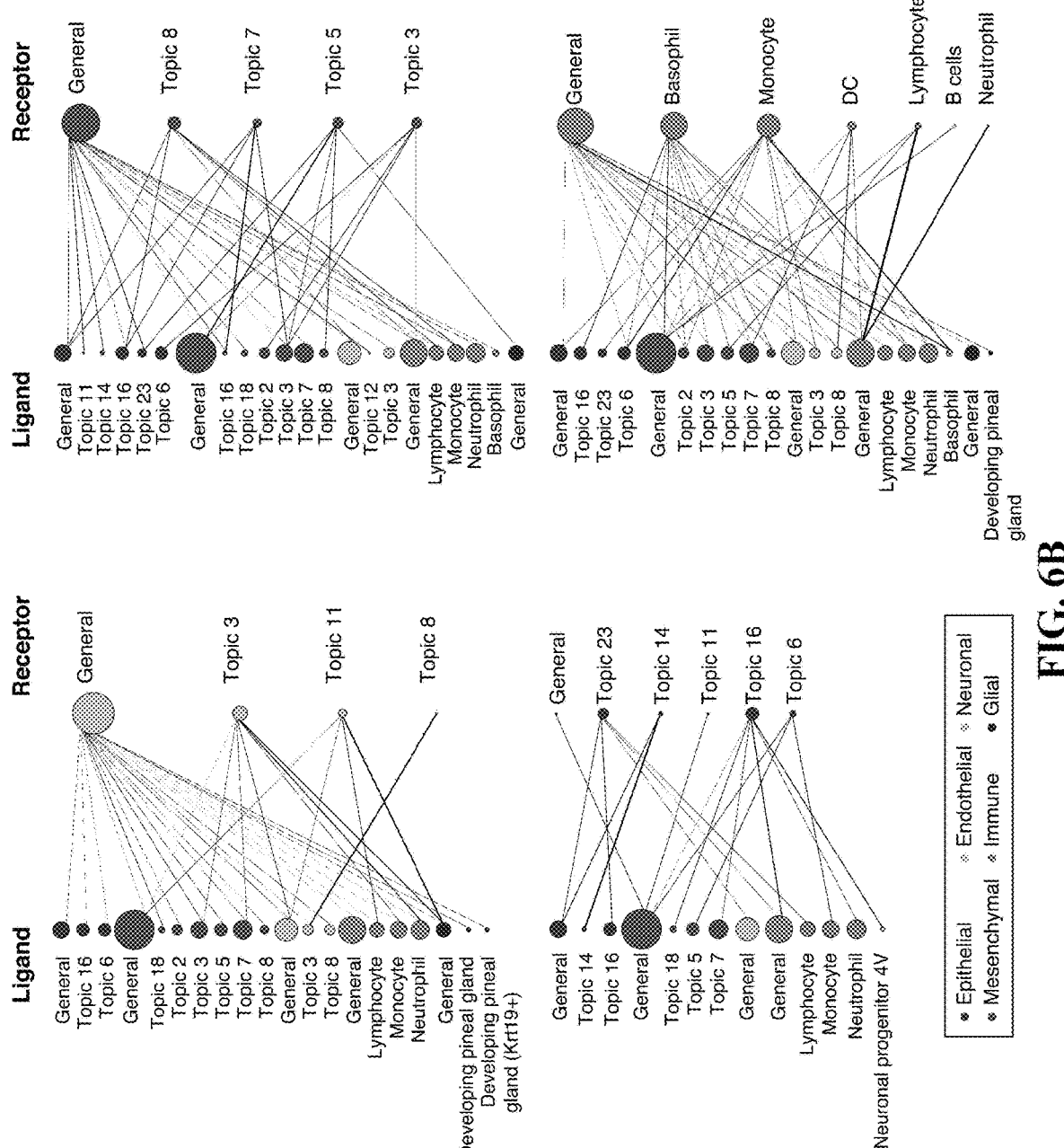
Figures 13A, 13B:
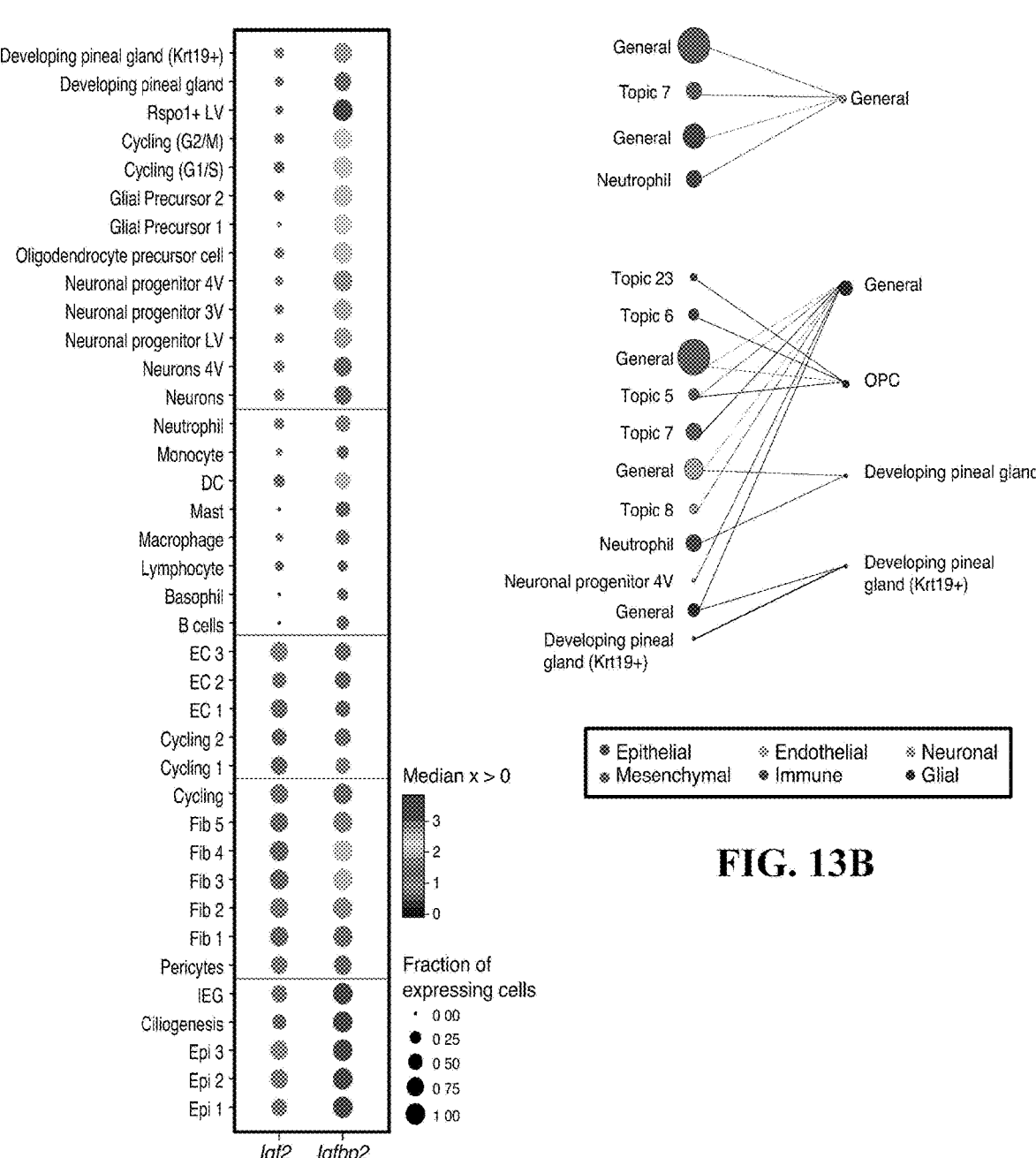
FIG. 13A-13B—Neuronal and glia-like cells do not play significant contribution in cellular crosstalk in the developing choroid plexus.

Each of the diverse cell types in the ChP expressed a large number of genes encoding secreted proteins, many with potential to impact cell-cell interactions within the ChP or the composition of the CSF. In addition to epithelial cells, a recognized source of CSF-distributed factors, additional potential cellular sources were identified for proteins that have been measured in CSF (FIG. 6A). For example, Insulin like growth factor 2 (Igf2), which is secreted into the CSF and regulates progenitor proliferation in the developing cerebral cortex (Lehtinen et al., 2011), was highly expressed in endothelial and mesenchymal cell subsets in addition to epithelial cells (FIG. 13A). A cell-cell interaction network based on cognate receptor-ligand pairs (STAR Methods), showed that endothelial and immune cells potentially receive much greater signal input from other cell types compared to epithelial, neuronal and glial subsets. Further, mesenchymal cells expressed ligands for cognate receptors found on all the major cell types (FIGS. 6B, 13B, Table 5).

TABLE 5

| Identified Interactions in Embryo - cognate ligand-receptor pairs. | | | | | |
|---|---|---|---|---|---|
| Receptor | Ligand | Ligand.Type | Receptor.Type | Cell_Type_Specificity.Ligand | Subtype.specificity.Ligand |
| ACVR2B | INHBA | Ligand | Receptor | Immune | Immune_Neutrophil |
| ACVR2B | SNX2 | Ligand | Receptor | Immune | Immune_General |
| ACVR2B | BMP7 | ECM/Ligand | Receptor | Fibroblast | Fibroblast_Topic 7 |
| ADRB2 | SLC9A3R1 | Ligand | Receptor | Immune | Immune_Lymphocyte |
| ADRB2 | PON2 | Ligand | Receptor | Endothelial | Endothelial_General |
| ADRB2 | IL1B | Ligand | Receptor | Immune | Immune_General |
| ADRB2 | ALDOA | Ligand | Receptor | Immune | Immune_Basophil |
| AGTR2 | ACE | Ligand | Receptor | Epithelial | Epithelial_Topic 16 |
| AGTR2 | TIMP3 | ECM/Ligand | Receptor | Fibroblast | Fibroblast_Topic 3 |
| ANXA2 | CTSB | Ligand | ECM/Receptor | Immune | Immune_General |
| ANXA2 | PCSK9 | Ligand | ECM/Receptor | Neuronal | Neuronal_Neuronal progenitor 4V |
| ANXA2 | ANXA1 | Ligand | ECM/Receptor | Immune | Immune_General |
| ANXA2 | FN1 | ECM/Ligand | ECM/Receptor | Fibroblast | Fibroblast_General |
| ANXA2 | PLAT | Ligand | ECM/Receptor | Fibroblast | Fibroblast_Topic 18 |
| APLNR | APLN | Ligand | Receptor | Endothelial | Endothelial_General |
| APLNR | APLN | Ligand | Receptor | Endothelial | Endothelial_General |
| AQP1 | EFEMP2 | ECM/Receptor/Ligand | Receptor | Fibroblast | Fibroblast_General |
| AQP1 | EFEMP2 | ECM/Receptor/Ligand | Receptor | Fibroblast | Fibroblast_General |
| CCR1 | CCL7 | Ligand | Receptor | Immune | Immune_General |
| CCR1 | CCL2 | Ligand | Receptor | Immune | Immune_General |
| CCR1 | CCL4 | Ligand | Receptor | Immune | Immune_General |
| CCR2 | CCL7 | Ligand | Receptor | Immune | Immune_General |
| CCR2 | CCL2 | Ligand | Receptor | Immune | Immune_General |
| CD14 | LBP | Ligand | Receptor | Epithelial | Epithelial_General |
| CD14 | LTF | Ligand | Receptor | Immune | Immune_Neutrophil |
| CD36 | COL2A1 | ECM/Ligand | Receptor | Glial | Glial_General |

TABLE 5-continued

Identified Interactions in Embryo - cognate ligand-receptor pairs.

| | | | | | |
|---|---|---|---|---|---|
| CD36 | COL1A1 | ECM/Ligand | Receptor | Fibroblast | Fibroblast_Topic 2 |
| CD36 | COL4A1 | ECM/Ligand | Receptor | Fibroblast | Fibroblast_Topic 3 |
| CD36 | FN1 | ECM/Ligand | Receptor | Fibroblast | Fibroblast_General |
| CD36 | COL1A1 | ECM/Ligand | Receptor | Fibroblast | Fibroblast_General |
| CD36 | COL6A1 | ECM/Ligand | Receptor | Fibroblast | Fibroblast_General |
| CD36 | THBS1 | ECM/Ligand | Receptor | Immune | Immune_Monocyte |
| CD40 | ERP44 | Ligand | Receptor | Fibroblast | Fibroblast_General |
| CD40 | SPP1 | Ligand | Receptor | Fibroblast | Fibroblast_Topic 8 |
| CD40 | CALR | ECM/Ligand | Receptor | Fibroblast | Fibroblast_General |
| CD40 | IGFBP5 | Ligand | Receptor | Glial | Glial_General |
| CD44 | HGF | Ligand | Receptor | Immune | Immune_Basophil |
| CD44 | FN1 | ECM/Ligand | Receptor | Fibroblast | Fibroblast_General |
| CD44 | COL1A1 | ECM/Ligand | Receptor | Fibroblast | Fibroblast_General |
| CD44 | COL1A1 | ECM/Ligand | Receptor | Fibroblast | Fibroblast_Topic 2 |
| CD44 | VCAN | ECM/Ligand | Receptor | Fibroblast | Fibroblast_Topic 2 |
| CD44 | IGFBP3 | Ligand | Receptor | Endothelial | Endothelial_General |
| CD44 | IGFBP3 | Ligand | Receptor | Endothelial | Endothelial_Topic 8 |
| CD44 | SPP1 | Ligand | Receptor | Fibroblast | Fibroblast_Topic 8 |
| CD74 | CTSF | Ligand | Receptor | Glial | Glial_Developing pineal gland |
| CD79A | FN1 | ECM/Ligand | Receptor | Fibroblast | Fibroblast_General |
| CD93 | COL4A1 | ECM/Ligand | Receptor | Fibroblast | Fibroblast_Topic 3 |
| CD93 | COL4A1 | ECM/Ligand | Receptor | Fibroblast | Fibroblast_Topic 3 |
| CD93 | COL4A3 | ECM/Ligand | Receptor | Epithelial | Epithelial_Topic 6 |
| CD93 | COL4A3 | ECM/Ligand | Receptor | Epithelial | Epithelial_Topic 6 |
| CD93 | C1QA | Ligand | Receptor | Immune | Immune_General |
| CD93 | C1QA | Ligand | Receptor | Immune | Immune_General |
| CD93 | COL1A1 | ECM/Ligand | Receptor | Fibroblast | Fibroblast_Topic 2 |
| CD93 | COL1A1 | ECM/Ligand | Receptor | Fibroblast | Fibroblast_Topic 2 |
| CD93 | COL1A1 | ECM/Ligand | Receptor | Fibroblast | Fibroblast_General |
| CD93 | COL1A1 | ECM/Ligand | Receptor | Fibroblast | Fibroblast_General |
| CDH1 | SFRP2 | ECM/Ligand | Receptor | Fibroblast | Fibroblast_General |
| CDH1 | LOXL2 | ECM/Receptor/Ligand | Receptor | Fibroblast | Fibroblast_General |
| CLEC5A | TYROBP | Ligand | Receptor | Immune | Immune_General |
| COLEC12 | COL8A2 | ECM/Ligand | Receptor | Epithelial | Epithelial_General |
| COLEC12 | COL8A2 | ECM/Ligand | Receptor | Epithelial | Epithelial_General |
| COLEC12 | COL8A2 | ECM/Ligand | Receptor | Epithelial | Epithelial_Topic 14 |
| COLEC12 | COL8A2 | ECM/Ligand | Receptor | Epithelial | Epithelial_Topic 14 |
| CSF1R | CSF1 | Receptor/Ligand | Receptor | Immune | Immune_Basophil |
| CSF3R | ELANE | Ligand | Receptor | Immune | Immune_Neutrophil |
| CXCR4 | CXCL12 | Ligand | Receptor | Endothelial | Endothelial_Topic 8 |
| CXCR4 | B2M | Ligand | Receptor | Fibroblast | Fibroblast_Topic 5 |
| CXCR4 | CXCL12 | Ligand | Receptor | Fibroblast | Fibroblast_General |
| CXCR4 | CXCL12 | Ligand | Receptor | Fibroblast | Fibroblast_Topic 7 Neuronal_Neuronal progenitor 4V |
| CXCR4 | CXCL14 | Ligand | Receptor | Neuronal | |
| CXCR4 | ELANE | Ligand | Receptor | Immune | Immune_Neutrophil |
| CXCR5 | CCL4 | Ligand | Receptor | Immune | Immune_General |
| DCC | SFRP2 | ECM/Ligand | Receptor | Fibroblast | Fibroblast_General |
| DPP4 | CXCL12 | Ligand | Receptor | Fibroblast | Fibroblast_Topic 7 |
| DPP4 | CXCL2 | Ligand | Receptor | Immune | Immune_General |
| DPP4 | CXCL12 | Ligand | Receptor | Endothelial | Endothelial_Topic 8 |
| DPP4 | CXCL12 | Ligand | Receptor | Fibroblast | Fibroblast_General |
| EDNRA | EDN3 | Ligand | Receptor | Fibroblast | Fibroblast_Topic 7 |
| ENG | BMP7 | ECM/Ligand | Receptor | Fibroblast | Fibroblast_Topic 7 |
| ENG | INHBA | Ligand | Receptor | Immune | Immune_Neutrophil |
| ENG | LRG1 | Ligand | Receptor | Endothelial | Endothelial_General |
| ENG | TGFB2 | ECM/Ligand | Receptor | Glial | Glial_General |
| EPHB2 | MMP2 | ECM/Ligand | Receptor | Fibroblast | Fibroblast_General |
| F2R | ELANE | Ligand | Receptor | Immune | Immune_Neutrophil |
| F2RL1 | ELANE | Ligand | Receptor | Immune | Immune_Neutrophil |
| F3 | F10 | Ligand | ECM/Receptor | Immune | Immune_Monocyte |
| F3 | F10 | Ligand | ECM/Receptor | Immune | Immune_Monocyte |
| FCER1A | ITIH2 | Ligand | Receptor | Fibroblast | Fibroblast_Topic 7 |
| FGFR1 | FGF8 | Ligand | Receptor | Glial | Glial_General |
| FGFR1 | FGF17 | Ligand | Receptor | Glial | Glial_General |
| FGFR1 | MMP2 | ECM/Ligand | Receptor | Fibroblast | Fibroblast_General |
| FGFR1 | HSPG2 | ECM/Ligand | Receptor | Endothelial | Endothelial_General |
| FGFR4 | FGF17 | Ligand | Receptor | Glial | Glial_General |
| FGFR4 | FGF8 | Ligand | Receptor | Glial | Glial_General |
| FGFR4 | ANGPTL4 | ECM/Ligand | Receptor | Fibroblast | Fibroblast_General |
| FGFR4 | LTA | Ligand | Receptor | Immune | Immune_Lymphocyte |
| FLT1 | HSPG2 | ECM/Ligand | Receptor | Endothelial | Endothelial_General |
| FLT1 | PGF | Ligand | Receptor | Fibroblast | Fibroblast_General |
| FLT1 | PGF | Ligand | Receptor | Fibroblast | Fibroblast_Topic 5 |
| FLT1 | S100A9 | Ligand | Receptor | Immune | Immune_Neutrophil |
| FZD2 | WNT5A | ECM/Ligand | Receptor | Epithelial | Epithelial_Topic 23 |
| FZD4 | SLC9A3R1 | Ligand | ECM/Receptor | Immune | Immune_Lymphocyte |

TABLE 5-continued

Identified Interactions in Embryo - cognate ligand-receptor pairs.

| | | | | | |
|---|---|---|---|---|---|
| GPR183 | GPC6 | ECM/Ligand | Receptor | Fibroblast | Fibroblast__Topic 8 |
| GPR183 | NID2 | ECM/Ligand | Receptor | Epithelial | Epithelial__Topic 6 |
| GPR183 | NID2 | ECM/Ligand | Receptor | Endothelial | Endothelial__General |
| HBEGF | FBLN1 | ECM/Ligand | Receptor | Fibroblast | Fibroblast__General |
| HBEGF | FBLN1 | ECM/Ligand | Receptor | Fibroblast | Fibroblast__Topic 7 |
| HFE | B2M | Ligand | Receptor | Fibroblast | Fibroblast__Topic 5 |
| HTR1B | NME2 | Ligand | Receptor | Endothelial | Endothelial__General |
| HYAL2 | PON2 | Ligand | Receptor | Endothelial | Endothelial__General |
| IGF2R | CREG1 | Ligand | Receptor | Immune | Immune_General |
| IGF2R | FN1 | ECM/Ligand | Receptor | Fibroblast | Fibroblast__General |
| IGSF1 | IGF1 | Ligand | Receptor | Fibroblast | Fibroblast__Topic 7 |
| IGSF1 | INHBA | Ligand | Receptor | Immune | Immune_Neutrophil |
| IGSF1 | IGF1 | Ligand | Receptor | Immune | Immune_General |
| IL17RA | DNASE2B | Ligand | Receptor | Immune | Immune_Basophil |
| IL18R1 | IL18 | Ligand | Receptor | Immune | Immune_General |
| IL18RAP | IL18 | Ligand | Receptor | Immune | Immune_General |
| IL1R1 | IL1B | Ligand | Receptor | Immune | Immune_General |
| IL2RB | ECM1 | ECM/Ligand | Receptor | Fibroblast | Fibroblast__General |
| IL2RB | ECM1 | ECM/Ligand | Receptor | Fibroblast | Fibroblast__Topic 5 |
| IL6ST | IL6 | Receptor/Ligand | Receptor | Immune | Immune_Basophil |
| ITGA3 | CALR | ECM/Ligand | Receptor | Fibroblast | Fibroblast__General |
| ITGA3 | FN1 | ECM/Ligand | Receptor | Fibroblast | Fibroblast__General |
| ITGA3 | THBS1 | ECM/Ligand | Receptor | Immune | Immune_Monocyte |
| ITGA4 | ANXA1 | Ligand | Receptor | Immune | Immune_General |
| ITGA4 | PNP | Ligand | Receptor | Epithelial | Epithelial__Topic 6 |
| ITGA4 | VCAN | ECM/Ligand | Receptor | Fibroblast | Fibroblast__Topic 2 |
| ITGA4 | ALDOA | Ligand | Receptor | Immune | Immune_Basophil |
| ITGA4 | PON2 | Ligand | Receptor | Endothelial | Endothelial__General |
| ITGA4 | FN1 | ECM/Ligand | Receptor | Fibroblast | Fibroblast__General |
| ITGA4 | THBS2 | ECM/Ligand | Receptor | Fibroblast | Fibroblast__General |
| ITGA4 | THBS1 | ECM/Ligand | Receptor | Immune | Immune_Monocyte |
| ITGA5 | COL1A1 | ECM/Ligand | Receptor | Fibroblast | Fibroblast__Topic 2 |
| ITGA5 | SFRP2 | ECM/Ligand | Receptor | Fibroblast | Fibroblast__General |
| ITGA5 | COL18A1 | ECM/Ligand | Receptor | Endothelial | Endothelial__Topic 8 |
| ITGA5 | SPP1 | Ligand | Receptor | Fibroblast | Fibroblast__Topic 8 |
| ITGA5 | COL6A3 | ECM/Ligand | Receptor | Fibroblast | Fibroblast__General |
| ITGA5 | FN1 | ECM/Ligand | Receptor | Fibroblast | Fibroblast__General |
| ITGA5 | ANGPT2 | Ligand | Receptor | Fibroblast | Fibroblast__Topic 18 |
| ITGA5 | IGFBP2 | Ligand | Receptor | Epithelial | Epithelial__General |
| ITGA5 | IGFBP2 | Ligand | Receptor | Fibroblast | Fibroblast__Topic 7 |
| ITGA5 | COL1A1 | ECM/Ligand | Receptor | Fibroblast | Fibroblast__General |
| ITGA8 | VTN | ECM/Receptor/Ligand | Receptor | Fibroblast | Fibroblast__Topic 3 |
| ITGA8 | VTN | ECM/Receptor/Ligand | Receptor | Fibroblast | Fibroblast__Topic 3 |
| ITGA8 | NPNT | ECM/Receptor/Ligand | Receptor | Epithelial | Epithelial__Topic 23 |
| ITGA8 | NPNT | ECM/Receptor/Ligand | Receptor | Epithelial | Epithelial__Topic 23 |
| ITGA8 | FN1 | ECM/Ligand | Receptor | Fibroblast | Fibroblast__General |
| ITGA8 | FN1 | ECM/Ligand | Receptor | Fibroblast | Fibroblast__General |
| ITGAL | ESM1 | Ligand | Receptor | Endothelial | Endothelial__Topic 3 |
| ITGAL | ESM1 | Ligand | Receptor | Endothelial | Endothelial_Topic 3 |
| ITGB2 | ESM1 | Ligand | Receptor | Endothelial | Endothelial_Topic 3 |
| ITGB3 | NOV | ECM/Ligand | Receptor | Fibroblast | Fibroblast__Topic 2 |
| ITGB3 | FBLN2 | ECM/Ligand | Receptor | Endothelial | Endothelial__Topic 8 |
| ITGB3 | NOV | ECM/Ligand | Receptor | Epithelial | Epithelial__Topic 16 |
| ITGB3 | THBS1 | ECM/Ligand | Receptor | Immune | Immune_Monocyte |
| ITGB3 | SPP1 | Ligand | Receptor | Fibroblast | Fibroblast__Topic 8 |
| ITGB3 | FN1 | ECM/Ligand | Receptor | Fibroblast | Fibroblast__General |
| ITGB3 | COL6A3 | ECM/Ligand | Receptor | Fibroblast | Fibroblast__General |
| ITGB3 | GSN | Ligand | Receptor | Fibroblast | Fibroblast__Topic 5 |
| ITGB3 | VTN | ECM/Receptor/Ligand | Receptor | Fibroblast | Fibroblast__Topic 3 |
| ITGB3 | GSN | Ligand | Receptor | Epithelial | Epithelial__Topic 16 |
| ITGB3 | COL4A3 | ECM/Ligand | Receptor | Epithelial | Epithelial__Topic 6 |
| ITGB3 | GSN | Ligand | Receptor | Fibroblast | Fibroblast__General |
| KDR | TIMP3 | ECM/Ligand | Receptor | Fibroblast | Fibroblast__Topic 3 |
| KDR | VEGFC | Ligand | Receptor | Endothelial | Endothelial__Topic 8 |
| KDR | COL18A1 | ECM/Ligand | Receptor | Endothelial | Endothelial__Topic 8 |
| KDR | HSPG2 | ECM/Ligand | Receptor | Endothelial | Endothelial__General |
| KDR | FIGF | Ligand | Receptor | Fibroblast | Fibroblast__Topic 5 |
| KDR | FIGF | Ligand | Receptor | Fibroblast | Fibroblast__General |
| KLRD1 | TYROBP | Ligand | Receptor | Immune | Immune_General |
| LRP1 | A2M | Ligand | Receptor | Epithelial | Epithelial__Topic 11 |
| LRP1 | THBS1 | ECM/Ligand | Receptor | Immune | Immune_Monocyte |
| LRP1 | C1QA | Ligand | Receptor | Immune | Immune_General |
| LRP1 | LTF | Ligand | Receptor | Immune | Immune_Neutrophil |
| LRP1 | C1QB | Ligand | Receptor | Immune | Immune_General |
| LRP1 | CALR | ECM/Ligand | Receptor | Fibroblast | Fibroblast__General |
| LRP1 | ELANE | Ligand | Receptor | Immune | Immune_Neutrophil |
| LRP1 | PLAT | Ligand | Receptor | Fibroblast | Fibroblast__Topic 18 |
| LRP1 | C1QC | Ligand | Receptor | Immune | Immune_General |

TABLE 5-continued

Identified Interactions in Embryo - cognate ligand-receptor pairs.

| | | | | | |
|---|---|---|---|---|---|
| LRP1 | PDGFB | Ligand | Receptor | Endothelial | Endothelial_General |
| LY96 | LY86 | Ligand | Receptor | Immune | Immune_General |
| LYVE1 | PDGFB | Ligand | Receptor | Endothelial | Endothelial_General |
| NOTCH1 | EGFL7 | ECM/Ligand | Receptor | Endothelial | Endothelial_General |
| NOTCH1 | NOV | ECM/Ligand | Receptor | Epithelial | Epithelia_Topic 16 |
| NOTCH1 | NOV | ECM/Ligand | Receptor | Fibroblast | Fibroblast_Topic 2 |
| NOTCH1 | RBP3 | ECM/Ligand | Receptor | Glial | Glial_Developing pineal gland |
| NR3C1 | HMGB2 | Ligand | Receptor | Endothelial | Endothelial_Topic 12 |
| NR3C1 | HMGB2 | Ligand | Receptor | Fibroblast | Fibroblast_Topic 16 |
| NR3C1 | CALR | ECM/Ligand | Receptor | Fibroblast | Fibroblast_General |
| NRP2 | PGF | Ligand | Receptor | Fibroblast | Fibroblast_Topic 5 |
| NRP2 | PGF | Ligand | Receptor | Fibroblast | Fibroblast_General |
| NRP2 | SEMA3C | Receptor/Ligand | Receptor | Epithelial | Epithelial_Topic 23 |
| NRP2 | SEMA3F | Receptor/Ligand | Receptor | Epithelial | Epithelial_Topic 6 |
| NRXN1 | NXPH1 | Ligand | Receptor | Glial | Glial_Developing pineal gland (Krt19+) |
| P2RX4 | WNT4 | ECM/Receptor/Ligand | Receptor | Fibroblast | Fibroblast_Topic 7 |
| P2RY1 | SLC9A3R1 | Ligand | Receptor | Immune | Immune_Lymphocyte |
| PDGFRA | SNX2 | Ligand | Receptor | Immune | Immune_General |
| PDGFRA | SNX2 | Ligand | Receptor | Immune | Immune_General |
| PDGFRA | SNX2 | Ligand | Receptor | Immune | Immune_General |
| PDGFRA | CLU | ECM/Ligand | Receptor | Epithelial | Epithelial_General |
| PDGFRA | CLU | ECM/Ligand | Receptor | Epithelial | Epithelial_General |
| PDGFRA | CLU | ECM/Ligand | Receptor | Epithelial | Epithelial_General |
| PDGFRA | SLC9A3R1 | Ligand | Receptor | Immune | Immune_Lymphocyte |
| PDGFRA | SLC9A3R1 | Ligand | Receptor | Immune | Immune_Lymphocyte |
| PDGFRA | SLC9A3R1 | Ligand | Receptor | Immune | Immune_Lymphocyte |
| PDGFRA | PDGFC | Ligand | Receptor | Epithelial | Epithelial_Topic 16 |
| PDGFRA | PDGFC | Ligand | Receptor | Epithelial | Epithelial_Topic 16 |
| PDGFRA | PDGFC | Ligand | Receptor | Epithelial | Epithelial_Topic 16 |
| PDGFRA | PDGFB | Ligand | Receptor | Endothelial | Endothelial_General |
| PDGFRA | PDGFB | Ligand | Receptor | Endothelial | Endothelial_General |
| PDGFRA | PDGFB | Ligand | Receptor | Endothelial | Endothelial_General |
| PDGFRB | PDGFC | Ligand | Receptor | Epithelial | Epithelial_Topic 16 |
| PDGFRB | SNX2 | Ligand | Receptor | Immune | Immune_General |
| PDGFRB | MFGE8 | ECM/Ligand | Receptor | Endothelial | Endothelial_Topic 3 |
| PDGFRB | SLC9A3R1 | Ligand | Receptor | Immune | Immune_Lymphocyte |
| PDGFRB | PDGFB | Ligand | Receptor | Endothelial | Endothelial_General |
| PILRA | NID2 | ECM/Ligand | Receptor | Epithelial | Epithelial_Topic 6 |
| PILRA | NID2 | ECM/Ligand | Receptor | Endothelial | Endothelial_General |
| PROCR | CTSB | Ligand | Receptor | Immune | Immune_General |
| PTGDR | PTGDS | Ligand | Receptor | Epithelial | Epithelial_General |
| PTGDR | PTGDS | Ligand | Receptor | Fibroblast | Fibroblast_Topic 16 |
| PTGER3 | EFEMP2 | ECM/Receptor/Ligand | Receptor | Fibroblast | Fibroblast_General |
| PTGER3 | EFEMP2 | ECM/Receptor/Ligand | Receptor | Fibroblast | Fibroblast_General |
| PTH1R | SLC9A3R1 | Ligand | Receptor | Immune | Immune_Lymphocyte |
| PTPRZ1 | PTN | Receptor/Ligand | ECM/Receptor | Fibroblast | Fibroblast_Topic 7 |
| RAMP3 | ADM | Ligand | Receptor | Fibroblast | Fibroblast_Topic 18 |
| RARA | FN1 | ECM/Ligand | Receptor | Fibroblast | Fibroblast_General |
| RARA | PENK | Ligand | Receptor | Epithelial | Epithelial_Topic 23 |
| RARA | CLU | ECM/Ligand | Receptor | Epithelial | Epithelial_General |
| ROBO2 | SLIT2 | Ligand | Receptor | Glial | Glial_General |
| ROBO4 | SLIT2 | Ligand | Receptor | Glial | Glial_General |
| ROBO4 | SLIT2 | Ligand | Receptor | Glial | Glial_General |
| RORA | NME2 | Ligand | Receptor | Endothelial | Endothelial_General |
| RORB | NME2 | Ligand | Receptor | Endothelial | Endothelial_General |
| SCARB1 | PON2 | Ligand | Receptor | Endothelial | Endothelial_General |
| SCARB1 | PON2 | Ligand | Receptor | Endothelial | Endothelial_General |
| SCARF1 | CALR | ECM/Ligand | Receptor | Fibroblast | Fibroblast_General |
| SELPLG | VCAN | ECM/Ligand | Receptor | Fibroblast | Fibroblast_Topic 2 |
| SLC40A1 | CP | Ligand | Receptor | Fibroblast | Fibroblast_General |
| SLC40A1 | CP | Ligand | Receptor | Fibroblast | Fibroblast_General |
| TBXA2R | PRDX4 | Ligand | Receptor | Glial | Glial_Developing pineal gland (Krt19+) |
| TBXA2R | NME2 | Ligand | Receptor | Endothelial | Endothelial_General |
| TEK | ANGPT2 | Ligand | Receptor | Fibroblast | Fibroblast_Topic 18 |
| TGFBR2 | CLU | ECM/Ligand | Receptor | Epithelial | Epithelial_General |
| TGFBR2 | LRG1 | Ligand | Receptor | Endothelial | Endothelial_General |
| TGFBR2 | SPARC | ECM/Ligand | Receptor | Endothelial | Endothelial_Topic 3 |
| TGFBR2 | TGFB2 | ECM/Ligand | Receptor | Glial | Glial_General |
| TMEM219 | PON2 | Ligand | Receptor | Endothelial | Endothelial_General |
| TNFRSF11B | THBS1 | ECM/Ligand | ECM/Receptor | Immune | Immune_Monocyte |
| TNFRSF11B | THBS1 | ECM/Ligand | ECM/Receptor | Immune | Immune_Monocyte |
| TNFRSF11B | FN1 | ECM/Ligand | ECM/Receptor | Fibroblast | Fibroblast_General |
| TNFRSF11B | FN1 | ECM/Ligand | ECM/Receptor | Fibroblast | Fibroblast_General |
| TNFRSF11B | VTN | ECM/Receptor/Ligand | ECM/Receptor | Fibroblast | Fibroblast_Topic 3 |
| TNFRSF11B | VTN | ECM/Receptor/Ligand | ECM/Receptor | Fibroblast | Fibroblast_Topic 3 |

TABLE 5-continued

| | | | | | | |
|---|---|---|---|---|---|---|
| | | | Identified Interactions in Embryo - cognate ligand-receptor pairs. | | | |
| TNFRSF25 | TNFSF12 | Ligand | Receptor | Fibroblast | Fibroblast_General | |
| TREM2 | TYROBP | Ligand | Receptor | Immune | Immune_General | |
| TREML2 | SNX2 | Ligand | Receptor | Immune | Immune_General | |

| Receptor | gene.Ligand | Cell_Type_Specificity.Receptor | Subtype.specificity.Receptor | gene.Receptor | wt | wt. final |
|---|---|---|---|---|---|---|
| ACVR2B | Inhba | Neuronal | Neuronal_General | Acvr2b | 1 | 1 |
| ACVR2B | Snx2 | Neuronal | Neuronal_General | Acvr2b | 1 | 1 |
| ACVR2B | Bmp7 | Neuronal | Neuronal_General | Acvr2b | 1 | 1 |
| ADRB2 | Slc9a3r1 | Immune | Immune_General | Adrb2 | 1 | 1 |
| ADRB2 | Pon2 | Immune | Immune_General | Adrb2 | 0.5 | 0.5 |
| ADRB2 | Il1b | Immune | Immune_General | Adrb2 | 1 | 1 |
| ADRB2 | Aldoa | Immune | Immune_General | Adrb2 | 1 | 1 |
| AGTR2 | Ace | Fibroblast | Fibroblast_Topic 7 | Agtr2 | 1 | 1 |
| AGTR2 | Timp3 | Fibroblast | Fibroblast_Topic 7 | Agtr2 | 1 | 1 |
| ANXA2 | Ctsb | Epithelial | Epithelial_Topic 16 | Anxa2 | 1 | 1 |
| ANXA2 | Pcsk9 | Epithelial | Epithelial_Topic 16 | Anxa2 | 1 | 1 |
| ANXA2 | Anxa1 | Epithelial | Epithelial_Topic 16 | Anxa2 | 1 | 1 |
| ANXA2 | Fn1 | Epithelial | Epithelial_Topic 16 | Anxa2 | 1 | 1 |
| ANXA2 | Plat | Epithelial | Epithelial_Topic 16 | Anxa2 | 1 | 1 |
| APLNR | Apln | Endothelial | Endothelial_Topic 11 | Aplnr | 1 | 1 |
| APLNR | Apln | Endothelial | Endothelial_General | Aplnr | 1 | 1 |
| AQP1 | Efemp2 | Epithelial | Epithelial_Topic 11 | Aqp1 | 1 | 1 |
| AQP1 | Efemp2 | Epithelial | Epithelial_General | Aqp1 | 1 | 1 |
| CCR1 | Ccl7 | Immune | Immune_General | Ccr1 | 0.5 | 0.67 |
| CCR1 | Ccl12 | Immune | Immune_General | Ccr1 | 0.5 | 0.67 |
| CCR1 | Ccl4 | Immune | Immune_General | Ccr1 | 1 | 0.67 |
| CCR2 | Ccl7 | Immune | Immune_General | Ccr2 | 0.5 | 0.5 |
| CCR2 | Ccl12 | Immune | Immune_General | Ccr2 | 0.5 | 0.5 |
| CD14 | Lbp | Immune | Immune_General | Cd14 | 1 | 1 |
| CD14 | Ltf | Immune | Immune_General | Cd14 | 1 | 1 |
| CD36 | Col2a1 | Immune | Immune_General | Cd36 | 1 | 1 |
| CD36 | Col1a1 | Immune | Immune_General | Cd36 | 0.5 | 0.5 |
| CD36 | Col4a1 | Immune | Immune_General | Cd36 | 1 | 1 |
| CD36 | Fn1 | Immune | Immune_General | Cd36 | 0.5 | 0.67 |
| CD36 | Col1a1 | Immune | Immune_General | Cd36 | 0.5 | 0.67 |
| CD36 | Col6a1 | Immune | Immune_General | Cd36 | 1 | 0.67 |
| CD36 | Thbs1 | Immune | Immune_General | Cd36 | 1 | 1 |
| CD40 | Erp44 | Fibroblast | Fibroblast_Topic 5 | Cd40 | 1 | 1 |
| CD40 | Spp1 | Fibroblast | Fibroblast_Topic 5 | Cd40 | 1 | 1 |
| CD40 | Calr | Fibroblast | Fibroblast_Topic 5 | Cd40 | 1 | 1 |
| CD40 | Igfbp5 | Fibroblast | Fibroblast_Topic 5 | Cd40 | 1 | 1 |
| CD44 | Hgf | Immune | Immune_General | Cd44 | 1 | 1 |
| CD44 | Fn1 | Immune | Immune_General | Cd44 | 0.5 | 0.5 |
| CD44 | Col1a1 | Immune | Immune_General | Cd44 | 0.5 | 0.5 |
| CD44 | Col1a1 | Immune | Immune_General | Cd44 | 0.5 | 0.5 |
| CD44 | Vcan | Immune | Immune_General | Cd44 | 0.5 | 0.5 |
| CD44 | Igfbp3 | Immune | Immune_General | Cd44 | 1 | 1 |
| CD44 | Igfbp3 | Immune | Immune_General | Cd44 | 1 | 1 |
| CD44 | Spp1 | Immune | Immune_General | Cd44 | 1 | 1 |
| CD74 | Ctsf | Immune | Immune_General | Cd74 | 1 | 1 |
| CD79A | Fn1 | Immune | Immune_B | Cd79a | 1 | 1 |
| CD93 | Col4a1 | Fibroblast | Fibroblast_Topic 3 | Cd93 | 1 | 1 |
| CD93 | Col4a1 | Endothelial | Endothelial_General | Cd93 | 1 | 1 |
| CD93 | Col4a3 | Fibroblast | Fibroblast_Topic 3 | Cd93 | 1 | 1 |
| CD93 | Col4a3 | Endothelial | Endothelial_General | Cd93 | 1 | 1 |
| CD93 | C1qa | Fibroblast | Fibroblast_Topic 3 | Cd93 | 1 | 1 |
| CD93 | C1qa | Endothelial | Endothelial_General | Cd93 | 1 | 1 |
| CD93 | Col1a1 | Fibroblast | Fibroblast_Topic 3 | Cd93 | 1 | 1 |
| CD93 | Col1a1 | Endothelial | Endothelial_General | Cd93 | 0.5 | 0.5 |
| CD93 | Col1a1 | Fibroblast | Fibroblast_Topic 3 | Cd93 | 1 | 1 |
| CD93 | Col1a1 | Endothelial | Endothelial_General | Cd93 | 0.5 | 0.5 |
| CDH1 | Sfrp2 | Immune | Immune_Basophil | Cdh1 | 1 | 1 |
| CDH1 | Loxl2 | Immune | Immune_Basophil | Cdh1 | 1 | 1 |
| CLEC5A | Tyrobp | Immune | Immune_Neutrophil | Clec5a | 1 | 1 |
| COLEC12 | Col8a2 | Epithelial | Epithelial_Topic 14 | Colec12 | 1 | 1 |
| COLEC12 | Col8a2 | Fibroblast | Fibroblast_General | Colec12 | 1 | 1 |
| COLEC12 | Col8a2 | Epithelial | Epithelial_Topic 14 | Colec12 | 1 | 1 |
| COLEC12 | Col8a2 | Fibroblast | Fibroblast_General | Colec12 | 1 | 1 |
| CSF1R | Csf1 | Immune | Immune_General | Csf1r | 1 | 1 |
| CSF3R | Elane | Immune | Immune_Monocyte | Csf3r | 1 | 1 |
| CXCR4 | Cxcl12 | Glial | Glial_General | Cxcr4 | 1 | 1 |
| CXCR4 | B2m | Glial | Glial_General | Cxcr4 | 1 | 1 |
| CXCR4 | Cxcl12 | Glial | Glial_General | Cxcr4 | 1 | 1 |
| CXCR4 | Cxcl12 | Glial | Glial_General | Cxcr4 | 1 | 1 |
| CXCR4 | Cxcl14 | Glial | Glial_General | Cxcr4 | 1 | 1 |
| CXCR4 | Elane | Glial | Glial_General | Cxcr4 | 1 | 1 |

TABLE 5-continued

| | | | Identified Interactions in Embryo - cognate ligand-receptor pairs. | | | |
|---|---|---|---|---|---|---|
| CXCR5 | Ccl4 | Immune | Immune__Lymphocyte | Cxcr5 | 1 | 1 |
| DCC | Sfrp2 | Neuronal | Neuronal__General | Dcc | 1 | 1 |
| DPP4 | Cxcl12 | Immune | Immune__DC | Dpp4 | 1 | 1 |
| DPP4 | Cxcl1 | Immune | Immune__DC | Dpp4 | 1 | 1 |
| DPP4 | Cxcl12 | Immune | Immune__DC | Dpp4 | 1 | 1 |
| DPP4 | Cxcl12 | Immune | Immune__DC | Dpp4 | 1 | 1 |
| EDNRA | Edn3 | Fibroblast | Fibroblast__General | Ednra | 1 | 1 |
| ENG | Bmp7 | Endothelial | Endothelial__Topic 3 | Eng | 1 | 1 |
| ENG | Inhba | Endothelial | Endothelial__Topic 3 | Eng | 1 | 1 |
| ENG | Lrg1 | Endothelial | Endothelial__Topic 3 | Eng | 1 | 1 |
| ENG | Tgfb2 | Endothelial | Endothelial__Topic 3 | Eng | 1 | 1 |
| EPHB2 | Mmp2 | Neuronal | Neuronal__General | Ephb2 | 1 | 1 |
| F2R | Elane | Endothelial | Endothelial__Topic 3 | F2r | 1 | 1 |
| F2RL1 | Elane | Glial | Glial__Developing pineal gland | F2rl1 | 1 | 1 |
| F3 | F10 | Fibroblast | Fibroblast__General | F3 | 1 | 1 |
| F3 | F10 | Fibroblast | Fibroblast__Topic 8 | F3 | 1 | 1 |
| FCER1A | Itih2 | Immune | Immune__Basophil | Fcer1a | 1 | 1 |
| FGFR1 | Fgf8 | Glial | Glial__General | Fgfr1 | 1 | 1 |
| FGFR1 | Fgf17 | Glial | Glial__General | Fgfr | 1 | 1 |
| FGFR1 | Mmp2 | Glial | Glial__General | Fgfr1 | 1 | 1 |
| FGFR1 | Hspg2 | Glial | Glial__General | Fgfr1 | 1 | 1 |
| FGFR4 | Fgf17 | Endothelial | Endothelial__Topic 11 | Fgfr4 | 1 | 1 |
| FGFR4 | Fgf8 | Endothelial | Endothelial__Topic 11 | Fgfr4 | 1 | 1 |
| FGFR4 | Angptl4 | Endothelial | Endothelial__Topic 11 | Fgfr4 | 1 | 1 |
| FGFR4 | Lta | Endothelial | Endothelial__Topic 11 | Fgfr4 | 1 | 1 |
| FLT1 | Hspg2 | Endothelial | Endothelial__General | Flt1 | 0.5 | 0.5 |
| FLT1 | Pgf | Endothelial | Endothelial__General | Flt1 | 1 | 1 |
| FLT1 | Pgf | Endothelial | Endothelial__General | Flt1 | 1 | 1 |
| FLT1 | S100a9 | Endothelial | Endothelial__General | Flt1 | 1 | 1 |
| FZD2 | Wnt5a | Fibroblast | Fibroblast__General | Fzd2 | 1 | 1 |
| FZD4 | Slc9a3r1 | Endothelial | Endothelial__General | Fzd4 | 1 | 1 |
| GPR183 | Gpc6 | Immune | Immune__General | Gpr183 | 1 | 1 |
| GPR183 | Nid2 | Immune | Immune__General | Gpr183 | 1 | 1 |
| GPR183 | Nid2 | Immune | Immune__Genral | Gpr183 | 1 | 1 |
| HBEGF | Fbln1 | Endothelial | Endothelial__General | Hbegf | 1 | 1 |
| HBEGF | Fbln1 | Endothelial | Endothelial__General | Hbegf | 1 | 1 |
| HFE | B2m | Epithelial | Epithelial__Topic 6 | Hfe | 1 | 1 |
| HTR1B | Nme2 | Immune | Immune__Basophil | Htr1b | 1 | 1 |
| HYAL2 | Pon2 | Endothelial | Endothelial__General | Hyal2 | 0.5 | 0.5 |
| IGF2R | Creg1 | Endothelial | Endothelial__General | Igf2r | 1 | 1 |
| IGF2R | Fn1 | Endothelial | Endothelial__General | Igf2r | 0.33 | 0.33 |
| IGSF1 | Igf1 | Epithelial | Epithelial__Topic 16 | Igsf1 | 1 | 1 |
| IGSF1 | Inhba | Epithelial | Epithelial__Topic 16 | Igsf1 | 1 | 1 |
| IGSF1 | Igf1 | Epithelial | Epithelial__Topic 16 | Igsf1 | 1 | 1 |
| IL17RA | Dnase2b | Immune | Immune__Monocyte | Il17ra | 1 | 1 |
| IL18R1 | Il18 | Immune | Immune__Lymphocyte | Il18r1 | 1 | 1 |
| IL18RAP | Il18 | Immune | Immune__Basophil | Il18rap | 1 | 1 |
| IL1R1 | Il1b | Immune | Immune__Lymphocyte | Il1r1 | 1 | 1 |
| IL2RB | Ecm1 | Immune | Immune__Lymphocyte | Il2rb | 1 | 1 |
| IL2RB | Ecm1 | Immune | Immune__Lymphocyte | Il2rb | 1 | 1 |
| IL6ST | Il6 | Fibroblast | Fibroblast__General | Il6st | 1 | 1 |
| ITGA3 | Calr | Epithelial | Epithelial__Topic 6 | Itga3 | 1 | 1 |
| ITGA3 | Fn1 | Epithelial | Epithelial__Topic 6 | Itga3 | 1 | 1 |
| ITGA3 | Thbs1 | Epithelial | Epithelial__Topic 6 | Itga3 | 1 | 1 |
| ITGA4 | Anxa1 | Immune | Immune__Monocyte | Itga4 | 1 | 1 |
| ITGA4 | Pnp | Immune | Immune__Monocyte | Itga4 | 1 | 1 |
| ITGA4 | Vcan | Immune | Immune__Monocyte | Itga4 | 1 | 1 |
| ITGA4 | Aldoa | Immune | Immune__Monocyte | Itga4 | 1 | 1 |
| ITGA4 | Pon2 | Immune | Immune__Monocyte | Itga4 | 1 | 1 |
| ITGA4 | Fn1 | Immune | Immune__Monocyte | Itga4 | 0.5 | 0.75 |
| ITGA4 | Thbs2 | Immune | Immune__Monocyte | Itga4 | 1 | 0.75 |
| ITGA4 | Thbs1 | Immune | Immune__Monocyte | Itga4 | 1 | 1 |
| ITGA5 | Col1a1 | Endothelial | Endothelial__General | Itga5 | 0.5 | 0.5 |
| ITGA5 | Sfrp2 | Endothelial | Endothelial__General | Itga5 | 1 | 0.71 |
| ITGA5 | Col18a1 | Endothelial | Endothelial__General | Itga5 | 0.5 | 0.5 |
| ITGA5 | Spp1 | Endothelial | Endothelial__General | Itga5 | 1 | 1 |
| ITGA5 | Col6a3 | Endothelial | Endothelial__General | Itga5 | 1 | 0.71 |
| ITGA5 | Fn1 | Endothelial | Endothelial__General | Itga5 | 0.33 | 0.71 |
| ITGA5 | Angpt2 | Endothelial | Endothelial__General | Itga5 | 0.5 | 0.5 |
| ITGA5 | IgfbP2 | Endothelial | Endothelial__General | Itga5 | 1 | 1 |
| ITGA5 | IgfbP2 | Endothelial | Endothelial__General | Itga5 | 1 | 1 |
| ITGA5 | Col1a1 | Endothelial | Endothelial__General | Itga5 | 0.5 | 0.71 |
| ITGA8 | Vtn | Fibroblast | Fibroblast__General | Itga8 | 1 | 1 |
| ITGA8 | Vtn | Fibroblast | Fibroblast__Topic 5 | Itga8 | 1 | 1 |
| ITGA8 | Npnt | Fibroblast | Fibroblast__General | Itga8 | 1 | 1 |
| ITGA8 | Npnt | Fibroblast | Fibroblast__Topic 5 | Itga8 | 1 | 1 |
| ITGA8 | Fn1 | Fibroblast | Fibroblast__General | Itga8 | 1 | 1 |

TABLE 5-continued

Identified Interactions in Embryo - cognate ligand-receptor pairs.

| | | | | | | |
|---|---|---|---|---|---|---|
| ITGA8 | Fn1 | Fibroblast | Fibroblast_Topic 5 | Itga8 | 1 | 1 |
| ITGAL | Esm1 | Immune | Immune_Monocyte | Itga1 | 1 | 1 |
| ITGAL | Esm1 | Endothelial | Endothelial_Topic 8 | Itga1 | 1 | 1 |
| ITGB2 | Esm1 | Immune | Immune_General | Itgb2 | 1 | 1 |
| ITGB3 | Nov | Immune | Immune_Basophil | Itgb3 | 1 | 1 |
| ITGB3 | Fbln2 | Immune | Immune_Basophil | Itgb3 | 1 | 1 |
| ITGB3 | Nov | Immune | Immune_Basophil | Itgb3 | 1 | 1 |
| ITGB3 | Thbs1 | Immune | Immune_Basophil | Itgb3 | 1 | 1 |
| ITGB3 | Spp1 | Immune | Immune_Basophil | Itgb3 | 1 | 1 |
| ITGB3 | Fn1 | Immune | Immune_Basophil | Itgb3 | 1 | 1 |
| ITGB3 | Col6a3 | Immune | Immune_Basophil | Itgb3 | 1 | 1 |
| ITGB3 | Gsn | Immune | Immune_Basophil | Itgb3 | 1 | 1 |
| ITGB3 | Vtn | Immune | Immune_Basophil | Itgb3 | 1 | 1 |
| ITGB3 | Gsn | Immune | Immune_Basophil | Itgb3 | 1 | 1 |
| ITGB3 | Col4a3 | Immune | Immune_Basophil | Itgb3 | 1 | 1 |
| ITGB3 | Gsn | Immune | Immune_Basophil | Itgb3 | 1 | 1 |
| KDR | Timp3 | Endothelial | Endothelial_General | Kdr | 1 | 1 |
| KDR | Vegfc | Endothelial | Endothelial_General | Kdr | 1 | 0.75 |
| KDR | Col18a1 | Endothelial | Endothelial_General | Kdr | 0.5 | 0.75 |
| KDR | Hspg2 | Endothelial | Endothelial_General | Kdr | 0.5 | 0.5 |
| KDR | Figf | Endothelial | Endothelial_General | Kdr | 1 | 1 |
| KDR | Figf | Endothelial | Endothelial_General | Kdr | 1 | 1 |
| KLRD1 | Tyrobp | Immune | Immune_Lymphocyte | Klrd1 | 1 | 1 |
| LRP1 | A2m | Fibroblast | Fibroblast_General | Lrp1 | 1 | 1 |
| LRP1 | Thbs1 | Fibroblast | Fibroblast_General | Lrp1 | 1 | 1 |
| LRP1 | C1qa | Fibroblast | Fibroblast_General | Lrp1 | 1 | 1 |
| LRP1 | Ltf | Fibroblast | Fibroblast_General | Lrp1 | 1 | 1 |
| LRP1 | C1qb | Fibroblast | Fibroblast_General | Lrp1 | 1 | 1 |
| LRP1 | Calr | Fibroblast | Fibroblast_General | Lrp1 | 0.5 | 0.5 |
| LRP1 | Elane | Fibroblast | Fibroblast_General | Lrp1 | 1 | 1 |
| LRP1 | Plat | Fibroblast | Fibroblast_General | Lrp1 | 1 | 1 |
| LRP1 | C1qc | Fibroblast | Fibroblast_General | Lrp1 | 1 | 1 |
| LRP1 | Pdgfb | Fibroblast | Fibroblast_General | Lrp1 | 0.33 | 0.33 |
| LY96 | Ly86 | Immune | Immune_General | Ly96 | 1 | 1 |
| LYVE1 | Pdgfb | Immune | Immune_General | Lyve1 | 1 | 1 |
| NOTCH1 | Egfl7 | Endothelial | Endothelial_General | Notch1 | 1 | 1 |
| NOTCH1 | Nov | Endothelial | Endothelial_General | Notch1 | 1 | 1 |
| NOTCH1 | Nov | Endothelial | Endothelial_General | Notch1 | 1 | 1 |
| NOTCH1 | Rbp3 | Endothelial | Endothelial_General | Notch1 | 1 | 1 |
| NR3C1 | Hmgb2 | Fibroblast | Fibroblast_General | Nr3c1 | 1 | 1 |
| NR3C1 | Hmgb2 | Fibroblast | Fibroblast_General | Nr3c1 | 1 | 1 |
| NR3C1 | Calr | Fibroblast | Fibroblast_General | Nr3c1 | 0.5 | 0.5 |
| NRP2 | Pgf | Glial | Glial_OPC | Nrp2 | 1 | 1 |
| NRP2 | Pgf | Glial | Glial_OPC | Nrp2 | 1 | 1 |
| NRP2 | Sema3c | Glial | Glial_OPC | Nrp2 | 1 | 1 |
| NRP2 | Sema3f | Glial | Glial_OPC | Nrp2 | 1 | 1 |
| NRXN1 | Nxph1 | Glial | Glial_Developing pineal gland (Krt19+) | Nrxn1 | 1 | 1 |
| P2RX4 | Wnt4 | Immune | Immune_General | P2rx4 | 1 | 1 |
| P2RY1 | Slc9a3r1 | Immune | Immune_Basophil | P2ry1 | 1 | 1 |
| PDGFRA | Snx2 | Epithelial | Epithelial_Topic 23 | Pdgfra | 1 | 1 |
| PDGFRA | Snx2 | Fibroblast | Fibroblast_Topic 8 | Pdgfra | 1 | 1 |
| PDGFRA | Snx2 | Fibroblast | Fibroblast_General | Pdgfra | 0.5 | 0.5 |
| PDGFRA | Clu | Epithelial | Epithelial_Topic 23 | Pdgfra | 1 | 1 |
| PDGFRA | Clu | Fibroblast | Fibroblast_Topic 8 | Pdgfra | 1 | 1 |
| PDGFRA | Clu | Fibroblast | Fibroblast_General | Pdgfra | 1 | 1 |
| PDGFRA | Slc9a3r1 | Epithelial | Epithelial_Topic 23 | Pdgfra | 1 | 1 |
| PDGFRA | Slc9a3r1 | Fibroblast | Fibroblast_Topic 8 | Pdgfra | 1 | 1 |
| PDGFRA | Slc9a3r1 | Fibroblast | Fibroblast_General | Pdgfra | 0.33 | 0.33 |
| PDGFRA | Pdgfc | Epithelial | Epithelial_Topic 23 | Pdgfra | 1 | 1 |
| PDGFRA | Pdgfc | Fibroblast | Fibroblast_Topic 8 | Pdgfra | 1 | 1 |
| PDGFRA | Pdgfc | Fibroblast | Fibroblast_General | Pdgfra | 0.5 | 0.5 |
| PDGFRA | Pdgfb | Epithelial | Epithelial_Topic 23 | Pdgfra | 1 | 1 |
| PDGFRA | Pdgfb | Fibroblast | Fibroblast_Topic 8 | Pdgfra | 1 | 1 |
| PDGFRA | Pdgfb | Fibroblast | Fibroblast_General | Pdgfra | 0.33 | 0.33 |
| PDGFRB | Pdgfc | Fibroblast | Fibroblast_General | Pdgfrb | 0.5 | 0.5 |
| PDGFRB | Snx2 | Fibroblast | Fibroblast_General | Pdgfrb | 0.5 | 0.5 |
| PDGFRB | Mfge8 | Fibroblast | Fibroblast_General | Pdgfrb | 1 | 1 |
| PDGFRB | Slc9a3r1 | Fibroblast | Fibroblast_General | Pdgfrb | 0.33 | 0.33 |
| PDGFRB | Pdgfb | Fibroblast | Fibroblast_General | Pdgfrb | 0.33 | 0.33 |
| PILRA | Nid2 | Immune | Immune_Monocyte | Pilra | 1 | 1 |
| PILRA | Nid2 | Immune | Immune_Monocyte | Pilra | 1 | 1 |
| PROCR | Ctsb | Endothelial | Endothelial_General | Procr | 1 | 1 |
| PTGDR | Ptgds | Fibroblast | Fibroblast_Topic 7 | Ptgdr | 1 | 1 |
| PTGDR | Ptgds | Fibroblast | Fibroblast_Topic 7 | Ptgdr | 1 | 1 |
| PTGER3 | Efemp2 | Fibroblast | Fibroblast_Topic 5 | Ptger3 | 1 | 1 |
| PTGER3 | Efemp2 | Immune | Immune_Basophil | Ptger3 | 1 | 1 |
| PTH1R | Slc9a3r1 | Fibroblast | Fibroblast_General | Pth1r | 0.33 | 0.33 |

TABLE 5-continued

| Identified Interactions in Embryo - cognate ligand-receptor pairs. | | | | | | |
|---|---|---|---|---|---|---|
| PTPRZ1 | Ptn | Glial | Glial_General | Ptprz1 | 1 | 1 |
| RAMP3 | Adm | Endothelial | Endothelial_General | Ramp3 | 1 | 1 |
| RARA | Fn1 | Immune | Immune_Monocyte | Rara | 0.5 | 0.5 |
| RARA | Penk | Immune | Immune_Monocyte | Rara | 1 | 1 |
| RARA | Clu | Immune | Immune_Monocyte | Rara | 1 | 1 |
| ROBO2 | Slit2 | Glial | Glial_Developing pineal gland (Krt19+) | Robo2 | 1 | 1 |
| ROBO4 | Slit2 | Endothelial | Endothelial_General | Robo4 | 1 | 1 |
| ROBO4 | Slit2 | Endothelial | Endothelial_Topic 3 | Robo4 | 1 | 1 |
| RORA | Nme2 | Fibroblast | Fibroblast_General | Rora | 1 | 1 |
| RORB | Nme2 | Glial | Glial_Developing pineal gland | Rorb | 1 | 1 |
| SCARB1 | Pon2 | Endothelial | Endothelial_General | Scarb1 | 0.5 | 0.5 |
| SCARB1 | Pon2 | Endothelial | Endothelial_Topic 3 | Scarb1 | 1 | 1 |
| SCARF1 | Calr | Endothelial | Endothelial_General | Scarf1 | 1 | 1 |
| SELPLG | Vcan | Immune | Immune_General | Selplg | 0.5 | 0.5 |
| SLC40A1 | Cp | Immune | Immune_General | Slc40a1 | 1 | 1 |
| SLC40A1 | Cp | Endothelial | Endothelial_Topic 11 | Slc40a1 | 1 | 1 |
| TBXA2R | Prdx4 | Endothelial | Endothelial_General | Tbxa2r | 1 | 1 |
| TBXA2R | Nme2 | Endothelial | Endothelial_General | Tbxa2r | 1 | 1 |
| TEK | Angpt2 | Endothelial | Endothelial_General | Tek | 0.5 | 0.5 |
| TGFBR2 | Clu | Endothelial | Endothelial_General | Tgfbr2 | 1 | 1 |
| TGFBR2 | Lrg1 | Endothelial | Endothelial_General | Tgfbr2 | 1 | 1 |
| TGFBR2 | Sparc | Endothelial | Endothelial_General | Tgfbr2 | 1 | 1 |
| TGFBR2 | Tgfb2 | Endothelial | Endothelial_General | Tgfbr2 | 1 | 1 |
| TMEM219 | Pon2 | Immune | Immune_General | Tmem219 | 0.5 | 0.5 |
| TNFRSF11B | Thbs1 | Endothelial | Endothelial_Topic 3 | Tnfrsf11b | 1 | 1 |
| TNFRSF11B | Thbs1 | Endothelial | Endothelial_General | Tnfrsf11b | 1 | 1 |
| TNFRSF11B | Fn1 | Endothelial | Endothelial_Topic 3 | Tnfrsf11b | 1 | 1 |
| TNFRSF11B | Fn1 | Endothelial | Endothelial_General | Tnfrsf11b | 0.33 | 0.33 |
| TNFRSF11B | Vtn | Endothelial | Endothelial_Topic 3 | Tnfrsf11b | 1 | 1 |
| TNFRSF11B | Vtn | Endothelial | Endothelial_General | Tnfrsf11b | 1 | 1 |
| TNFRSF25 | Tnfsf12 | Immune | Immune_Lymphocyte | Tnfrsf25 | 1 | 1 |
| TREM2 | Tyrobp | Immune | Immune_General | Trem2 | 1 | 1 |
| TREML2 | Snx2 | Immune | Immune_Neutrophil | Treml2 | 1 | 1 |

Figure 6C:
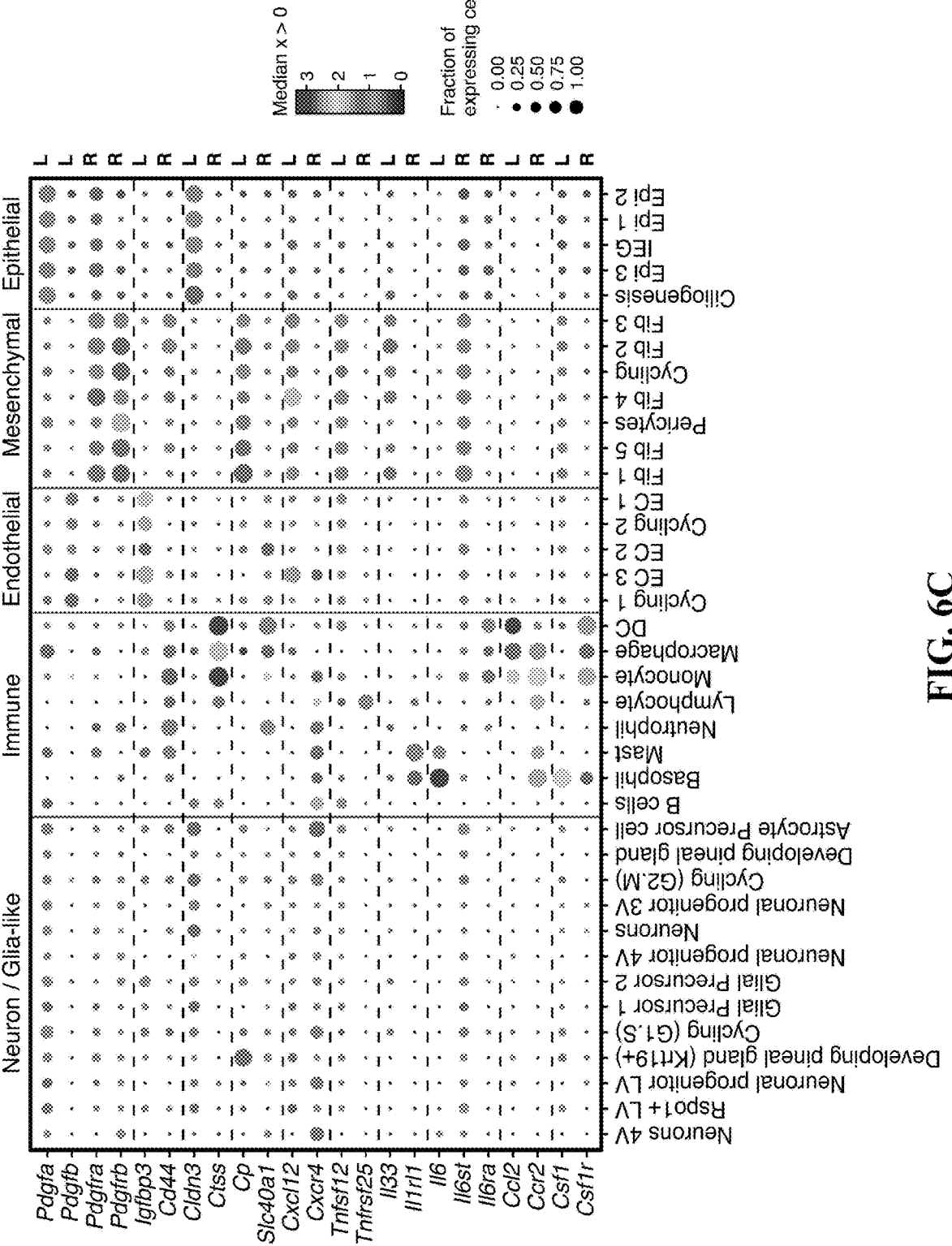

Examining cell specific interactions highlighted key potential roles for specific cell types. For example, basophils expressed colony stimulating factor 1 (Csf1), while macrophages and monocytes expressed its receptor Csf1R, suggesting a signaling axis for myeloid cell maturation (FIG. 6C), similar to basophil-macrophage communication in the lung (Cohen et al., 2018). In another example, basophils, and to a lesser extent mast cells, expressed 16, whereas one of the IL6 receptors, Il6st, was predominantly expressed by mesenchymal cells, and another, Il6ra, was enriched in monocytes, macrophages and DCs (FIG. 6C). Basophils and mast cells also specifically expressed Ilr1i (ST2), the receptor for the alarmin 1133 (Schmitz et al., 2005), which in turn was expressed by fibroblasts and enriched in the 3V ChP (FIG. 6C). Finally, the growth factor receptors Pdgfra and Pdgfrb were uniquely expressed in fibroblasts and pericytes, respectively, while their ligands, Pdgfa and Pdgfb, were uniquely expressed by epithelial and endothelial cells, respectively (FIG. 6C).

Maturation of the Choroid Plexus Brain Barrier in the Adult Brain

Figure 7B:
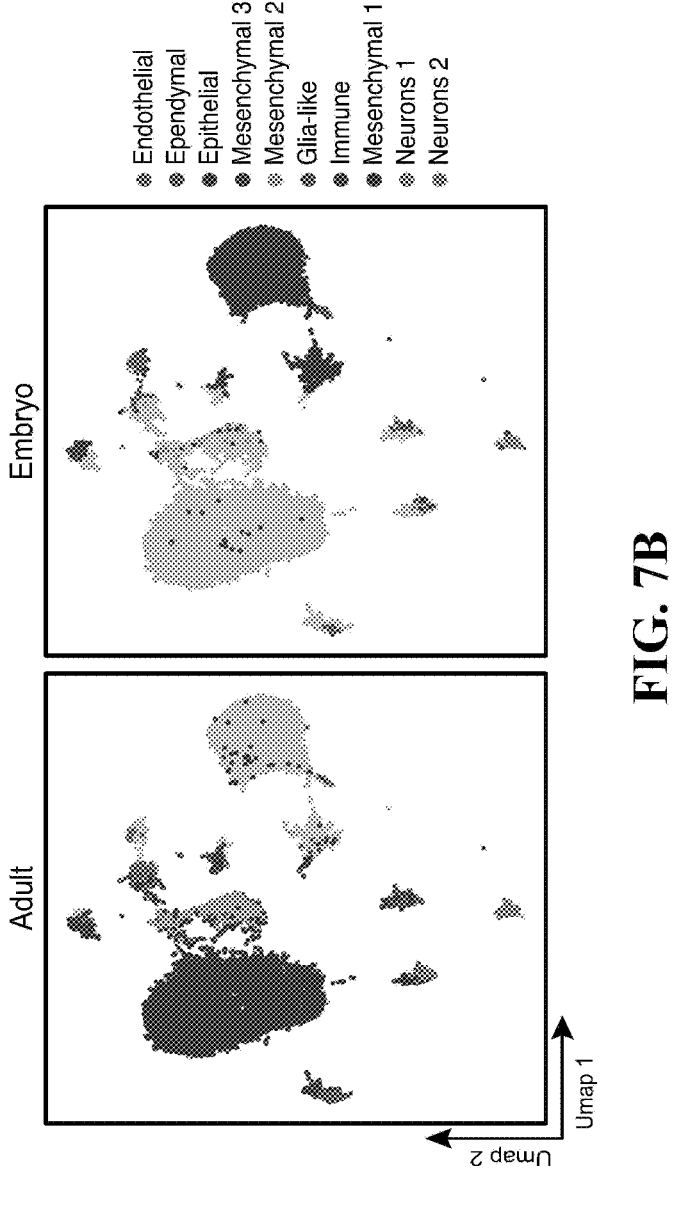
FIG. 7A-7F—Maturation of ChP brain barrier in adulthood.
Figure 7A:
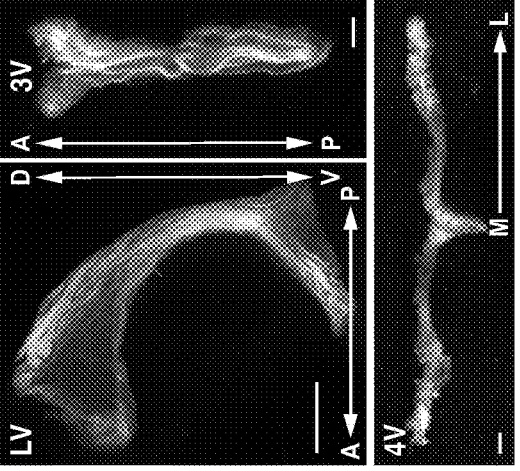

To assess to what extent the cellular diversity established within and across ChP of the developing brain is maintained in the adult, single nucleus RNA-seq was performed (snRNA-Seq) (Habib et al., 2017) (STAR Methods) of 52,629 nuclei across the three ventricles of the ChP from adult (4-6 month old) mice (n=13 number of animals, in 3 pools for each ventricle, performed in two separate experiments) (FIGS. 7A, 7B). 9,845 nuclei from developing LV ChP from E16.5 embryonic brains (n=3 animals) were also profiled for comparison. To relate adult and embryonic profiles, 62,474 nuclei from developing and adult ChP (STAR Methods, FIG. 14B) were jointly clustered and partitioned cells into ten clusters (FIG. 7B). As an alternative approach to compare adult and embryonic profiles, random forest classifier was used (as in (Habib et al., 2017), STAR Methods, FIG. 14A). All cell types observed in the embryonic atlas were present in the adult ChP, along with additional adult-specific cell subsets (FIGS. 7B, 14B-14D), such as ependymocytes. While snRNA-Seq allowed Applicants to overcome the challenge of dissociating adult tissue (Habib et al., 2017), it under-represented immune cells and might have over-represented epithelial cells (FIG. 14E, STAR Methods).

Figures 7C, 7D:
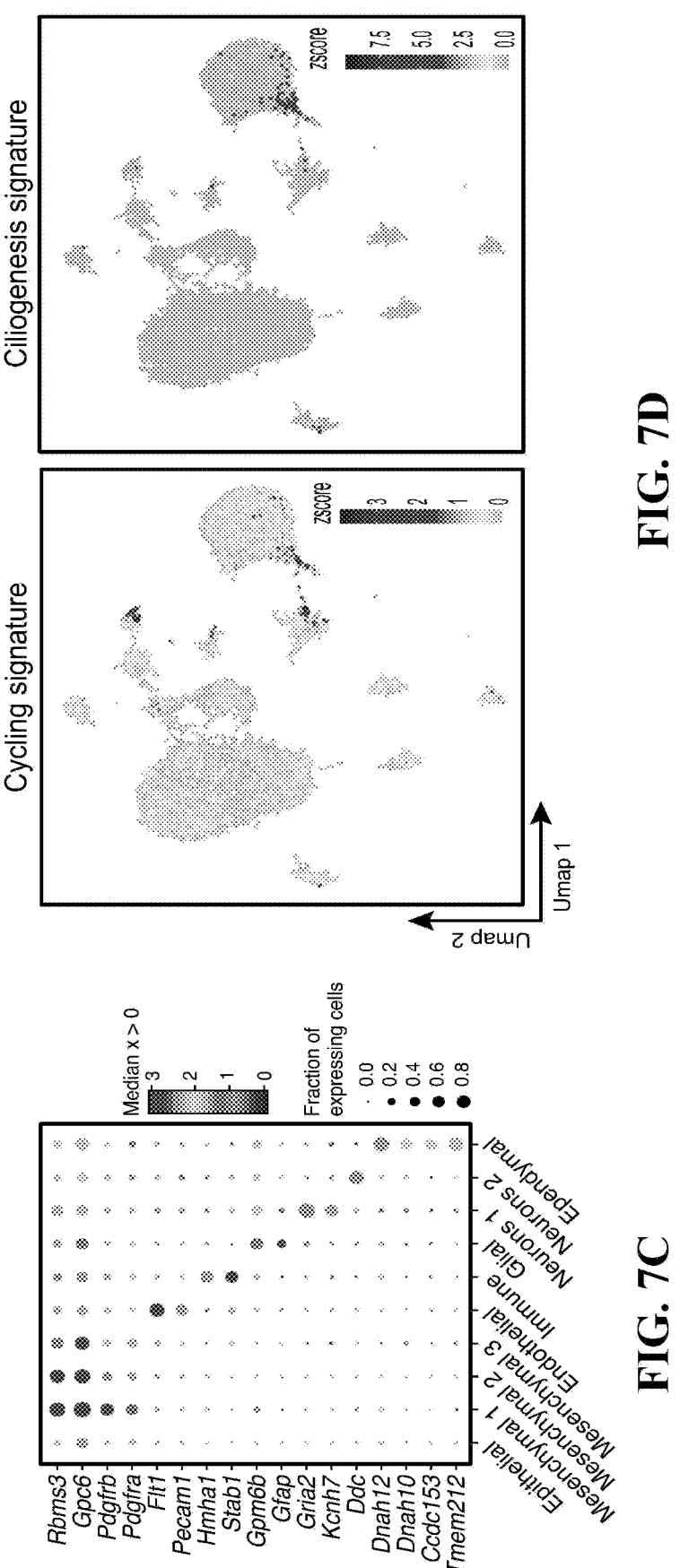
Figures 14A, 14B, 14C, 14D:
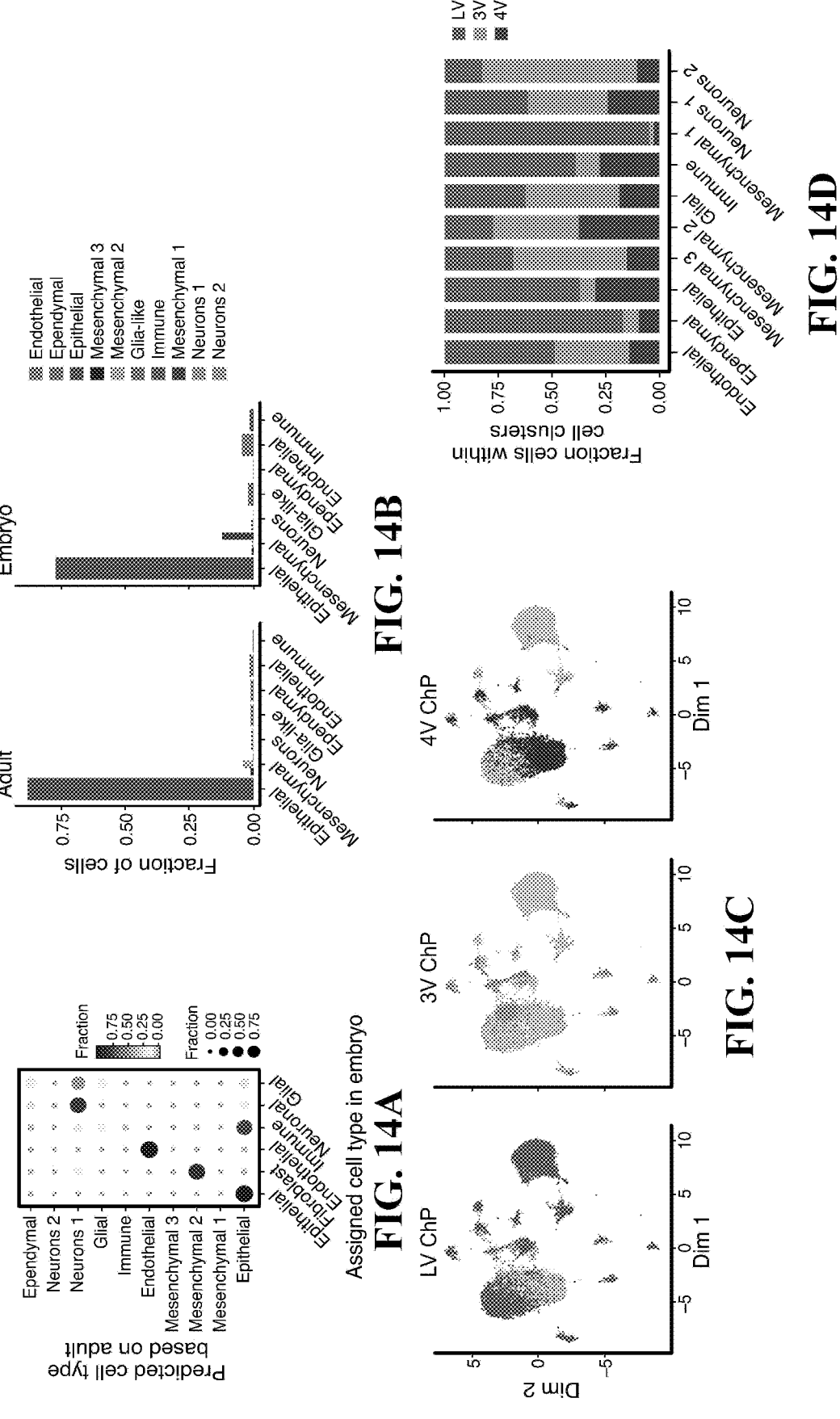
FIG. 14A-14I-Molecular heterogeneity across adult ChP cell types.

Adult and embryonic nuclei showed differences in transcriptional profiles, proportions, maturation states and regionalization. For example, while in the embryonic brain lia and neuronal precursors and immature neurons were found (FIG. 1F), in the adult ChP distinct populations of mature neuronal cells (Gria2 and Kcnh7, or the Ddc expressing subsets; FIG. 7C), and astrocyte-like cells expressing GFAP with ramified processes embedded in the choroid plexus stromal space were found (FIG. 14F). Other age-specific differences included lack of proliferating and ciliogenesis epithelial cells in the adult cell types, suggesting low proliferation under homeostatic conditions in the adult ChP (FIG. 7D). Finally, mesenchymal cells clustered into three subtypes, an embryonically enriched cluster (mesenchymal 1), an adult enriched cluster (mesenchymal 2), and one shared cluster (mesenchymal 3) (FIGS. 7B, 14B).

Figure 7E:
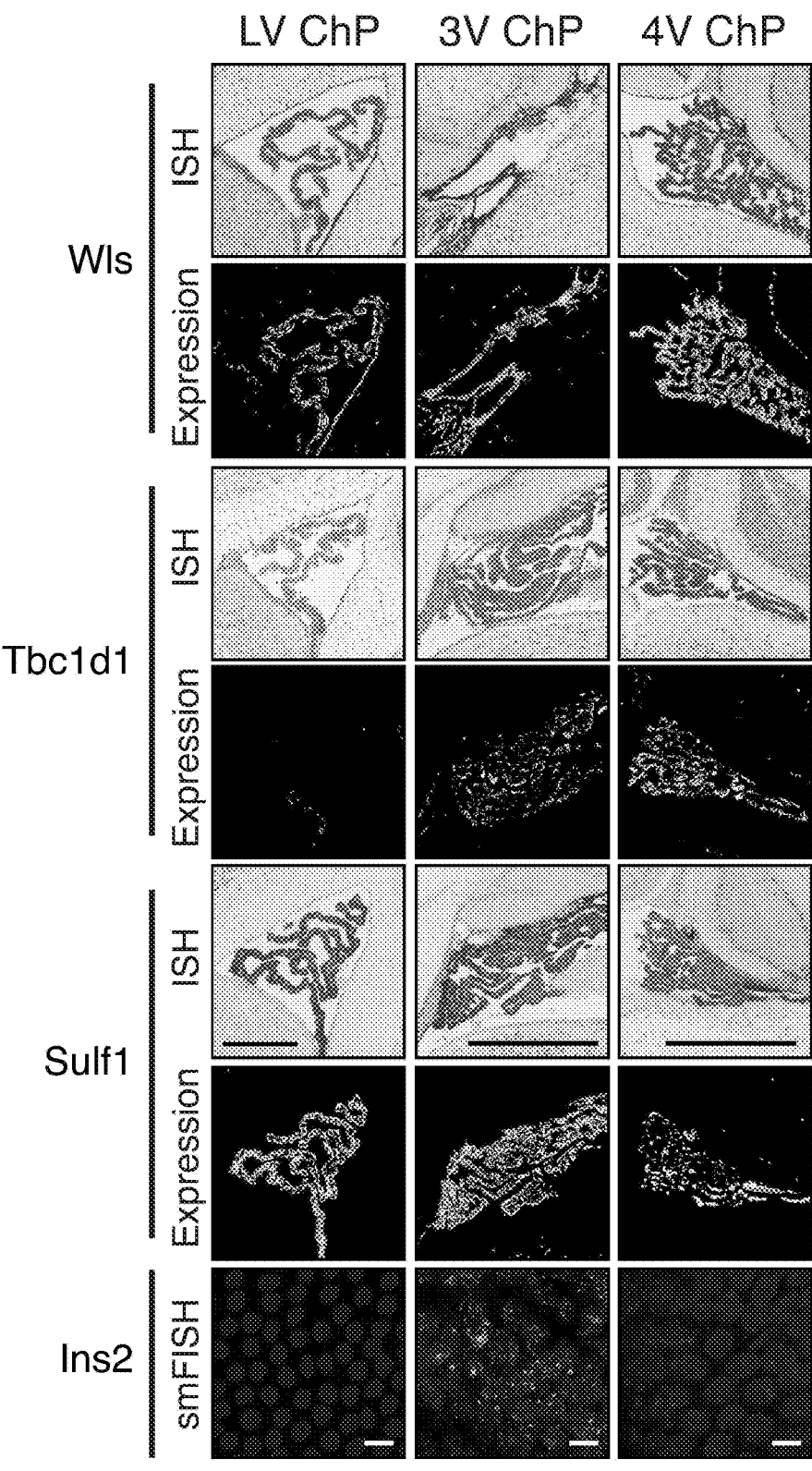
Figure 7F:
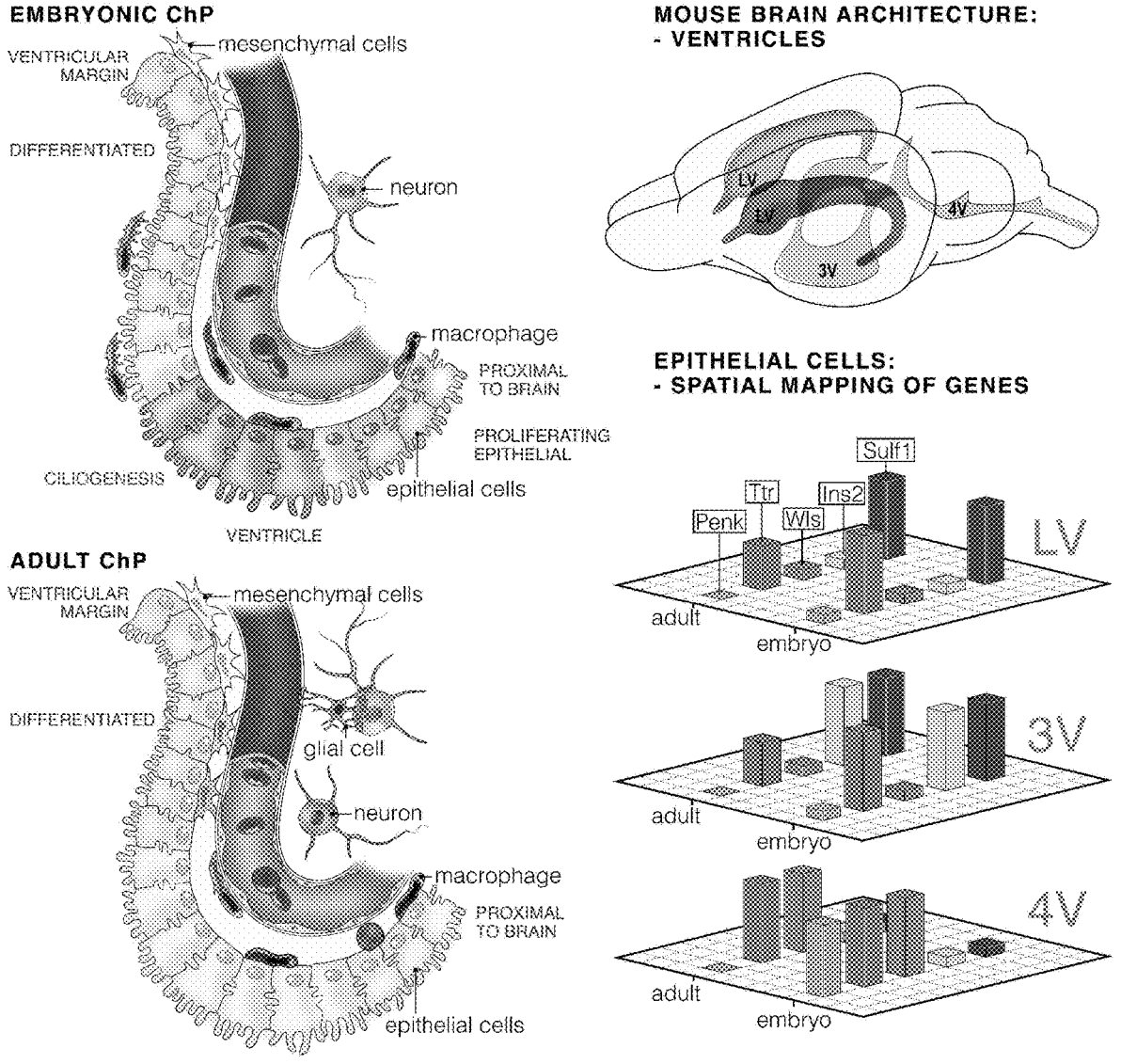
Figures 14E, 14F, 14G, 14H:
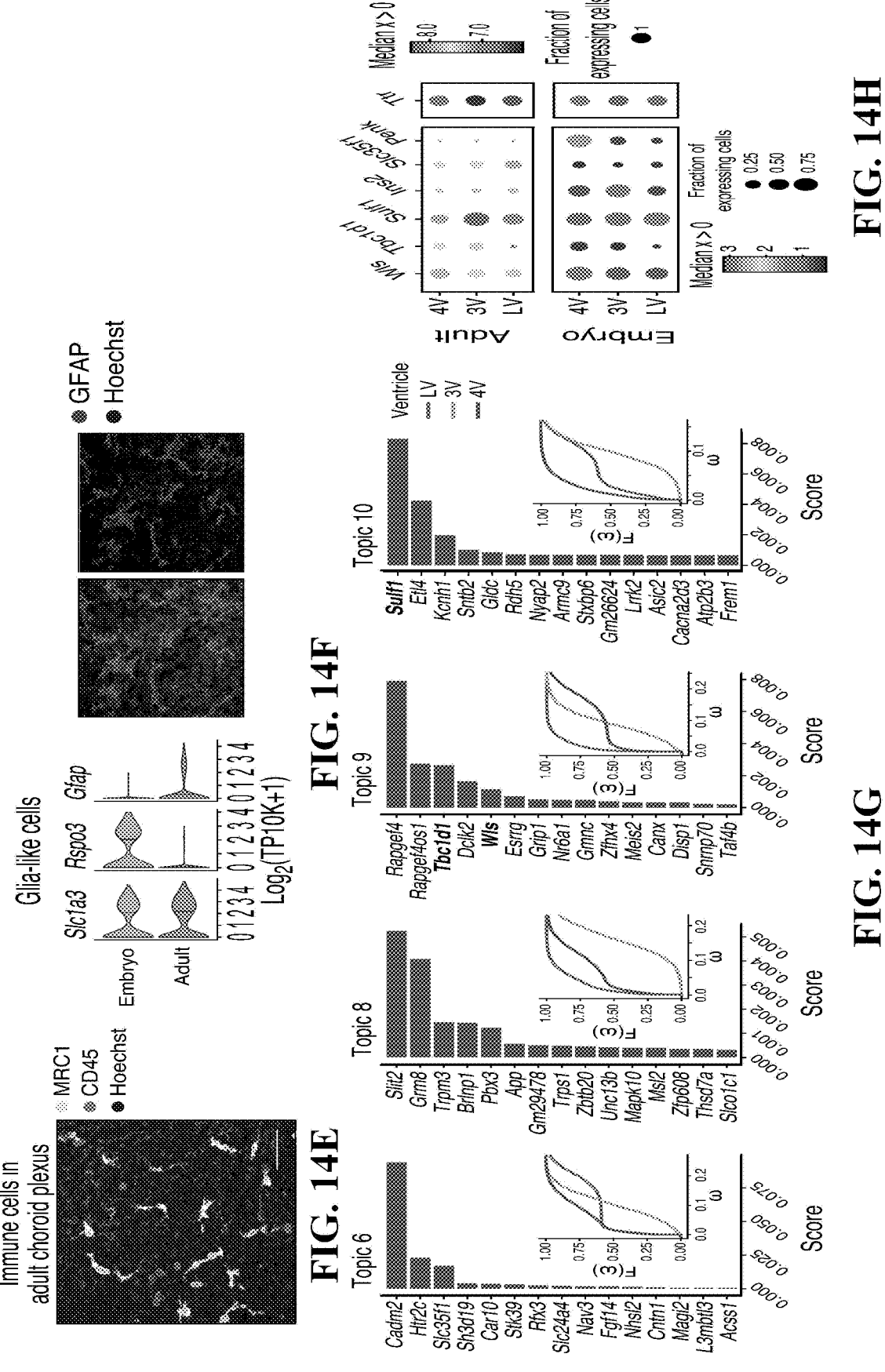
Figure 14I:
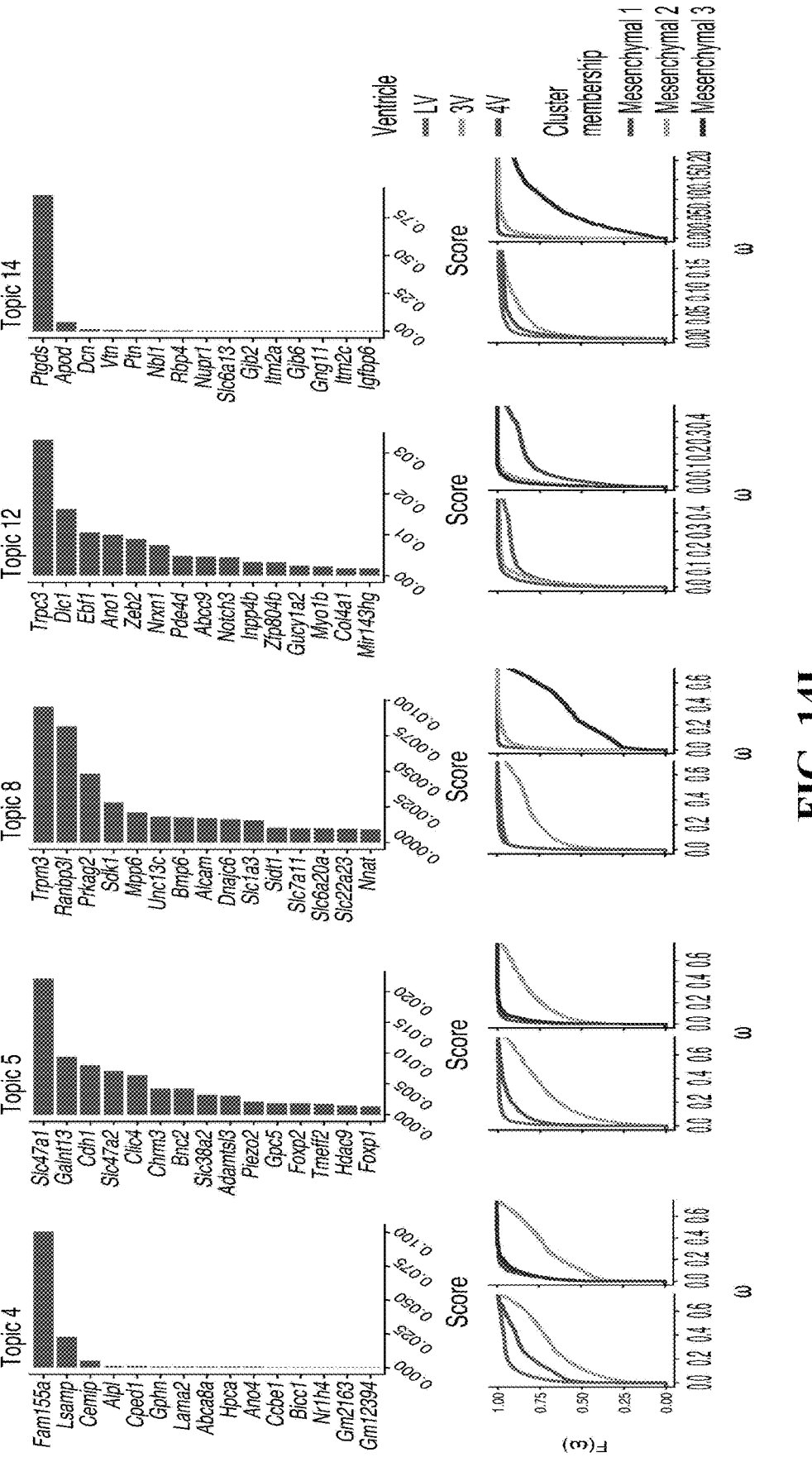
Figures 15A, 15B, 15C:
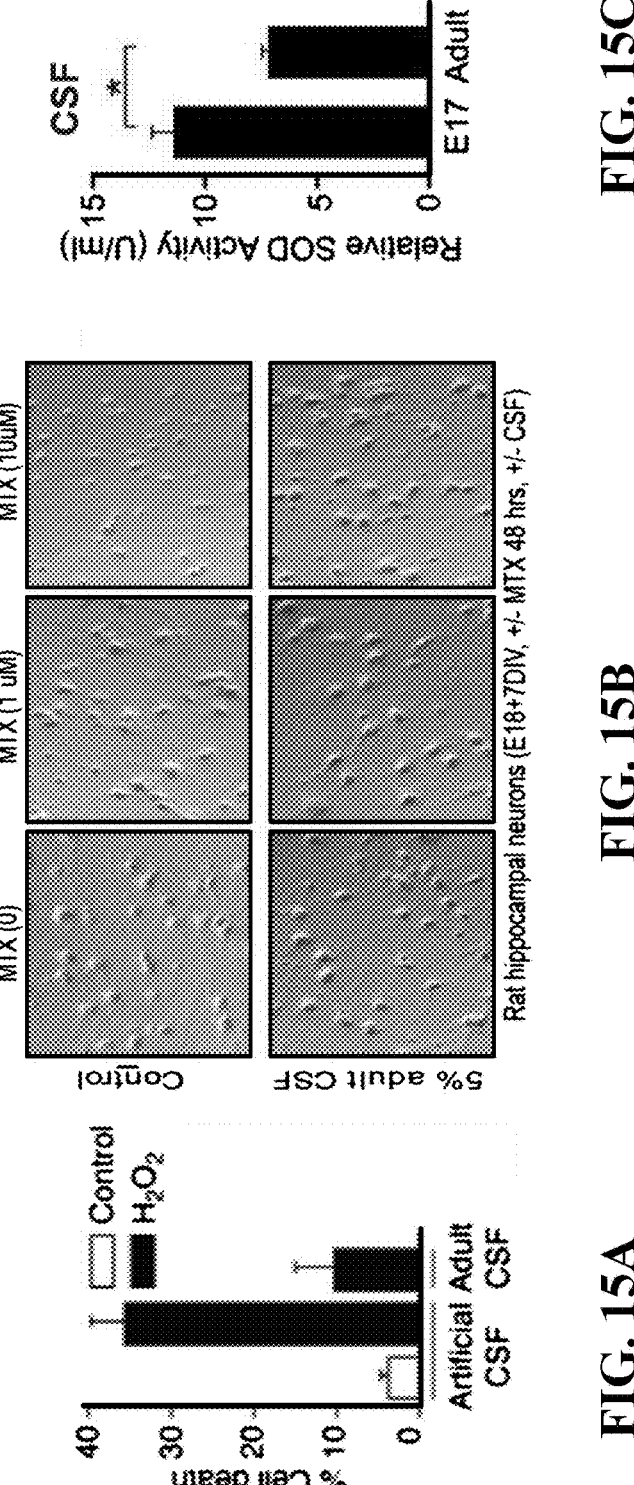
FIG. 15A-15E—explores whether CSF contains factors to protect neurons from oxidative stress (FIG. 15A) measurement of cell death in artificial and adult CSF.
Figures 15D, 15E:
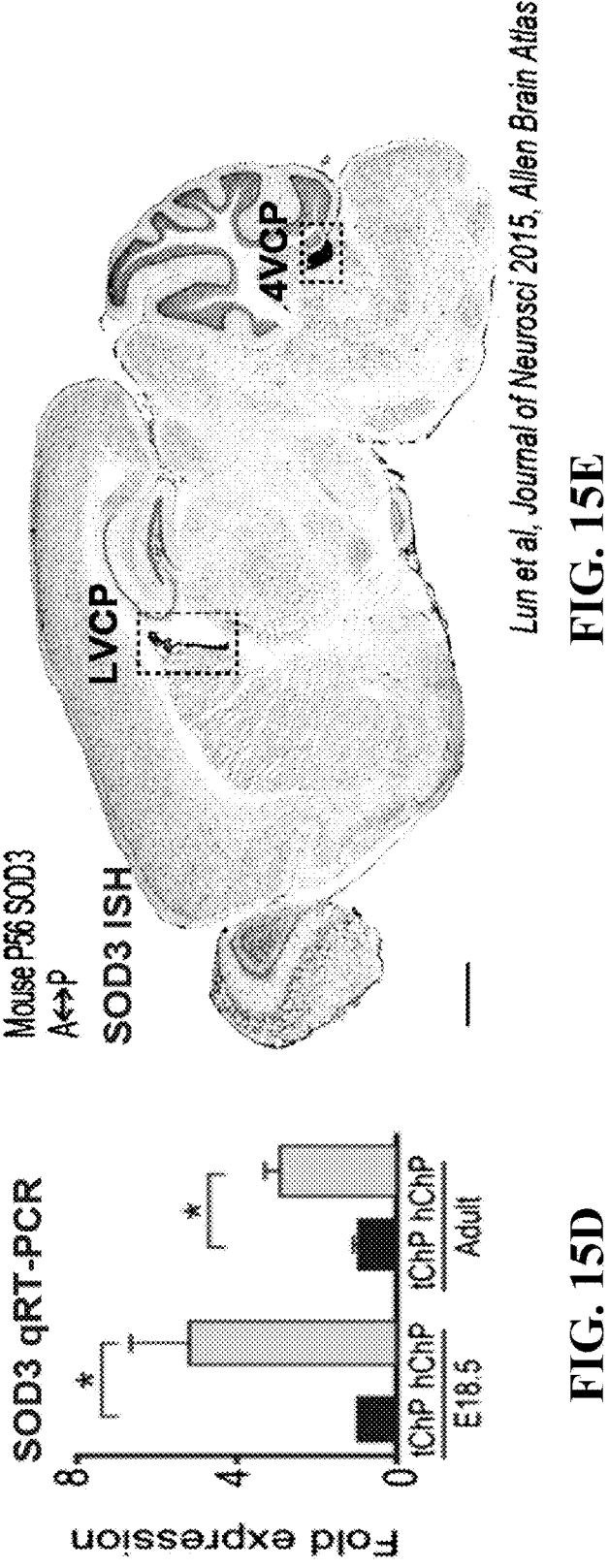
Figures 16A, 16B:
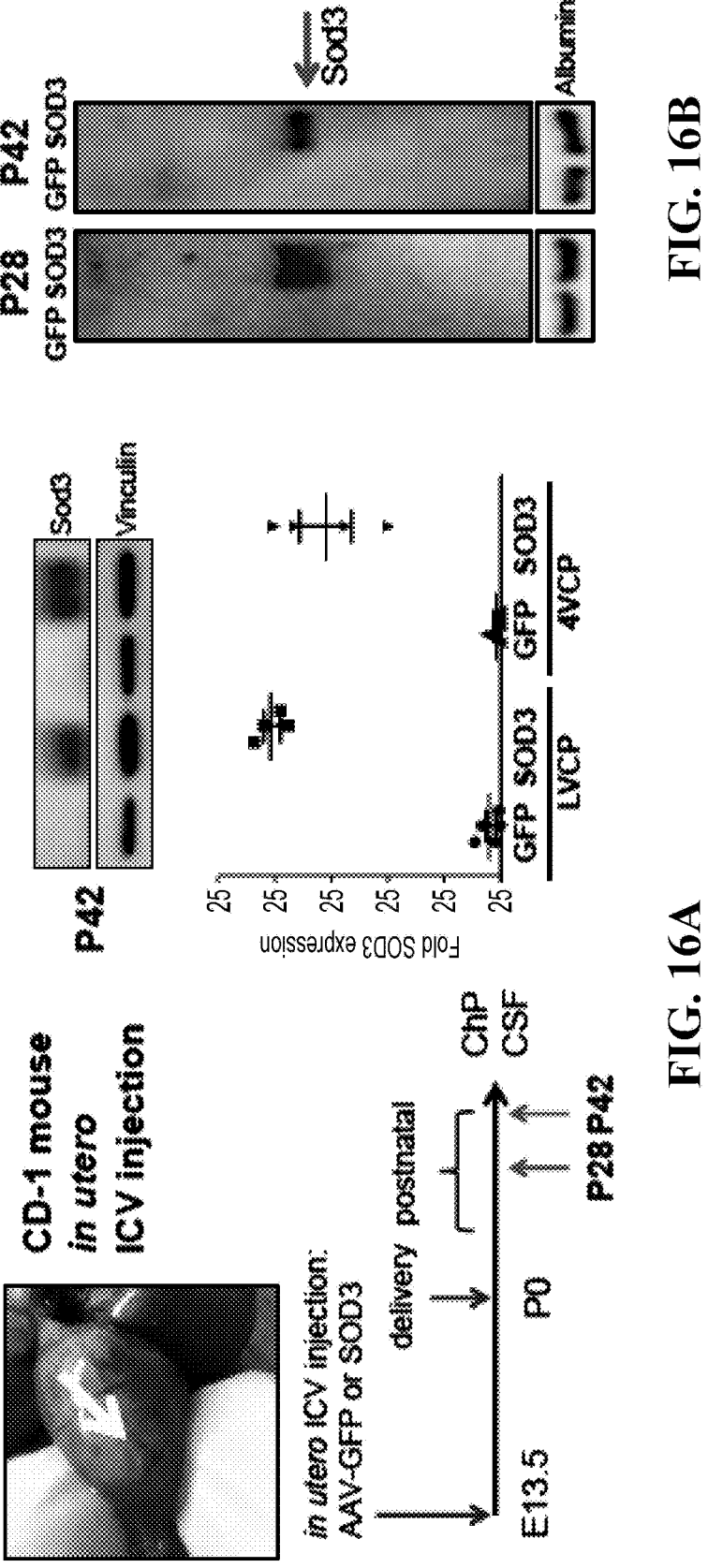
FIG. 16A-16B—includes timing and development of method of in utero ICV injection for ChP-mediated gene therapy to secrete SOD3 in CSF.
Figures 20A, 20B, 20C, 20D, 20E:
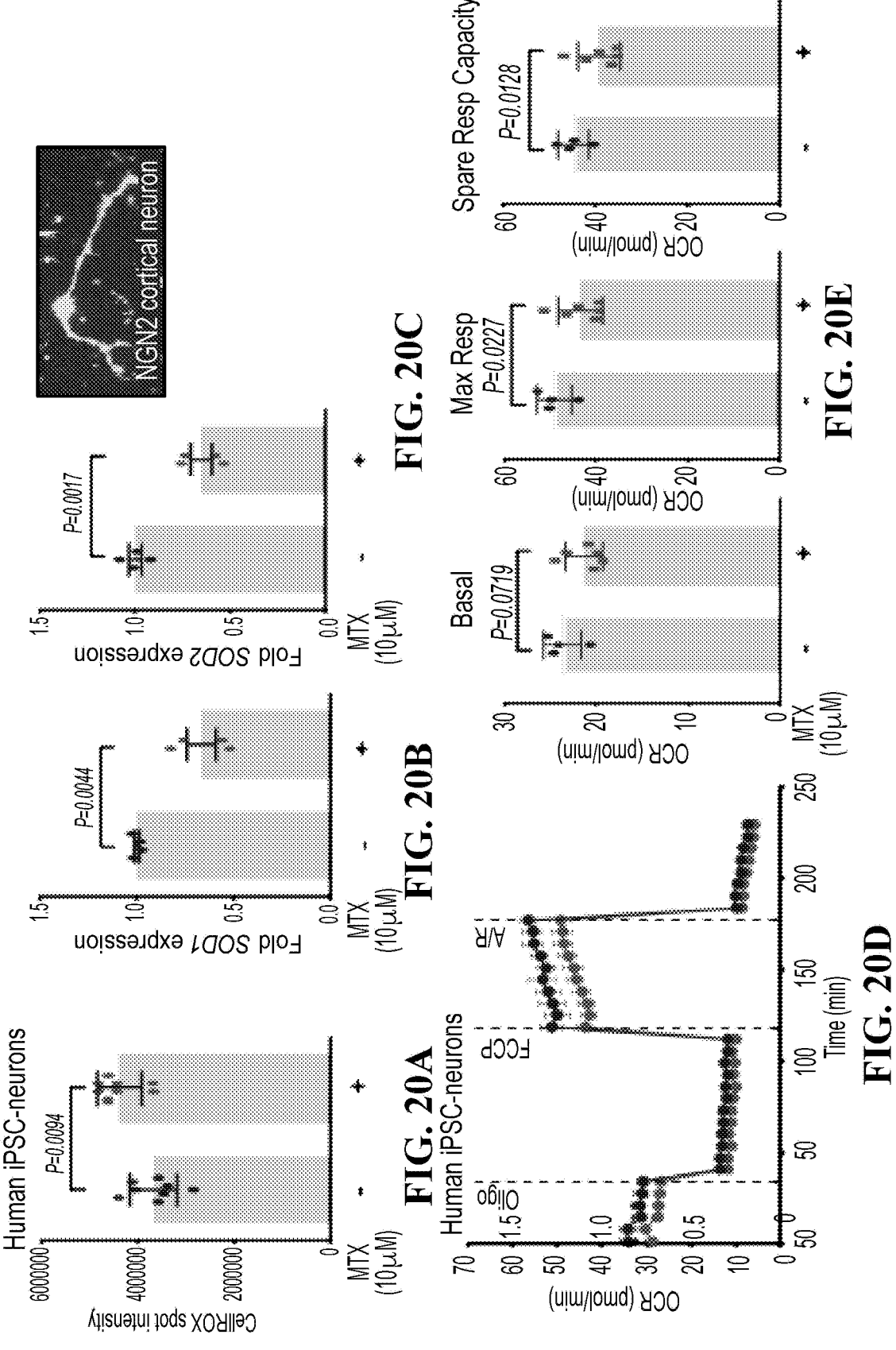
FIG. 20A-20E—MTX induces oxidative stress in Human iPSC-derived neurons charted in 20A-20E, FIG. 20A—CellROX spot intensity, FIG. 20B—SOD1 expression, FIG. 20C—SOD2 expression, FIG. 20D OCR (pmol/min) over time, and FIG. 20E measures Basal, Maz Rrep and Spare Resp Capacity.
Figures 22A, 22B, 22C, 22D, 23:
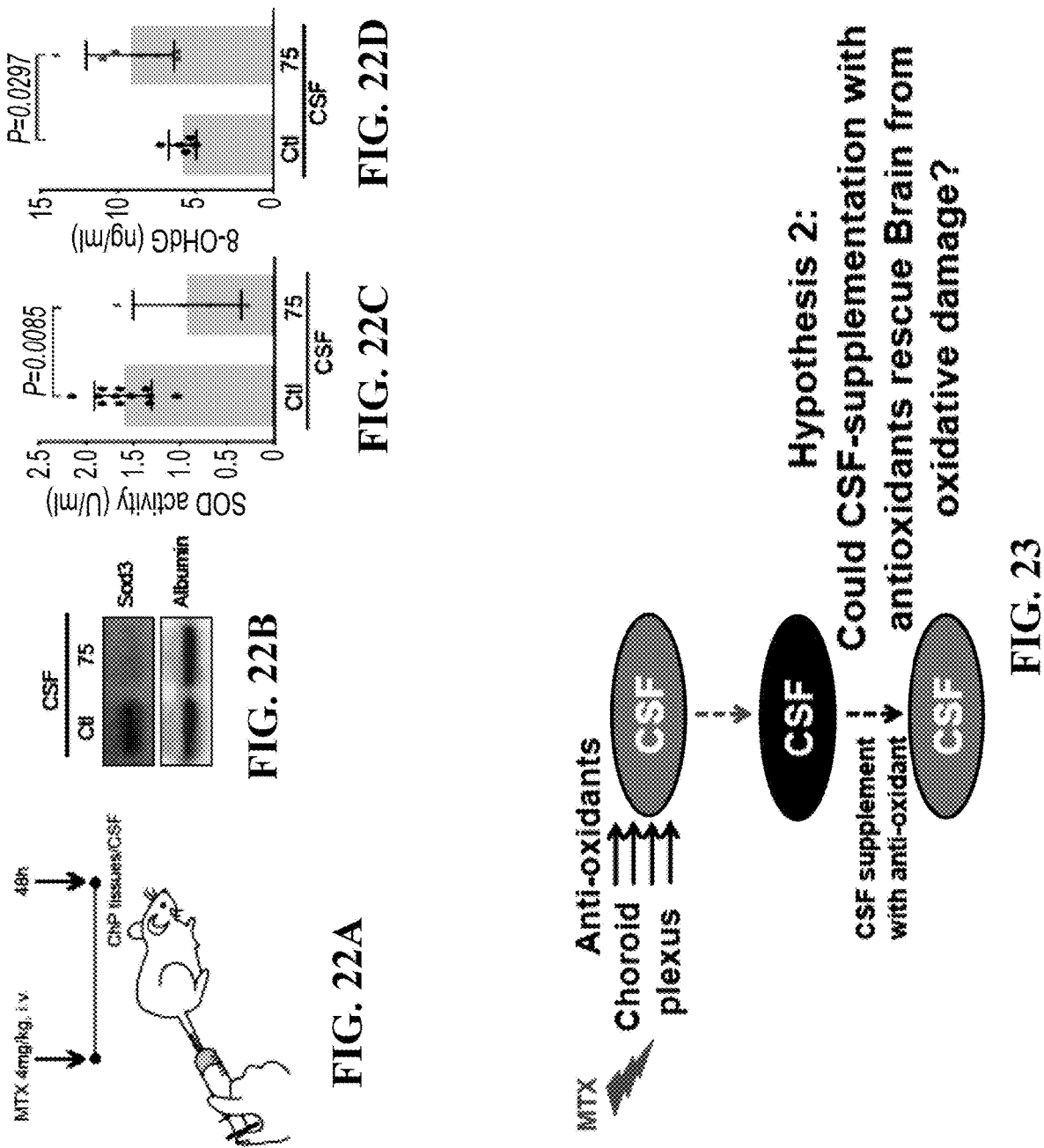
FIG. 22A-22D—MTX decreases SOD expression and increases oxidative damage in vivo
FIG. 23—depiction of the objective to test if CSF-SOD supplementation protects the brain from chemotherapy-induced oxidative damage.
Figures 25A, 25B, 25C, 25D, 25E:
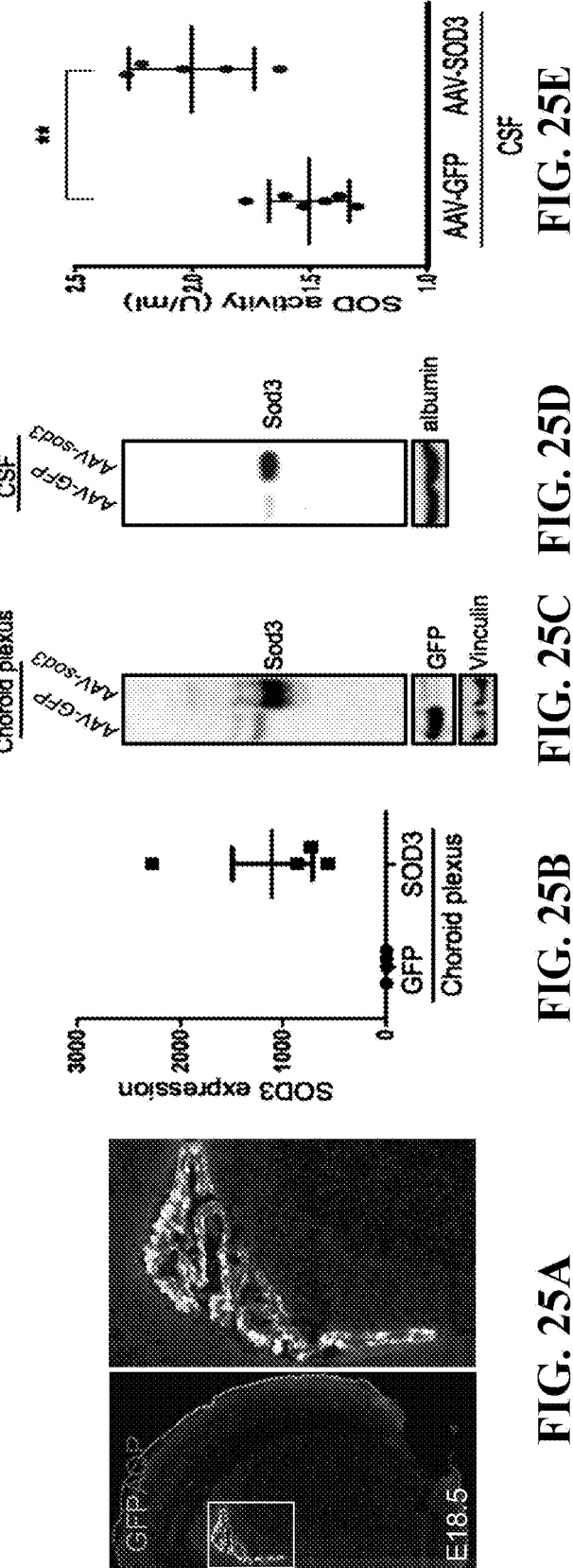
FIG. 25A-25E—(FIG. 25A) AAV2/5-GFP infection in E13.5 mouse embryos shows efficient GFP expression in lateral ventricle (LV) ChP epithelial cells by E18.5. AAV2/5-SOD3 transduced embryos show sustained SOD3 expression in postnatal 14 LV ChP by (FIG. 25B) qPCR, (FIG. 25C) immunoblotting, and (FIG. 25D) CSF.
Figures 26A, 26B, 26C, 26D, 26E, 26F:
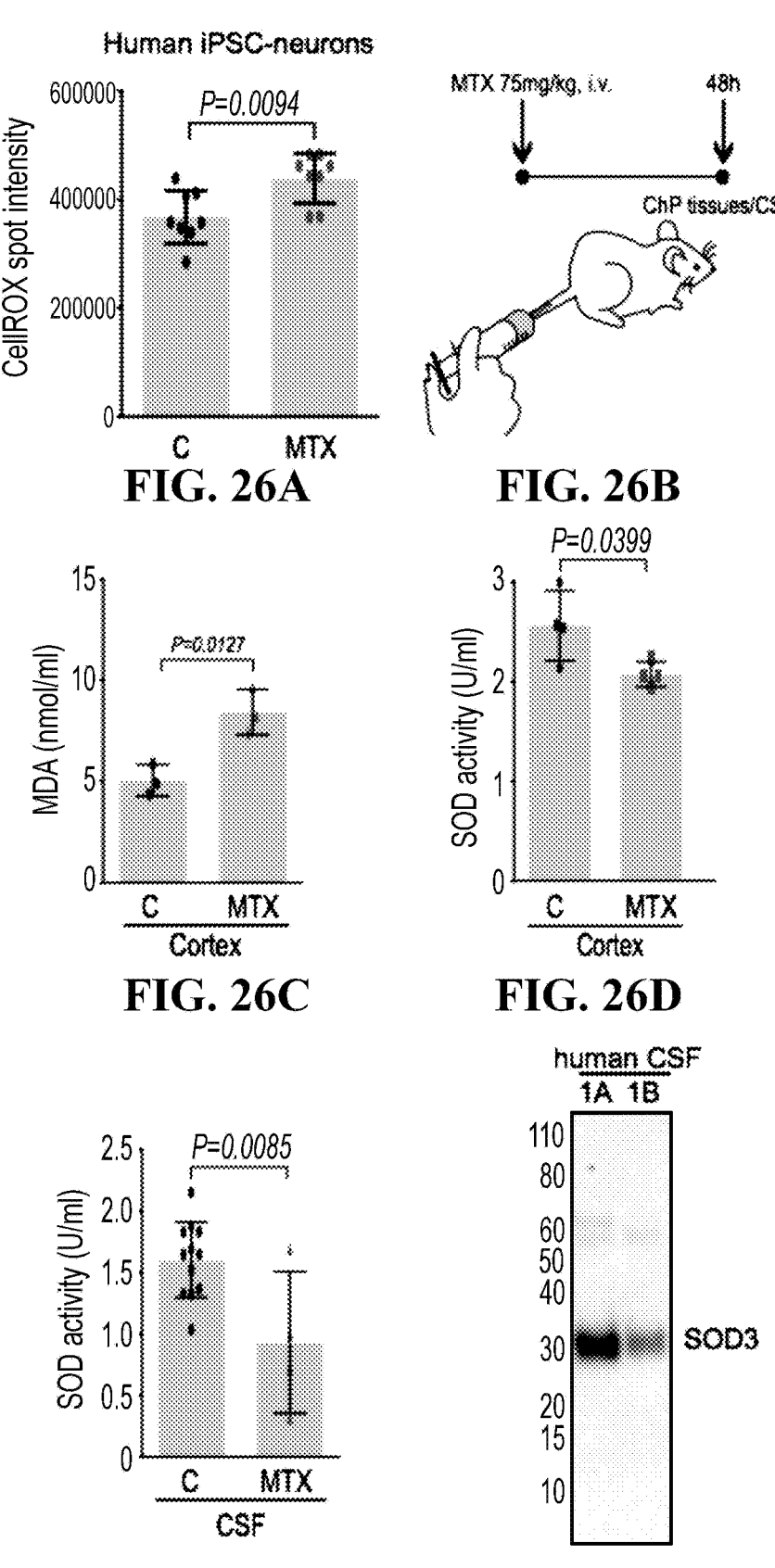
FIG. 26A-26F—(FIG. 26A) MTX (10 uM) triggers oxidative stress in human iPSC cortical neurons.
Figure 27A:
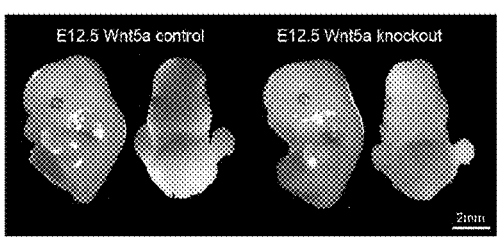
FIG. 27A-27E Wnt5a deficiency impairs hindbrain choroid plexus development.
Figure 27B:
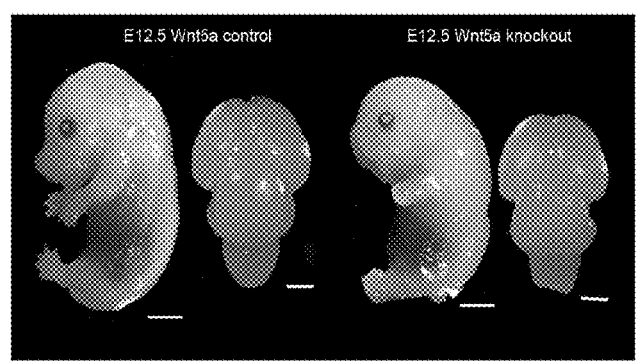
Figure 27C:
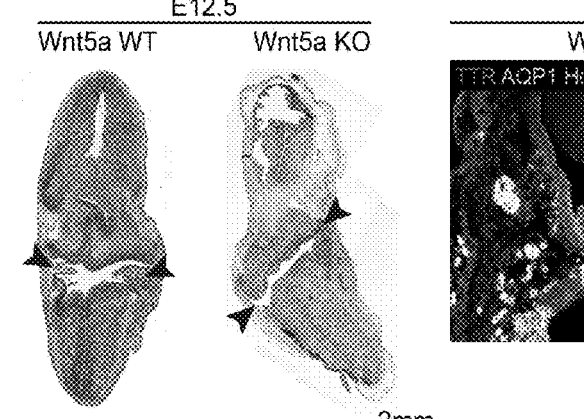
Figure 27D:
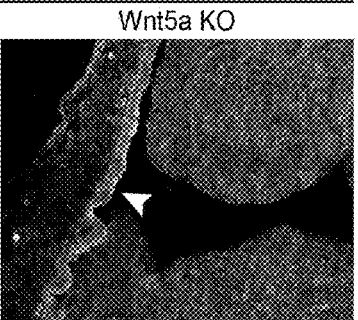
Figure 27E:
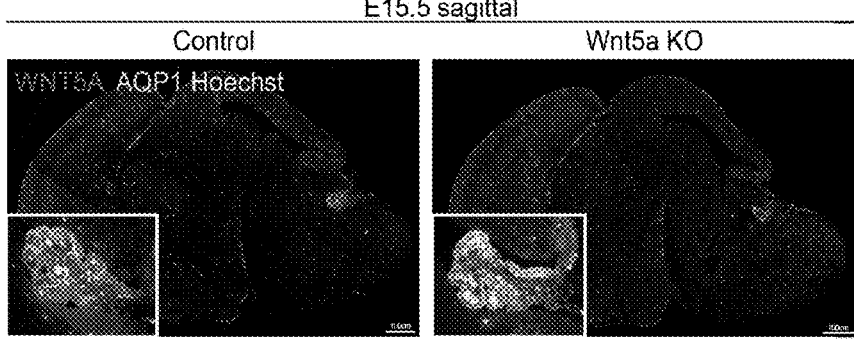

Interestingly, regionalized expression in adult epithelial cells was found, as also observed during development (FIG. 14G, Table 6). Some genes maintained regionalized expression as in the embryo (e.g. Wls, Tbcld1, Sulf1, and Ins2, FIGS. 7E, 14H), such as Ins2, which retained its enriched expression in the 3V ChP epithelial cells (confirmed using single molecule fluorescence in situ hybridization (sm-FISH), FIG. 7E). Other genes lost expression altogether in adult epithelial cells, including Penk and Shh, which were no longer detected in the adult ChP (FIG. 14H) (Lun et al., 2015b). Finally, newly regionalized genes emerged in the adult epithelial ChP, including Ttr (Lun et al., 2015b) and Slc35f1 (FIG. 14H). There was also some inconclusive ventricle specific regionalization of mesenchymal cell programs (FIG. 14I, Table 7). Overall, there were adult-specific cellular subtypes and regionalized gene expression programs, along with retention of embryonic properties of the ChP, which altogether, reflect conserved and maturing functions of the ChP-CSF system.

TABLE 6

Top 50 genes in each topic revealed by topic modeling on epithelial cells of adult ChPs.

| topic_6 | topic_8 | topic_9 | topic_10 |
| --- | --- | --- | --- |
| Cadm2 | Slit2 | Rapgef4 | Sulf1 |
| Htr2c | Grm8 | Rapgef4os1 | Etl4 |
| Slc35f1 | Trpm3 | Tbc1d1 | Kcnh1 |
| Sh3d19 | Brinp1 | Dclk2 | Sntb2 |
| Car10 | Pbx3 | Wls | Gldc |
| Stk39 | App | Esrrg | Rdh5 |
| Rfx3 | Gm29478 | Grip1 | Nyap2 |
| Slc24a4 | Trps1 | Nr6a1 | Armc9 |
| Nav3 | Zbtb20 | Gmnc | Stxbp6 |
| Fgfl4 | Unc13b | Zfhx4 | Gm26624 |
| Nhsl2 | Mapk10 | Meis2 | Lrrk2 |
| Cntn1 | Msi2 | Canx | Asic2 |
| Magi2 | Zfp608 | Disp1 | Cacna2d3 |
| L3mbtl3 | Thsd7a | Snrnp70 | Atp2b3 |
| Acss1 | Slco1c1 | Taf4b | Frem1 |
| Rims2 | Mettl24 | Aff3 | Clybl |
| 5730522E02Rik | Cacnb4 | 4921511C10Rik | Gtf2i |
| Gulp1 | Ccdc88c | 1810034E14Rik | Clic6 |
| Vps54 | Ppp2r2b | A2m | Slit3 |
| Dennd1b | Spata13 | Gm26804 | Pcolce2 |
| Fam110b | Per2 | Prkd1 | Strip2 |
| Brwd3 | Mcu | Gm26733 | Fbxo33 |
| Sptlc3 | Prdm16 | Lamb1 | Nckap5 |
| Dgki | Heg1 | Cdyl | Ptgis |
| P3h2 | Fap | Efna5 | Tspan9 |
| Elovl6 | Sox6 | Tanc2 | Oxct1 |
| Samd4 | Maob | Gm13963 | F5 |
| Atrnl1 | Eya4 | Lrrfip1 | Edar |
| Mpp7 | Per1 | Sycp3 | Chst11 |
| Gpm6a | Sgms2 | Sycp2 | Mtss1 |
| Gabra4 | Pdzd2 | Ormdl2 | A830018L16Rik |
| Baiap2l1 | Zfp521 | Itga6 | Lepr |
| Psd3 | Pdk4 | Ermard | St5 |
| Mapk9 | Acad10 | Gm43713 | Tmem181a |
| Gm5934 | Abca4 | Rnf150 | Pcx |
| Inadl | Airn | 4930469G21Rik | Asb3 |
| Arhgap10 | 4732471J01Rik | Fat1 | Spop |
| Map7 | 0610040J01Rik | Rnf26 | Sgk1 |
| Tmem135 | Sil1 | Meis1 | Dnah2 |
| Zfp148 | Exoc6 | Tm9sf4 | Tns3 |
| Prlr | Galnt7 | Gm11099 | Armc3 |
| B4galt6 | Il17rd | Thyn1 | Olfr1507 |
| Acsl4 | Mgat5 | Grb14 | Tmprss11a |
| Aim1 | Mitf | Dtnbos | Pgpep11 |
| Stk3 | Gm16432 | Cbfb | Nedd4 |
| Flrt2 | Slc12a2 | Dnaaf3 | Map2k6 |
| Maml2 | Ptpn13 | Elovl5 | Ephx1 |
| Tox | Abliml | Slc4a10 | Gtf3c1 |
| Zfp652 | Actn2 | Atp7a | Dawl |
| Ppmle | Clstn3 | Defb9 | Ncor2 |

TABLE 7

Top 50 genes in each topic revealed by topic modeling on mesenchymal cells of developing and adult ChPs (on snRNA-seq data).

| topic_4 | topic_5 | topic_8 | topic_12 | topic_14 |
| --- | --- | --- | --- | --- |
| Fam155a | Slc47a1 | Trpm3 | Trpc3 | Ptgds |
| Lsamp | Galnt13 | Ranbp31 | Dlc1 | Apod |
| Cemip | Cdh1 | Prkag2 | Ebf1 | Dcn |
| Alpl | Slc47a2 | Sdk1 | Ano1 | Vtn |
| Cped1 | Clic4 | Mpp6 | Zeb2 | Ptn |
| Gphn | Chrm3 | Unc13c | Nrxn1 | Nbl1 |
| Lama2 | Bnc2 | Bmp6 | Pde4d | Rbp4 |
| Abca8a | Slc38a2 | Alcam | Abcc9 | Nupr1 |
| Hpca | Adamtsl3 | Dnajc6 | Notch3 | Slc6a13 |
| Ano4 | Piezo2 | Slc1a3 | Inpp4b | Gjb2 |
| Ccbe1 | Gpc5 | Sidt1 | Zfp804b | Itm2a |
| Bicc1 | Foxp2 | Slc7a11 | Gucy1a2 | Gjb6 |
| Nr1h4 | Tmeff2 | Slc6a20a | Myo1b | Gng11 |
| Gm2163 | Hdac9 | Slc22a23 | Col4a1 | Itm2c |
| Gm12394 | Foxp1 | Nnat | Mir143hg | Igfbp6 |
| Cfh | Tmtc1 | Rapgef5 | Ednra | Aebp1 |
| Ank | Abi1 | Hlf | Dmd | Osr1 |
| Atxn1 | Fbxl7 | Camk1d | Dock10 | Islr |
| Rbms1 | Grid2 | Dcdc2a | Tbx3os1 | Ifitm1 |
| Adh1 | Cacna2d3 | Ntrk3 | Vcl | Rcn3 |
| Slc9a9 | Lrrtm4 | Pde1a | Kcnq5 | Fcgrt |
| 4833422C13Rik | Slc2a13 | Kcnk2 | Gpc6 | Vwa1 |
| Slco3a1 | Slc4a4 | Celf2 | Cacnb2 | Lum |
| Rgs7bp | Thsd4 | 6-Mar | Lims1 | Serping1 |
| Sult5a1 | Pcdh11x | Dpyd | Errfi1 | Glul |
| 4930578G10Rik | Sh3pxd2a | Gm4477 | Eya4 | Emp3 |
| Cnksr2 | Mmp16 | Elmo1 | Kcnt2 | Fmod |
| Lamc3 | Nr3c2 | 1700112E06Rik | Pde3a | Cxcl12 |
| Enpep | Slc4a10 | Rora | Kazn | Apoe |
| Fnbp1 | Eya2 | Slc6a1 | Lhfp | Cldn11 |
| Scube1 | Pcsk5 | Mcc | Slc38a11 | Pmp22 |
| Ptprd | Dock5 | Robo1 | Myh9 | Slc16a11 |
| Edil3 | Slc26a7 | Slc6a9 | Arhgap10 | Jund |
| Cntfr | Abcb1a | Nadk2 | Specc1 | Mgp |
| Pknox2 | Slc9a2 | Col4a6 | Ccdc3 | Laptm4a |
| Etv6 | Kcnb2 | Slc16a12 | Arhgap42 | Serpinf1 |
| Cdh6 | Nebl | Slc13a3 | Clstn2 | Srgn |
| Adam12 | Plpp3 | Tgfbr3 | Cacna2d1 | Plat |
| Matn2 | Wwp1 | Pdzrn3 | Grm7 | Foxc1 |
| Plekha6 | Fn1 | Sesn1 | Fbn2 | Nkain4 |
| Rgs7 | Tll1 | Negr1 | Zfhx3 | Ogn |
| Myo1e | Ctnnd2 | Tcte2 | Zeb1 | Ifitm3 |
| Cacng4 | Tcf7l2 | Tcf4 | Chn1 | Itih5 |
| Ppp3ca | Dlg2 | Prkca | Mast4 | Cyba |
| Clmp | Ccdc85a | Lpar1 | Cobll1 | Tsc22d1 |
| Tgfbi | Tbc1d8 | Kdm7a | Pde5a | Wnt4 |
| Tshz2 | Adamts2 | Lepr | Airn | Steap3 |
| App | Gm20400 | Zkscan2 | Arhgef17 | Gja1 |
| Mitf | Ildr2 | Lrrk1 | Fry | Uqcc3 |
| Cdh19 | Rad51b | Ccr9 | Frmd4a | Cd248 |

Discussion

The choroid plexus (ChP) is a critical yet understudied brain barrier. The lack of a cellular and molecular parts list for the ChP has been a major obstacle to dissecting its roles in instructing brain development and health and unlocking its therapeutic potential. The comprehensive cell atlas allows Applicants to chart all major cell classes in the developing and adult ChP, including epithelial, endothelial, mesenchymal (mural and fibroblasts), immune (innate and adaptive), neuronal and glial cells. Applicants characterized similarities and distinctions across brain ventricles and developmental states, and the extensive analyses and validations provide a molecular launchpad for defining the functional roles of each cell type and their interactions.

Establishing this resource required new solutions to several technical challenges unique to the choroid plexus, including tissue isolation, dissociation, and imaging. While gene expression has been analyzed previously from the LV and/or 4V ChP (Liddelow et al., 2010; Lun et al., 2015b;

Silva-Vargas et al., 2016), such analyses were not performed for the 3V ChP, likely due to the difficulty of reliably dissecting this tissue. Here, micro-dissection techniques were optimized to isolate ChP from each ventricle, with minimal contamination from adjacent brain tissue. Next, enzymatic dissociation of embryonic tissue into single cells was optimized by employing combinations of enzymes, temperatures, and mechanical dissociation. Nuclei from adult tissue were isolated, which failed to yield viable cells by dissociation. Analyzing embryonic tissue at both the single cell and single nucleus level allowed assessment of some of the similarities and differences between embryonic and adult ChP tissues.

This work builds on previous findings (Lun et al., 2015b) to demonstrate that epithelial expression programs in the developing and adult brain are ventricle-specific. In the adult 4V ChP, cells retain differential expression of classic patterning genes (e.g., Hoxa2, Hoxb3os, Meis1) as transcriptional memories of their early hindbrain development along the rostro-caudal body axis. Such regionalization may help drive ventricle-specific synthesis of factors to be secreted into the CSF on extracellular vesicles for delivery to distal targets (Coulter et al., 2018; Huang et al., 2010). Local paracrine signaling networks may be supported by Shh receptor Ptch1 enrichment in 4V ChP stromal cells and epithelial cells, in addition to earlier reports that showed that Shh-Ptch1 pericyte signaling instructs the coordinated vascular outgrowth of the fourth ventricle ChP (Nielsen and Dymecki, 2010).

The data revealed several putative signaling axes across cell types, highlighting endothelial and mesenchymal cells as additional potential sources of signals within the ChP. These results open new hypotheses about paracrine signaling within the ChP that may contribute to functions beyond immune cell recruitment and tissue development. This cell atlas provides a first opportunity to identify specific cell types within and across ventricles responsible for the production of secreted factors that promote the health and growth of the brain (Ghersi-Egea et al., 2018; Lun et al., 2015a; Saunders et al., 2018a). Previous studies predicted ChP epithelial cells to be the primary producers of a multitude of secreted factors for distribution throughout the developing brain via the CSF. However, it was shown that essentially all major ChP cell types, and in particular ChP fibroblasts, also express many secreted factors. It remains to be determined if these secreted factors of non-epithelial origin are restricted to targets within ChP stromal space, or whether transport mechanisms allow them to be delivered into the CSF.

In particular, it was found that Ins2 expression was enriched in 3V ChP epithelial cells, suggesting the ChP as a potential internal source of insulin for the brain. While CSF-insulin levels are well documented (Gray et al., 2014), the potential for a brain-derived source of functional insulin has been long debated (Kleinridders et al., 2014). Receptors and signaling machinery for insulin are found widely throughout the brain, the hypothalamus and ventral third ventricle—major centers involved in regulation of body metabolism—are located in the immediate neighborhood of the 3V ChP and could be nearby target sites (Baskin et al., 1983; van Houten et al., 1979), where local fluid flows distribute factors (Faubel et al., 2016). ChP-derived insulin could also act more distally, including on neural progenitor cells to regulate neurogenesis (as has been shown for IGF family members (Lehtinen et al., 2011)).

Ventricle-specific regionalization of mesenchymal cells in developing brains is accompanied by ventricle-specific expression of different ECM components including collagens, and could contribute to differential tissue stiffness and elasticity, which is apparent upon tissue dissection. For other tissues of the body such as the developing muscle and bone, ECM properties impart instructive cues to stem cells (Gattazzo et al., 2014), suggesting that spatially heterogeneous ECM niche in ChP may guide cell-cell interactions and even cell migration (Hallmann et al., 2015).

These profiles of embryonic ChP immune cell populations under homeostatic conditions are largely in agreement with recent single cell profiling studies of adult ChP macrophages, and revealed spatial organization of several macrophage archetypes across ventricles and within the choroid plexus. The vast majority of the ChP macrophages shared 5 of 6 signature genes (Mrc1, Ms4a7, Pf4, Stab1, Fcrls) recently described for adult ChP macrophages (Jordao et al., 2019) and are Sall1 negative (Hammond et al., 2019). Analyses further revealed unique spatial positioning for Spic-expressing cells in the 4V ChP, where they localized to the medial core of the ChP. Spic expression correlated with that of Clec4n, a proposed marker of juvenile ChP macrophages (Li et al., 2019). Slc40a1 Fpn-expressing macrophages closely positioned along larger blood vessels. In other epithelia such as the intestine, Slc40a1 Fpn is an essential iron exporter that removes iron from cells into the blood (Donovan et al., 2005). The present findings suggest that Slc40a1/Fpn-expressing macrophages may participate in maintenance of brain iron homeostasis essential for brain development (Mao et al., 2010).

Overall ventricle-specific regionalization of epithelial cells was maintained in the adult tissue. Many of the genes underlying regionalization differed from those in embryonic samples. While Ins2 retained in 3V ChP epithelial cells of the adult, some embryonically regionalized genes were no longer regionalized in the adult brain, and vice versa. Except for proliferating and differentiating epithelial cell states in the developing embryo, the conservative clustering did not identify distinct clusters of cells within each ventricle of either embryonic or adult, but rather, uncovered ventricle-specific expression, as reflected by "topics" enrichment. Topics as well as graded gene expression patterns, particularly across 4V epithelial cells, may arise from the segmental development of the 4V ChP from distinct rhombomeres (Awatramani et al., 2003; Hunter and Dymecki, 2007). Further heterogeneity in all cell types may emerge in response to state-dependent changes including circadian rhythms (Myung et al., 2018) or in disease (Hammond et al., 2019; Jordão et al., 2019).

The present study provides a first comprehensive map of the molecular, cellular and spatial diversity of the ChP from each ventricle of the developing and adult brain. Revealing a rich network of cells, with expression regionalization across ventricles in epithelial and mesenchymal cells, and suggesting a previously unappreciated role for mesenchymal, vascular and immune cells in shaping the tissue and potentially the CSF. These data will facilitate the design of tools to access and control specific cell populations in the ChP by genetic, optogenetic, and chemogenetic means. Since the ChP-CSF system is implicated in a growing number of neurologic conditions, the dataset offers molecular insight that will accelerate future studies investigating the lifelong, active regulation of the ChP brain-body barrier in health and disease.

Star Methods

Experimental Model and Subject Details

Animal Models

All mouse work was performed accordance with the Institutional Animal Care and Use Committees (IACUC) and relevant guidelines at the Boston Children's Hospital, Broad Institute and MIT, with protocols 17-10-3547R.

Embryonic day (E) 16.5 embryos were obtained from time-pregnant CD-1 dams for all embryonic ChP analyses. Adult ChP were harvested from 4-6 months old CD-1 males. All animals were housed under 12 hr/12 hr day night cycle with access to standard chow and water ad libitum. Embryonic day (E) 16.5 Cx3cr1-GFP mice were used to visualize macrophage distribution in the embryonic ChP.

CD1(ICR)—Charles River Labs Strain 022.

Cx3cr1-GFP (catalog #: 005582, The Jackson Laboratory)

Method Details

Embryonic ChP Tissue Dissection

Whole ChP from each ventricle were harvested using #5 forceps and fine-dissection scissors. To collect the 4V ChP, the developing hindbrain was separated from the mid- and forebrain structures using a scalpel. Next, using a scalpel the cisterna magna was exposed by gently pushing away the developing cerebellum to expose the 4V ChP. Lateral arms and medial core of the 4V ChP were teased away using forceps. Next, the 3V and LV ChP were collected from the rest of the developing brain structures. 3V ChP was found along the dorsal midline between the developing cerebral cortices, which were gently separated to expose the tissue and using a scalpel was cut away from developing pial membranes. After collecting the 3V ChP, a scalpel was used to perform a bilateral cut along the midline to separate the developing cortex into two hemispheres. Each hemisphere was stabilized with forceps and a third of the rostral end was cut, the developing hippocampus was rolled out using the flat surface of a scalpel and the attached LV ChP was gently separated from the hippocampus/fornix using forceps.

FACS Purification of Healthy Embryonic Cells

Lateral, third and four ventricles of three litters of embryonic E16.5 dpc embryos were rapidly dissected and pooled together in dissecting medium (HBSS+06% Glucose+1× Pen/Strep+Filtered medium 0.22 filter) (Corning, Cat:21-023-CV)+ glucose (Sigma, Cat:7021-100G). Dissected ChPs were spun down at 300×G for 3 mins in a centrifuge. Whole ChP was dissociated enzymatically by preparing fresh solution of collagenase II (Gibco, 17101-015) supplemented with 3 mM calcium (Sigma, C3881) for 15 minutes at room temperature. Next, CP was tapped and flicked 30 times and incubated at 37° C. incubator 3 consecutive times. The enzymatic solution with digested ChP tissue was then diluted using 1×HBSS, followed by pelleting down cells at 300×G for 3 mins. TrypLE (Life Technologies, TrypLE, Catalog: 12604) was then added and samples were incubated for 5 minutes followed by trituration using a micropipette. Samples were finally washed with ChP epithelial cell (CPEC) medium (DMEM+10% FBS+1×Pen/strep) and re-suspended in 1×HBSS+ glucose+ LIVE/DEAD staining kit (Thermo Fisher, Catalog: L-3; 224). Live cells identified by green fluorescence (calcein-AM) (LifeTechnologies, Catalog L3224A) and lack of EtD-1 homodimer staining (L3224B) were selected and sorted by a MoFlo Astrios cell sorter (Beckman Coulter) into 500 μL filled into dissecting medium.

Single Cell RNA-Seq

Single cells were processed through the 10×Genomics Single Cell 3' platform using the Chromium Single Cell 3' Library & Gel Bead Kit V1 and V2 kit (10× Genomics), as per the manufacturer's protocol. Briefly, 7,000 cells were loaded on each channel and partitioned into Gel Beads in Emulsion in the Chromium instrument where cell lysis and barcoding occur. This was followed by amplification, fragmentation, adaptor ligation and index library PCR. Libraries were sequenced on an Illumina HiSeqX at a read length of 98 base pairs.

Tissue Fixation and Processing

Dissected ChP were fixed in 4% paraformaldehyde (in 1× phosphate-buffered saline, pH 7.4). For microtome sectioning, embryonic brains were drop fixed in 4% paraformaldehyde, and incubated in the following series of solutions in 1× phosphate-buffered saline: 10% sucrose, 20% sucrose, 30% sucrose, 1:1 mixture of 30% sucrose and Optimal Cutting Temperature (OCT) compound (overnight) and finally in OCT compound alone (1 hour). Samples were then frozen in OCT compound.

Immunohistochemical Analysis

Cryosections were permeabilized with 0.1% Triton X-100 in phosphate-buffered saline, and incubated with primary antibodies overnight and then with secondary antibodies for 2 hours. Sections were counterstained with Hoechst 33342 (Thermo Fisher Scientific) and mounted on slides using Fluoromount-G (SouthemBiotech, Birmingham, AL).

For Ki67 staining, an antigen retrieval step was included: A food steamer (catalog number 5712, Oster, Boca Raton, FL) was filled with water and preheated until the chamber temperature reached 100° C.; sections were then immersed in boiling citric acid buffer (10 mmol/L sodium citrate, 0.05% Tween 20, pH 6) and placed in the steamer for 20 minutes. Sections were then cooled to room temperature.

Antibodies and Probes

Applicants used the following antibodies: AQP1—mouse (1:100)—Santa Cruz—sc-32737; PECAM1—rat (1:200)—BD Pharmingen—Cat. 550274; COL1A1—rabbit (1:250)-Abcam-ab34710; Spil/PU.1—rat (1:250)—Novus Bio—MAB7124-SP; KI67—mouse (1:50)-BD Pharmingen—550609; Ac-Tubulin—(1:250)-mouse-Sigma; Ccdc67-rabbit (1:500)-Proteintech-24579-1-AP; Shisa8-rabbit (1:500)-abcam-ab188621; Rtnl-rabbit (1:1000)-abcam-ab83049; Tubb3-mouse (1:250)-Biolegend-801202; 5-HT-goat (1:3000)-Sigma Aldrich-S5545; Slc40al-rabbit (1:250)-Alpha Diagnostic International-MTP11-A; LYVE-1-rat (1:300)-R and D-AF2125; Spi-C-rabbit (1:35)-Thermo Fisher-PA5-67537; CLDN5-488-mouse (1:400)-Invitrogen-Cat. 331588; VWF-rabbit (1:200)-Thermo Fisher-Cat. MA5-14029; ACTA2-Cy3-mouse (1:200); MRC1/CD206-rabbit (1:250) -Abcam-ab64693; Erg-rabbit (1:300); GFAP-mouse (1:1000).

The following RNAscope probes were used: Ins2, Slc38a5, Collal

Whole Explant RNAscope In Situ Hybridization and Immunohistochemistry

For whole mount smFISH, lateral, third, and fourth ventricle choroid plexus explants were dissected from E16.5 embryos and fixed with 4% paraformaldehyde (PFA) for 10 minutes at room temperature in a 9-well glass plate before beginning the manufacturer's provided protocol for RNAscope Fluorescent Multiplex (ACD). Free-floating explants were incubated with Target Retrieval Reagent (ACD) in a vegetable steamer for 12 minutes. Subsequently, explants were washed 3×3 minutes in double distilled water prior to incubation with Protease III Reagent (ACD) for 8 minutes at 40° C., followed by another 3×3 minute wash cycle in double distilled water. Target Probes (ACD) were then hybridized and amplified according to the manufacturer's specifications. After hybridization, immunohistochemical staining was performed in a subset of explants and described above. Allen Brain Atlas (Lein et al., 2007) and Gene-paint (Diez-Roux et al., 2011) were used to obtain in situ hybridization images of transcript localization within embryonic and adult brains.

Scanning and Transmission Electron Microscopy

Lateral ventricle choroid plexus tissue from embryonic and adult brain was micro-dissected in HBSS (Thermo Fisher Scientific) and drop-fixed immediately in FGP fixative (5% Glutaraldehyde, 2.5% Paraformaldehyde and 0.06% picric acid in 0.2 M sodium cacodylate buffer, pH 7.4). After 2 hour fixation at room temperature, the choroid plexus tissue was washed in 0.1M cacodylate buffer and postfixed with 1% Osmiumtetroxide $(OsO4)/1.5\%$ Potassiumferrocyanide (KFeCN6) for 1 hour, washed twice in water, and once in 50 mM Maleate buffer pH 5.15 (MB) and incubated in 1% uranyl acetate in MB for 1 hr followed by 1 wash in MB, 2 washes in water and subsequent dehydration in grades of alcohol (10 min each; 50%, 70%, 90%, 2×10 min 100%). The samples were then put in propyleneoxide for 1 hr and infiltrated ON in a 1:1 mixture of propyleneoxide and TAAB Epon (TAAB Laboratories Equipment Ltd, https://taab.co.uk). The following day, the samples were embedded in TAAB Epon and polymerized at 60° C. for 48 hrs. Ultrathin sections (about 80 nm) were cut on a Reichert Ultracut-S microtome, picked up on to copper grids stained with lead citrate. Images were acquired with a JEOL 1200EX transmission electron microscope, and recorded with an AMT 2k CCD camera (Biological Electron Microscopy Facility, Harvard Medical School).

Whole Explant Viral Transduction

Whole ChP were isolated and floated on Polycarbonate Track-Etched membranes (Whatman, Nucleopore, 8.0 μm Pore Size, Diameter, 13 mm) membranes in DMEM and infected with AAV-Syn1-GFP (AAV1.Syn.GCaMP6s.WPRE.SV40) (Penn Vector P2824), while incubated in DMEM for 48 hours in 37° C. incubators under $(95\%02/5\%0^2)$. Explants were then stained with antibodies against Tubb3 (Tuj 1, Biolegend, 1:250) and with corresponding secondary antibodies to visualize neurons, while native fluorescence was used to visualize Syn1 expression. Imaging was performed with a Zeiss LSM 700 confocal laser scanning microscope.

Hematoxylin and Eosin (H&E) Staining

Paraffin-embedded brains were sectioned to a thickness of 5 microns. The sections were de-paraffinized in xylene and then re-hydrated via successive incubation in 100% ethanol, 95% ethanol and water. Sections were incubated in Gill 3 hematoxylin (Sigma Aldrich, St. Louis, MO) for 2 minutes, followed by a 5-second incubation in 0.5% ammonia water to increase the contrast of the hematoxylin stain. Next, sections were rinsed in water and incubated in 1% alcoholic eosin for 3 minutes. Finally, sections were dehydrated via successive incubation in 95% ethanol, 100% ethanol and mounted using Permount (Thermo Fisher Scientific).

Adult ChP Tissue Dissection

Adult brain was first separated into hindbrain and connected mid/forebrain. From the hindbrain unit, the cerebellum was lifted to expose the cisterna magna and lateral arms of each ChP were separated using a scalpel. The 3V ChP was found in the medial space between in cerebral cortices and was exposed using a scalpel to gently separate the cortices and cut contra-lateral projections from each hemisphere. Next, irrigating this space with 1×HBSS revealed the ChP, which was clearly identifiable by a blood vessel running along its rostro-caudal axis. The 3V ChP travels ventrally as it extends into the rostral region of the brain, to connect to the ventral roots of the LV ChP in each hemisphere. The 3V ChP was separated from each of these connecting structures using scalpels. Next, to collect the LV ChP, cortices were separated into the two hemispheres by a bilateral cut along the midline. A third of each hemisphere from the rostral end was cut, and the hippocampus was rolled out using the flat surface of a scalpel and the attached LV ChP was separated from the hippocampus/fornix using a scalpel.

Single Nucleus RNA-Seq

Working on ice throughout, ChP tissue was transferred into the dounce homogenizer (Sigma Cat No: D8938) with 2 mL of EZ Lysis Buffer (Sigma-Aldrich: NUC101-1KT). Tissue was carefully dounced while on ice 25 times with Pestle A followed by 25 times with Pestle B, then transferred to a 15 mL conical tube. 2 mL of EZ lysis buffer were added to the dounce homogenizer to rinse residual nuclei and transferred to 15 mL tube for a final volume of 4 mL. Homogenate was incubated on ice for 10 mins and then centrifuged with a swing bucket rotor at 500 g for 5 mins at 4° C. Supernatant was removed and the pellet was resuspended in 100 μl of ice cold PBS+0.04% BSA (NEB B9000S). 40 μm FlowMi cell strainers were pre-wetted with ice cold 200 μl of PBS and the resuspended nuclei were gently filtered through the FlowMi into 1.5 mL Eppendorf tubes. Nuclei were counted using the Nexcelom Cellometer Vision and a DAPI stain. DAPI was diluted to 2.5 pg/μl in PBS and 20 μl of the DAPI was pipette mixed with 20 μl of the filtered nuclei suspension, then 20 μl of the stained nuclei were pipetted into the cellometer cell counting chamber (Nexcelom CHT4-SD100-002). Nuclei were counted using a custom assay with dilution factor set to 2. 10,000 nuclei were the input to 10× Genomics single-cell 3' Gene Expression v2 assay. cDNA was amplified for 12 cycles and resulting WTA measured by Qubit HS DNA (Thermo Fisher Scientific: Q32851) and quality assessed by BioAnalyzer (Agilent: 5067-4626). This WTA material was diluted to <8 ng/μl and processed through v2 library construction according the manufacturer's protocol, and resulting libraries were quantified again by Qubit and BioAnalzyer. Libraries were pooled and sequenced on 2 lanes of Illumina HiSeqX by The Broad Institute's Genomics Platform.

Quantification and Statistical Analysis

Regionalized Proliferation in the LV ChP

To quantify the proliferating front of the LV ChP, tissue was stained with Ki67 and Hoechst. Immuno-stained explants were imaged using LSM 710 laser scanning confocal microscope (Zeiss) with tiling function to collect images of whole LV ChP. The tissue was divided into three equal regions along the dorso-ventral axis of each LV ChP, into brain-proximal, medial and distal regions (excluding the distalmost ventricular of the tissue). Hoechst staining was used to identify cellular nuclei and proliferating cells were identified by overlapped Ki67 staining. Percentage of proliferating cells were counted in each region. A total of four independent explants were quantified. Multiple comparisons ANOVA was employed using statistical software package Graphpad PRISM. Data are represented as means±SEM. P<0.05 was considered significant.

Computational Analysis

Pre-Processing of Droplet-Based scRNA-Seq

De-multiplexing, alignment to the mm10 transcriptome and unique molecular identifier (UMI)-collapsing were performed using the Cellranger toolkit from 10× Genomics (version 1.1.0 for the first experiment, which was V1 chemistry, and version 2.0. for experiments two and three, which were V2 chemistry). For each cell, the number of genes for which at least one read was mapped were quantified, and then all cells with fewer than 500 detected genes were excluded. Since the total number of UMI and genes detected varies across cell types (FIG. 8A), further excluded were epithelial cells with fewer than 10,000 total UMI and mesenchymal cells with fewer than 6,000 total UMIs. Genes that were detected in less than 5 cells were excluded. Expression values $E_{i,j}$ for gene i in cell j were calculated by dividing UMI counts for gene i by the sum of the UMI counts in cell j, to normalize for differences in coverage, and then multiplying by 10,000 to create TPM-like values (TP10K), and finally computing $\log_2(TP10K+1)$. Batch correction was performed for each cell type separately using ComBat as implemented in the R package sva (Leek et al., 2012), using the default parametric adjustment mode. The output was a corrected expression matrix, which was used as an input to further analysis.

Pre-Processing of Droplet-Based snRNA-Seq Data

De-multiplexing, alignment to the mm10 transcriptome and unique molecular identifier (UMI)-collapsing were performed using the Cellranger toolkit (version 2.1.1, chemistry V2) provided by 10× Genomics. For each cell, the number of genes for which at least one read was mapped was quantified, and then excluded all cells with fewer than 400 detected genes. Genes that were detected in less than 10 cells were excluded. Expression values $E_{i,j}$ for gene i in cell j were calculated by dividing UMI counts for gene i by the sum of the UMI counts in cell j, to normalize for differences in coverage, and then multiplying by 10,000 to create TPM-like values (TP10K), and finally computing $\log_2(TP10K+1)$. For ease of data handling, and since ~80% of cells were epithelial cells, epithelial cells from the second batch of the adult data were randomly down-sampled to 6,000 cells. To address batch effects, canonical correlation analysis (CCA) from the Seurat package (Butler et al., 2018) was used on the union of the top 2,000 variable genes of batch 1 and batch 2 of all nuclei data, including embryo and adult. When aligning the CCA subspaces, 20 dimensions were used. Dimensionality reduction to 2D for visualization was performed using UMAP (McInnes et al., 2018) on the first 11 CCA dimensions. Clustering of cells was performed using the FindClusters( ) function from the Seurat package in R on the first 20 CCA dimensions, with a resolution of 0.8.

Identifying Variable Genes

Selection of variable genes was performed by fitting a logistic regression to the cellular detection fraction (often referred to as a), using the total number of UMIs per cell as a predictor as in (Montoro et al., 2018). Outliers from this curve are genes that are expressed in a lower fraction of cells than would be expected given the total number of UMIs mapping to that gene, that is, likely cell-type or state-specific genes. A threshold of deviance between $<-0.15$ and $<-0.3$ was used. In order to further correct for batch effect, if there were enough cells from all three batches, variable genes were calculated within each batch, and only the intersection of variable genes in each batch were taken for downstream analysis. This was the case when analyzing all cells (FIG. 1), and epithelial and mesenchymal cells. Batch was ignored for computing variable genes for immune, endothelial and neuro-/glia-like cells. The expression matrix was restricted to this subset of variable genes and values were centered and scaled and capped at a z-score of 10.

Dimensionality Reduction Using PCA and Visualization Using t-SNE or UMAP

The expression matrix to the subsets of variable genes and high-quality cells was restricted as noted above, and then centered and scaled values were implemented before inputting them into principal component analysis (PCA), using 'RunPCA' in Seurat which runs the irlba function. The cell embeddings were either the singular vectors themselves or the singular vectors multiplied with the singular values depending on the cells. After PCA, significant principal components were identified using the elbow-method when looking at the distribution of singular values. Scores from only those significant principal components were used as the input to further analysis. For visualization purposes, the dimensionality of the datasets was further reduced to 2D embeddings using the RunTSNE( ) function of the Seurat package in R on the significant PCs.

Clustering and Removing Doublets

To cluster single cells by their expression, an unsupervised clustering approach was used, based on the Infomap graph-clustering algorithm (Girvan and Newman, 2002). In brief, a k-nearest-neighbor graph on the data was constructed using, for each pair of cells, the Euclidean distance between the scores of significant principal components to identify k nearest neighbors. The parameter k was chosen to be consistent with the size of the dataset. Specifically, k was set to 40 for neuronal/glia-like cells and to 20 for immune cells, for which subclusters of macrophages were post-hoc merged together based on expression of canonical markers. The nearest-neighbor graph was computed using the function nng from the R package cccd. The k-nearest-neighbor graph was then used as the input to Infomap (Girvan and Newman, 2002) implemented using the infomap.community function from the igraph R package. For major cell types (FIG. 1C), clusters were post-hoc merged to six major cell populations using canonical markers for all cell types detected.

Doublets would form their own clusters and were clearly identifiable by dual expression of e.g. epithelial genes and endothelial genes and were removed from further analysis and any visualizations in the paper.

Scoring Cells Using Signature Gene Sets

In order to score cells using a gene sets, such as cell cycle (FIG. 2A) or arterial/venous gene expression (FIG. 12A), Applicants averaged over genes in the gene set after centering and scaling gene expression across cells. For cycling cells, cells with a z-score above 2 were classified as cycling cells.

Topic Modeling

LDA was computed on epithelial, mesenchymal and endothelial cells separately in the embryo, and on epithelial cells in adult. Specifically, the FitGoMO function from the CountClust R package (Dey et al., 2017) was used to fit LDA topic models to the UMI counts (Bielecki et al., 2018). To improve topic signals, genes expressed in more than 98% of cells or less than 2% of cells were removed from the count matrix prior to fitting the topic models (analogous to the removal of highly abundant words or extremely rare words in document analysis), except for endothelial cells. The number of topics to fit (K) and the tolerance value are required to run FitGoMO function. Thus, for each cell type and developmental status, a range of K and tolerance values were fit, picking values that gave robust topics and where the number of informative topics found were mostly saturated. For the embryo data, this was achieved with a tolerance of 0.1, and a K of 16 for endothelial cells, K of 20 for epithelial and mesenchymal cells, and K of 14 and tolerance of 0.01 for adult epithelial nuclei. The top genes to highlight for each topic were selected using the ExtractTopFeatureso function.

Defining Cell-Type or Cluster Signatures

Differential expression between cell types in scRNA-Seq of Embryo (FIG. 1) or snRNA-Seq of adult (FIG. 7), and between clusters of immune cells and neuro-/glia-like cells was performed using MAST (Finak et al., 2015), which fits a hurdle model to the expression of each gene, consisting of logistic regression for the zero component (i.e. whether the gene is expressed) and linear regression for the continuous component (i.e. the expression level). The regression model includes terms to capture the effects of the cell subset or cluster, while controlling for cell complexity (i.e. the total number of unique molecular identifiers (nUMI)). Specifically, the regression formula, $Yi \sim X+N$, where Yi is the standardized $\log_2(TP10K+1)$ expression vector for gene i across all cells, X is a factor variable reflecting cell subset or cluster membership, Nis the scaled nUMI in each cell was used. In all cases, the discrete and continuous coefficients of the model were retrieved and p-values were calculated using the likelihood ratio test in MAST. Q-values were estimated using the Benjamini-Hochberg correction. In order to identify cell-type specific or cluster specific markers, a FDR cutoff for the hurdle model was chosen using the elbow-method and a small mastfc cutoff to exclude genes with very small effect sizes. If a gene passed the FDR and the mastfc cutoff in only one cluster/cell type, it was considered to be specific.

Diffusion Map

For macrophages, cells of replicate 3 were excluded for this analysis because they had very high expression of mitochondrial genes. Diffusion components were calculated on a gene expression matrix limited to variable genes within the macrophages (not correcting for batch). Diffusion components were calculated using the DiffusionMap function from the destiny package in R (Angerer et al., 2016) with a k of 20 and a local sigma.

For diffusion analysis of epithelial and neuronal cells, cells from only 3V ChP were selected, where most neuronal cells were sampled from, only from replicate 3, because of strong batch effects between replicates. Furthermore, the epithelial cell cluster scoring highly for IEG genes (Figure S2D) and Oligodendrocyte precursor cells were also excluded from this analysis. Of the remaining cells, variable genes were computed as described above. Diffusion components were calculated as described for macrophages with a k of 30 and a local sigma.

Cell-Cell Interactions

First, a gene set table was created where cell type markers from FIG. 1C (Table 1) were considered to be general markers, and then subtype specific gene sets were added. For neuronal/glia-like cells and immune cells, cluster specific genes were added (Table 1). For the endothelial, epithelial and mesenchymal cells, the top 50 scoring feature genes from the topics used in this paper were added (Table 2-4). Gene names were then converted to their human homologs. The data in baderlab.org/CellCellInteractions/was used as a source of cognate ligand-receptor interactions. First, ligand-receptor pairs between any two gene sets (Table 5) were identified. Then, between two given gene sets, the weights per ligand and then per receptor was normalized to 1, as there is redundancy. All the weights between two gene sets were then summed. In order to assess the significance for the strength of two gene sets interacting with each other, the gene to gene-set assignment was shuffled $10^4$ times, and each time recomputed the overall interaction strength between any two gene sets. This formed the null distribution against which the empirical p-value was computed.

Cell Type Classification Across Embryo or Adult

To compare the embryo scRNA-seq dataset to the adult snRNA-seq dataset, a random forest classifier was used from the R package 'randomForest'. First, common variable genes were computed between the two datasets by taking the intersection of the variable genes in each dataset. Then, the classifier was trained on the scaled expression matrix of the common variable genes in the adult snRNA-seq dataset. The out-of-bag error was 0.15. The classifier then ran on the scaled expression matrix of the common variable genes in the embryo scRNA-seq dataset. Applicants then compared the predicted cell type assignment of the random forest classifier to the cell type assignment shown in FIG. 1C.

Data and Software Availability scRNA-seq and snRNA-seq data will be deposited in GEO and the Single Cell Portal (URL). Accession numbers have been requested.

Example 2—Harnessing Choroid Plexus Epithelial Cells to Secrete Anti-Oxidant Therapeutics into the Cerebrospinal Fluid for Distribution Throughout the Brain Despite remarkable progress in the diagnosis and treatment of human illness, access to the brain for drug delivery remains elusive. Oxidative stress—the accumulation of toxic cellular byproducts that would typically be neutralized by anti-oxidants—represents an insidious process that plays a pivotal role in normal aging as well as in the pathophysiology of many neurologic diseases. Anti-oxidant therapy is commonly prescribed for many conditions including age-associated neurologic disease, movement disorders, and motor neuron diseases. Therefore, sustained anti-oxidant delivery could favorably impact the course of several diseases.

The choroid plexus is an epithelial sheet located in each brain ventricle that secretes health-promoting factors that are distributed to all brain tissues via the cerebrospinal fluid (CSF). Proteins in healthy CSF protect neurons from oxidative-stress-induced damage. However, the availability of many protective secreted factors including the anti-oxidant SOD3 diminishes naturally with age.

While the exact combination of proteins in the CSF that mediate its neuroprotective effects it not elucidated, the RNAseq studies as well as in situ hybridization analyses from the Allen Brain Atlas suggest that the ChP is the principal source of the antioxidant Sod3 for the brain. Sod3 encodes Extracellular superoxide dismutase (EC-SOD), which catalyzes the dismutation of two superoxide radicals into hydrogen peroxide and oxygen. SOD3 is robustly secreted into CSF [8], where it interacts with extracellular matrix or freely distributes as enzymatically active tetramers. The ChP actively secretes many health-promoting factors into the CSF. Convective exchange between CSF and the brain's interstitial fluid then actively clears toxins from the brain, particularly during sleep or anesthesia [9]. Together, these data raise the hypothesis that restoring ChP-SOD secretion into the adult CSF may have therapeutic benefit on the brain.

Applicants previously found that chemotherapy triggers oxidative stress and damage in cultured human neurons. In parallel, chemotherapy dampens the ChP's ability to produce SOD3, contributing to diminished antioxidant levels in the CSF. CSF from patients receiving chemotherapeutics including methotrexate have reduced anti-oxidant capacity in their CSF, despite thiol supplementation (e.g. Leucovorin; [10-13] see also Preliminary data, FIG. 4.

It was hypothesized that the harmful effects of oxidative stress can be mitigated by restoring choroid plexus secretion of SOD3. Adeno-associated virus (AAV)-based augmentation of SOD3 production in choroid plexus was used.

Results:

AAV2/5-SOD3 transduction increased SOD3 expression and secretion into CSF in adult mice and rats. In parallel, MTX induced markers of oxidative damage to cultured human neurons, patient CSF, and rodent brain. Healthy adult CSF protected cultured rodent neurons from oxidative-stress-induced death. In vivo, intravenous MTX administered to mice and rats decreased choroid plexus anti-oxidant gene transcription and reduced antioxidant availability in CSF was confirmed. Finally, initial results suggest AAV2/5-SOD3 transduction may confer benefits to hippocampal tissue from MTX-induced oxidative damage to lipids. Applicants are currently increasing sample numbers and completing analyses of oxidative damage in other brain regions including cortex, white matter, and CSF.

Methods:

AAV2/5-SOD3 or control AAV2/5-GFP was injected into embryonic (E) 13.5 mouse lateral ventricles, and offspring were raised to 4-6 weeks of age. Applicants quantified choroid plexus-SOD3 expression (qRT-PCR), CSF-SOD protein levels (immunoblotting), and CSF-anti-oxidant capacity (ELISA). In parallel, Applicants tested if Methotrexate (MTX) exposure induced signatures of oxidative damage in cultured human cortical neurons (iPSCs), in patient CSF, and in vivo rodent brain. To test if supplemental choroid plexus-SOD3 protects the brain from acute oxidative stress, intravenous MTX was administered to mice previously transduced with AAV2/5-SOD3 or control AAV2/5-GFP, and analyzed cortex, hippocampus, and corpus callosum for markers of oxidative damage 48 hours later.

Figures 1, 2, 3, 29C:
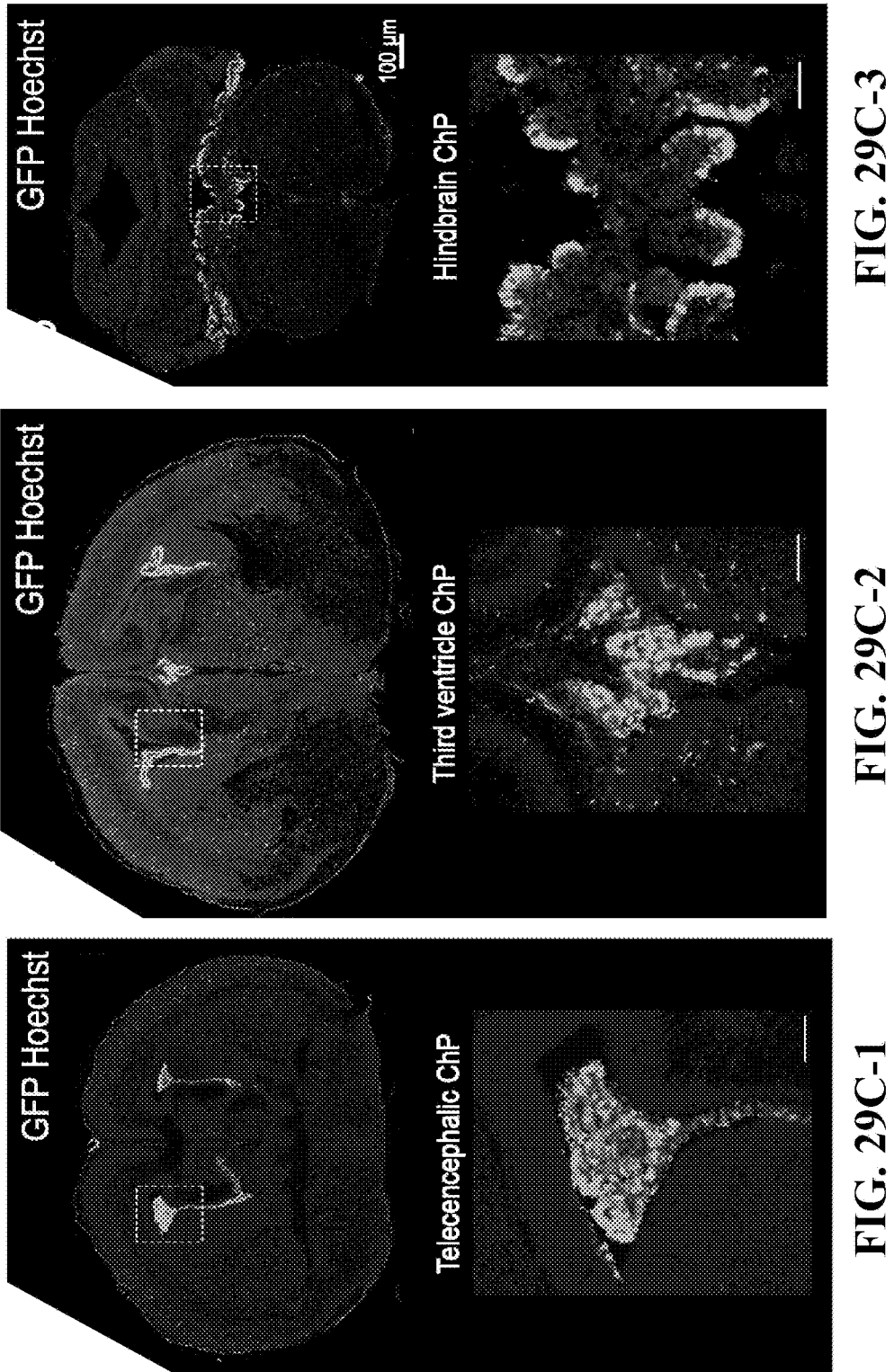

The human SOD3 expression vector was obtained (shared by Yasuhiko Kizuka [31]). Applcicants subcloned the SOD3 coding sequence into AAV2/5 plasmid, which shows tropism for ChP, generated high titer virus, and performed intra-ventricular injections into E13.5 mice and adult rats (FIG. 3). In both sets of experiments, SOD3 expression was observed in ChP, and increased SOD3 in CSF, likely due primarily increased SOD secretion by ChP (given the selective infection of ChP using the AAV2/5 serotype, which exhibits a strong tropism for ChP, FIG. 3A and not shown). In mouse experiments, expression at late embryonic ages was observed (not shown) and confirmed sustained expression and secretion up to P14. Applicants are currently aging parallel litters to obtain additional adult time points. In adult rat experiments, ChP SOD expression one week following intraventricular infection was confirmed (not shown). Importantly, the supplemental CSF-SOD demonstrated enhanced enzymatic activity in vivo (FIG. 3E). In an unrelated experiment, AAV2/5-GCaMP6 (a variant of GFP) was injected into adult mice at 5 weeks of age and achieved expression by ChP epithelial cells (data not shown), thereby providing proof-of-concept for AAV-mediated ChP targeting in adult mice. SOD3 represents a good target for these initial studies given the availability of reliable, commercially available reagents (qPCR primers, antibodies, ELISA kits). Applicants have extensive experience with all proposed techniques.

Optimized assays for evaluating redox homeostasis and oxidative damage to cells, lipids, and DNA and found chemotherapy (MTX)-induced oxidative damage in human neurons in vitro and in rodent brain in vivo, and rodent ChP in vitro and in vivo was performed (FIG. 4; data not shown). In other experiments (with Eric Wong, BIDMC/HMS), Applicants confirmed reports that MTX diminishes antioxidant capacity of human CSF.

Conclusions:

The choroid plexus is a secretory epithelial sheet that is poised to distribute health-promoting factors throughout the brain. Following AAV-based SOD supplementation, CSF-SOD levels are increased, as the antioxidant capacity of the CSF. As a first test of this broadly clinically approach, a chemotherapy model was used that leads to off-target effects in non-cancerous brain cells. Specifically, the preliminary studies demonstrate that exposure to chemotherapy triggers oxidative damage in brain cells, likely via direct effects as well as via a chemotherapy-induced drop in CSF antioxidant levels.

The findings suggest AAV-based gene therapy via the choroid plexus as may represent effective target tissue for achieving sustained gene therapy and anti-oxidant delivery via the CSF for the central nervous system. Initial results suggest that when challenged with the chemotherapeutic methotrexate, AAV-SOD supplementation confers benefits to some areas of the brain (e.g. hippocampus). However, this approach could pave the way to a more generalized gene therapy approach that harnesses the choroid plexus in service of neurologic disease.

Recent years have witnessed the innovation of AAV-based gene therapy approaches for the treatment of neurologic conditions including spinal muscular atrophy, Batten disease, and even genetic hearing loss. Because the choroid plexus is a secretory epithelial sheet that is poised to distribute factors throughout the brain, the approach could provide a valuable demonstration of an effective and less invasive target tissue for achieving sustained gene therapy for nervous system repair and maintenance.

Additional Studies

After 48 hours (based on preliminary studies), Applicants will collect CSF for measuring anti-oxidant capacity and SOD3 expression levels, isolate ChP for gene expression assays, and isolate cortex and hippocampus, which will be analyzed for changes in redox homeostasis using glutathione peroxidase assays (Cayman Chemicals). Preliminary results show that ChP-SOD3 rescues oxidative stress against MTX in the hippocampus. FIG. 24. Because lipid modifications have been implicated in MTX-associated chemobrain [28], Applicants will also test for changes in levels of malondialdehyde—the most prevalent byproduct of lipid peroxidation during oxidative stress. A minimum of 4 male and 4 female mice will be tested per group in an initial cohort. Applicants focus on MTX given the extensive preliminary data, but are by no means limited to working with this reagent, and recognize that other mechanisms and cell (e.g. tri-glial response) also contribute to chemotherapy-associated brain damage [29]. This approach provides an opportunity to test if a ChP with blunted antioxidant expression (due to MTX exposure) can be harnessed to produce excess anti-oxidant with benefits throughout the brain. If successful, collaborative projects will be pursued to test if the "super-ChP" confers benefits to other neurologic diseases in which oxidative stress is a hallmark of disease pathophysiology. In parallel, testing this approach in concert with other chemotherapeutics also implicated in triggering oxidative damage to the brain (e.g. Paclitaxel) have been discussed.

On the one hand, previous attempts for alleviating neurologic disease with sustained anti-oxidant-type therapies have had mixed results. It also remains to be determined how long-term AAV-mediated gene delivery would eventually be optimized in the adult human population, especially in the case of cells broadly targeted throughout the brain. On the other hand, there is reason to be optimistic since AAV-mediated gene therapy has recently been harnessed for intervention in severe neurological disorders (e.g. spinal muscular atrophy [14], Batten disease [15], and Usher syndrome [16]). If successful, this strategy will provide a new means for delivering anti-oxidants to the brain. It is anticipated that this approach can then be generalized for testing similar therapeutic delivery in mouse models with relevance to oxidative-stress associated neurologic diseases with particularly poor prognosis such as motor neuron disease. For human therapeutic purposes, the advent of more selective AAV vectors could soon enable more specific and even less-invasive delivery methods using intravenous injective and/or via intranasal spray with ability to decelerate progressive disease burden and possibly even the process of natural aging. Future studies could also incorporate combinatorial approaches, including N-acetylcysteine (NAC), by direct infusion into CSF [30], or microglial interference [29].

These preliminary data strongly suggest that chemotherapy directly damages secretory cells in the choroid plexus, leading to impoverished CSF lacking critical anti-oxidants and other health-promoting factors, thereby compounding the adverse effects of chemotherapy on non-cancerous cells throughout the brain. Applicants will test this hypothesis by assessing chemotherapy-induced oxidative stress responses in (1) human neurons, (2) rat brain and choroid plexus, as well as (3) altered redox capacity of CSF from rats and humans exposed to chemotherapy cocktails including MTX, Paclitaxel, and Adriamycin (Aim 1). Applicants will then engineer a biologically inspired CSF supplement, and test if CSF supplementation mitigates side effects of chemotherapy on: a] human neurons in vitro, b] rodent neuronal stem cells, neurons, and choroid plexus in vivo.

Identify neuroprotective factors in FDA-approved libraries that protect cultured human cortical neurons 2c. Test if intraventricular infusion of candidate neuroprotective factors identified in Aim 2b further protect the rat brain from chemotherapy-induced damage caused by oxidative stress.

Given the tremendous efforts to develop even more powerful chemotherapeutics that readily cross the BBB for aggressive treatment of brain cancers, as well as cancers that metastasize into the CNS, it is anticipated that the neurotoxic effects of chemotherapeutics will increasingly become a key factor limiting treatment dosage and efficacy. Because convective exchange between CSF and the brain's interstitial fluid actively delivers health-promoting signals to brain cells while clearing toxins from the brain (e.g. (18)), Applicants predict that intervention at the level of the choroid plexus and/or CSF supplementation will provide fresh, new avenues for protecting noncancerous cells in the brain and preserving cognitive health in the face of intense chemotherapy.

Experimental Methods and Data Analysis. Applicants will culture induced human cortical neurons (Südhof protocol (34)) in neuronal growth medium (including growth factors such as BDNF (10 ng/ml), NT3 (10 ng/ml), and laminin (0.2 g/ml) for 5 days in vitro (DIV) at 1-2X104 cells in 96 wells (BCH Human Neuron Core, see LETTER). Applicants will treat with increasing doses of chemotherapeutics (1 nM-10 uM; MTX, Paclitaxel, and Adriamycin), and evaluate neurons for morphological changes, oxidative damage, mitochondrial health, and cell viability (35) at 24 hour time intervals over 3 DIV. Leucovorin, Donepezil (36), Capecitabine (37) (10 M) will be included as controls. Applicants will treat iPSCs with the chemotherapeutics at peri-threshold doses identified above, and test their effects on mitochondrial respiration using Seahorse technology (Agilent; Department core instrument; 104 iPSCs/microplate; n=4 wells/condition). After 2 hours of chemotherapy exposure, distinct fluorescent indicators will be used to quantify basal respiration, maximal respiration, and spare respiratory capacity (Seahorse XF Cell Mito Stress Test). In parallel, mRNA will be extracted to test the effect of chemotherapeutics on neuronal antioxidant expression levels. A minimum of five biological replicates will be performed. ANOVA with Tukey multiple comparison post test will be used. The human CSF cancer patient cohort will also be extended beyond CNS lymphoma to other brain tumors that use MTX, Paclitaxel and Adriamycin as principal course of therapy (with Dr. Eric Wong, BIDMC, see LETTER). CSF is aliquoted and snap frozen immediately following collection, and will be used in experiments without freeze/thaw cycles. Applicants will pair broader expression assays that capture health, and growth-promoting activities in CSF will be quantified (SomaScan, BIDMC Genomics, Proteomics, Bioinformatics, and Systems Biology Center Core) (38, 39) with more targeted assays for overall SOD activity (Cayman Chemical, #706002). Specific changes in proteins will be further validated by immunoblotting (e.g. SOD3; Abcam, ab80946).

Harness the ChP-CSF System to Protect Brain from Chemotherapy-Induced Damage

Augmented ChP Antioxidant Secretion Help Prevent Chemotherapy-Associated Damage

Rationale and Preliminary Studies. Because the ChP-CSF system is easily accessible in humans (e.g. via intranasal sprays, intravenous injections), and because the CSF can penetrate deep into the brain via convective exchange with interstitial fluid (especially during sleep (18, 46)), the ChP and CSF are prime targets for therapeutic intervention. In rodents, intraventricular AAV delivery provides a direct method for inducing gene expression in ChP. AAV2/5 shows tropism for ChP epithelial cells (FIG. 6) (47). ChP can be infected during development or postnatally, thereby providing a means to augment production and release of antioxidants into the CSF. While chemotherapy likely influences expression of many genes, Applicants begin with Sod3 as it is highly secreted by ChP into the brain, and excellent reagents are commercially available. The human SOD3 expression vector was obtained (kindly shared by Yasuhiko Kizuka (48)). The SOD3 coding sequence was subcloned into AAV2/5 plasmid, the construct expresses well in culture, and Applicants are generating high titer virus for the proposed studies (with Chen Wang, BCH Viral Core; FIG. 7).

Experimental Methods and Data Analysis. AAV2/5-SOD3 or control AAV2/5-GFP will be injected into the rat lateral ventricle (−0.8 mm posterior, 1.5 mm lateral, 3.5 mm ventral to Bregma), resulting in expression beginning 48 hours later. Group 1: SOD3 expression will be confirmed by qRT-PCR and immunostaining one week after injection. Group 2: Chemotherapeutic cocktails, or vehicle controls, will be delivered by intravenous route as in Aim 1b (1 week post-injection). 48 hours later, Applicants will isolate CSF and ChP to assess antioxidant capacity and targeted gene expression (Aim 1b). At the same time, brain tissues (e.g. cortex, hippocampus, lipids) will be evaluated for oxidative damage. Based on statistical power analysis using preliminary SOD activity data after intravenous MTX injection (average and standard deviation), it is estimated that at least N=4 rats are required to achieve alpha=0.05 and beta=0.3.

Expected Results and Interpretation. AAV vectors have high efficiency of stable transduction of post-mitotic tissues in vivo, which is appealing for gene therapy applications. These studies will provide, for the first time, direct evidence regarding the degree to which anti-oxidant overexpression by the ChP protects non-cancerous brain cells from damage induced by existing chemotherapeutics. This viral approach will facilitate rapid testing of additional protective compounds that can be applied individually or in combination during chemotherapy.

Potential Pitfalls and Alternative Approaches. (1) In future studies, Applicants will assess efficacy of this approach for preventing chemotherapy-induced decline in cognitive function in rodent models. (2) While AAV-mediated gene therapy has been harnessed for intervention in several neurological disorders (e.g. spinal muscular atrophy; Batten's disease), it is unclear if long-term AAV-mediated gene delivery would be optimal in surviving cancer patients. Because CSF is accessible in humans via intranasal spray, Applicants can consider a complementary approach to test for efficacy of neuroprotective factors, including N-acetyl-cysteine (NAC), by direct infusion into CSF (see Aim 2c) (49). (3) SOD3 may not be a dominant health-promoting factor at all levels tested. This can be tested by application of human CSF to chemotherapy-treated cells, with and without prior immunodepletion of SOD3 (similar to the approach involving immunodepletion of IGF2 from human CSF (15)).

Aim 2b. Identify Neuroprotective Factors for Cultured Human Cortical Neurons (iPSCs) from FDA-Approved Libraries Rationale and Preliminary Studies. As described above in Aim 1a, initial dose-response studies with MTX performed in iPSCs suggest chemotherapy triggers an oxidative stress response in human cortical neurons. Applicants will build on these data to screen a Redox library to identify compounds that protect neurons from damage, and to identity pathways activated by MTX treatment in human neurons (50, 51).

Experimental Methods and Data Analysis. Human iPSCs (cortical neurons) will be obtained and cultured as in Aim 1a. Using the threshold responses from Aim 1a for identifying which concentrations trigger oxidative stress (1 nM-10 uM; MTX, Paclitaxel, and Adriamycin), Applicants will screen a Redox library of 84 factors (Screen-well Redox Library; Enzo BML-2835) to identify compounds that protect neurons. Applicants begin with an initial evaluation of oxidative stress quantified by CellRox. Favorable compounds will also be tested for effects on neuronal morphology, mitochondrial health, and cell viability. For controls, ACSF alone, and native CSF will also be tested. The supplement may benefit from additional anti-oxidants, including NAC, which improves chemobrain in rats (52), or leucovorin (22) and Capecitabine, an anti-metabolite administered with Adriamycin.

Expected Results and Interpretation. This approach should uncover available compounds that may help offset the deleterious consequences of chemotherapy on non-cancerous cells in the brain. Top candidates will be tested individually and in combination, and promising candidates with then be tested in vivo (Aim 2c).

Potential Pitfalls and Alternative Approaches. (1) Applicants recognize that the in vitro assays are limited in scope and that candidate factors that do not test as positive in this assay may nevertheless have important activities (e.g. by acting as pro- or anti-inflammatory mediators) and may therefore be missed. However, on balance, this is a highly feasible approach and is likely to result in the discovery of some true protective factors for proof-of-principle testing in vivo in Aim 2c. (2) If protective factors are not identified using the Redox library, Applicants can expand to test other libraries (e.g. Tocris), or deduce new candidates by performing RNAseq on ChP to identify pathways with reduced gene expression in addition to SOD3.

Aim 2c. Test if Intraventricular Infusion of Candidate Neuroprotective Factors Identified in Aim 2b Protect the Rat Brain from Oxidative Damage Rationale and Preliminary Studies. To complement the gene therapy approach (Aim 2a), candidates identified to have potentially favorable effects protecting neurons from oxidative stress (Aim 2b) will be directly infused into rat CSF space. In future, promising candidate compounds can be optimized for pharmacological treatment in humans, under the guidance of collaborator Dr. Eric Wong (BIDMC).

Experimental Methods and Data Analysis. Candidate compounds will be delivered using a chronically implanted Alzet osmotic minipump, targeted to the lateral ventricle (Aim 2a) to achieve slow release of compounds into the rat CSF. A Hamilton syringe pump controls injection rate. Based on Applicants' previous work, 2 ul of the compound will be injected in solution or of a control compound, daily for 7 days (leucovorin; 0.4 ul/min infusion rate to prevent tissue injury; (53, 54)). At 1 week following onset of compound delivery, chemotherapeutic cocktails or saline controls will be delivered via tail vein injection (see Aim 1b). 48 hours later, CSF will be collected and antioxidant capacity tested and brain tissues collected for analysis of redox state (as in Aim 2a). A minimum 4 male and 4 female rats per group will be used for MTX, leucovorin and control groups.

Expected Results and Interpretation. If successful, this strategy will provide new candidate factors with the potential for lessening adverse neurocognitive sequelae following cancer therapy (55). The proposed strategy to identify new compounds and to harness the ChP-CSF system to offset the deleterious effects of chemotherapy may ultimately benefit cancer survivorship in both children and adults.

Potential Pitfalls and Alternative Approaches. (1) If necessary, timelines and doses of compound infusion will be adapted and expanded, as well as the time points for analysis of brain tissue following MTX delivery. (2) While useful compounds from Aim 2b are anticipated, if individual candidates in Aim 2b are not sufficient to achieve full protection, Applicants will work towards a synthetic CSF supplement that comprises multiple antioxidant compounds that will work in parallel and may yield synergistic effects.

The aims are fully achievable due to existing preliminary data, existing or available tools for all aims, strong PI expertise in oxidative stress (45, 56, 57), and local collaborations with leading cancer specialists.

References for Example 2

1. Saunders, N. R., et al., *The rights and wrongs of blood-brain barrier permeability studies: a walk through* 100 *years of history.* Front Neurosci, 2014. 8: p. 404.
2. Chow, B. W. and C. Gu, *The molecular constituents of the blood-brain barrier.* Trends Neurosci, 2015. 38(10): p. 598-608.
3. Patel, M., *Targeting Oxidative Stress in Central Nervous System Disorders.* Trends Pharmacol Sci, 2016. 37(9): p. 768-778.
4. Lehtinen, M. K. and A. Bonni, *Modeling oxidative stress in the central nervous system.* Curr Mol Med, 2006. 6(8): p. 871-81.
5. Lehtinen, M. K., et al., *The cerebrospinal fluid provides a proliferative niche for neural progenitor cells.* Neuron, 2011. 69(5): p. 893-905.

6. Lehtinen, M. K., et al., *The choroid plexus and cerebrospinal fluid: emerging roles in development, disease, and therapy.* J Neurosci, 2013. 33(45): p. 17553-9.

7. Chau, K. F., et al., *Progressive Differentiation and Instructive Capacities of Amniotic Fluid and Cerebrospinal Fluid Proteomes following Neural Tube Closure.* Dev Cell, 2015. 35(6): p. 789-802.

8. Lun, M. P., et al., *Spatially heterogeneous choroid plexus transcriptomes encode positional identity and contribute to regional CSF production.* J Neurosci, 2015. 35(12): p. 4903-16.

9. Xie, L., et al., *Sleep drives metabolite clearance from the adult brain.* Science, 2013. 342(6156): p. 373-7.

10. Fardell, J. E., et al., *Chemotherapy and cognitive impairment: treatment options.* Clin Pharmacol Ther, 2011. 90(3): p. 366-76.

11. Dietrich, J., et al., *Clinical patterns and biological correlates of cognitive dysfunction associated with cancer therapy.* Oncologist, 2008. 13(12): p. 1285-95.

12. Moore, I. M. K., et al., *Changes in Oxidant Defense, Apoptosis, and Cognitive Abilities During Treatment for Childhood Leukemia.* Biol Res Nurs, 2018. 20(4): p. 393-402.

13. Ki Moore, I. M., et al., *Increase in oxidative stress as measured by cerebrospinal fluid lipid peroxidation during treatment for childhood acute lymphoblastic leukemia.* J Pediatr Hematol Oncol, 2015. 37(2): p. e86-93.

14. Shababi, M., et al., *A Direct Comparison of IV and ICV Delivery Methods for Gene Replacement Therapy in a Mouse Model of SMARD1.* Mol Ther Methods Clin Dev, 2018. 10: p. 348-360.

15. Geraets, R. D., et al., *Moving towards effective therapeutic strategies for Neuronal Ceroid Lipofuscinosis.* Orphanet J Rare Dis, 2016. 11: p. 40.

16. Pan, B., et al., *Gene therapy restores auditory and vestibular function in a mouse model of Usher syndrome type 1c.* Nat Biotechnol, 2017. 35(3): p. 264-272.

17. Gao, X., et al., *Treatment of autosomal dominant hearing loss by in vivo delivery of genome editing agents.* Nature, 2018. 553(7687): p. 217-221.

18. Donsante, A., et al., *ATP7A gene addition to the choroid plexus results in long-term rescue of the lethal copper transport defect in a Menkes disease mouse model.* Mol Ther, 2011. 19(12): p. 2114-23.

19. Watson, D. J., M. A. Passini, and J. H. Wolfe, *Transduction of the choroid plexus and ependyma in neonatal mouse brain by vesicular stomatitis virus glycoprotein-pseudotyped lentivirus and adeno-associated virus type 5 vectors.* Hum Gene Ther, 2005. 16(1): p. 49-56.

20. Haddad, M. R., et al., *Fetal Brain-directed AAV Gene Therapy Results in Rapid, Robust, and Persistent Transduction of Mouse Choroid Plexus Epithelia.* Mol Ther Nucleic Acids, 2013. 2: p. e101.

21. Shannon, M. L., et al., *Mice Expressing Myc in Neural Precursors Develop Choroid Plexus and Ciliary Body Tumors.* Am J Pathol, 2018.

22. Lehtinen, M. K., et al., *Cystatin B deficiency sensitizes neurons to oxidative stress in progressive myoclonus epilepsy, EPM1.* J Neurosci, 2009. 29(18): p. 5910-5.

23. Protas, P. T., et al., *Cerebrospinal fluid oxidative stress during chemotherapy of acute lymphoblastic leukemia in children.* Pediatr Hematol Oncol, 2010. 27(4): p. 306-13.

24. Rodgers, C., et al., *Fatigue and Oxidative Stress in Children Undergoing Leukemia Treatment.* Biol Res Nurs, 2016. 18(5): p. 515-20.

25. Nakayama, A., et al., *Systematic review: generating evidence-based guidelines on the concurrent use of dietary antioxidants and chemotherapy or radiotherapy.* Cancer Invest, 2011. 29(10): p. 655-67.

26. Seigers, R., et al., *Long-lasting suppression of hippocampal cell proliferation and impaired cognitive performance by methotrexate in the rat.* Behav Brain Res, 2008. 186(2): p. 168-75.

27. Seigers, R., et al., *Methotrexate decreases hippocampal cell proliferation and induces memory deficits in rats.* Behav Brain Res, 2009. 201(2): p. 279-84.

28. Horowitz, T. S., J. Suls, and M. Trevino, *A Call for a Neuroscience Approach to Cancer-Related Cognitive Impairment.* Trends Neurosci, 2018. 41(8): p. 493-496.

29. Gibson, E. M., et al., *Methotrexate Chemotherapy Induces Persistent Tri-glial Dysregulation that Underlies Chemotherapy-Related Cognitive Impairment.* Cell, 2018.

30. Choi, Y., et al., *Minocycline attenuates neuronal cell death and improves cognitive impairment in Alzheimer's disease models.* Neuropsychopharmacology, 2007. 32(11): p. 2393-404.

31. Ota, F., et al., *N-Glycosylation is essential for the secretion of extracellular superoxide dismutase.* FEBS Lett, 2016. 590(19): p. 3357-3367.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of reducing brain oxidative stress in a subject in need thereof, comprising:

delivering, by intraventricular injection, to a choroid plexus (ChP) exhibiting age, drug, or disease induced reduction of anti-oxidant enzyme expression levels and/or activity, a vector encoding superoxide dismutase 3 (SOD3), whereby expression of the SOD3 in the ChP results in reduced oxidative stress in a brain of the subject, wherein the viral vector is an adeno-associated virus (AAV) 2/5 vector.

2. The method of claim 1, wherein the subject suffers from a neurodegenerative or inflammatory disease.

3. The method of claim 2, wherein the neurodegenerative or inflammatory disease is selected from Alzheimer's disease (AD), familial AD, Creutzfeldt-Jacob disease, dementia pugilistica, Down's Syndrome, Gerstmann-Straussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), Parkinson's disease, HIV-related dementia, adult onset diabetes, senile cardiac amyloidosis, endocrine tumors, glaucoma, ocular amyloidosis, primary retinal degeneration, macular degeneration, optic nerve drusen, optic neuropathy, optic neuritis, and lattice dystrophy, or atypical parkinsonism, acute disseminated encephalomyelitis (ADEM); Addison's disease; ankylosing spondylitis; antiphospholipid antibody syndrome (APS); aplastic anemia; autoimmune-associated infertility; autoimmune gastritis; autoimmune hepatitis; autoimmune hemophilia; autoimmune lymphoproliferative syndrome (ALPS); autoimmune thrombocytopenia; autoimmune uveoretinitis; Behget's disease; bullous pemphigoid; celiac disease; dermatomyositis; diabetes mellitus type I; glomerulonephritis; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; insulin resistance; mixed connective tissue disease; multiple sclerosis (MS); myasthenia gravis (MG); opsoclonus myoclonus syndrome (OMS); Ord's thyroiditis; pemphigus; pernicious anemia; polyarteritis nodosa; polymyositis; primary biliary cirrhosis; primary myxedema; psoriasis; rheumatic fever; rheumatoid arthritis; Reiter's syndrome; scleroderma with anti-collagen antibodies; Sjögren's syndrome; systemic lupus erythematosus (SLE); Takayasu's arteritis; temporal arteritis; vitiligo; warm autoimmune hemolytic anemia; or Wegener's granulomatosis.

4. The method of claim 1, wherein the subject is receiving a chemotherapeutic.

5. The method of claim 4, wherein the chemotherapeutic is selected from methotrexate, Paclitaxel, and Adriamycin, or a combination thereof.

6. The method of claim 1, wherein reduced oxidative stress in the brain of the subject comprises reduced levels of 8-hydroxyguanosine (8-OHdG) and/or malondialdehyde (MDA).

7. A method of reducing brain oxidative stress in a subject in need thereof, comprising delivering, by intraventricular injection, to a choroid plexus (ChP) exhibiting age-, drug-, or disease-induced reduction of anti-oxidant enzyme expression levels and/or activity, a viral vector comprising an adeno-associated virus (AAV) 2/5 vector encoding superoxide dismutase 3 (SOD3), wherein expression of the SOD3 in the ChP results a reduction in oxidative stress markers selected from the group consisting of 8-hydroxyguanosine (8-OHdG) and malondialdehyde (MDA).

\* \* \* \* \*